US007781484B2

(12) United States Patent
Byers et al.

(10) Patent No.: US 7,781,484 B2
(45) Date of Patent: Aug. 24, 2010

(54) THIOL ESTER COMPOSITIONS AND PROCESSES FOR MAKING AND USING SAME

(75) Inventors: Jim D. Byers, Bartlesville, OK (US); Mitchell D. Refvik, Bartlesville, OK (US); Chad W. Brown, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 1454 days.

(21) Appl. No.: 11/059,792

(22) Filed: Feb. 17, 2005

(65) Prior Publication Data

US 2005/0197390 A1     Sep. 8, 2005

Related U.S. Application Data

(60) Provisional application No. 60/545,260, filed on Feb. 17, 2004, provisional application No. 60/561,614, filed on Apr. 13, 2004, provisional application No. 60/561,685, filed on Apr. 13, 2004, provisional application No. 60/561,855, filed on Apr. 13, 2004.

(51) Int. Cl.
*A61K 31/21* (2006.01)
*C07C 327/08* (2006.01)

(52) U.S. Cl. ..................................... 514/513; 558/250

(58) Field of Classification Search ................. 558/250; 514/513
See application file for complete search history.

(56) References Cited

U.S. PATENT DOCUMENTS

| 3,041,284 | A |   | 6/1962  | Calhoun et al.   |
|-----------|---|---|---------|------------------|
| 3,114,734 | A |   | 12/1963 | Gobrad et al.    |
| 3,211,674 | A |   | 10/1965 | Sandridge        |
| 3,278,496 | A |   | 10/1966 | LeFave et al.    |
| 3,446,780 | A |   | 5/1969  | Bertozzi         |
| 3,465,057 | A |   | 9/1969  | Cameron et al.   |
| 3,686,326 | A |   | 8/1972  | Oswald et al.    |
| 3,707,552 | A |   | 12/1972 | Dobinson et al.  |
| 3,742,006 | A |   | 6/1973  | Doss             |
| 3,746,685 | A |   | 7/1973  | Dobinson et al.  |
| 3,853,959 | A |   | 12/1974 | Dobinson et al.  |
| 3,884,951 | A |   | 5/1975  | Oswald           |
| 3,914,288 | A |   | 10/1975 | Gamish et al.    |
| 3,916,067 | A |   | 10/1975 | Jones et al.     |
| 3,926,822 | A |   | 12/1975 | Habiby           |
| 3,953,347 | A |   | 4/1976  | Habiby           |
| 3,981,901 | A |   | 9/1976  | Guthrie et al.   |
| 3,986,966 | A |   | 10/1976 | Wakim            |
| 3,991,089 | A |   | 11/1976 | Schwab et al.    |
| 4,045,472 | A |   | 8/1977  | Guthrie et al.   |
| 4,119,640 | A |   | 10/1978 | Hodakowski et al.|
| 4,218,332 | A |   | 8/1980  | Schwab et al.    |
| 4,231,956 | A |   | 11/1980 | Sullivan et al.  |
| 4,254,185 | A |   | 3/1981  | Buter            |
| 4,340,707 | A |   | 7/1982  | Queis et al.     |
| 4,504,651 | A |   | 3/1985  | Yamaguchi et al. |
| 4,566,878 | A |   | 1/1986  | Karol et al.     |
| 4,626,562 | A |   | 12/1986 | Motomura et al.  |
| 4,636,242 | A |   | 1/1987  | Timmons          |
| 5,126,425 | A |   | 6/1992  | Sesagawa et al.  |
| 5,405,426 | A |   | 4/1995  | Timmons et al.   |
| 5,411,776 | A | * | 5/1995  | Schmidt et al. ............... 428/34 |
| 5,422,422 | A |   | 6/1995  | Bader et al.     |
| 5,454,851 | A |   | 10/1995 | Zlotnikov et al. |
| 5,538,531 | A |   | 7/1996  | Hudson et al.    |
| 5,925,726 | A |   | 7/1999  | Seppala et al.   |
| 5,932,681 | A |   | 8/1999  | Herold et al.    |
| 6,039,781 | A |   | 3/2000  | Goertz et al.    |
| 6,221,994 | B1 |  | 4/2001  | Galblati et al.  |
| 6,231,633 | B1 |  | 5/2001  | Hirano et al.    |
| 6,358,296 | B1 |  | 3/2002  | Markusch et al.  |
| 6,583,302 | B1 |  | 6/2003  | Erhan et al.     |
| 7,585,932 | B2 | * | 9/2009 | Byers et al. ................. 528/376 |
| 2003/0204030 | A1 | | 10/2003 | Higuchi et al. |
| 2005/0197390 | A1 | | 9/2005 | Byers et al. |
| 2005/0197391 | A1 | | 9/2005 | Refvik et al. |
| 2006/0000252 | A1 | | 1/2006 | Carstens et al. |
| 2006/0009365 | A1 | | 1/2006 | Erhan et al. |
| 2006/0036110 | A1 | | 2/2006 | Brown et al. |
| 2006/0111520 | A1 | | 5/2006 | Byers et al. |
| 2007/0055033 | A1 | | 3/2007 | Byers et al. |
| 2007/0112100 | A1 | | 5/2007 | Byers et al. |

FOREIGN PATENT DOCUMENTS

DE         300174         5/1992

(Continued)

OTHER PUBLICATIONS

Stokes et al., Fat metabolism in higher Plants, Archives of Biochemistry and Biophysics (1974), 162 (2), 638-48.*
Kanemura, Y, et al. "Dithiols as Improvers for Polyurethanes," Chemical Abstracts, American Chemical Society, vol. 11, No. 22, Nov. 27, 1989 (XP000251903).
Search Report from International Patent Application No. PCT/US2006/031393, dated Jan. 1, 2007.
Search Report from Internatinal Patent Application No. PCT/US2006/031901 dated Nov. 11, 2006.

(Continued)

*Primary Examiner*—James O Wilson
*Assistant Examiner*—Ebenezer Sackey
(74) *Attorney, Agent, or Firm*—Stephen R. Jenkins

(57) ABSTRACT

Thiol ester compositions, methods of making the thiol ester compositions, and methods of using the thiol ester compositions are provided. In some embodiments, the thiol ester compositions include thiol esters, hydroxy thiol esters and cross-linked thiol esters. The thiol ester composition can be used to produce cross-linked thiol esters, sulfonic acid-containing esters, sulfonate containing esters and thioacrylate containing esters. The thiol ester compositions can be used to produce polythiourethanes. The polythiourethanes can be used in fertilizers and fertilizer coatings.

53 Claims, 14 Drawing Sheets

FOREIGN PATENT DOCUMENTS

| | | |
|---|---|---|
| EP | 0 308 664 | 8/1988 |
| EP | 0 716 057 | 6/1996 |
| FR | 1 194 553 | 11/1959 |
| GB | 908986 | 10/1962 |
| GB | 1 292 214 | 10/1972 |
| GB | 1 312 821 | 4/1973 |
| GB | 1 312 822 | 4/1973 |
| GB | 1 484 062 | 8/1977 |
| GB | 2188327 | 9/1987 |
| JP | 60123506 | 7/1985 |
| JP | 1 090169 | 4/1989 |
| JP | 1090167 | 6/1989 |
| JP | 1090168 | 6/1989 |
| JP | 1090170 | 6/1989 |
| JP | 2003-252956 | 9/2003 |
| WO | WO 86/06371 | 11/1986 |
| WO | WO 02/053672 | 7/2002 |
| WO | WO 03/006569 | 1/2003 |
| WO | WO 03/082958 | 10/2003 |
| WO | WO 2005/080325 | 1/2005 |
| WO | WO 2005/014564 | 2/2005 |
| WO | WO 2005/022217 | 3/2005 |
| WO | WO 2005/123862 | 12/2005 |
| WO | WO 2007/021960 | 2/2007 |
| WO | WO 2007/035215 | 3/2007 |

OTHER PUBLICATIONS

Kanemura, Y, et al, Dithiols as Improvers for Polyurethanes, Chemical Abstracts, American Chemical Society, vol. 11, No. 22, Nov. 27, 2989.

Stokes, Archives of Biochemistry and Biophysics (1974) 162(2), 638-48.

Olsen, Scand. Symp. Lipids, [Proc.], 11$^{th}$ (1982), Meeting Date 1981, 173-8.

Peppard, Proceedings of the Congress—European Brewery Conventions (1979), 17$^{th}$ 91-104.

http://www.brunobock.org/modules.php?name=Content&pa=showpage&pid=49.

Dyer, et al, The Kinetics of the Reactions of Phenyl Isocyanate with Thiols, J. Org. Chem., Aug. 26, 1961, 2919-2925.

Dyer, et al., The Kinetics of the Reactions of Phenyl Isocyanate with Certain Thiols, J. Am. Chem. Soc., 79, Aug. 13, 1957, 366-369.

Robins, Metal Ion Catalysis in Mercaptan Isocyanate Reactions, Adv. In Urethane Science and Tech., 12, 1993, 25-58.

Silva, et al, Recent Developments in Polyurethane Catalysis: Catalytic Mechanisms Review, Catalysis Reviews, 46, 2004, 31-52.

http://www.cognis.com/NR/rdonlyres/FDE0E9E1-DAE2-4950-B7FA-5EAF67B40C18/0/Folder_26.pdf.

Office Action dated Jun. 18, 2008, 8 pages, U.S. Appl. No. 11/060,696, filed Feb. 17, 2005.

Office Action dated Jun. 27, 2008, 8 pages, U.S. Appl. No. 11/059,792, filed Feb. 17, 2005.

Office Action dated Mar. 19, 2009, 8 pages, U.S. Appl. No. 11/059,792, filed Feb. 17, 2005.

Office Action dated Sep. 24, 2008, 8 pages, U.S. Appl. No. 11/464,318, filed Aug. 14, 2008.

Office Action dated Jun. 24, 2008, 5 pages, U.S. Appl. No. 11/060,675, filed Feb. 17, 2005.

Office Action dated Dec. 21, 2007, 5 pages, U.S. Appl. No. 11/060,675, filed Feb. 17, 2005.

Office Action dated Jul. 16, 2007, 8 pages, U.S. Appl. No. 11/060,675, filed Feb. 17, 2005.

Office Action dated Dec. 19, 2006, 7 pages, U.S. Appl. No. 11/060,675, filed Feb. 17, 2005.

Office Action dated Jun. 23, 2008, 8 pages, U.S. Appl. No. 11/204,728, filed Aug. 16, 2005.

Search Report for International Patent Application No. PCT/US2005/005110 dated Jan. 24, 2006.

Elchueva, A.D., et al., "Influence of the Type of Oligoisocyanate on the Properties of Thiourethane Compounds," Russian J of Applied Chem, vol. 74 (2001) pp. 1040-1043.

Fitt, Peter S., et al., "Dithiols. Part XIX. Further Studies on the Deacetylation of Acetylated Dithiols," J of the Chem Society No. 5 (1957) pp. 2240-2249.

Derkach, N. Ya, et al., "Mercapto Derivatives of Alkylmalonic Esters," Chemical Abstracts, vol. 54, No. 22, (1960), Abstract No. 24386a.

Blackman L.C.F., et al. "Promoters for the Dropwise Condensation of Steam. Part II . . . ," J of the Chem Society, No. 1 (1957) pp. 165-169.

Mazaev, V.E., et al., "Preparation Reflux Mercaptoethanol Appropriate Acid," Derwent Publications, Week 197442, Abstract No. SU410010 (1974).

Demchuk, Dmitry V., et al. "Synthesis of 12- and 13-Membered Sulfur-Containing Lactones by Homolytic Macrocyclization . . . ," Synthesis, (1995) pp. 307-311.

Sudmeier, James L., et al. "Fast Kinetics by Stopped-Flow Chlorine-35 Nuclear Magnetic Resonance . . . " Inorganic Chem vol. 10 No. 4 (1971) pp. 860-863.

Tanaka, Kiyoshi, et al., "Oxidation of Thiol by 5-Arylidene, 1,3-Dimethylbarbituric Acid and Its Application . . . ," Tetrahedron Letters, vol. 28, No. 36 (1987) pp. 4173-4176.

Troyansky, Emmanuil I., et al. "Stereoselective Free Radical Cycloaddition-Macrocyclization in Facile Synthesis . . . ," Tetrahedron, vol. 51, No. 42 (1995) pp. 11431-11444.

Chavdarian, Charles G., et al. "Synthesis, Redox Characteristics, and in Vitro Norepinephrine Uptake . . . " J of Medicinal Chem, vol. 22, No. 11 (1979) pp. 1317-1322.

Sjoberg, Bertil, "Uber Thioglycerine and einige verwandte Schwefelverbindungen," Berichte der Deutschen Chemischen Gesellschaft, vol. 75, No. 1 (1942) pp. 13-29.

Mayadunne, Roshan T.A., et al. "Multiarm organic compounds for use as reversible chain-transfer agents . . . ," Tetrahedron Letters, vol. 43, No. 38 (2002) pp. 6811-6814.

Miyake, Y., et al., "Enantioselective conversion of meso-cyclic disulfides to chiral cyclic sulfides . . . " J of the Chem Society, Perkin Trans 1, No. 10 (2000) pp. 1595-1599.

Bhattacharya, S., et al., "Synthesis of Macrocyclic Diacy/Dialkyl Glycerols Containing Disulfide Tether and Studies . . . " J Org Chem vol. 63, No. 25 (1998) pp. 9232-9242.

Apitzsch, et al. "Uber Sulfide aus alfa,alfa1-Disulfhydryl-thio-gamma-pyron-beta, beta1- . . . ," Berichte der Deutschen Chemischen Gesellschaft, vol. 42 (1909) pp. 2940-2943.

Teplenicheva, Y.L., et al., "Ethyl 2-(alpha-hydroxyhexafluoroisopropyl)acrylate as a potential . . . " Russian Chemical Bulletin, vol. 46, No. 4 (1997) pp. 755-758.

Gala, D., et al., "A Practical Conversion of a Azetidinone to Penem: Synthesis of Sch 34343," Tetrahedron, vol. 48, No. 7, (1992) pp. 1175-1182.

Schonberg, A., et al., "Konstitution und Umsetzungen des Produktes aus Aceton-dicarbonsaure-diathylester . . . ," Chemische Berichte, vol. 99, No. 10 (1966) pp. 3327-3330.

Apitzsch, H., "Uber die Einwirkungvon Schwefelkohlenstoff und Atzkali auf Ketone," Berichte der Deutschen Chemischen Gesellschaft, vol. 41 (1908) pp. 4028-4039.

Fischer, G.C., et al., "Irreducible Analogues of Mevaldic Acid Coenzyme a Hemithioacetal as Potential Inhibitors, . . . " J Org Chem, vol. 50 No. 12 (1985) pp. 2011-2019.

Ferres, H., et al., "A diastereoselective sysnthesis of 4(RS), 6(SR)-mercaptomethylmevalonolactone, . . . " Tetrahedron Letters, vol. 24, No. 35 (1983) pp. 3769-3772.

Schwab, A.W., et al., "Hydrogen Sulfide Adducts of Methyl Oleate and Linoleate," J of the America Oil Chemists' Society, vol. 50 (1973) pp. 364-366.

Schwab, A.W., et al. "Free Radical Addition of Hydrogen Sulfide to Conjugated . . . ," J of the American Oil Chemists' Society, vol. 47 (1970) pp. 371-373.

International Application No. PCT/US2006/031419 Search Report, Mar. 8, 2007.

* cited by examiner

¹³C NMRs of Soybean Oil (top) and a Thiol Containing Ester Produced from Soybean Oil (bottom)

¹H NMRs of Epoxidized Soybean Oil (top)
and a Thiol Containing Ester Produced from Epoxidized Soybean Oil (bottom)

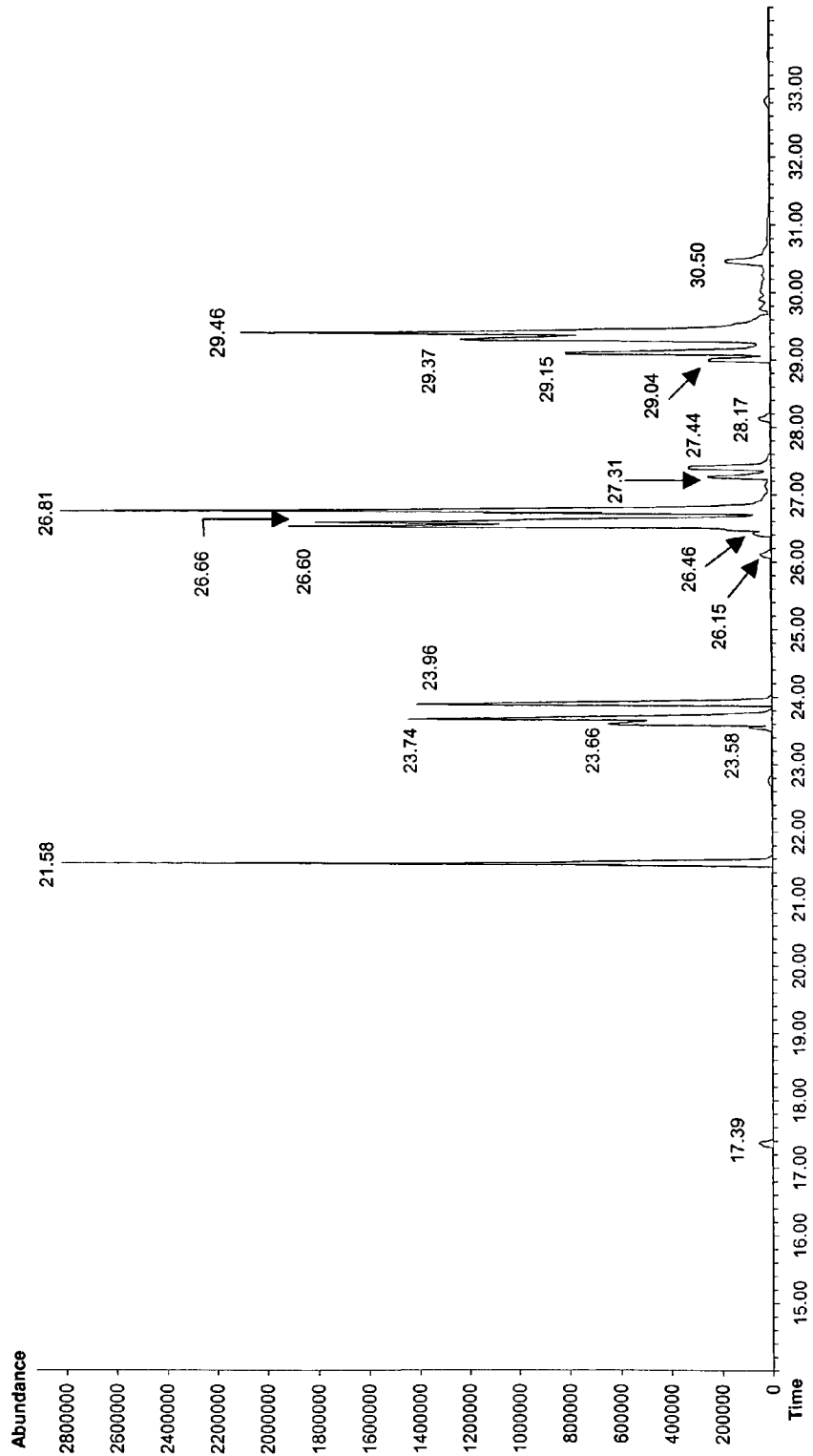
Figure 3 – GC/MS Trace of Thiol Containing Ester Produced from Soybean Oil and Treated by Methanolysis

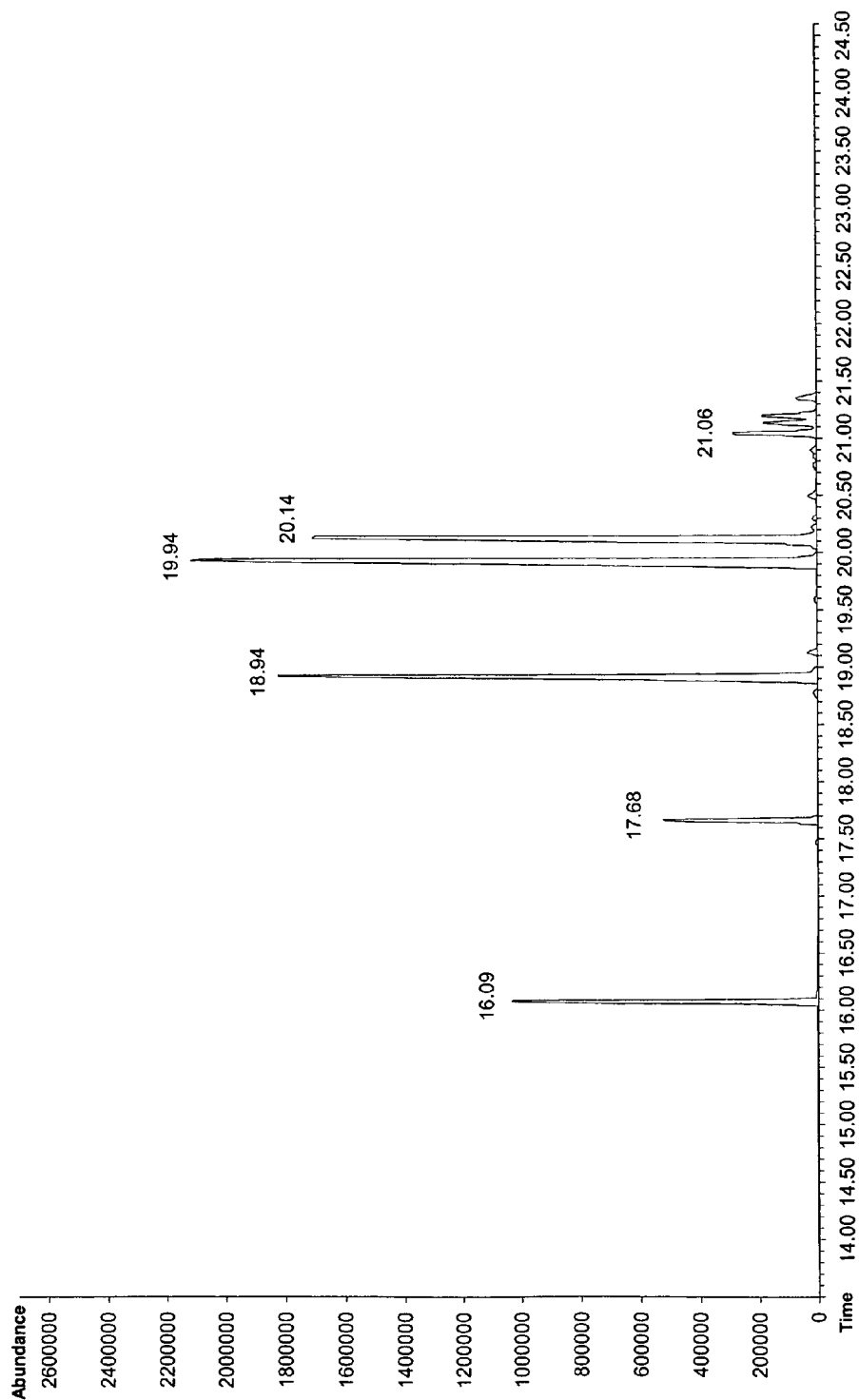
Figure 4 – GC/MS Trace of Epoxidized Soybean Oil and Treated by Methanolysis

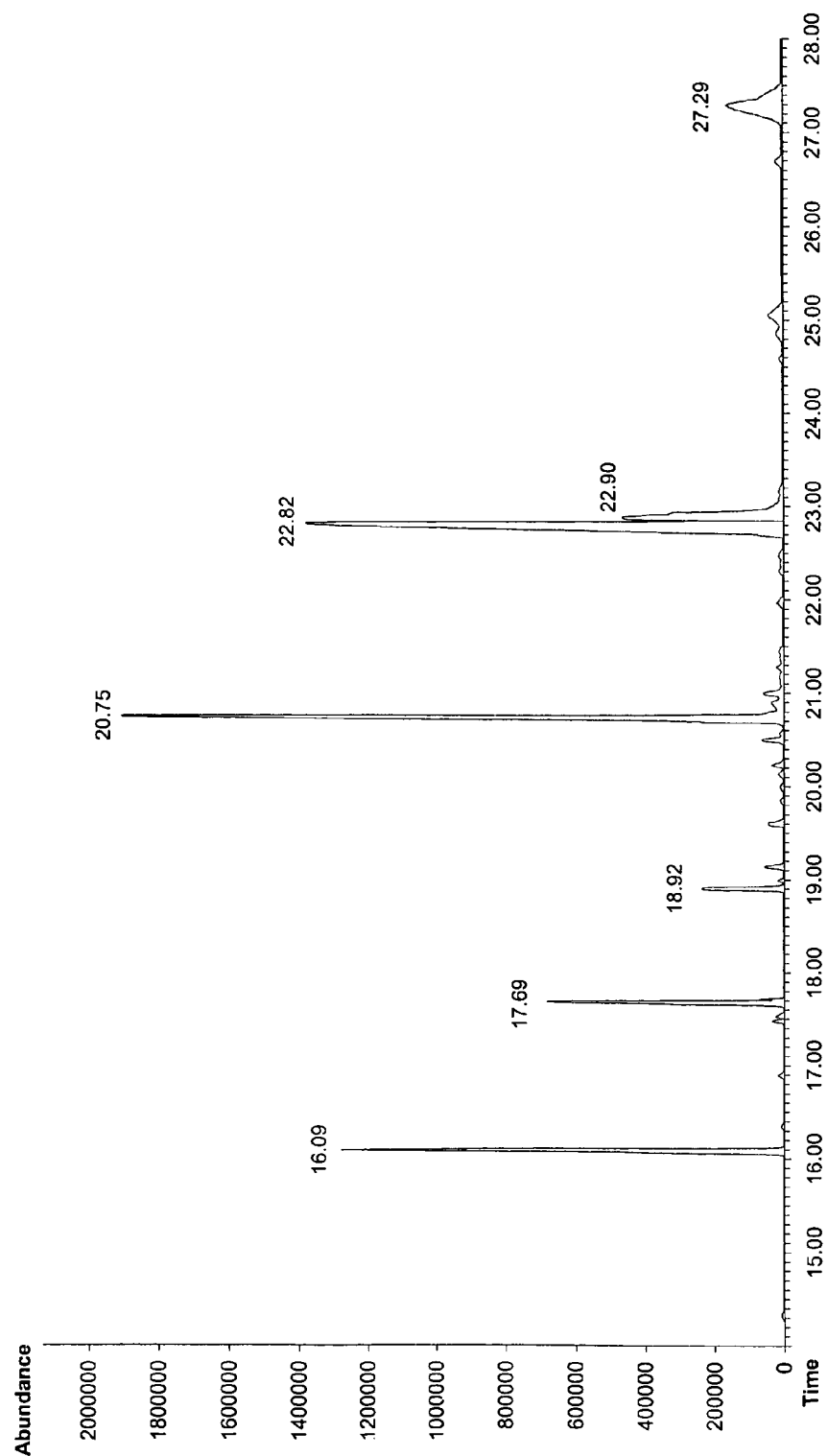
Figure 5 – GC/MS Trace of Hydroxy Thiol Containing Ester Produced from Epoxidized Soybean Oil and Treated by Methanolysis

| Lab ID | Thiol Ester | Iso-cyanate | Catalyst | SH+OH/Iso Equiv. ratio | Catalyst Amount (g) | Catalyst wt% of Reagents | Curing Profile | % THIOL SULFUR (Raman) | Shore Hardness | Glass Transition Temp (°C) | CTE 1 (ppm) | CTE 2 (ppm) | Comments |
|---|---|---|---|---|---|---|---|---|---|---|---|---|---|
| RC-029 | CMSO | Lupranate M20S | Jeffol A-480 | 0.90 | 0.160 | 2.000 | A | 6.25 | 83A | 30.83 | 117.36 | 201.24 | tough+slippery |
| RC-050 | CMSO (lab) | Lupranate M20S | Jeffol A-480 | 0.90 | 0.160 | 2.000 | A | 7.97 | 55D | 52.48 | 117.12 | 452.98 | hard elastomer/tough |
| RC-090 | MHSO | Lupranate M20S | Jeffol A-480 | 0.96 | 0.004 | 0.050 | A | 8.60 | 80D | 100.94 | 98.13 | 183.15 | rigid |
| RC-091 | MHSO | Lupranate M20S | DBTDL | 0.96 | 0.008 | 0.100 | B | 8.60 | 83D | 110/137.6 | 93.22 | | very tough rigid |
| RC-007 | MHSO | TDI (80%) | BDMA | 0.88 | 0.001 | 0.013 | B | 6.50 | 80D | 114.66 | 112.65 | 129.39 | |
| RC-033 | CMSO | HMDI (90%) | Jeffol A-480 | 0.81 | 0.160 | 2.000 | A | 6.25 | 55A | 19.36 | 27.08 | 216.22 | tough |
| RC-031 | CMSO | TDI (80%) | DBTDL | 0.81 | 0.064 | 0.800 | B | 6.25 | 75A | -37.33 | 226.23 | | tough |
| RC-049 | CMSO (lab) | Lupranate M20S | Jeffol A-480 | 1.00 | 0.160 | 2.000 | A | 7.97 | 43A | 50.85 | 167.11 | 244.93 | |
| RC-025 | MSO | HMDI (90%) | DBTDL | 0.92 | 0.064 | 0.800 | B | 5.31 | 50A | 13.90 | 148.50 | 273.57 | tough |
| RC-026 | MSO | HMDI (90%) | DBTDL | 0.83 | 0.064 | 0.800 | B | 5.31 | 64A | 31.18 | 155.96 | 273.71 | tough |
| RC-088 | MHSO | HDI (98%) | Jeffol A-480 | 0.96 | 0.004 | 0.050 | B | 8.60 | 76D | 73.35 | 118.34 | 209.05 | rigid tough |
| RC-089 | MHSO | HDI (98%) | DBTDL | 0.96 | 0.008 | 0.100 | B | 8.60 | 78D | 76.67 | 107.74 | 453.26 | rigid tough |
| RC-086 | MHSO | HMDI (90%) | Jeffol A-480 | 0.96 | 0.004 | 0.050 | B | 8.60 | 73D | 62.80 | 102.31 | 230.51 | rigid |
| RC-087 | MHSO | HMDI (90%) | DBTDL | 0.96 | 0.008 | 0.100 | B | 8.60 | 74D | 62.86 | 109.13 | 241.97 | rigid |
| RC-092 | MHSO | HMDI (90%) | BDMA | 1.09 | 0.001 | 0.013 | C | 9.10 | 77D | 76.77 | 108.85 | 211.59 | rigid clear |
| RC-094 | MHSO | IPDI (98%) | Jeffol A-480 | 1.09 | 0.004 | 0.050 | A | 9.10 | 78D | 79.16 | 92.47 | 204.05 | rigid |
| RC-095 | MHSO | IPDI (98%) | BDMA | 1.09 | 0.001 | 0.013 | B | 9.10 | 80D | 102.92 | 89.47 | 197.99 | rigid |
| RC-096 | MHSO | IPDI (98%) | DBTDL | 1.09 | 0.008 | 0.100 | B | 9.10 | 82D | 96.05 | 96.41 | 196.47 | rigid |
| RC-115 | MHSO | IPDI (98%) | DBTDL | 0.87 | 0.008 | 0.100 | B | 6.50 | 72D | 79.19 | 111.34 | 233.73 | hard rigid |
| RC-009 | MHSO | Lupranate M20S | BDMA | 0.87 | 0.001 | 0.013 | B | 6.50 | 82D | 52.42 | 91.68 | 146.02 | |
| RC-093 | MHSO | Lupranate M20S | BDMA | 1.09 | 0.001 | 0.013 | B | 9.10 | 82D | 35.65 | 76.73 | 100.18 | very hard rigid |
| RC-003 | MHSO | TDI (80%) | DBTDL | 0.88 | 0.008 | 0.100 | B | 6.50 | 79D | 53.99 | 95.51 | 164.04 | |
| RC-085 | MHSO | TDI (80%) | Jeffol A-480 | 1.07 | 0.004 | 0.050 | A | 8.60 | 80D | 58.57 | 80.82 | 129.58 | hard + stiff |

FIG. 6A

| Lab ID | Thiol Ester | Isocyanate | Catalyst | SH+OH/Iso Equiv. ratio | Catalyst Amount (g) | Catalyst wt% of Reagents | Curing Profile | % THIOL SULFUR (Raman) | Shore Hardness | Glass Transition Temp (° C) | CTE 1 (ppm) | CTE 2 (ppm) | Comments |
|---|---|---|---|---|---|---|---|---|---|---|---|---|---|
| RC-001 | MSO (TBP/PP) | IPDI (98%) | Jeffol A-480 | 0.96 | 0.160 | 2.000 | A | 7.56 | 42A | 14.28 | 146.03 | 222.05 | |
| RC-041 | MSO (TBP/PP) | Lupranate M20S | Jeffol A-481 | 0.86 | 0.160 | 2.000 | A | 7.56 | 47D | 54.36 | 121.89 | 259.58 | hard elastomer/tough |
| RC-108 | MSO lab | Lupranate M20S | DBTDL | 0.79 | 0.064 | 0.800 | B | 7.25 | 48D | 38.46 | 152.01 | 233.13 | tough |
| RC-063 | MSO-lab TBP | TDI (80%) | Jeffol A-480 | 0.68 | 0.160 | 2.000 | A | 7.93 | 48D | 54.66 | 271.27 | | semi-rigid tough |
| RC-034 | CMSO | HMDI (90%) | DBTDL | 0.90 | 0.064 | 0.800 | B | 6.25 | 58A | 18.16 | 99.19 | 256.05 | tough+flexible |
| RC-114 | CMSO | IPDI (98%) | DBTDL | 0.81 | 0.064 | 0.800 | B | 6.25 | 66A | 25.89 | 156.97 | 256.06 | flexible tough |
| RC-098 | CMSO | Lupranate M20S | BDMA | 0.81 | 0.020 | 0.250 | B | 6.25 | 34D | 47.27 | 146.92 | 226.64 | tough |
| RC-030 | CMSO | TDI (80%) | DBTDL | 0.90 | 0.064 | 0.800 | B | 6.25 | 70A | 14.46 | 134.54 | 229.86 | tough |
| RC-046 | CMSO | TDI (80%) | Jeffol A-480 | 1.00 | 0.160 | 2.000 | A | 7.97 | 76A | 25.12 | 88.89 | 215.20 | very tough |
| RC-028 | CMSO | TDI (80%) | Jeffol A-480 | 0.90 | 0.160 | 2.000 | A | 6.25 | 67A | 16.73 | 124.66 | 225.64 | tough |
| RC-048 | CMSO (lab) | HMDI (90%) | Jeffol A-480 | 1.00 | 0.160 | 2.000 | A | 7.97 | 78A | 30.86 | 96.73 | 228.51 | tough+viscous |
| RC-084 | CMSO (lab) | Lupranate M20S | BDMA | 1.00 | 0.011 | 0.138 | B | 7.97 | 40D | 44.12 | 114.85 | 209.26 | semi-flexible tough |
| RC-083 | CMSO (lab) | TDI (80%) | BDMA | 1.00 | 0.220 | 0.275 | B | 7.97 | 79A | 28.61 | 134.08 | 212.93 | tough |
| RC-005 | MHSO | HMDI (90%) | DBTDL | 0.87 | 0.008 | 0.100 | B | 6.50 | 72D | 65.90 | 102.49 | 889.27 | |
| RC-008 | MHSO | HMDI (90%) | BDMA | 0.87 | 0.001 | 0.013 | B | 6.50 | 63D | 54.80 | 104.68 | 601.86 | |
| RC-010 | MHSO | IPDI (98%) | BDMA | 0.87 | 0.001 | 0.013 | B | 6.50 | 72D | 62.01 | 96.27 | 230.62 | |
| RC-011 | MHSO | IPDI (98%) | Jeffol A-480 | 0.87 | 0.004 | 0.050 | A | 6.50 | 68D | 70.20 | 106.92 | 489.63 | |
| RC-002 | MHSO | Lupranate M20S | Jeffol A-480 | 0.87 | 0.004 | 0.050 | A | 6.50 | 81D | 38.48 | 73.29 | 121.61 | rigid/tough |
| RC-004 | MHSO | Lupranate M20S | DBTDL | 0.87 | 0.008 | 0.100 | B | 6.50 | 80D | 49.92 | 87.61 | 141.54 | |
| RC-006 | MHSO | TDI (80%) | Jeffol A-480 | 0.88 | 0.004 | 0.050 | A | 6.50 | 78D | 53.88 | 84.68 | 174.17 | |

FIG. 6B

| Lab ID | Thiol Ester | Isocyanate | Catalyst | SH+OH/Iso Equiv. ratio | Catalyst Amount (g) | Catalyst wt% of Reagents | Curing Profile | % THIOL SULFUR (Raman) | Shore Hardness | Glass Transition Temp (° C) | CTE 1 (ppm) | CTE 2 (ppm) | Comments |
|---|---|---|---|---|---|---|---|---|---|---|---|---|---|
| RC-044 | MSO (TBP/PP) | HMDI (90%) | Jeffcat A-480 | 0.96 | 0.160 | 2.000 | A | 7.56 | 68A | 26.63 | 92.45 | 225.36 | tough |
| RC-045 | MSO (TBP/PP) | HMDI (90%) | DBTDL | 0.96 | 0.064 | 0.800 | B | 7.56 | 63A | 31.63 | 148.54 | 270.37 | very tough |
| RC-079 | MSO (TBP/PP) | IPDI (98%) | BDMA | 0.86 | 0.064 | 0.800 | B | 7.56 | 55A | 17.16 | 132.08 | 228.78 | tough |
| RC-080 | MSO (TBP/PP) | IPDI (98%) | Jeffcat A-480 | 0.86 | 0.160 | 2.000 | A | 7.56 | 49A | 20.00 | 194.71 |  | tough |
| RC-081 | MSO (TBP/PP) | IPDI (98%) | DBTDL | 0.86 | 0.064 | 0.800 | B | 7.56 | 80A | 23.69 | 135.78 | 225.11 | tough |
| RC-043 | MSO (TBP/PP) | TDI (80%) | DBTDL | 0.96 | 0.064 | 0.800 | B | 7.56 | 77A | 16.62 | 207.90 |  |  |
| RC-078 | MSO (TBP/PP) | TDI (80%) | BDMA | 0.86 | 0.020 | 0.250 | B | 7.56 | 34D | 40.07 | 131.66 | 213.96 | tough |
| RC-100 | MSO lab | HMDI (90%) | DBTDL | 0.88 | 0.064 | 0.800 | B | 7.25 | 28D | 54.18 | 172.80 | 227.62 | semi-tough slippery |
| RC-111 | MSO lab | IPDI (98%) | Jeffcat A-480 | 0.79 | 0.160 | 2.000 | A | 7.25 | 46A | 5.27 | 160.37 | 223.79 | flexible tough |
| RC-104 | MSO lab | Lupranate M20S | BDMA | 0.88 | 0.020 | 0.250 | A | 7.25 | 39D | 51.12 | 143.20 | 227.48 | semi-tough |
| RC-105 | MSO lab | Lupranate M20S | Jeffcat A-480 | 0.88 | 0.160 | 2.000 | A | 7.25 | 38D | 51.26 | 153.02 | 232.55 | tough |
| RC-102 | MSO lab | TDI (80%) | Jeffcat A-480 | 0.79 | 0.160 | 2.000 | A | 7.25 | 81A | 29.97 | 133.24 | 221.53 | tough slippery |
| RC-068 | MSO-lab TBP | HMDI (90%) | DBTDL | 0.94 | 0.064 | 0.800 | B | 7.93 | 48A | 36.95 | 277.75 |  | tough |
| RC-066 | MSO-lab TBP | Lupranate M20S | Jeffcat A-480 | 0.94 | 0.160 | 2.000 | A | 7.93 | 35D | 38.46 | 226.57 |  | semi-rigid tough |
| RC-082 |  | IPDI (98%) | BDMA |  |  |  |  |  | 57A | 16.40 | 124.43 | 217.72 | flexible tough |
| RC-032 | CMSO | HMDI (90%) | Jeffcat A-480 | 0.90 | 0.160 | 2.000 | A | 6.25 | 51A | 16.94 | 123.58 | 250.05 | tough |
| RC-035 | CMSO | HMDI (90%) | DBTDL | 0.81 | 0.064 | 0.800 | B | 6.25 | 84A | 50.66 | 179.55 | 255.23 | fragile |
| RC-060 | CMSO | HMDI (90%) | DBTDL | 1.01 | 0.064 | 0.800 | B | 5.28 | 45A | 16.57 | 136.11 | 248.71 | fragile |

FIG. 6C

| Lab ID | Thiol Ester | Isocyanate | Catalyst | SH+OH/Iso Equiv. ratio | Catalyst Amount (g) | Catalyst wt% of Reagents | Curing Profile | % THIOL SULFUR (Raman) | Shore Hardness | Glass Transition Temp (°C) | CTE 1 (ppm) | CTE 2 (ppm) | Comments |
|---|---|---|---|---|---|---|---|---|---|---|---|---|---|
| RC-097 | CMSO | Lupranate M20S | BDMA | 0.90 | 0.020 | 0.250 | B | 6.25 | 28D | 26.53 | 120.69 | 213.14 | fragile |
| RC-047 | CMSO | TDI (80%) | Jeffol A-480 | 0.90 | 0.160 | 2.000 | A | 7.97 | 35D | 42.98 | 160.55 | 238.36 | easily broken |
| RC-053 | CMSO | TDI (80%) | DBTDL | 1.00 | 0.064 | 0.800 | B | 7.97 | 80A | 26.41 | 106.56 | 213.61 | tough |
| RC-055 | CMSO | TDI (80%) | Jeffol A-480 | 0.91 | 0.160 | 2.000 | A | 5.28 | 55A | 7.95 | 75.50 | 222.02 | easily broken |
| RC-099 | CMSO | TDI (80%) | BDMA | 0.90 | 0.020 | 0.250 | B | 6.25 | 67A | 14.85 | 148.73 | 239.75 | semi-tough |
| RC-074 | CMSO (lab) | IPDI (98%) | Jeffol A-480 | 1.00 | 0.160 | 2.000 | A | 7.97 | 58A | 18.88 | 116.84 | 218.45 | tough |
| RC-075 | CMSO (lab) | IPDI (98%) | Jeffol A-480 | 0.90 | 0.160 | 2.000 | A | 7.97 | 56A | 14.46 | 110.62 | 228.12 | tough |
| RC-076 | CMSO (lab) | IPDI (98%) | BDMA | 0.90 | 0.064 | 0.800 | B | 7.97 | 49A | 18.80 | 115.80 | 208.39 | tough |
| RC-077 | CMSO (lab) | IPDI (98%) | DBTDL | 0.90 | 0.064 | 0.800 | B | 7.97 | 80A | 27.06 | 119.69 | 228.02 | tough |
| RC-051 | CMSO (lab) | Lupranate M20S | DBTDL | 1.00 | 0.064 | 0.800 | B | 7.97 | 45D | 53.53 | 134.14 | 225.60 | tough |
| RC-022 | MSO | HMDI (90%) | Jeffol A-480 | 0.92 | 0.160 | 2.000 | A | 5.31 | 44A | 5.64 | 192.47 | 274.97 | rubbery/easily torn |
| RC-024 | MSO | TDI (80%) | DBTDL | 0.83 | 0.064 | 0.800 | B | 5.31 | 54A | 6.72 | 207.15 | 302.37 | fragile |
| RC-019 | MHSO | HMDI (90%) | Jeffol A-480 | 1.00 | 0.004 | 0.050 | B | 6.50 | 68D | 70.85 | 97.72 | 269.73 | nothing more |
| RC-040 | MSO (TBP/PP) | Lupranate M20S | Jeffol A-480 | 0.96 | 0.160 | 2.000 | A | 7.56 | 42D | 53.07 | 121.12 | 239.90 | easily broken |
| RC-042 | MSO (TBP/PP) | Lupranate M20S | DBTDL | 0.96 | 0.064 | 0.800 | B | 7.56 | 43D | 49.20 | 97.07 | 229.89 | easily broken |
| RC-038 | MSO (TBP/PP) | TDI (80%) | Jeffol A-480 | 0.96 | 0.160 | 2.000 | A | 7.56 | 76A | 38.19 | 172.55 | 230.25 | semi-tough |
| RC-039 | MSO (TBP/PP) | TDI (80%) | Jeffol A-480 | 0.86 | 0.160 | 2.000 | A | 7.56 | 82A | 25.00 | 72.47 | 206.14 | easily broken |
| RC-106 | MSO lab | HMDI (90%) | Jeffol A-480 | 0.88 | 0.160 | 2.000 | A | 7.25 | 60A | 22.05 | 127.53 | 243.03 | flexible tough |
| RC-110 | MSO lab | IPDI (98%) | DBTDL | 0.79 | 0.064 | 0.800 | B | 7.25 | 73A | 28.45 | 147.84 | 235.65 | flexible tough |
| RC-101 | MSO lab | TDI (80%) | Jeffol A-480 | 0.87 | 0.080 | 1.000 | A | 7.25 | 72A | 33.31 | 208.24 | 291.72 | tough slippery |

FIG. 6D

| Lab ID | Thiol Ester | Isocyanate | Catalyst | SH+OH/Iso Equiv. ratio | Catalyst Amount (g) | Catalyst wt% of Reagents | Curing Profile | % THIOL SULFUR (Raman) | Shore Hardness | Glass Transition Temp (°C) | CTE 1 (ppm) | CTE 2 (ppm) | Comments |
|---|---|---|---|---|---|---|---|---|---|---|---|---|---|
| RC-103 | MSO lab | TDI (80%) | BDMA | 0.87 | 0.020 | 0.250 | A | 7.25 | 76A | 26.68 | 158.43 | 222.16 | fragile |
| RC-109 | MSO lab | TDI (80%) | DBTDL | 0.79 | 0.064 | 0.800 | B | 7.25 | 26D | 45.71 | 156.21 | 233.01 | fragile |
| RC-064 | MSO-lab TBP | HMDI (90%) | Jeffol A-480 | 0.94 | 0.160 | 2.000 | A | 7.93 | 53A | 15.49 | | | tough |
| RC-065 | MSO-lab TBP | HMDI (90%) | Jeffol A-480 | 0.84 | 0.160 | 2.000 | A | 7.93 | 55A | 22.29 | 235.80 | | tough |
| RC-072 | MSO-lab TBP | IPDI (98%) | Jeffol A-480 | 0.94 | 0.160 | 2.000 | A | 7.93 | 46A | 15.61 | 218.86 | | tough |
| RC-073 | MSO-lab TBP | IPDI (98%) | Jeffol A-480 | 0.85 | 0.160 | 2.000 | A | 7.93 | 45A | 34.05 | 217.13 | | tough |
| RC-062 | MSO-lab TBP | TDI (80%) | Jeffol A-480 | 0.94 | 0.160 | 2.000 | A | 7.93 | 74A | 24.74 | 227.15 | | tough |
| RC-067 | MSO-lab TBP | TDI (80%) | DBTDL | 0.94 | 0.064 | 0.800 | B | 7.93 | 75A | 16.41 | 222.62 | | tough |
| RC-070 | MSO-lab TBP | TDI (80%) | BDMA | 0.94 | 0.064 | 0.800 | B | 7.93 | 77A | 20.98 | 224.47 | | tough |
| RC-059 | CMSO | HMDI (90%) | Jeffol A-480 | 1.01 | 0.160 | 2.000 | A | 5.28 | 35A | 10.73 | 103.04 | 264.09 | |
| RC-036 | CMSO | Lupranate M20S | DBTDL | 0.90 | 0.064 | 0.800 | B | 6.25 | 86A | 18.07 | 65.23 | 208.95 | fragile |
| RC-037 | CMSO | Lupranate M20S | DBTDL | 0.81 | 0.064 | 0.800 | B | 6.25 | 33D | 51.67 | 167.57 | 251.00 | brittle |
| RC-056 | CMSO | Lupranate M20S | Jeffol A-480 | 1.01 | 0.160 | 2.000 | A | 5.28 | 69A | 14.43 | 138.52 | 222.45 | brittle + opaque |
| RC-057 | CMSO | Lupranate M20S | Jeffol A-480 | 0.91 | 0.160 | 2.000 | A | 5.28 | 74A | 15.73 | 114.59 | 213.85 | brittle + opaque |
| RC-061 | CMSO | Lupranate M20S | DBTDL | 1.01 | 0.064 | 0.800 | B | 5.28 | 67A | 3.95 | 214.02 | | fragile |
| RC-054 | CMSO | TDI (80%) | Jeffol A-480 | 1.00 | 0.160 | 2.000 | A | 5.28 | 46A | 16.84 | 199.28 | 241.53 | fragile |
| RC-058 | CMSO | TDI (80%) | DBTDL | 1.00 | 0.064 | 0.800 | B | 5.28 | 50A | -0.92 | 222.94 | | brittle |
| RC-052 | CMSO (lab) | HMDI (90%) | DBTDL | 1.00 | 0.064 | 0.800 | B | 7.97 | 65A | 46.54 | 171.76 | 228.39 | tough |
| RC-112 | CMSO (PP) | IPDI (98%) | DBTDL | 0.83 | 0.064 | 0.800 | B | 5.31 | 40A | 8.95 | 187.65 | 252.67 | soft brittle |

FIG. 6E

| Lab ID | Thiol Ester | Isocyanate | Catalyst | SH+OH/Iso Equiv. ratio | Catalyst Amount (g) | Catalyst wt% of Reagents | Curing Profile | % THIOL SULFUR (Raman) | Shore Hardness | Glass Transition Temp (° C) | CTE 1 (ppm) | CTE 2 (ppm) | Comments |
|---|---|---|---|---|---|---|---|---|---|---|---|---|---|
| RC-021 | MSO | Lupranate M20S | Jeffol A-480 | 0.92 | 0.160 | 2.000 | A | 5.31 | 70A | 46.70 | 161.56 | 273.49 | fragile |
| RC-027 | MSO | Lupranate M20S | DBTDL | 0.92 | 0.064 | 0.800 | B | 5.31 | 64A | -21.08 | 121.06 | 212.23 | brittle |
| RC-113 | CMSO (PP) | Lupranate M20S | BDMA | 0.83 | 0.020 | 0.250 | A | 5.31 | 75A | 15.35 | 121.01 | 192.97 | fragile |
| RC-020 | MSO | TDI (80%) | Jeffol A-480 | 0.92 | 0.160 | 2.000 | A | 7.56 | 47A | 5.52 | 143.98 | 225.20 | fragile |
| RC-023 | MSO | TDI (80%) | DBTDL | 0.92 | 0.064 | 0.800 | B | 5.31 | 45A | -1.60 | 126.48 | 284.15 | fragile |
| RC-107 | MSO lab | Lupranate M20S | DBTDL | 0.88 | 0.064 | 0.800 | B | 7.25 | 40D | 46.23 | 157.91 | 230.63 | brittle |
| RC-069 | MSO-lab TBP | Lupranate M20S | DBTDL | 0.94 | 0.064 | 0.800 | B | 7.93 | 42D | 34.57 | 243.09 |  | fragile |
| RC-071 | MSO-lab TBP | Lupranate M20S | BDMA | 0.94 | 0.021 | 0.263 | B | 7.93 | 37D | 43.52 | 197.83 |  | fragile |
| RC-116 | Caster Oil | IPDI (98%) | Jeffol A-480 | 1.00 | 0.160 | 2.000 | A | -- | 50A | -11.65 | 110.61 | 228.58 | -- |
| RC-015 | Castor Oil | HMDI (90%) | Jeffol A-480 | 1.00 | 0.160 | 2.000 | A | -- | 60A | -8.06 | 96.95 | 222.01 | -- |
| RC-016 | Castor Oil | HMDI (90%) | DBTDL | 1.00 | 0.064 | 0.800 | B | -- | 67A | -4.48 | 91.15 | 244.86 | -- |
| RC-119 | Castor Oil | HMDI (90%) | BDMA | 1.00 | 0.064 | 0.800 | B | -- | 55A | -6.46 | 102.29 | 219.90 | -- |
| RC-012 | Castor Oil | IPDI (98%) | DBTDL | 1.00 | 0.005 | 0.063 | B | -- | 58A | -10.91 | 89.01 | 221.48 | -- |
| RC-117 | Castor Oil | IPDI (98%) | BDMA | 1.00 | 0.064 | 0.800 | B | -- | 55A | -11.10 | 92.75 | 224.24 | -- |
| RC-014 | Castor Oil | Lupranate M20S | Jeffol A-480 | 1.00 | 0.160 | 2.000 | A | -- | 81A | -8.00 | 80.93 | 205.28 | -- |
| RC-018 | Castor Oil | Lupranate M20S | DBTDL | 1.00 | 0.010 | 0.125 | B | -- | 82A | -2.37 | 80.69 | 201.27 | -- |
| RC-118 | Castor Oil | Lupranate M20S | BDMA | 1.00 | 0.064 | 0.800 | B | -- | 75A | -2.57 | 121.68 | 220.36 | -- |
| RC-013 | Castor Oil | TDI (80%) | Jeffol A-480 | 1.00 | 0.160 | 2.000 | A | -- | 60A | -13.37 | 100.93 | 220.34 | -- |
| RC-017 | Castor Oil | TDI (80%) | DBTDL | 1.00 | 0.064 | 0.800 | B | -- | 66A | -9.29 | 114.23 | 225.92 | -- |
| RC-120 | Castor Oil | TDI (80%) | BDMA | 1.00 | 0.064 | 0.800 | B | -- | 57A | -13.98 | 133.59 | 238.42 | -- |
| 812-10-1 | MCO | Lupranate M20S | DBTDL | 0.95 | 0.012 | 0.125 | B |  |  |  |  |  |  |
| 810-12-15 | MCO | Lupranate M20S | DBTDL | 1.00 | 0.015 | 0.125 | B |  |  |  |  |  |  |

THIOL ESTER COMPOSITIONS AND PROCESSES FOR MAKING AND USING SAME

CROSS REFERENCE TO RELATED APPLICATIONS

This application claims the benefit of four provisional patent applications having U.S. Ser. No. 60/545,260 filed on Feb. 17, 2004; U.S. Ser. No. 60/561,614 filed on Apr. 13, 2004; U.S. Ser. No. 60/561,685 filed on Apr. 13, 2004; and U.S. Ser. No. 60/561,855 filed on Apr. 13, 2004, which hereby are incorporated by reference in their entirety.

BACKGROUND OF THE INVENTION

1. Field of the Invention

The invention relates to thiol containing ester compositions generally made from a reaction of unsaturated ester compositions and a material capable of forming a thiol group. The invention also relates to the processes for preparing such thiol containing compositions and uses for the thiol containing compositions.

2. Description of Related Art

The chemical industry strives to make products, such as polymers, fertilizers, and fuels, with less expensive feedstocks that are in abundant supply. As the fossil fuels slowly deplete over time, alternative sources are always being sought as replacements for fuels. Additionally, the chemical industry continuously strives to produce products and use feedstocks that are environmentally friendly in order to reduce potential hazards and risks related to safety and environmental issues.

SUMMARY OF THE INVENTION

The present invention advantageously provides thiol containing compositions and methods of making such compositions. In addition to the compositions and methods of making such compositions, products that include such compositions are also provided.

As an embodiment of the present invention, a thiol ester composition is advantageously provided. In this embodiment, the thiol ester composition includes thiol ester molecules that have an average of at least 1.5 ester groups per thiol ester molecule. The thiol ester molecules also have an average of at least 1.5 thiol groups per thiol ester molecule. The thiol ester molecules also have a molar ratio of cyclic sulfides to thiol groups of less than 1.5.

In some aspects, the thiol ester molecules have a molar ratio of cyclic sulfides to thiol groups ranging from 0 to 1.0. In some aspects, the thiol ester molecules have an average ranging from 1.5 to 9 thiol groups per thiol ester molecule. In some embodiments, the thiol ester molecules have a molar ratio of carbon-carbon double bonds to thiol groups of less than 1.5.

The amount of thiol sulfur or mercaptan sulfur contained within the thiol ester molecules can also vary. For example, in some embodiments, the thiol ester molecules have an average of greater than 5 weight percent thiol sulfur. In other embodiments, the thiol ester molecules have an average ranging from 8 to 10 weight percent thiol sulfur. In some embodiments, the thiol ester molecules have an average of less than 30 mole percent sulfur, which is present as cyclic sulfides. Alternatively, the thiol ester molecules have an average of less than 2 mole percent sulfur present as cyclic sulfides.

In some embodiments, the thiol ester molecules are produced from unsaturated esters that have an average of less than 25 weight percent of side chains that include 3 contiguous methylene interrupted carbon-carbon double bonds. In another aspect, greater than 40 percent of the total side chains contained within the thiol ester molecules contain sulfur.

In addition to the thiol ester composition, a process for producing the thiol ester composition is advantageously provided as another embodiment of the present invention. To produce the thiol ester composition, hydrogen sulfide is contacted with an unsaturated ester composition. The unsaturated ester composition includes unsaturated esters that have an average of at least 1.5 ester groups per unsaturated ester molecule. The unsaturated esters also have an average of at least 1.5 carbon-carbon double bonds per unsaturated ester molecule. The hydrogen sulfide and the unsaturated esters are reacted to produce or form the thiol ester composition. The thiol ester composition advantageously includes thiol ester molecules that have a molar ratio of cyclic sulfides to thiol groups of less than 1.5.

Process variables related to the step of reacting the hydrogen sulfide and the unsaturated ester can be varied in embodiments in the present invention. In an aspect, the step of reacting the hydrogen sulfide and the unsaturated esters occurs in the presence of a solvent. In another aspect, the step of reacting the hydrogen sulfide and the unsaturated esters occurs in the substantial absence of a solvent. In some embodiments, the step of reacting the hydrogen sulfide and the unsaturated esters is catalyzed by a heterogeneous catalyst. Alternatively, the reaction of the hydrogen sulfide and the unsaturated esters is initiated by a free-radical initiator or UV radiation. The temperature at which the hydrogen sulfide and the unsaturated ester are reacted can be varied. In some embodiments, reacting the hydrogen sulfide and the unsaturated esters occurs at a temperature of greater than −20° C. As another example, the process is a continuous process and the reaction of the hydrogen sulfide and the unsaturated esters is performed in an absence of a solvent, at a temperature of greater than −20° C., and is initiated by UV radiation. Other types and combinations of process variables can be changed in embodiments of the present invention, as will be understood by those of skill in the art.

Another process for producing the thiol ester composition is advantageously provided as another embodiment of the present invention. In this process embodiment, the hydrogen sulfide and the unsaturated ester composition are contacted. The unsaturated ester composition includes unsaturated esters having an average of at least 1.5 ester groups per unsaturated ester molecule and having an average of at least 1.5 carbon-carbon double bonds per unsaturated ester molecule. The hydrogen sulfide and the unsaturated esters are then reacted in a substantial absence of a solvent to form the thiol ester composition. The thiol ester composition includes thiol ester molecules. The thiol ester composition advantageously includes thiol ester molecules that have a molar ratio of cyclic sulfides to thiol groups of less than 1.5.

Process variables related to the step of reacting the hydrogen sulfide and the unsaturated ester can be varied in embodiments in the present invention. In an aspect, the step of reacting the hydrogen sulfide and the unsaturated esters occurs in the presence of a solvent. In another aspect, the step of reacting the hydrogen sulfide and the unsaturated esters occurs in the substantial absence of a solvent. In some embodiments, the step of reacting the hydrogen sulfide and the unsaturated esters is catalyzed by a heterogeneous catalyst. Alternatively, the reaction of the hydrogen sulfide and the unsaturated esters is initiated by a free-radical initiator or UV radiation. The temperature at which the hydrogen sulfide and the unsaturated ester are reacted can be varied. In some embodiments, reacting the hydrogen sulfide and the unsaturated esters occurs at a temperature of greater than −20° C.

In embodiments of the present invention, the unsaturated ester composition includes a natural source oil, as described herein. In some embodiments, the unsaturated ester composition includes soybean oil. Other types of unsaturated ester compositions are described herein.

The resulting thiol ester molecules produced by this process possess advantageous characteristics. For example, in some embodiments, the thiol ester molecules have a molar ratio of the hydrogen sulfide to carbon-carbon double bonds of greater than 2. As another example, in other embodiments, the thiol ester molecules have an average of greater than 5 weight percent thiol sulfur. In some aspects, greater than 40 percent of the thiol ester molecule total side chains contain sulfur.

As another embodiment of the present invention, another process for preparing the thiol ester composition is advantageously provided. In this embodiment, a polyol composition and a thiol carboxylic acid composition are contacted and reacted to produce the thiol ester composition. The thiol ester composition includes thiol ester molecules having an average of at least 1.5 ester groups per thiol ester molecule and having an average of at least 1.5 thiol groups per thiol ester molecule.

In addition to the thiol ester composition, other compositions are advantageously provided as embodiments of the present invention. For example, a hydroxy thiol ester composition is provided as another embodiment of the present invention. The hydroxyl thiol ester composition includes hydroxy thiol ester molecules having an average of at least 1.5 ester groups per hydroxy thiol ester molecule and having an average of at least 1.5 α-hydroxy thiol groups per hydroxy thiol ester molecule.

As described herein, the α-hydroxy thiol groups contain an alcohol or hydroxy group and a thiol group within the same group. In embodiments of the present invention, the α-hydroxy thiol groups can be replaced with separate alcohol and thiol groups. In these embodiments, the same number of α-hydroxy groups can be used for the separate alcohol and thiol groups. For example, in some embodiments, the hydroxy thiol ester molecules have an average of at least 1.5 α-hydroxy thiol groups. In embodiments that contain separate alcohol and thiol groups, the hydroxy thiol ester molecules would contain an average of at least 1.5 alcohol groups and an average of at least 1.5 thiol groups.

In some aspects, the hydroxy thiol ester molecules have an average ranging from 1.5 to 9 α-hydroxy thiol groups per hydroxy thiol ester molecule. In some embodiments, the thiol ester molecules have a molar ratio of carbon-carbon double bonds to thiol groups of less than 1.5.

In some embodiments, the thiol ester molecules are produced from unsaturated esters that have an average of less than 25 weight percent of side chains that include 3 contiguous methylene interrupted carbon-carbon double bonds. In another aspect, greater than 40 percent of the total side chains contained within the α-hydroxy thiol ester molecules contain sulfur.

The amount of thiol sulfur contained within the hydroxy thiol ester molecules can also vary. For example, in some embodiments, the hydroxy thiol ester molecules have an average of greater than 5 weight percent thiol sulfur. In other embodiments, the hydroxy thiol ester molecules have an average ranging from 8 to 10 weight percent thiol sulfur.

In some embodiments, the hydroxy thiol ester molecules have a molar ratio of epoxide groups to the α-hydroxy thiol groups of less than 2. In other aspects, the composition is substantially free of epoxide groups.

In addition to the hydroxy thiol ester composition, methods or processes for making the hydroxy thiol ester composition are advantageously provided as embodiments of the present invention. In an embodiment, a process for preparing the hydroxy thiol ester composition is provided that includes the step of contacting the hydrogen sulfide and an epoxidized unsaturated ester composition. The epoxidized unsaturated ester composition includes epoxidized unsaturated esters having an average of at least 1.5 ester groups per epoxidized unsaturated ester molecule and having an average of at least 1.5 epoxide groups per epoxidized unsaturated ester molecule. The hydrogen sulfide and the epoxidized unsaturated esters are then reacted to form the hydroxy thiol ester composition.

In embodiments of the present invention, the epoxidized unsaturated ester composition includes an epoxidized natural source oil, as described herein. In some embodiments, the epoxidized unsaturated ester composition includes an epoxidized soybean oil. Other types of epoxidized unsaturated ester compositions are described herein.

In some embodiments, a molar ratio of the hydrogen sulfide to epoxide groups in the epoxidized unsaturated esters is greater than 1.

In an aspect, the step of the hydrogen sulfide and the epoxidized unsaturated esters is performed in the presence of a catalyst.

Another process for preparing the hydroxy thiol ester composition is advantageously provided as another embodiment of the present invention. In this process embodiment, a polyol composition and a hydroxy thiol carboxylic acid composition are contacted and reacted to produce the hydroxy thiol ester composition. In this embodiment, the hydroxy thiol ester composition includes hydroxy thiol ester molecules having an average of at least 1.5 ester groups per hydroxy thiol ester molecule and having an average of at least 1.5 α-hydroxy thiol groups per hydroxy thiol ester molecule.

A cross-linked thiol ester composition is advantageously provided as another embodiment of the present invention. The cross-linked thiol ester composition includes thiol ester oligomers having at least two thiol ester monomers connected by a polysulfide linkage having a structure —$S_Q$—, wherein Q is greater than 1. In some embodiments, the thiol ester oligomers have at least three thiol ester monomers connected by polysulfide linkages. In another aspect, the thiol ester oligomers have from 3 to 20 thiol ester monomers connected by polysulfide linkages.

In an aspect, the cross-linked thiol ester composition includes both thiol ester monomers and thiol ester oligomers. In some embodiments, the thiol ester monomers and thiol ester oligomers have a total thiol sulfur content ranging from 0.5 to 8 weight percent; or alternatively, ranging from 8 to 15 weight percent. The combined thiol ester monomers and thiol ester oligomers can have an average molecular weight greater than 2000; or alternatively, in a range from 2000 to 20,000.

As another embodiment of the present invention, a cross-linked thiol ester composition produced by the process comprising the steps of contacting the thiol ester composition with an oxidizing agent and reacting the thiol ester and the oxidizing agent to form thiol ester oligomers is advantageously provided. In this embodiment, the thiol ester oligomers have at least two thiol ester monomers connected by a polysulfide linkage having a structure —$S_Q$—, wherein Q is greater than 1.

A process to produce the cross-linked thiol ester composition is also advantageously provided as another embodiment of the present invention. In this process, a thiol ester composition is contacted and reacted with an oxidizing agent to form thiol ester oligomers having at least two thiol ester monomers connected by a polysulfide linkage having a structure —S$_Q$—, wherein Q is greater than 1. In some embodiments, the oxidizing agent is elemental sulfur, oxygen, or hydrogen peroxide. In an aspect, the oxidizing agent is elemental sulfur.

In an aspect, the thiol ester is a hydroxy thiol ester. In other aspects, a weight ratio of elemental sulfur to thiol sulfur in the thiol ester molecules ranges from 0.5 to 32.

The step of the reacting the thiol ester and the oxidizing agent can be performed at a temperature ranging from 25° C. to 150° C. The process for producing the cross-linked thiol ester composition can also include the step of stripping residual hydrogen sulfide from the cross-linked thiol ester composition produced. In another aspect, the reaction of the thiol ester and the elemental sulfur is catalyzed. In some embodiments, the catalyst is an amine.

It is another object of the present invention to provide a novel fertilizer material.

It is another object of the present invention to provide a novel process for production of a fertilizer material.

Accordingly, in one of its aspects, the present invention relates to an abrasion resistant polythiourethane and/or epoxy polymer encapsulated controlled release fertilizer material.

In another of its aspects, the present invention relates to a controlled release fertilizer material comprising a particulate plant nutrient surrounded by a coating which is the reaction product of a mixture comprising: (i) a first component selected from an isocyanate and/or an epoxy resin, and (ii) a first active hydrogen-containing compound selected from the group consisting of a thiol ester composition; a hydroxy thiol ester composition; a cross-linked thiol ester composition and mixtures thereof.

In another of its aspects, the present invention relates to a controlled release fertilizer material comprising a particulate plant nutrient surrounded by a coating which is the reaction product of a mixture comprising: (i) an isocyanate and/or an epoxy resin; and (ii) a sulfur-containing vegetable oil.

In another of its aspects, the present invention relates to a controlled release fertilizer material comprising a particulate plant nutrient surrounded by a coating which is the reaction product of a mixture comprising: (i) an isocyanate and/or an epoxy resin, and (ii) a sulfur-containing soybean oil.

In another of its aspects, the present invention relates to a controlled release fertilizer material comprising a particulate plant nutrient surrounded by at least one coating comprising a polythiourethane and/or an epoxy polymer.

In another of its aspects, the present invention relates to a controlled release fertilizer material comprising a particulate plant nutrient surrounded by at least one coating comprising the reaction product of a mixture comprising an isocyanate, a wax and an active hydrogen-containing compound comprising a sulfur-containing vegetable oil.

In another of its aspects, the present invention relates to a process for the production of abrasion resistant polythiourethane and/or epoxy polymer encapsulated controlled release fertilizer particles by incorporating in urethane and/or epoxy polymer forming reaction mixture a sulfur-containing compound such as one or more of a thiol ester composition; a hydroxy thiol ester composition; a cross-linked thiol ester composition, other sulfur-based compounds described herein below and mixtures thereof.

Preferably, for the production of the present polythiourethane encapsulated controlled release fertilizer material, a sulfur-containing compound (e.g., one or more of a thiol ester composition; a hydroxy thiol ester composition; a cross-linked thiol ester composition) is used as one of the isocyanate-reactive components (alone or in combination with other active hydrogen-containing compounds). Preferably, the sulfur-containing compound comprises a sulfur-containing vegetable oil. In one preferred embodiment, the sulfur-containing vegetable oil comprises a mercaptanized vegetable oil (MVO), more preferably as described in more detail herein, even more preferably an MVO produced by the addition of hydrogen sulfide to a vegetable oil. In another preferred embodiment, the sulfur-containing vegetable oil comprises mercapto-hydroxy vegetable oil (MHVO), more preferably as described in more detail herein, even more preferably an MHVO produced by the addition of hydrogen sulfide to epoxidized vegetable oil. In yet another preferred embodiment, the sulfur containing vegetable oil comprises sulfur cross-linked mercaptanized vegetable oil (CMVO), more preferably as described in more detail herein, even more preferably an CMVO produced by the addition of elemental sulfur to mercaptanized vegetable oil (MVO).

Preferably, for the production of epoxy polymer encapsulated controlled release fertilizer material, a sulfur-containing compound (e.g., one or more of a thiol ester composition; a hydroxy thiol ester composition; a cross-linked thiol ester composition) is used as one of the isocyanate-reactive components (alone or in combination with other active hydrogen-containing compounds). Preferably, the sulfur-containing compound comprises a sulfur-containing vegetable oil (e.g., MVO and/or MHVO and/or CMVO) is used as one of the epoxy resin-reactive components.

In one preferred embodiment of the present process, a polythiourethane encapsulated controlled release fertilizer material is produced by employing the following steps:

(i) applying an isocyanate-reactive component comprising a sulfur-containing vegetable oil (preferably one or more of MVO, MHVO and CMVO described herein) to fertilizer particles to form coated fertilizer particles, and (ii) applying an isocyanate to the coated fertilizer particles to form the fertilizer material.

Steps (i) and (ii) are optionally repeated successively a number of times (e.g., 2-10) to form a desired thickness of the polythiourethane coating which encapsulates the fertilizer particles. The controlled release fertilizer material produced by this process preferably contains from about 1.5 to 20% by weight, more preferably from about 2 to 15% by weight, most preferably from about 2.5 to 10% by weight, of polythiourethane coating, based upon the total weight of the coated fertilizer material.

In another embodiment, a polythiourethane encapsulated controlled release fertilizer material is produced by employing the following steps:

(i) applying an isocyanate component to fertilizer particles to form coated fertilizer particles, and (ii) applying an active hydrogen-containing compound comprising a sulfur-containing vegetable oil (preferably one or more of MVO, MHVO and CMVO described herein) to the coated fertilizer particles to form the fertilizer material.

Again, Steps (i) and (ii) are optionally repeated successively a number of times (e.g., 2-10) to form a desired thickness of the polythiourethane coating which encapsulates the fertilizer particles. The controlled release fertilizer material produced by this process preferably contains from about 1.5 to 20% by weight, more preferably from about 2 to 15% by weight, most preferably from about 2.5 to 10% by weight, of polythiourethane coating, based upon the total weight of the coated fertilizer material.

In yet a further embodiment, a polythiourethane encapsulated controlled release fertilizer material is produced by employing the following steps:

(i) applying to fertilizer particles a prepolymer of an isocyanate and an active hydrogen-containing compound comprising a sulfur-containing vegetable oil (preferably one or more of MVO, MHVO and CMVO described herein) to form coated fertilizer particle to form the fertilizer material;

(ii) converting the prepolymer to a polythiourethane to form the fertilizer material.

The prepolymer used in Step (i) may be produced by contacting: (a) an active hydrogen-containing compound comprising a sulfur-containing vegetable oil (preferably one or more of MVO, MHVO and CMVO described herein) and (b) an isocyanate to produce a prepolymer either continuously or in a batch process in quantities such that the ratio of free (i.e., unreacted) isocyanate groups contained in component (b) to free (i.e., unreacted) active hydrogen moieties in component (a) is from about 0.8:1 to about 2.0:1, preferably from about 0.9:1 to about 1.5:1, more preferably from about 0.95:1 to about 1.3:1.

Thus, in one embodiment, the prepolymer used in Step (i) has excess isocyanate groups. In this case, the conversion in Step (ii) comprises adding further active hydrogen-containing compound which is the same or different than that used in Step (i). In another embodiment, the prepolymer used in Step (i) has excess active hydrogen groups. In this case, the conversion in Step (ii) comprises adding further isocyanate which is the same or different than that used in Step (i). It is preferred that Step (ii) comprises addition of sufficient active hydrogen-containing compound or isocyanate (as the case may be) to compensate for substantially all free isocyanate or active hydrogen reactive groups on the prepolymer.

The embodiment involving prepolymers should be conducted carefully since, once the co-reactants are mixed together the reaction starts to form polythiourethane and the viscosity of the mixture increases, which can reduce the spreadability of the components over the fertilizer particles. However, this viscosity increase can be managed by limiting the mixing time and temperature of the co-reactants prior to being applied to the fertilizer particles.

In a further preferred embodiment, organic additives can be: (1) added to one or more of the co-reactants (premix) and/or (2) first applied to the fertilizer particles prior to the co-reactants (precoat) and/or 3) applied to the polythiourethane coated fertilizer particles as a last step (overcoat). Non-limiting examples of suitable organic additives may be selected from the group comprising waxes, petrolatums, asphalts, fatty acids, fatty acid salts, fatty acid esters, higher alcohols, silicones and mixtures thereof.

In addition, the coating formulation may contain cross-linking agents, commonly used by those skilled in the art of producing polyurethane polymers. Suitable cross-linking agents may be selected from the group comprising low molecular weight diols, amine initiated polyethylene and polypropylene glycols, glycerol, sorbitol, neopentyl glycol, alkyl diamines, aryldiammines and mixtures thereof.

In addition the use of catalysts, commonly used for the polyurethane production, can be used in the present process to increase the rate of cure of the polythiourethane coating. Suitable catalysts may be selected from the group comprising tertiary amines, organo-tin compounds and mixtures thereof.

Optionally, other additives for increasing flowability and/or spreadability of the coating materials can be used in the present process. These include flow and spread agents conventionally used by those skilled in the art of polyurethane production.

In a preferred embodiment, the process for producing epoxy polymer encapsulated controlled release fertilizer material comprises the following steps:

(i) applying an epoxy-reactive component comprising a sulfur-containing vegetable oil (preferably one or more of MVO, MHVO and CMVO described herein) to fertilizer particles to form coated fertilizer particles; and (ii) applying an epoxy resin component to the coated fertilizer particles to the fertilizer material.

Steps (i) and (ii) are optionally repeated successively a number of times (e.g., 2-10) to form a desired thickness of the epoxy polymer coating which encapsulates the fertilizer particles. The controlled release fertilizer material produced by this process preferably contains from about 1.5 to 20% by weight, more preferably from about 2 to 15% by weight, most preferably from about 2.5 to 10% by weight, of epoxy polymer coating, based upon the total weight of the coated fertilizer material.

For epoxy polymers produced from mercaptanized vegetable oils it has been found that the use of a tertiary amine catalyst is highly preferred. The amine catalyst forms the mercaptide anion of the mercaptanized vegetable oil. It is the mercaptide anion form of the mercaptanized vegetable oil that is reactive with epoxy resins, as described by Wicks, Z. W. et al in "Organic Coatings: Science and Technology", Vol. 1, John Wiley & Sons, 1992, p. 179.

The present invention also relates to encapsulated fertilizer compositions produced by these processes.

The preferred sulfur-containing vegetable oils useful in the aspects of the invention relating to fertilizer material are those discussed in more detail herein. A particularly preferred sulfur-containing vegetable oil is Polymercaptan 358 available from Chevron Phillips Chemical Co. and which is the reaction product of soybean oil and hydrogen sulfide.

It has been surprisingly and unexpectedly discovered that that improved controlled (e.g., slow) release fertilizer material can be produced when a sulfur-containing vegetable oil is used as an isocyanate-reactive component for forming polythiourethane encapsulated fertilizer material. Further, it has been surprisingly and unexpectedly discovered that that improved controlled (e.g., slow) release fertilizer material can be produced when a sulfur-containing vegetable oil is used in the epoxy-reactive component for forming epoxy polymer encapsulated fertilizer material. The use of such a sulfur-containing vegetable oil results in a number of advantages, including: the resulting fertilizer material as improved resistance to abrasion (i.e., it has improved durability during production and/or handling); the sulfur-containing vegetable oil is derived from a natural, renewable resource materials; the sulfur-containing vegetable oil has increased hydrophobicity due to the sulfur content compared with conventional polyols which contain more polar oxygen functional groups; and it is possible to achieve a prescribed release rate profile for a fertilizer material using lower coat weights (e.g., as compared to those described in U.S. Pat. No. 5,538,531 [Hudson] and U.S. Pat. No. 6,358,296 [Markusch]) thereby significantly reducing the cost of produce the finished fertilizer material.

BRIEF DESCRIPTION OF THE DRAWINGS

So that the manner in which the features, advantages and objects of the invention, as well as others that will become apparent, can be understood in more detail, more particular description of the invention briefly summarized above can be had by reference to the embodiment thereof that is illustrated in the appended drawings, which form a part of this specification. It is to be noted, however, that the drawings illustrate only particular embodiments of the invention and are therefore not to be considered limiting of the invention's scope as it may admit to other equally effective embodiments.

FIG. 3 is a gas chromatograph (GC)/mass spectrometer (MS) trace of a thiol containing ester that was produced from soybean oil in accordance with an embodiment of the present invention and then treated by methanolysis;

FIG. 4 is a GC/MS trace of epoxidized soybean oil treated by methanolysis;

FIG. 5 is a GC/MS trace of hydroxy thiol containing ester produced from epoxidized soybean oil in accordance with an embodiment of the present invention and then treated by methanolysis;

FIGS. 6A-6F are tables that contain physical property data for numerous polythiourethane compositions prepared in accordance with embodiments of the present invention;

DETAILED DESCRIPTION OF THE INVENTION

Figure 1:
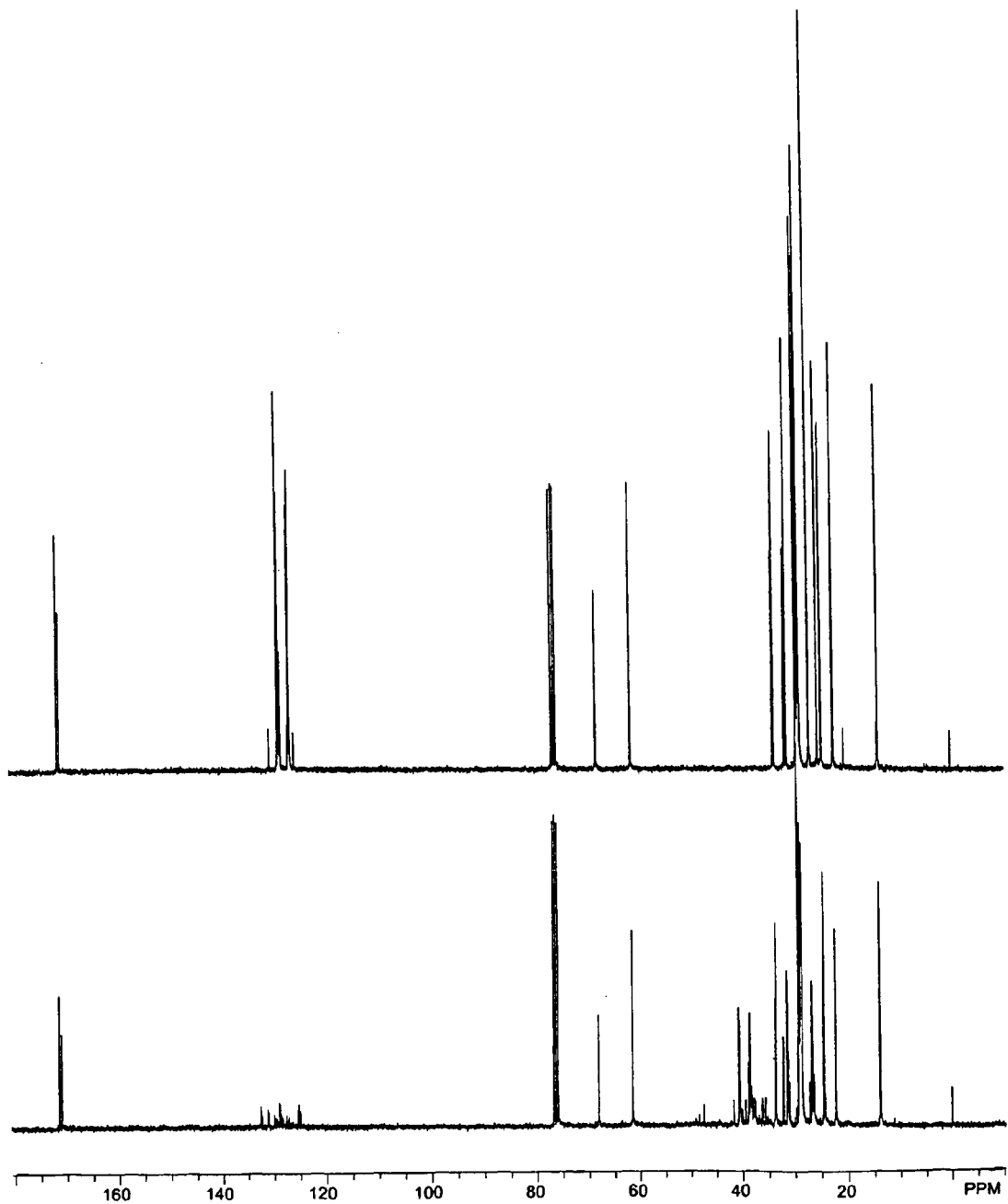
FIG. 1 includes two graphs that compare the NMR's of soybean oil, which is shown in the top graph, and a thiol containing ester produced from soybean oil in accordance with an embodiment of the present invention, which is shown in the bottom graph.

In the following description, all numbers disclosed herein are approximate values, regardless whether the word "about" or "approximate" is used in connection therewith. They can vary by 1%, 2%, 5%, and sometimes, 10 to 20%. Whenever a numerical range with a lower limit, $R_L$ and an upper limit, $R_U$, is disclosed, any number falling within the range is specifically disclosed. In particular, the following numbers within the range are specifically disclosed: $R=R_L+k*(R_U-R_L)$, wherein k is a variable ranging from 1% to 100% with a 1% increment, i.e., k is 1%, 2%, 3%, 4%, 5%, . . . , 50%, 51%, 52%, . . . , 95%, 96%, 97%, 98%, 99%, or 100%. Moreover, any numerical range defined by two R numbers as defined in the above is also specifically disclosed.

In this specification "natural" refers to materials obtained, by any method, from naturally occurring fruits, nuts, vegetables, plants and animals. As an example, natural source oil refers to source oils extracted, and optionally purified, from naturally occurring fruits, nuts, vegetables, plants and animals. Additionally, unsaturated natural source oil refers to unsaturated source oils extracted, and optionally purified, from naturally occurring fruits, nuts, vegetables, plants, and animals.

In this specification, "natural source raw material" refers to materials obtained by extraction, chemical breakdown, or chemical processing of "natural" materials. A nonlimiting example includes natural source oils that can be extracted from naturally occurring fruits, nuts, vegetables, plants and animals. As another non-limiting example, glycerol and carboxylic acids or carboxylic acid esters, saturated or unsaturated, can be produced and isolated by the chemical processing of triglycerides extracted from naturally occurring fruits, nuts, vegetables, plants, and animals.

In this specification "synthetic" refers to materials produced from chemical building blocks not directly derived from natural sources. For example synthetic unsaturated ester oil can be produced by the reaction of synthetic ethylene glycol and a synthetic carboxylic acid, i.e. acrylic acid or propionic acid. Other types of synthetic materials will be apparent to those of skill in the art and are to be considered within the scope of the present invention.

Regardless of the definitions of natural and synthetic, the materials described herein can be produced from a combination of natural and synthetic materials, "semi-synthetic". As a non-limiting example, the unsaturated ester oils described in this specification can be obtained or produced from a combination of synthetic and natural source raw materials. For example, the unsaturated ester oil can be produced by the reaction of synthetic ethylene glycerol and oleic acid isolated from a natural source oil. Alternatively, the unsaturated ester oil can be produced from the reaction of glycerol isolated from natural source oils and a synthetic carboxylic acid, i.e. acrylic acid. Alternatively, the unsaturated ester oil can be produced from glycerol and oleic acid isolated from natural source oils.

In this specification, "thiol ester composition" refers to an ester composition that includes "thiol ester molecules." The thiol ester molecule has at least one thiol group and at least one ester group within the thiol ester molecule.

In this specification, "hydroxy thiol ester composition" refers to an ester composition that includes "hydroxy thiol ester molecules." The hydroxy thiol ester molecule has at least one thiol group, at least one ester group, and at least one hydroxy or alcohol group within the hydroxy thiol ester molecule. Alternatively, the alcohol group and the thiol group can be combined in the same group, which is referred to as an "α-hydroxy thiol group."

In this specification, "sulfonic acid-containing ester composition" refers to a composition that includes sulfonic acid-containing ester molecules. The sulfonic acid-containing ester molecules have at least one sulfonic acid group and at least one ester group within the sulfonic acid-containing ester molecule.

In this specification, "sulfonate-containing ester composition" refers to an ester composition that includes sulfonate-containing ester molecules. The sulfonate-containing ester molecules have at least one sulfonate group and at least one ester group within the sulfonate-containing ester molecule.

In this specification, "unsaturated ester composition" refers to an ester composition that includes unsaturated ester molecules. The unsaturated ester molecules have at least one ester group and at least one carbon-carbon double bond within the sulfonate-containing ester molecule.

In this specification, "epoxidized unsaturated ester composition" refers to an ester composition that has been produced by epoxidizing an unsaturated ester composition.

In this specification, "polythiourethane" refers to a urethane composition that includes more than one of the following structure:

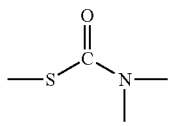

The presence of the thiourethane group can be determined by method known to those skilled in the art (for example infrared spectroscopy, Raman spectroscopy, and/or NMR).

Thiol Ester Composition

The present invention advantageously provides a thiol ester composition as an embodiment of the present invention. The thiol ester composition includes thiol ester molecules that have an average of at least 1.5 ester groups and an average of at least 1.5 thiol groups per thiol ester molecule. The thiol ester composition also has a molar ratio of cyclic sulfides to thiol groups of less than 1.5, as described herein.

Generally, the thiol ester composition contains molecules having at least one ester group and at least one thiol group. The thiol ester composition of this invention can be produced from any unsaturated ester, as described herein. Because the feedstock unsaturated esters can contain multiple carbon-carbon double bonds per unsaturated ester molecule, carbon-carbon double bond reactivity and statistical probability dictate that each thiol ester molecule of the thiol ester composition produced from the unsaturated ester composition will not have the same number of thiol groups, number of unreacted carbon-carbon double bonds, number of cyclic sulfides, molar ratio of carbon-carbon double bonds to thiol groups, molar ratio of cyclic sulfides to thiol groups and other quantities of functional groups and molar ratios disclosed herein as the feedstock unsaturated ester. Additionally, the feedstock unsaturated esters can also comprise a mixture of individual unsaturated esters having a different number of carbon-carbon double bonds and/or ester groups. Thus, many of these properties will be discussed as an average number of the groups per thiol ester molecule within the thiol ester composition or average ratio per thiol ester molecule within the thiol ester composition. In other embodiments, it is desired to control the content of thiol sulfur present in the thiol ester. Because it is difficult to ensure that the hydrogen sulfide reacts with every carbon-carbon double bond within the unsaturated ester, certain molecules of thiol ester can have more or less thiol groups than other molecules. Thus, the weight percent of thiol groups is stated as an average across all thiol ester molecules of the thiol ester composition.

The thiol ester can be derived from any unsaturated ester described herein.

The thiol ester compositions can be described as comprising one or more separate or discreet functional groups of the thiol ester molecule and/or thiol ester composition. These independent functional groups can include: the number of (or average number of) ester groups per thiol ester molecule, thiol containing the number of (or average number of) thiol groups per thiol ester molecule, the number of (or average number of) unreacted carbon-carbon double bonds per thiol ester molecule, the average thiol sulfur content of the thiol ester composition, the percentage (or average percentage) of sulfide linkages per thiol ester molecule, and the percentage (or average percentage) of cyclic sulfide groups per thiol ester molecule. Additionally, the thiol ester compositions can be described using individual or a combination of ratios including the ratio of double bonds to thiol groups, the ratio of cyclic sulfides to mercaptan group, and the like. As separate elements, these functional groups of the thiol composition will be described separately.

Minimally, in some embodiments, the thiol ester contains thiol ester molecules having at least one ester group and one thiol group per thiol ester molecule. As the thiol ester is prepared from unsaturated esters, the thiol ester can contain the same number of ester groups as the unsaturated esters described herein. In an embodiment, the thiol ester molecules have an average of at least 1.5 ester groups per thiol ester molecule. Alternatively, the thiol ester molecules have an average of at least 2 ester groups per thiol ester molecule; alternatively, an average of at least 2.5 ester groups per thiol ester molecule; or alternatively, an average of at least 3 ester groups per thiol ester molecule. In other embodiments, the thiol esters have an average of from 1.5 to 8 ester groups per thiol ester molecule; alternatively, an average of from 2 to 7 ester groups per thiol ester molecule; alternatively, an average of from 2.5 to 5 ester groups per thiol ester molecule; or alternatively, an average of from 3 to 4 ester groups per thiol ester molecule. In yet other embodiments, the thiol ester comprises an average of 3 ester groups per thiol ester molecule or alternatively, an average of 4 ester groups per unsaturated ester molecule.

Minimally, the thiol ester comprises an average of at least one thiol group per thiol ester molecule. In an embodiment, the thiol ester molecules have an average of at least 1.5 thiol groups per thiol ester molecule; alternatively, thiol containing an average of at least 2 thiol groups per thiol ester molecule; alternatively, an average of at least 2.5 thiol groups per thiol ester molecule; or alternatively, an average of at least 3 thiol groups per thiol ester molecule. In other embodiments, the thiol ester molecules have an average of from 1.5 to 9 thiol groups per thiol ester molecule; alternatively, an average of from 3 to 8 thiol groups per thiol ester molecule; alternatively, thiol containing an average of from 2 to 4 thiol groups per thiol ester molecule, or alternatively, an average of from 4 to 8 thiol groups per thiol ester molecule.

In other embodiments, the thiol ester can be described by the average amount of thiol sulfur present in thiol ester. In an embodiment, the thiol ester molecules have an average of at least 5 weight percent thiol sulfur per thiol ester molecule; alternatively, an average of at least 10 weight percent thiol sulfur per thiol ester molecule, or alternatively, an average of greater than 15 weight percent thiol sulfur per thiol ester molecule. In an embodiment, the thiol ester molecules have an average of from 5 to 25 weight percent thiol sulfur per thiol ester molecule; alternatively, an average of from 5 to 20 weight percent thiol sulfur per thiol ester molecule; alternatively, an average of from 6 to 15 weight percent thiol sulfur per thiol ester molecule; or alternatively, an average of from 8 to 10 weight percent thiol sulfur per thiol ester molecule.

Generally, the location of the thiol group of the thiol ester is not particularly important and will be dictated by the method used to produce the thiol ester. In embodiments wherein the thiol ester is produced by contacting an unsaturated ester, the position of the thiol group will be dictated by the position of the carbon-carbon double bond. When the carbon-carbon double bond is an internal carbon-carbon double bond, the method of producing the thiol ester will result in a secondary thiol group. However, when the double bond is located at a terminal position it is possible to choose reaction conditions to produce a thiol ester comprising either a primary thiol group or a secondary thiol group.

Some methods of producing the thiol ester composition can additionally create sulfur containing functional groups other than a thiol group. For example, in some thiol ester production methods, an introduced thiol group can react with a carbon-carbon double bond within the same unsaturated ester to produce a sulfide linkage. When the reaction is with a double bond of a second unsaturated ester, this produces a simple sulfide linkage. However, in some instances, the second carbon-carbon double bond is located in the same unsaturated ester molecule. When the thiol group reacts with a second carbon-carbon double bond within the same unsaturated ester molecule, a sulfide linkage is produced. In some instances, the carbon-carbon double bond can be within a second ester group of the unsaturated ester molecule. While in other instances, the carbon-carbon double bond can be within the same ester group of the unsaturated ester molecule.

When the thiol group reacts with the carbon-carbon double bond in a second ester group of the same unsaturated ester molecule, the cyclic sulfide would contain two ester groups contained within a ring structure. When the thiol group reacts with the carbon-carbon double bond within the same ester group, the cyclic sulfide would not contain an ester group within the ring structure. Within this specification, this second type of cyclic sulfide is referred to as a cyclic sulfide. Within this specification, the first type of cyclic sulfide is referred to as a simple sulfide. In the cyclic sulfide case, the sulfide linkage produces a cyclic sulfide functionality within a single ester group of the thiol ester. This linkage is termed a cyclic sulfide for purposes of this application. One such sulfide group that can be produced is a cyclic sulfide. The cyclic sulfide rings that can be produced include a tetrahydrothiopyran ring, a thietane ring, or a thiophane ring (tetrahydrothiophene ring).

In some embodiments, it is desirable to control the average amount of sulfur present as cyclic sulfide in the thiol ester. In an embodiment the average amount of sulfur present as cyclic sulfide in the thiol ester molecules comprises less than 30 mole percent. Alternatively, the average amount of sulfur present as cyclic sulfide in the thiol esters comprises less than 20 mole percent; alternatively, less than 10 mole percent; alternatively, less than 5 mole percent; or alternatively, less than 2 mole percent. In other embodiments, it is desired to control the molar ratio of cyclic sulfides to thiol groups. In other embodiments, it is desirable to have molar ratios of cyclic sulfide to thiol group. In an embodiment, the average molar ratio of cyclic sulfide groups to thiol group per thiol ester is less than 1.5. Alternatively, the average molar ratio of cyclic sulfide groups to thiol group per thiol ester is less than 1; alternatively, less than 0.5; alternatively, less than 0.25; or alternatively, 0.1. In some embodiments, the ratio of cyclic sulfide groups to thiol group per thiol ester ranges from 0 to 1; or alternatively, the average molar ratio of cyclic sulfide groups to thiol group per thiol ester ranges between 0.05 and 1.

In some instances it can desirable to have carbon-carbon double bonds present in the thiol ester composition while in other embodiments it can be desirable to minimize the number of carbon-carbon double bonds present in the thiol ester composition. The presence of carbon-carbon double bonds present in the thiol ester can be stated as an average molar ratio of carbon-carbon double bonds to thiol-sulfur. In an embodiment, the average ratio of the remaining unreacted carbon-carbon double bond in the thiol ester composition to thiol sulfur is less than 1.5 per thiol ester molecule. Alternatively, the average ratio of carbon-carbon double bond to thiol sulfur is less than 1.2 per thiol ester molecule; alternatively, less than 1.0 per thiol ester molecule; alternatively, less than 0.75 per thiol ester molecule; alternatively, less than 0.5 per thiol ester molecule; alternatively, less than 0.2 per thiol ester molecule; or alternatively, less than 0.1 per thiol ester molecule.

In particular embodiments, the thiol ester is produced from unsaturated ester compositions. Because the feedstock unsaturated ester has particular compositions having a certain number of ester groups present, the product thiol ester composition will have about the same number of ester groups per thiol ester molecule as the feedstock unsaturated ester. Other, independent thiol ester properties described herein can be used to further describe the thiol ester composition.

In some embodiments, the thiol ester molecules are produced from unsaturated esters having an average of less than 25 weight percent of side chains having 3 contiguous methylene interrupted carbon-carbon double bonds, as described herein. In some embodiments, greater than 40 percent of the thiol containing natural source total side chains can include sulfur. In some embodiments, greater than 60 percent of the thiol ester molecule total side chains can include sulfur. In other embodiments, greater than 50, 70, or 80 percent of the thiol ester molecule total side chains can include sulfur.

In an embodiment, the thiol ester is a thiol containing natural source oil, as described herein. When the thiol ester is a thiol containing natural source oil, functional groups that are present in the thiol containing natural source oil can be described in a "per thiol ester molecule" basis or in a "per triglyceride" basis. The thiol containing natural source oil can have substantially the same properties as the thiol ester composition, such as the molar ratios and other independent descriptive elements described herein.

The average number of thiol groups per triglyceride in the thiol containing natural source oil is greater than about 1.5. In some embodiments, the average number of thiol groups per triglyceride can range from about 1.5 to about 9.

The thiol ester compositions can also be described as a product produced by the process comprising contacting hydrogen sulfide and an unsaturated ester composition and can be further limited by the process as described herein. The thiol containing natural source oil can also be described using a molecular weight or an average molecular weight of the side chains.

Hydroxy Thiol Ester Composition

In embodiments of the present invention, the thiol ester compositions can also contain a hydroxy or alcohol group. When the thiol ester composition includes the hydroxy group, the thiol ester composition is referred to herein as the hydroxy thiol ester composition. The quantity or number of alcohol groups present in the hydroxy thiol ester composition can be independent of the quantity of other functional groups present in the hydroxy thiol ester composition (i.e. thiol groups, ester groups, sulfides, cyclic sulfides). Additionally, the weight percent of thiol sulfur and functional group ratios (i.e. molar ratio of cyclic sulfides to thiol groups, molar ratio of epoxide groups to thiol groups, molar ratio of epoxide groups to α-hydroxy thiol groups and other disclosed quantities of functional groups and their molar ratios to the thiol groups) are separate or discreet elements that can be used to describe the hydroxy thiol ester composition. The hydroxy thiol ester composition can be described using any combination of the hydroxy thiol ester composition separate functional groups or ratios described herein.

In an embodiment, the hydroxy thiol ester composition is produced by reacting hydrogen sulfide with an epoxidized unsaturated ester composition as described herein. Because the epoxidized unsaturated ester can contain multiple epoxide groups, epoxide group reactivity and statistical probability dictate that not all hydroxy thiol ester molecules of the hydroxy thiol ester composition will have the same number of hydroxy groups, thiol groups, α-hydroxy thiol groups, sulfides, cyclic sulfides, molar ratio of cyclic sulfides to thiol groups, molar ratio of epoxide groups to thiol groups, molar ratio of epoxide groups to α-hydroxy thiol groups, weight percent thiol sulfur and other disclosed quantities of functional groups and their molar ratios as the epoxidized unsaturated ester composition. Thus, many of these properties will be discussed as an average number or ratio per hydroxy thiol ester molecule. In other embodiments, it is desired to control the content of thiol sulfur present in the hydroxy thiol ester. Because it is difficult to ensure that the hydrogen sulfide reacts with every epoxide group within the epoxidized unsaturated ester, certain hydroxy thiol ester molecules can have more or less thiol groups than other molecules within the hydroxy thiol ester composition. Thus, the weight percent of thiol groups can be stated as an average weight percent across all hydroxy thiol ester molecules.

As an embodiment of the present invention, the hydroxy thiol ester composition includes hydroxy thiol ester molecules that have an average of at least 1 ester groups and an average of at least 1 α-hydroxy thiol groups per hydroxy thiol ester molecule. As an embodiment of the present invention, the hydroxy thiol ester composition includes hydroxy thiol ester molecules that have an average of at least 1.5 ester groups and an average of at least 1.5 α-hydroxy thiol groups per hydroxy thiol ester molecule.

Minimally, in some embodiments, the hydroxy thiol ester comprises at least one ester, at least one thiol group, and at least one hydroxy group. Because the hydroxy thiol ester is prepared from epoxidized unsaturated esters, the hydroxy thiol ester can contain the same number of ester groups as the epoxidized unsaturated esters. In an embodiment, the hydroxy thiol ester molecules have an average of at least 1.5 ester groups per hydroxy thiol ester molecule. Alternatively, the hydroxy thiol ester molecules have an average of at least 2 ester groups per hydroxy thiol ester molecule; alternatively, an average of at least 2.5 ester groups per hydroxy thiol ester molecule; or alternatively, an average of at least 3 ester groups per hydroxy thiol ester molecule. In other embodiments, the hydroxy thiol esters have an average of from 1.5 to 8 ester groups per hydroxy thiol ester molecule; alternatively, an average of from 2 to 7 ester groups per hydroxy thiol ester molecule; alternatively, an average of from 2.5 to 5 ester groups per hydroxy thiol ester molecule; or alternatively, an average of from 3 to 4 ester groups per hydroxy thiol ester molecule. In yet other embodiments, the α-hydroxy thiol ester comprises an average of 3 ester groups per hydroxy thiol ester molecule or alternatively, an average of 4 ester groups per hydroxy thiol ester molecule.

In some embodiments, the hydroxy group and the thiol group are combined in the same group, which produces the α-hydroxy thiol group. In other embodiments, the thiol group and the hydroxy or alcohol group are not in the same group. When this occurs, to produce the hydroxy thiol ester composition, the alcohol group is added independently of the thiol group. For example, as another embodiment of the present invention, the hydroxy thiol ester composition advantageously includes hydroxy thiol ester molecules. The hydroxy thiol ester molecules have an average of at least 1.5 ester groups, an average of at least 1.5 thiol groups, and an average of at least 1.5 alcohol groups per hydroxy thiol ester molecule.

Minimally, in some embodiments, the hydroxy thiol ester comprises at least one thiol group per hydroxy thiol ester molecule. In an embodiment, the hydroxy thiol ester molecules have an average of at least 1.5 thiol groups per hydroxy thiol ester molecule; alternatively, an average of at least 2 thiol groups per hydroxy thiol ester molecule; alternatively, an average of at least 2.5 thiol groups per hydroxy thiol ester molecule; or alternatively, an average of at least 3 thiol groups per hydroxy thiol ester molecule. In other embodiments, the hydroxy thiol ester molecules have an average of from 1.5 to 9 thiol groups per hydroxy thiol ester molecule; alternatively, an average of from 3 to 8 thiol groups per hydroxy thiol ester molecule; alternatively, an average of from 2 to 4 thiol groups per hydroxy thiol ester molecule; or alternatively, an average of from 4 to 8 thiol groups per hydroxy thiol ester.

Minimally, in some embodiments, the hydroxy thiol ester composition comprises an average of at least 1 hydroxy or alcohol group per hydroxy thiol ester molecule. In some embodiments, the hydroxy thiol ester composition comprises an average of at least 1.5 hydroxy groups per hydroxy thiol ester molecule; alternatively, average of at least 2 hydroxy groups per hydroxy thiol ester molecule; alternatively, an average of at least 2.5 hydroxy groups per hydroxy thiol ester molecule; or alternatively, an average of at least 3 hydroxy groups per thiol ester molecule. In other embodiments, the thiol ester composition comprises an average of from 1.5 to 9 hydroxy groups per hydroxy thiol ester molecule; alternatively, an average of from 3 to 8 hydroxy groups per hydroxy thiol ester molecule; alternatively, an average of from 2 to 4 hydroxy groups per hydroxy thiol ester molecule; or alternatively, an average of from 4 to 8 hydroxy groups per hydroxy thiol ester molecule.

In yet other embodiments, the number of hydroxy groups can be stated as an average molar ratio of hydroxy group to thiol groups. Minimally, in some embodiments, the molar ratio of hydroxy groups to thiol groups is at least 0.25. In some embodiments, the molar ratio of hydroxy groups to thiol groups is at least 0.5; alternatively, at least 0.75; alternatively, at least 1.0; alternatively, at least 1.25; or alternatively, at least 1.5. In other embodiments, the molar ratio of hydroxy groups to thiol groups ranges from 0.25 to 2.0; alternatively, from 0.5 to 1.5; or alternatively, from 0.75 to 1.25.

In embodiments where the hydroxy thiol esters are produced from an epoxidized unsaturated ester, the hydroxy thiol esters can be described as containing ester groups and α-hydroxy thiol groups. The number of ester groups and the number of α-hydroxy thiol groups are independent elements and as such the hydroxy thiol esters can be described as having any combination of ester groups and α-hydroxy thiol groups described herein. Minimally, the hydroxy thiol ester comprises an average of at least 1 α-hydroxy thiol group per hydroxy thiol ester molecule. In some embodiments, the hydroxy thiol ester composition comprises an average of at least 1.5 α-hydroxy thiol groups per hydroxy thiol ester molecule; alternatively, an average of at least 2 α-hydroxy thiol groups per hydroxy thiol ester molecule; alternatively, an average of at least 2.5 α-hydroxy thiol groups per hydroxy thiol ester molecule; or alternatively, an average of at least 3 α-hydroxy thiol groups per hydroxy thiol ester molecule. In other embodiments, the hydroxy thiol ester composition comprises an average of from 1.5 to 9 α-hydroxy thiol groups per hydroxy thiol ester molecule; alternatively, an average of from 3 to 8 α-hydroxy thiol groups per hydroxy thiol ester molecule; alternatively, an average of from 2 to 4 α-hydroxy thiol groups per hydroxy thiol ester molecule; or alternatively, an average of from 4 to 8 α-hydroxy thiol groups per hydroxy thiol ester molecule.

The hydroxy thiol esters can be produced by contacting an epoxidized ester derived from an unsaturated ester (i.e., epoxidized unsaturated ester), as described herein. In some instances it can desirable to have epoxide groups present in the hydroxy thiol ester composition. While in other embodiments, it can be desirable to minimize the number of epoxy groups present in the hydroxy thiol ester composition. Thus, the presence of residual epoxide groups can be another separate functional group used to describe the hydroxy thiol ester.

The presence of epoxide groups in the hydroxy thiol ester can be independently described as an average number of epoxide groups per hydroxy thiol ester, a molar ratio of epoxide groups to thiol groups, a molar ratio of epoxide groups to α-hydroxy thiol groups, or any combination thereof. In some embodiments, the hydroxy thiol ester molecules comprise an average of less than 2 epoxide groups per hydroxy thiol ester molecule, i.e., the hydroxy thiol ester molecules have a molar ratio of epoxide groups to α-hydroxy thiol groups of less than 2. Alternatively, the hydroxy thiol ester comprises an average of less than 1.5 epoxide groups per hydroxy thiol ester molecule; alternatively, an average of less than 1 epoxide group per hydroxy thiol ester molecule; alternatively, an average of less than 0.75 epoxide groups per hydroxy thiol ester molecule; or alternatively, an average of less than 0.5 epoxide groups per hydroxy thiol ester molecule. In other embodiments, the molar ratio of epoxide groups to thiol groups averages less than 1.5. Alternatively, the molar ratio of epoxide groups to thiol groups averages less than 1; alternatively, averages less than 0.75; alternatively, averages less than 0.5; alternatively, averages less than 0.25; or alternatively, averages less than 0.1. In yet other embodiments, the molar ratio of epoxide groups to α-hydroxy thiol groups averages less than 1.5. Alternatively, the molar ratio of epoxide groups to α-hydroxy thiol groups averages less than 1; alternatively, averages less than 0.75; alternatively, averages less than 0.5; alternatively, averages less than 0.25; or alternatively, averages less than 0.1.

In some embodiments, the hydroxy thiol ester composition is substantially free of epoxide groups.

In other embodiments, the hydroxy thiol ester can be described by the average amount of thiol sulfur present in hydroxy thiol ester. In an embodiment, the hydroxy thiol ester molecules have an average of at least 2.5 weight percent thiol sulfur per hydroxy thiol ester molecule; alternatively, an average of at least 5 weight percent thiol sulfur per hydroxy thiol ester molecule; alternatively, an average of at least 10 weight percent thiol sulfur per hydroxy thiol ester molecule; or alternatively, an average of greater than 15 weight percent thiol sulfur per hydroxy thiol ester molecule. In an embodiment, the hydroxy thiol ester molecules have an average of from 5 to 25 weight percent thiol sulfur per hydroxy thiol ester molecule; alternatively, an average of from 5 to 20 weight percent thiol sulfur per hydroxy thiol ester molecule; alternatively, an average of from 6 to 15 weight percent thiol sulfur per hydroxy thiol ester molecule; or alternatively, an average of from 8 to 10 weight percent thiol sulfur per hydroxy thiol ester molecule.

In some embodiments, at least 20 percent of the total side chains include the α-hydroxy thiol group. In some embodiments, at least 20 percent of the total side chains include the α-hydroxy thiol group. In some embodiments, at least 60 percent of the total side chains include the α-hydroxy thiol group; alternatively, at least 70 percent of the total side chains include the α-hydroxy thiol group. Yet in other embodiments, at least 80 percent of the total side chains include the α-hydroxy thiol group.

In some aspects, greater than 20 percent of the hydroxy thiol ester molecule total side chains contain sulfur. In some aspects, greater than 40 percent of the hydroxy thiol ester molecule total side chains contain sulfur. In some aspects, greater than 60 percent of the hydroxy thiol ester molecule total side chains contain sulfur; alternatively, greater than 70 percent of the total side chains contain sulfur; or alternatively, greater than 80 percent of the total side chains contain sulfur.

In particular embodiments, the epoxidized unsaturated ester used in the synthesis of the hydroxy thiol ester is produced from the epoxidized unsaturated ester composition that includes an epoxidized natural source oil. Because the natural source oils have particular compositions regarding the number of ester groups present, the hydroxy thiol ester will have about the same number of ester groups as the feedstock natural source oil. Other independent properties that are described herein can be used to further describe the hydroxy thiol ester.

In other embodiments, the epoxidized unsaturated ester used to produce the hydroxy thiol ester is produced from synthetic (or semi-synthetic) unsaturated ester oils. Because the synthetic ester oils can have particular compositions regarding the number of ester groups present, the hydroxy thiol ester would have about the same number of ester groups as the synthetic ester oil. Other, independent properties of the unsaturated ester, whether the unsaturated ester includes natural source or synthetic oils, can be used to further describe the hydroxy thiol ester composition.

The hydroxy thiol ester compositions can also be described as a product produced by the process comprising contacting hydrogen sulfide and an epoxidized unsaturated ester composition and can be further limited by the process as described herein. The hydroxy thiol containing natural source oil can also be described using an average molecular weight or an average molecular weight of the side chains.

Cross-Linked Thiol Ester Compositions

In an aspect, the present invention relates to a cross-linked thiol ester composition. Generally, the cross-linked thiol ester molecules are oligomers of thiol esters that are connected together by polysulfide linkages —$S_x$— wherein x is an integer greater 1. As the cross-linked thiol ester is described as an oligomer of thiol esters, the thiol esters can be described as the monomer from which the cross-linked thiol esters are produced.

In an aspect, the cross-linked thiol ester composition comprises a thiol ester oligomer having at least two thiol ester monomers connected by a polysulfide linkage having a structure —$S_Q$—, wherein Q is an integer greater than 1. In an aspect, the polysulfide linkage may be the polysulfide linkage —$S_Q$—, wherein Q is 2, 3, 4, or mixtures thereof. In other embodiments, Q can be 2; alternatively, 3; or alternatively, 4.

In an aspect, the cross-linked thiol ester composition comprises a thiol ester oligomer having at least 3 thiol ester monomers connected by polysulfide linkages; alternatively, 5 thiol ester monomers connected by polysulfide linkages; alternatively, 7 thiol ester monomers connected by polysulfide linkages; or alternatively, 10 thiol ester monomers connected by polysulfide linkages. In yet other embodiments, the cross-linked thiol ester composition comprises a thiol ester oligomer having from 3 to 20 thiol ester monomers connected by polysulfide linkages; alternatively, from 5 to 15 thiol ester monomers connected by polysulfide linkages; or alternatively, from 7 to 12 thiol ester monomers connected by polysulfide linkages.

In an aspect, the cross-linked thiol ester composition comprises thiol ester monomers and thiol ester oligomers. In some embodiments, the cross-linked thiol ester composition has a combined thiol ester monomer and thiol ester oligomer average molecular weight greater than 2,000. In other embodiments, the cross-linked thiol ester composition has a combined thiol ester monomer and thiol ester oligomer average molecular weight greater than 5,000; or alternatively, greater than 10,000. In yet other embodiments, the cross-linked thiol ester composition has a combined thiol ester monomer and thiol ester oligomer average molecular weight ranging from 2,000 to 20,000; alternatively, from 3,000 to 15,000; or alternatively, from 7,500 to 12,500.

In an aspect, the thiol ester monomers and thiol ester oligomers have a total thiol sulfur content greater than 0.5. In other embodiments, the thiol ester monomers and thiol ester oligomers have a total thiol sulfur content greater than 1; alternatively, greater than 2; alternatively, greater than 4. In yet other embodiments, the thiol ester monomers and the thiol ester oligomers have a total thiol sulfur content from 0.5 to 8; alternatively, from 4 to 8; or alternatively, 0.5 to 4.

In an aspect, the thiol ester monomers and thiol ester oligomers have a total sulfur content greater than 8. In some embodiments, the thiol ester monomers and thiol ester oligomers have a total sulfur content greater than 10; alternatively, greater than 12. In yet other embodiments, the thiol ester monomers and thiol ester oligomers have a total sulfur content ranging from 8 to 15 weight percent; alternatively, from 9 to 14; or alternatively, from 10 to 13.

The cross-linked thiol ester compositions can also be described as a product produced by the process comprising contacting a thiol ester with oxidizing agent and can be further limited by the process as described herein.

Sulfide-Containing Ester Compositions

The present invention advantageously includes sulfide-containing ester compositions as embodiments of the present invention. Generally, the sulfide-containing ester compositions can be described as containing molecules having at least one ester group and a least one sulfide group within each molecule. The sulfide-containing esters used in the present invention can be produced by contacting either an unsaturated ester or an epoxidized unsaturated ester with a thiol containing compound as described herein.

In addition to sulfide groups and ester groups, the sulfide-containing esters can further be described by including other functional groups and ratios described herein. Each of the other functional groups, ratios, the number of sulfide groups, and the number of ester groups are separate elements that allow the sulfide-containing ester to be described using any combination of the sulfide-containing ester separate elements described herein. A non-limiting list of the sulfide-containing separate elements include the average number of ester groups per sulfide-containing ester molecule, the number of sulfide groups per sulfide-containing ester molecule, the average number of moiety X per sulfide-containing ester molecule, the average number of moiety Y per sulfide-containing ester molecule, the average number of moiety Z per sulfide-containing ester molecule, and the like.

The feedstock unsaturated esters can contain multiple carbon-carbon double bonds per unsaturated ester molecule. The carbon-carbon double bond reactivity and statistical probability, however, dictate that each sulfide-containing ester molecule of the thiol-containing ester composition produced from the unsaturated ester composition will not have the same number of sulfide groups, number of unreacted carbon-carbon double bonds, molar ratio of carbon-carbon double bonds to sulfide groups, molar ratio of cyclic sulfides to thiol groups and other herein disclosed quantities of functional groups and molar ratios. Additionally, the feedstock unsaturated esters can also comprise a mixture of individual unsaturated esters having a different number of carbon-carbon double bonds and/or ester groups. Many of these properties are discussed herein as an average number of the groups per sulfide-containing ester molecule within the sulfide-containing ester composition or average ratio per thiol-containing ester molecule within the sulfide-containing ester composition.

In embodiments related to the sulfide-containing ester that is produced from an epoxidized unsaturated ester, the feedstock epoxidized unsaturated esters can contain multiple epoxide groups per unsaturated ester molecule. Individual epoxide group reactivity and statistical probability dictate that each sulfide-containing ester molecule of the sulfide-containing ester composition produced from the unsaturated ester composition will not have the same number of sulfide groups, number of unreacted epoxide groups, molar ratio of epoxide groups to sulfide groups, and other herein disclosed quantities of functional groups and molar ratios. Additionally, the feedstock epoxidized unsaturated esters can also comprise a mixture of individual epoxidized unsaturated ester molecules having a different number of epoxide groups and/or ester groups. Thus, many of these properties are described as an average number of the groups per sulfide-containing ester molecules within the sulfide-containing ester composition or average ratio per thiol-containing ester molecule within the sulfide-containing ester composition.

Minimally, in some embodiments, the sulfide-containing esters comprise at least one ester group per sulfide-containing ester molecule. In some embodiments, the sulfide-containing ester has an average of at least 1.5 ester groups per sulfide-containing ester molecule. Alternatively, the sulfide-containing ester molecules have an average of at least 2 ester groups per sulfide-containing ester molecule; alternatively, an average of at least 2.5 ester groups per sulfide-containing ester molecule; or alternatively, an average of at least 3 ester groups per sulfide-containing ester molecule. In other embodiments, the sulfide-containing esters have an average of from 1.5 to 9 ester groups per sulfide-containing ester molecule; alternatively, an average of from 1.5 to 8 ester groups per sulfide-containing ester molecule; alternatively, an average of from 2 to 8 ester groups per sulfide-containing ester molecule; alternatively, an average of from 2 to 7 ester groups per sulfide-containing ester molecule; alternatively, an average of from 2.5 to 5 ester groups per sulfide-containing ester molecule; alternatively, an average of from 3 to 5 ester groups per sulfide-containing ester molecule; or alternatively, an average of from 3 to 4 ester groups per sulfide-containing ester molecule. In yet other embodiments, the hydroxy thiol-containing ester comprises an average of about 3 ester groups per sulfide-containing ester molecule; or alternatively, an average of about 4 ester groups per sulfide-containing ester molecule.

Minimally, in some embodiments, the sulfide-containing ester molecule composition comprises sulfide-containing ester molecules having at least one sulfide group per sulfide-containing ester molecule. In some embodiments, the sulfide-containing ester molecules have an average of at least 1.5 sulfide groups per sulfide-containing ester molecule. In other embodiments, the sulfide-containing ester molecules have an average of at least 2 sulfide groups per sulfide-containing ester molecule; alternatively, an average of at least 2.5 sulfide groups per sulfide-containing ester molecule; or alternatively, an average of at least 3 sulfide groups per sulfide-containing ester molecule. In other aspects, the sulfide-containing ester molecules have an average of from 1.5 to 9 sulfide groups per sulfide-containing ester molecule. Alternatively, the sulfide-containing ester molecules have an average of from 3 to 8 sulfide groups per sulfide-containing ester molecule; alternatively, an average of from 2 to 4 sulfide groups per sulfide-containing ester molecule; or alternatively, an average of from 4 to 8 sulfide groups per sulfide-containing ester molecule.

In another independent aspect, the sulfide-containing ester composition comprising molecules having the moiety X:

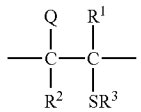

In this moiety X structure, Q is hydrogen or a hydroxy group; $R^1$ and $R^2$ are independently selected from the group consisting of hydrogen, $C_1$ to $C_{20}$ organyl groups, and $C_1$ to $C_{20}$ hydrocarbyl groups; $R^3$ is a $C_1$ to $C_{20}$ organyl groups or a $C_1$ to $C_{20}$ hydrocarbyl groups; and the unspecified valences of moiety X represent the remainder of the sulfide-containing ester molecule. Q, $R^1$, $R^2$, and $R^3$ are separate elements of moiety X that allow moiety X to have any combination of further Q, $R^1$, $R^2$, and $R^3$ elements described herein. In some particular embodiments, $R^1$ and $R^2$ are hydrogen and $R^3$ is a $C_1$ to $C_{20}$ organyl groups selected from the groups described herein.

In particular embodiments, the sulfide-containing ester molecules have an average of at least 1.5 moiety X's per sulfide-containing ester molecule. In other embodiments, the sulfide-containing ester molecules have an average of at least 2 moiety X's per sulfide-containing ester molecule; alternatively, an average of at least 2.5 moiety X's per sulfide-containing ester molecule; or alternatively, an average of at least 3 moiety X's per sulfide-containing ester molecule. In other aspects, the sulfide-containing ester molecules have an average of from 1.5 to 9 moiety X's per sulfide-containing ester molecule. Alternatively, the sulfide-containing ester molecules have an average of from 3 to 8 moiety X's per sulfide-containing ester molecule; alternatively, an average of from 2 to 4 moiety X's per sulfide-containing ester molecule; or alternatively, an average of from 4 to 8 moiety X's per sulfide-containing ester molecule.

In a particular aspect, the sulfide-containing ester composition comprising molecules having the moiety Y:

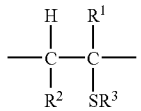

In this moiety Y structure, $R^1$ and $R^2$ are independently selected from the group consisting of hydrogen and $C_1$ to $C_{20}$ hydrocarbyl groups; $R^3$ is a $C_1$ to $C_{20}$ organyl groups or a $C_1$ to $C_{20}$ hydrocarbyl groups; and the unspecified valences of moiety Y represent the remainder of the sulfide-containing ester molecule. $R^1$, $R^2$, and $R^3$ are separate elements of moiety Y that allow moiety Y to have any combination of further $R^1$, $R^2$, and $R^3$ embodiments as described herein. In some embodiments, $R^1$ and $R^2$ are hydrogen and $R^3$ is a $C_1$ to $C_{20}$ organyl groups selected from the groups described herein.

In particular embodiments, the sulfide-containing ester molecules have an average of at least 1.5 moiety Y's per sulfide-containing ester molecule. In other embodiments, the sulfide-containing ester molecules have an average of at least 2 moiety Y's per sulfide-containing ester molecule; alternatively, an average of at least 2.5 moiety Y's per sulfide-containing ester molecule; or alternatively, an average of at least 3 moiety Y's per sulfide-containing ester molecule. In other aspects, the sulfide-containing ester molecules have an average of from 1.5 to 9 moiety Y's per sulfide-containing ester molecule. Alternatively, the sulfide-containing ester molecules have an average of from 3 to 8 moiety Y's per sulfide-containing ester molecule; alternatively, an average of from 2 to 4 moiety Y's per sulfide-containing ester molecule; or alternatively, an average of from 4 to 8 moiety Y's per sulfide-containing ester molecule.

In another particular aspect, the sulfide-containing ester composition comprising molecules having the moiety Z:

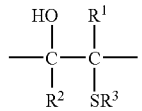

In this moiety Z structure, $R^1$ and $R^2$ are independently selected from the consisting of hydrogen and $C_1$ to $C_{20}$ hydrocarbyl groups; $R^3$ is a $C_1$ to $C_{20}$ organyl groups or a $C_1$ to $C_{20}$ hydrocarbyl groups; and the unspecified valences of moiety Z represent the remainder of the sulfide-containing ester molecule. $R^1$, $R^2$ and $R^3$ are separate elements of moiety Z that allow moiety Z to have any combination of further $R^1$, $R^2$, and $R^3$ elements described herein. In some embodiments, $R^1$ and $R^2$ are hydrogen and $R^3$ is a $C_1$ to $C_{20}$ organyl groups selected from the groups described herein.

In particular embodiments, the sulfide-containing ester molecules have an average of at least 1.5 moiety Z's per sulfide-containing ester molecule. In other embodiments, the sulfide-containing ester molecules have an average of at least 2 moiety Z's per sulfide-containing ester molecule; alternatively, an average of at least 2.5 moiety Z's per sulfide-containing ester molecule; or alternatively, an average of at least 3 moiety Z's per sulfide-containing ester molecule. In other aspects, the sulfide-containing ester molecules have an average of from 1.5 to 9 moiety Z's per sulfide-containing ester molecule. Alternatively, the sulfide-containing ester molecules have an average of from 3 to 8 moiety Z's per sulfide-containing ester molecule; alternatively, an average of from 2 to 4 moiety Z's per sulfide-containing ester molecule; or alternatively, an average of from 4 to 8 moiety Z's per sulfide-containing ester molecule.

In some embodiments, $R^3$ comprises at least one functional group. In one aspect, the functional group is selected from the group consisting of a hydroxy group, a carboxylic acid group, a carboxylic ester group, an amine group, a sulfide group, and a second thiol group. In some aspects, $R^3$ comprises at least two functional groups. In some aspects, the functional groups are selected from the group consisting of a hydroxy group, carboxylic acid group, a carboxylic ester group, an amine group, a sulfide group, a second thiol group, and mixtures thereof.

As another embodiment of the present invention, a sulfide-containing ester composition comprising sulfide-containing ester molecules is advantageously provided. In this embodiment, the sulfide-containing ester molecules have an average of at least 1 ester group per sulfide-containing ester molecule and have an average of at least 1 moiety X per sulfide-containing ester molecule. The moiety X has the structure as described herein. Additionally, the average number of ester groups and the average number of moiety X's are separate elements. Thus, the sulfide-containing ester molecules of the sulfide-containing ester composition can have any combination of the average number of ester groups and the average number of moiety X's described herein.

As another embodiment of the present invention, a sulfide-containing ester composition comprising sulfide-containing ester molecules is advantageously provided. In this embodiment, the sulfide-containing ester molecules have an average of least 1 ester group per sulfide-containing ester molecule and have an average of at least 1 moiety Y per sulfide-containing ester molecule. The moiety Y has the structure as described herein. Additionally, the average number of ester groups and the average number of moiety Y's are separate elements. Thus, the sulfide-containing ester molecules of the sulfide-containing ester composition can have any combination of the average number of ester groups and the average number of moiety Y's as described herein.

As another embodiment of the present invention, a sulfide-containing ester composition comprising sulfide-containing ester molecules is advantageously provided. In this embodiment, the sulfide-containing ester molecules have an average of at least 1 ester group per sulfide-containing ester molecule and have an average of at least 1 moiety Z per sulfide-containing ester molecule. The moiety Z has the structure as described herein. Additionally, the average number of ester groups and the average number of moiety Z's are separate elements. Thus, the sulfide-containing ester molecules of the sulfide-containing ester composition can have any combination of the average number of ester groups and the average number of moiety Z's as described herein.

The sulfide-containing ester compositions can also be described as a product produced by the process comprising contacting an unsaturated ester with a mercaptan and can be further limited by the process as described herein. In other embodiments, the sulfide-containing ester composition can also be described as a product produced by a process comprising contacting an epoxidized unsaturated ester with a mercaptan and can be further limited by the process as described herein.

Thioacrylate Ester Composition

As an embodiment of the present invention, a thioacrylate ester composition is advantageously provided Within the thioacrylate ester composition descriptions, the terms "acrylate" and "thioacrylate" can be used to describe elements of the thioacrylate esters. Although thioacrylate groups could be considered as a member of the class of acrylates, for the purposes of this thioacrylate ester composition description contained herein, the term acrylate refers to the group having the general structure:

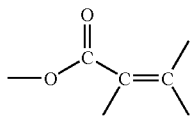

The term thioacrylate refers to the group having the general structure:

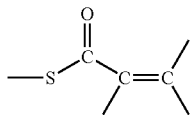

Within this general thioacrylate structure, the unspecified valences on the acrylate and thioacrylate carbon-carbon double bonds are further defined herein.

Generally, the thioacrylate ester composition can be described as comprising thioacrylate molecules having at least one ester group in addition to any acrylate or thioacrylate ester groups present in the thioacrylate molecule and at least one thioacrylate group. The ester group(s) that are in addition to any acrylate or thioacrylate ester groups present in the thioacrylate molecule are hereinafter referred to as "supplementary ester group(s)." The thioacrylate ester composition described herein can be produced by contacting an acrylate composition with a thiol-containing ester composition and/or a hydroxy thiol-containing ester composition, both of which are described herein.

In addition to thioacrylate groups and supplementary ester groups, the thioacrylate ester composition can further be described by including other functional groups and molar ratios described herein. The thioacrylate groups, supplementary ester groups, the other functional group, and molar ratios between functional groups present in the thioacrylate molecule represent separate elements of the thioacrylate ester molecules that allow the thioacrylate ester composition to be described using any combination of the thioacrylate ester separate elements described herein. A non-limiting list of the thioacrylate ester independent elements include: the number of supplementary ester groups, the average number of supplementary ester groups per thioacrylate ester molecule, the number of thioacrylate groups, the number of thioacrylate groups per thioacrylate ester molecule, the number of acrylate groups, the average number of acrylate groups per thioacrylate ester molecule, the number of moiety $X^1$'s, the average number of moiety $X^1$'s per thioacrylate ester molecule, the number of moiety $Y^1$'s, the average number of moiety $Y^1$'s per thioacrylate ester molecule, the number of moiety $Z^1$'s, the average number of moiety $Z^1$'s per thioacrylate ester molecule, and the like.

The feedstock thiol ester compositions and/or hydroxy thiol ester compositions can comprise a mixture of molecules that have an average quantity of ester groups, thiol groups, hydroxy groups, and other groups and molar ratios described herein. Additionally, individual thiol and hydroxy group reactivity within the thiol-containing ester compositions and/or hydroxy thiol ester compositions and statistical probability dictate that each thioacrylate ester molecule of the thioacrylate ester composition produced may not have the same number of ester groups, thioacrylate groups, acrylate groups, and other herein disclosed quantities of functional groups, moieties, and molar ratios. Thus, many of the properties of the thioacrylate ester molecules within the thioacrylate ester composition are described as using an average number of the groups per thioacrylate ester molecule within the thioacrylate ester composition or as an average ratio per thioacrylate ester molecule within the thioacrylate ester composition.

Minimally, in some embodiments, the thioacrylate ester composition comprises at least 1 supplementary ester group per thioacrylate ester molecule. In some embodiments, the thioacrylate ester has an average of at least 1.5 supplementary ester groups per thioacrylate ester molecule. Alternatively, the thioacrylate ester molecules have an average of at least 2 supplementary ester groups per thioacrylate ester molecule; alternatively, an average of at least 2.5 supplementary ester groups per thioacrylate ester molecule; or alternatively, an average of at least 3 supplementary ester groups per thioacrylate ester molecule. In other embodiments, the thioacrylate ester has an average of from 1.5 to 9 supplementary ester groups per thioacrylate ester molecule; alternatively, an average of from 1.5 to 8 supplementary ester groups per thioacrylate ester molecule; alternatively, an average of from 2 to 8 supplementary ester groups per thioacrylate ester molecule; alternatively, an average of from 2 to 7 supplementary ester groups per thioacrylate ester molecule; alternatively, an average of from 2.5 to 5 supplementary ester groups per thioacrylate ester molecule; alternatively, an average of from 3 to 5 supplementary ester groups per thioacrylate ester molecule; or alternatively, an average of from 3 to 4 supplementary ester groups per thioacrylate ester molecule. In yet other embodiments, the thioacrylate ester comprises an average of about 3 supplementary ester groups per thioacrylate ester molecule; or alternatively, an average of about 4 supplementary ester groups per thioacrylate ester molecule.

Minimally, in some embodiments, the thioacrylate ester comprises at least 1 thioacrylate group. In some embodiments of the present invention, the thioacrylate ester molecules have an average of at least 1.5 thioacrylate groups per thioacrylate ester molecule. In other embodiments, the thioacrylate ester molecules have an average of at least 2 thioacrylate groups per thioacrylate ester molecule; alternatively, an average of at least 2.5 thioacrylate groups per thioacrylate ester molecule; or alternatively, an average of at least 3 thioacrylate groups per thioacrylate ester molecule. In an aspect, the thioacrylate ester molecules have an average of from 1.5 to 9 thioacrylate groups per thioacrylate ester molecule; alternatively, an average of from 3 to 8 thioacrylate groups per thioacrylate ester molecule; alternatively, an average of from 2 to 4 thioacrylate groups per thioacrylate ester molecule; or alternatively, an average of from 4 to 8 thioacrylate groups per thioacrylate ester molecule.

In some aspects of the present invention, the thioacrylate ester molecules further comprise acrylate groups. In some embodiments, the thioacrylate ester molecules have an average of at least 1 acrylate group per thioacrylate ester molecule. In other embodiments, the thioacrylate ester molecules have an average of at least 1.5 acrylate groups per thioacrylate ester molecule; alternatively, an average of at least 2 acrylate groups per thioacrylate ester molecule; alternatively, an average of at least 2.5 acrylate groups per thioacrylate ester molecule; or alternatively, an average of at least 3 acrylate groups per thioacrylate ester molecule. In an aspect, the thioacrylate ester molecules have an average of from 1.5 to 9 acrylate groups per thioacrylate ester molecule; alternatively, an average of from 3 to 8 acrylate groups per thioacrylate ester molecule; alternatively, an average of from 2 to 4 acrylate groups per thioacrylate ester molecule; or alternatively, an average of from 4 to 8 acrylate groups per thioacrylate ester molecule.

As another embodiment of the present invention, a thioacrylate composition comprising thioacrylate ester molecules have an average of at least 1 supplementary ester group per thioacrylate ester molecule and an average of at least 1 moiety $X^1$ per thioacrylate ester molecule, the moiety $X^1$ having the structure:

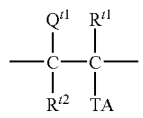

In the moiety $X^1$ structure, $R^{t1}$ and $R^{t2}$ are independently selected from the group consisting of consisting of hydrogen, $C_1$ to $C_{20}$ organyl groups, and $C_1$ to $C_{20}$ hydrocarbyl groups; $Q^{t1}$ is independently selected from the group consisting of hydrogen and an acrylate group; and TA represents a thioacrylate group having the structure:

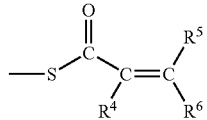

The unspecified valences of moiety $X^1$ represent the remainder of the thioacrylate ester molecule. Within the embodiments wherein the thioacrylate ester molecules contain the moiety $X^1$, the average number of supplementary ester groups per thioacrylate ester and the average number of moiety $X^1$ present in the thioacrylate molecules per thioacrylate ester molecule are separate elements.

In further embodiments, the thioacrylate ester molecules have an average of at least 1.5 moiety $X^1$'s per thioacrylate ester molecule. In other embodiments, the thioacrylate ester molecules have an average of at least 2 moiety $X^1$'s per thioacrylate ester molecule; alternatively, an average of at least 2.5 moiety $X^1$'s per thioacrylate ester molecule; or alternatively, an average of at least 3 moiety $X^1$'s per thioacrylate ester molecule. In an aspect, the thioacrylate ester molecules have an average of from 1.5 to 9 moiety $X^1$'s per thioacrylate ester molecule; alternatively, an average of from 3 to 8 moiety $X^1$'s per thioacrylate ester molecule; alternatively, an average of from 2 to 4 moiety $X^1$'s per thioacrylate ester molecule; or alternatively, an average of from 4 to 8 moiety $X^1$'s per thioacrylate ester molecule.

In some embodiments the thioacrylate ester has a thioacrylate group having the structure:

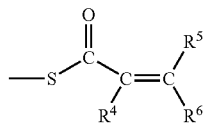

Generally, within the thioacrylate group structure, $R^4$, $R^5$, and $R^6$ are independently selected from the group consisting of hydrogen, $C_1$ to $C_{20}$ organyl groups, and $C_1$ to $C_{20}$ hydrocarbyl groups. In further embodiments, $R^4$, $R^5$, and $R^6$ are selected from hydrogen, $C_1$ to $C_{10}$ organyl groups, and $C_1$ to $C_{10}$ hydrocarbyl groups; or alternatively, selected from $C_1$ to $C_5$ organyl groups, and $C_1$ to $C_5$ hydrocarbyl groups. In certain embodiments, $R^4$, $R^5$, and $R^6$ are independently selected from the group consisting of hydrogen and a methyl group. In some specific embodiments, $R^5$ and $R^6$ are hydrogen and $R^4$ is selected from hydrogen, a methyl group, or a mixture thereof; alternatively, $R^5$ and $R^6$ are hydrogen and $R^4$ is a methyl group; or alternatively, $R^4$, $R^5$, and $R^6$ are hydrogen.

In some embodiments the thioacrylate ester has an acrylate group having the structure:

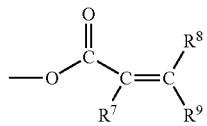

Generally, within the acrylate group structure, $R^7$, $R^8$, and $R^9$ are independently selected from the group consisting of hydrogen, $C_1$ to $C_{20}$ organyl groups, and $C_1$ to $C_{20}$ hydrocarbyl groups. In further embodiments, $R^7$, $R^8$, and $R^9$ are selected from hydrogen, $C_1$ to $C_{10}$ organyl groups, and $C_1$ to $C_{10}$ hydrocarbyl groups; or alternatively, selected from $C_1$ to $C_5$ organyl groups and $C_1$ to $C_5$ hydrocarbyl groups. In certain embodiments, $R^7$, $R^8$, and $R^9$ are independently selected from the group consisting of hydrogen and a methyl group. In some specific embodiments, $R^8$ and $R^9$ are hydrogen and $R^7$ is selected from hydrogen, a methyl group, or a mixture thereof; alternatively, $R^8$ and $R^9$ are hydrogen and $R^7$ is a methyl group; or alternatively, $R^7$, $R^8$, and $R^9$ are hydrogen.

As another embodiment of the present invention, a thioacrylate composition comprising thioacrylate ester molecules is advantageously provided. In this embodiment, the thioacrylate ester molecules have an average of at least 1 supplementary ester group per thioacrylate ester molecule and an average of at least 1 moiety $Y^1$ per thioacrylate ester molecule, the moiety $Y^1$ having the structure:

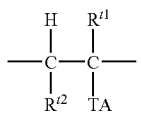

In the moiety $Y^1$ structure, $R^{t1}$ and $R^{t2}$ are independently selected from the group consisting of hydrogen, $C_1$ to $C_{20}$ organyl groups, and $C_1$ to $C_{20}$ hydrocarbyl groups, and TA represents a thioacrylate group having the structure:

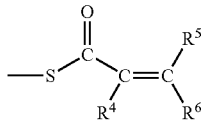

The unspecified valences of moiety $Y^1$ represent the remainder of the thioacrylate ester molecule. Within the embodiments related to the thioacrylate ester molecules containing the moiety $Y^1$, the average number of supplementary ester groups per thioacrylate ester and the average number of moiety $Y^1$ present in the thioacrylate molecules per thioacrylate ester molecule are separate elements.

In further embodiments, the thioacrylate ester molecules have an average of at least 1.5 moiety $Y^1$'s per thioacrylate ester molecule. In other embodiments, the thioacrylate ester molecules have an average of at least 2 moiety $Y^1$'s per thioacrylate ester molecule; alternatively, an average of at least 2.5 moiety $Y^1$'s per thioacrylate ester molecule; or alternatively, an average of at least 3 moiety $Y^1$'s per thioacrylate ester molecule. In an aspect, the thioacrylate ester molecules have an average of from 1.5 to 9 moiety $Y^1$'s per thioacrylate ester molecule; alternatively, an average of from 3 to 8 moiety $Y^1$'s per thioacrylate ester molecule; alternatively, an average of from 2 to 4 moiety $Y^1$'s per thioacrylate ester molecule; or alternatively, an average of from 4 to 8 moiety $Y^1$'s per thioacrylate ester molecule.

As another embodiment of the present invention, a thioacrylate composition comprising thioacrylate ester molecules is advantageously provided. In this embodiment, the thioacrylate ester molecules have an average of at least 1 supplementary ester group per thioacrylate ester molecule and an average of at least 1 moiety $Z^1$ per thioacrylate ester molecule, the moiety $Z^1$ having the structure:

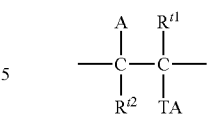

In the moiety $Z^1$ structure, $R^{t1}$ and $R^{t2}$ are independently selected from the group consisting of consisting of hydrogen, $C_1$ to $C_{20}$ organyl groups, and $C_1$ to $C_{20}$ hydrocarbyl groups; $Q^{t1}$ is independently selected from the group consisting of hydrogen and an acrylate group; TA represents a thioacrylate group having the structure:

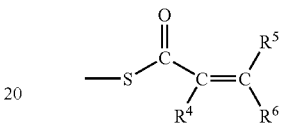

and A represents a acrylate group having the structure:

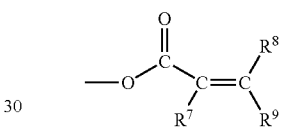

The unspecified valences of moiety $Z^1$ represent the remainder of the thioacrylate ester molecule. Within the embodiments where the thioacrylate ester molecules contain the moiety $Z^1$, the average number of supplementary ester groups per thioacrylate ester and the average number of moiety $Z^1$'s present in the thioacrylate molecules per thioacrylate ester molecule are independent elements.

In further embodiments, the thioacrylate ester molecules have an average of at least 1.5 moiety $Z^1$'s per thioacrylate ester molecule. In other embodiments, the thioacrylate ester molecules have an average of at least 2 moiety $Z^1$'s per thioacrylate ester molecule; alternatively, an average of at least 2.5 moiety $Z^1$'s per thioacrylate ester molecule; or alternatively, an average of at least 3 moiety $Z^1$'s per thioacrylate ester molecule. In an aspect, the thioacrylate ester molecules have an average of from 1.5 to 9 moiety $Z^1$'s per thioacrylate ester molecule; alternatively, an average of from 3 to 8 moiety $Z^1$'s per thioacrylate ester molecule; alternatively, an average of from 2 to 4 moiety $Z^1$'s per thioacrylate ester molecule; or alternatively, an average of from 4 to 8 moiety $Z^1$'s per thioacrylate ester molecule.

As another embodiment of the present invention, a thioacrylate ester composition comprising thioacrylate ester molecules is advantageously provided. In this embodiment, the thioacrylate ester molecules have an average of least 1 supplementary ester group per thioacrylate ester molecule and have an average of at least 1 moiety $X^1$ per thioacrylate ester molecule. The moiety $X^1$ has the structure as described herein. Additionally, the average number of supplementary ester groups per thioacrylate ester molecule and the average number of moiety $X^1$'s are independent elements.

As another embodiment of the present invention, a thioacrylate ester composition comprising thioacrylate ester molecules is advantageously provided. In this embodiment, the thioacrylate ester molecules have an average of least 1 supplementary ester group per thioacrylate ester molecule and have an average of at least 1 moiety $Y^1$ per thioacrylate ester molecule. The moiety $Y^1$ has the structure described herein. Additionally, the average number of supplementary ester groups per thioacrylate ester molecule and the average number of moiety $Y^1$'s are independent elements.

As another embodiment of the present invention, a thioacrylate ester composition comprising thioacrylate ester molecules is advantageously provided. In this embodiment, the thioacrylate ester molecules have an average of least 1 supplementary ester group per thioacrylate ester molecule and have an average of at least 1 moiety $Z^1$ per thioacrylate ester molecule. The moiety $Z^1$ has the structure described herein. Additionally, the average number of supplementary ester groups per thioacrylate ester molecule and the average number of moiety $Z^1$'s are independent elements.

In some embodiments, there is provided a thioacrylate molecule comprising one supplementary ester group and a thioacrylate group having the structure:

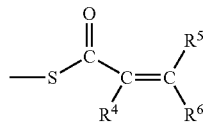

In this thioacrylate group structure, $R^4$, $R^5$, and $R^6$ are independently selected from the group consisting of hydrogen, $C_1$ to $C_{20}$ organyl groups, and $C_1$ to $C_{20}$ hydrocarbyl groups. The supplementary ester group and the thioacrylate group of the thioacrylate molecule represent independent elements. The thioacrylate molecule can have any combination of these elements described herein. Additionally, each $R^4$, $R^5$, and $R^6$ group of the thioacrylate structure represents an independent element. The thioacrylate structure described herein can have any combination of the $R^4$, $R^5$, and $R^6$ groups.

In some embodiments, the thioacrylate ester molecule comprising supplementary ester groups and a thioacrylate group has at least 1 supplementary ester group. In other embodiments the thioacrylate molecule has at least 2 supplementary ester groups; or alternatively, at least 3 supplementary ester groups. In other embodiments, the thioacrylate ester molecule that includes supplementary ester groups and a thioacrylate group has from 2 to 9 supplementary ester groups; alternatively, from 2 to 8 supplementary ester groups; alternatively, from 2 to 7 supplementary ester groups; alternatively, from 3 to 5 supplementary ester groups; or alternatively, from 3 to 4 supplementary ester groups. In yet other embodiments, the thioacrylate ester includes 3 supplementary ester groups or alternatively, includes 4 supplementary ester groups.

In further embodiments, the thioacrylate ester molecule that includes supplementary ester groups and a thioacrylate group can further include at least 1 thioacrylate groups; alternatively, at least 2 thioacrylate groups; or alternatively, at least three thioacrylate groups. In other embodiments, the thioacrylate ester molecule comprises from 2 to 9 thioacrylate groups; alternatively, from 3 to 8 thioacrylate groups; alternatively, from 2 to 4 thioacrylate groups; or alternatively, from 4 to 8 thioacrylate groups.

In other embodiments, the thioacrylate ester molecule that includes supplementary ester groups and a thioacrylate group can further include acrylate groups having the structure:

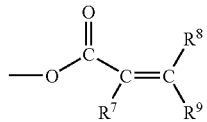

In this acrylate group structure, $R^7$, $R^8$, and $R^9$ are independently selected from the group consisting of hydrogen, $C_1$ to $C_{20}$ organyl groups, and $C_1$ to $C_{20}$ hydrocarbyl groups. In some embodiments the thioacrylate ester molecule comprises at least 2 acrylate groups; or alternatively, at least three acrylate groups. In other embodiments, the thioacrylate ester molecule comprises from 2 to 9 acrylate groups; alternatively, from 3 to 8 acrylate groups; alternatively, from 2 to 4 acrylate groups; or alternatively, from 4 to 8 acrylate groups.

In some embodiments, the thioacrylate ester molecule includes at least one supplementary ester group and a least one moiety $Y^1$ having the structure:

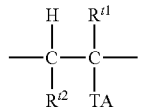

In this moiety $Y^1$ structure, $R^{r1}$ and $R^{r2}$ are independently selected from the group consisting of consisting of hydrogen, $C_1$ to $C_{20}$ organyl groups, and $C_1$ to $C_{20}$ hydrocarbyl groups, and TA represents a thioacrylate group having the structure:

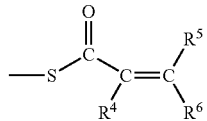

The unspecified valences of moiety $Y^1$ represent the remainder of the thioacrylate ester molecule. The supplementary ester groups and the moiety $Y^1$ of the thioacrylate molecule represent independent elements. The thioacrylate molecule can have any combination of these elements described herein. Other embodiments of the number of supplementary ester groups have been described herein. Additional embodiments of the $R^4$, $R^5$, and $R^6$ groups containing the thioacrylate structure are described herein.

The thioacrylate ester molecule that includes supplementary ester groups and moiety $Y^1$ can include any combination of the number of supplementary ester groups and any number of moiety $Y^1$'s described herein. The number of ester groups within the thioacrylate ester molecule that includes supplementary ester groups and moiety $Y^1$ are described herein. In further embodiments, the thioacrylate ester molecule that includes supplementary ester groups and moiety $Y^1$ can include at least 1 moiety $Y^1$; alternatively, at least 2 moiety $Y^1$'s; or alternatively, at least 3 moiety $Y^1$'s. In other embodiments, the thioacrylate ester molecule that includes supplementary ester groups and moiety $Y^1$ includes from 2 to 9 moiety $Y^1$'s; alternatively, from 3 to 8 moiety $Y^1$'s; alternatively, from 2 to 4 moiety $Y^1$'s; or alternatively, from 4 to 8 moiety $Y^1$'s.

The thioacrylate ester can also be described as a product produced by the process that includes contacting a thiol-containing ester composition with an acrylate composition and can be further limited by the process described herein. In other embodiments, the thioacrylate ester composition can also be described as a product produced by a process that includes contacting a hydroxy thiol-containing ester composition with an acrylate composition and can be further limited by the process described herein.

Sulfonic Acid-Containing Esters

The present invention advantageously provides a sulfonic acid-containing ester as an embodiment of the present invention. Generally, the sulfonic acid-containing ester of the present invention includes sulfonic acid-containing ester molecules having at least one ester group and a least one sulfonic acid group. The sulfonic acid-containing ester described herein can be produced by contacting a thiol ester with an oxidizing agent as described herein. Because the feedstock for the production of the sulfonic acid-containing ester can include multiple thiols groups, thiol group reactivity and statistical probability dictate that each sulfonic acid-containing ester molecule of the sulfonic acid-containing ester will not have the same number of sulfonic acid groups. Additionally, the feedstock thiol ester can also include a mixture of individual thiol ester molecules having different numbers of thiol groups and/or ester groups. Thus, many of the groups present in the sulfonic acid-containing ester are described herein as an average number of the groups per sulfonic acid-containing ester molecule or an average ratio per sulfonic acid-containing ester molecule within the sulfonic acid-containing ester.

The number of sulfonic acid groups and the number of ester groups contained within the sulfonic acid-containing ester are separate elements that allow the sulfonic acid-containing ester to be described using any combination of the sulfonic acid-containing ester separate elements described herein. A non-limiting list of the sulfonic acid-containing ester separate elements include the number of ester groups, the average number of ester groups per sulfonic acid-containing ester molecule, the number of sulfonic acid groups, the average number of sulfonic acid groups per sulfonic acid-containing ester molecule, the number of moiety $X^2$'s, the average number of moiety $X^2$'s per sulfonic acid-containing ester molecule, ester molecule, the number of moiety $Y^2$'s, the average number of $Y^2$ per sulfonic acid-containing ester molecule, ester molecule, the number of moiety $Z^2$'s, the average number of moiety $Z^2$'s per sulfonic acid-containing ester molecule, and the like.

Minimally, the sulfonic acid-containing ester includes at least one ester group per sulfonic acid-containing ester molecule. In some embodiments, the sulfonic acid-containing ester has an average of at least 1.5 ester groups per sulfonic acid-containing ester molecule. Alternatively, the sulfonic acid-containing ester has an average of at least 2 ester groups per sulfonic acid-containing ester molecule; alternatively, an average of at least 2.5 ester groups per sulfonic acid-containing ester molecule; or alternatively, an average of at least 3 ester groups per sulfonic acid-containing ester molecule. In other embodiments, the sulfonic acid-containing ester has an average of from 1.5 to 9 ester groups per sulfonic acid-containing ester molecule; alternatively, an average of from 1.5 to 8 ester groups per sulfonic acid-containing ester molecule; alternatively, an average of from 2 to 8 ester groups per sulfonic acid-containing ester molecule; alternatively, an average of from 2 to 7 ester groups per sulfonic acid-containing ester molecule; alternatively, an average of from 2.5 to 5 ester groups per sulfonic acid-containing ester molecule; alternatively, an average of from 3 to 5 ester groups per sulfonic acid-containing ester molecule; or alternatively, an average of from 3 to 4 ester groups per sulfonic acid-containing ester molecule. In yet other embodiments, the sulfonic acid-containing ester comprises an average of 3 ester groups per sulfonic acid-containing ester molecule or alternatively, an average of 4 ester groups per sulfonic acid-containing ester molecule.

Minimally, the sulfonic acid-containing ester molecules have an average of at least one sulfonic acid group per sulfonic acid-containing ester molecule. In some embodiments, the sulfonic acid ester has an average of at least 1.5 sulfonic acid groups per sulfonic acid-containing ester molecule; alternatively, have an average of at least 2 sulfonic acid groups per sulfonic acid-containing ester molecule; alternatively, an average of at least 2.5 sulfonic acid groups per sulfonic acid-containing ester molecule; or alternatively, an average of at least 3 sulfonic acid groups per sulfonic acid-containing ester molecule. In other embodiments, the sulfonic acid-containing ester has an average of from 1.5 to 9 sulfonic acid groups per sulfonic acid-containing ester molecule; alternatively, an average of from 3 to 8 sulfonic acid groups per sulfonic acid-containing ester molecule; alternatively, an average of from 2 to 4 sulfonic acid groups per sulfonic acid-containing ester molecule; or alternatively, an average of from 4 to 8 sulfonic acid groups per sulfonic acid-containing ester molecule.

In another aspect, the sulfonic acid-containing ester further includes a hydroxy group. In some embodiments, the sulfonic acid-containing ester comprises an average of at least 1 hydroxy group per sulfonic acid-containing ester molecule.

In some embodiments of the present invention, the sulfonic acid ester is substantially free of thiol groups.

In another independent aspect, the sulfonic acid-containing ester includes an average of at least one ester group per sulfonic acid-containing ester molecule and an average of at least one moiety $X^2$ per sulfonic acid-containing ester molecule wherein the moiety $X^2$ has the structure:

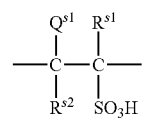

In this moiety $X^2$ structure, $Q^{s1}$ is hydrogen or a hydroxy group; $R^{s1}$ and $R^{s2}$ are independently selected from the group consisting of hydrogen, $C_1$ to $C_{20}$ organyl groups, and $C_1$ to $C_{20}$ hydrocarbyl groups; and the unspecified valences of moiety $X^2$ represent the remainder of the sulfonic acid-containing ester molecule. $Q^{s1}$, $R^{s1}$, and $R^{s2}$ are separate elements of moiety $X^2$ that allow moiety $X^2$ to have any combination of further $Q^{s1}$, $R^{s1}$, and $R^{s2}$ elements described herein. In some particular embodiments, $R^{s1}$ and $R^{s2}$ are hydrogen.

In particular embodiments, the sulfonic acid-containing ester has an average of at least 1.5 moiety $X^2$'s per sulfonic acid-containing ester molecule. In other embodiments, the sulfonic acid-containing ester has an average of at least 2 moiety $X^2$'s per sulfonic acid ester molecule; alternatively, an average of at least 2.5 moiety $X^2$'s per sulfonic acid-containing ester molecule; or alternatively, an average of at least 3 moiety $X^2$'s per sulfonic acid-containing ester molecule. In other aspects, the sulfonic acid-containing ester has an average of from 1.5 to 9 moiety $X^2$'s per sulfonic acid-containing ester molecule. Alternatively, the sulfonic acid-containing ester have an average of from 3 to 8 moiety $X^2$'s per sulfonic acid-containing ester molecule; alternatively, an average of from 2 to 4 moiety $X^2$'s per sulfonic acid-containing ester molecule; or alternatively, an average of from 4 to 8 moiety $X^2$'s per sulfonic acid-containing ester molecule.

In another independent aspect, the sulfonic acid-containing ester includes an average of at least one ester group per sulfonic acid-containing ester molecule and an average of at least one moiety $Y^2$ per sulfonic acid-containing ester molecule wherein the moiety $Y^2$ has the structure:

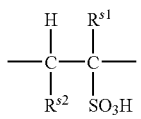

In this moiety $Y^2$ structure, $R^{s1}$ and $R^{s2}$ are independently selected from the group consisting of hydrogen, $C_1$ to $C_{20}$ organyl groups, and $C_1$ to $C_{20}$ hydrocarbyl groups, and the unspecified valences of moiety $Y^2$ represent the remainder of the sulfonic acid-containing ester molecule. $R^{s1}$ and $R^{s2}$ are separate elements of moiety $Y^2$ that allow moiety $Y^2$ to have any combination of further $R^{s1}$, and $R^{s2}$ elements described herein. In some particular embodiments, $R^{s1}$ and $R^{s2}$ are hydrogen.

In particular embodiments, the sulfonic acid-containing ester has an average of at least 1.5 moiety $Y^2$'s per sulfonic acid-containing ester molecule. In other embodiments, the sulfonic acid-containing ester has an average of at least 2 moiety $Y^2$'s per sulfonic acid ester molecule; alternatively, an average of at least 2.5 moiety $Y^2$'s per sulfonic acid-containing ester molecule; or alternatively, an average of at least 3 moiety $Y^2$'s per sulfonic acid-containing ester molecule. In other aspects, the sulfonic acid-containing ester has an average of from 1.5 to 9 moiety $Y^2$'s per sulfonic acid-containing ester molecule. Alternatively, the sulfonic acid-containing ester has an average of from 3 to 8 moiety $Y^2$'s per sulfonic acid-containing ester molecule; alternatively, an average of from 2 to 4 moiety $Y^2$'s per sulfonic acid-containing ester molecule; or alternatively, an average of from 4 to 8 moiety $Y^2$'s per sulfonic acid-containing ester molecule.

In another independent aspect, the sulfonic acid-containing ester includes an average of at least one ester group per sulfonic acid-containing ester molecule and an average of at least one moiety $Z^2$ per sulfonic acid-containing ester molecule wherein the moiety $Z^2$ has the structure:

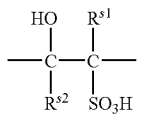

In the moiety $Z^2$ structure, $R^{s1}$ and $R^{s2}$ are independently selected from the group consisting of hydrogen, $C_1$ to $C_{20}$ organyl groups, and $C_1$ to $C_{20}$ hydrocarbyl groups, and the unspecified valences of moiety $Y^2$ represent the remainder of the sulfonic acid-containing ester molecule. $R^{s1}$, and $R^{s2}$ are separate elements of moiety $Z^2$ that allow moiety $Z^2$ to have any combination of further $R^{s1}$, and $R^{s2}$ elements described herein. In some particular embodiments, $R^{s1}$ and $R^{s2}$ are hydrogen.

In particular embodiments, the sulfonic acid-containing ester has an average of at least 1.5 moiety $Z^2$'s per sulfonic acid-containing ester molecule. In other embodiments, the sulfonic acid-containing ester has an average of at least 2 moiety $Z^2$'s per sulfonic acid ester molecule; alternatively, an average of at least 2.5 moiety $Z^2$'s per sulfonic acid-containing ester molecule; or alternatively, an average of at least 3 moiety $Z^2$'s per sulfonic acid-containing ester molecule. In other aspects, the sulfonic acid-containing ester has an average of from 1.5 to 9 moiety $Z^2$'s per sulfonic acid-containing ester molecule. Alternatively, the sulfonic acid-containing ester has an average of from 3 to 8 moiety $Z^2$'s per sulfonic acid-containing ester molecule; alternatively, an average of from 2 to 4 moiety $Z^2$'s per sulfonic acid-containing ester molecule; or alternatively, an average of from 4 to 8 moiety $Z^2$'s per sulfonic acid-containing ester molecule.

As another embodiment of the present invention, a sulfonic acid-containing ester comprising sulfonic acid-containing ester molecules is advantageously provided. In this embodiment, the sulfonic acid-containing ester molecules have an average of least 1 ester group per sulfonic acid-containing ester molecule and have an average of at least 1 moiety $X^2$ per sulfonic acid-containing ester molecule. The moiety $X^2$ has the structure described herein. Additionally, the average number of ester groups and the average number of moiety $X^2$'s are separate elements that allow the sulfonic acid-containing ester molecules of the sulfonic acid-containing ester to have any combination of the average number of ester groups and the average number of moiety $X^2$'s described herein.

As another embodiment of the present invention, a sulfonic acid-containing ester comprising sulfonic acid-containing ester molecules is advantageously provided. In this embodiment, the sulfonic acid-containing ester has an average of least 1 ester group per sulfonic acid-containing ester molecule and have an average of at least 1 moiety $Y^2$ per sulfonic acid-containing ester molecule. The moiety $Y^2$ has the structure described herein. Additionally, the average number of ester groups and the average number of moiety $Y^2$'s are separate elements that allow the sulfonic acid-containing ester molecules of the sulfonic acid-containing ester composition to have any combination of the average number of ester groups and the average number of moiety $Y^2$'s described herein.

As another embodiment of the present invention, a sulfonic acid-containing ester comprising sulfonic acid-containing ester molecules is advantageously provided. In this embodiment, the sulfonic acid-containing ester has an average of least 1 ester group per sulfonic acid-containing ester molecule and have an average of at least 1 moiety $Z^2$ per sulfonic acid-containing ester molecule. The moiety $Z^2$ has the structure described herein. Additionally, the average number of ester groups and the average number of moiety $Z^2$'s are separate elements that allow the sulfonic acid-containing ester molecules of the sulfonic acid-containing ester to have any combination of the average number of ester groups and the average number of moiety $Z^2$'s described herein.

In some embodiments, there is provided a sulfonic acid-containing ester molecule comprising at least one ester group and at least one sulfonic acid group. The number of ester groups and the number of sulfonic acid groups are separate elements that allow the sulfonic acid-containing ester molecule to contain any number of ester groups and sulfonic acid groups described herein.

In some embodiments, the sulfonic acid-containing ester molecule comprises at least 2 ester groups. Alternatively, in some embodiments, the sulfonic acid-containing ester molecule comprises at least 3 ester groups. In one aspect, the sulfonic acid-containing ester molecule comprises from 2 to 9 ester groups per sulfonic acid-containing ester molecule. In one aspect, the sulfonic acid-containing ester molecule comprises from 2 to 8 ester groups per sulfonic acid-containing ester molecule; alternatively, from 2 to 7 ester groups; alternatively, from 3 to 5 ester groups per sulfonic acid-containing ester molecule; or alternatively, from 3 to 4 ester groups. In yet other embodiments, the sulfonic acid-containing ester molecule comprises 3 ester groups; or alternatively, comprises 4 ester groups.

In further embodiments, the sulfonic acid-containing ester molecule comprises at least one ester group and at least one sulfonic acid. In other embodiments, the sulfonic acid-containing ester molecule comprises at least 2 sulfonic acid groups; or alternatively, at least three sulfonic acid groups. In other embodiments, the sulfonic acid-containing ester molecule comprises from 2 to 9 sulfonic acid groups; alternatively, from 3 to 8 sulfonic acid groups; alternatively, from 2 to 4 sulfonic acid groups; or alternatively, from 4 to 8 sulfonic acid groups.

In some embodiments, the sulfonic acid-containing ester molecule comprises at least one ester group and a least one moiety $X^2$. The sulfonic acid-containing ester molecule comprising ester groups and moiety $X^2$ may comprise any combination of the number of ester groups and any number of moiety $X^2$'s as described herein. The number of ester groups within the sulfonic acid-containing ester molecule comprising ester groups and moiety $X^2$ has been described previously. In further embodiments, the sulfonic acid-containing ester molecule comprising ester groups and moiety $X^2$ can comprise at least 1 moiety $X^2$; alternatively, at least 2 moiety $X^2$'s; or alternatively, at least 3 moiety $X^2$'s. In other embodiments, the sulfonic acid-containing ester molecule that includes ester groups and moiety $X^2$ comprises from 2 to 9 moiety $X^2$'s; alternatively, from 3 to 8 moiety $X^2$'s; alternatively, from 2 to 4 moiety $X^2$'s; or alternatively, from 4 to 8 moiety $X^2$'s.

In some embodiments, the sulfonic-containing acid ester molecule comprises at least one ester group and a least one moiety $Y^2$. The sulfonic acid-containing ester molecule comprising ester groups and moiety $Y^2$ can include any combination of the number of ester groups and any number of moiety $Y^2$'s described herein. The number of ester groups within the sulfonic acid-containing ester molecule comprising ester groups and moiety $Y^2$ has been described previously. In further embodiments, the sulfonic acid-containing ester molecule comprising ester groups and moiety $Y^2$ can include at least 1 moiety $Y^2$; alternatively, at least 2 moiety $Y^2$'s; or alternatively, at least 3 moiety $Y^2$'s. In other embodiments, the sulfonic acid-containing ester molecule comprising ester groups and moiety $Y^2$ includes from 2 to 9 moiety $Y^2$'s; alternatively, from 3 to 8 moiety $Y^2$'s; alternatively, from 2 to 4 moiety $Y^2$'s; or alternatively, from 4 to 8 moiety $Y^2$'s.

In some embodiments, the sulfonic acid-containing ester molecule comprises at least one ester group and a least one moiety $Z^2$. The sulfonic acid-containing ester molecule comprising ester groups and moiety $Z^2$ may comprise any combination of the number of ester groups and any number of moiety $Z^2$'s as described herein. The number of ester groups within the sulfonic acid-containing ester molecule comprising ester groups and moiety $Z^2$ has been described previously. In further embodiments, the sulfonic acid-containing ester molecule comprising ester groups and moiety $Z^2$ can include at least 1 moiety $Z^2$; alternatively, at least 2 moiety $Z^2$'s; or alternatively, at least 3 moiety $Z^2$'s. In other embodiments, the sulfonic acid-containing ester molecule comprising ester groups and moiety $Z^2$ includes from 2 to 9 moiety $Z^2$'s; alternatively, from 3 to 8 moiety $Z^2$'s; alternatively, from 2 to 4 moiety $Z^2$'s; or alternatively, from 4 to 8 moiety $Z^2$'s.

The sulfonic acid-containing ester can also be described as a product produced by the process comprising contacting a thiol ester with an oxidizing agent described herein.

Sulfonate-Containing Ester Compositions

Minimally, in some embodiments, the sulfonate-containing esters have an average of at least one ester group per sulfonate-containing ester molecule and at least one sulfonate per sulfonate-containing ester molecule. Generally, the sulfonate-containing esters are produced by reacting the herein described sulfonic acid-containing esters with a base. Because the feedstock sulfonic acid-containing esters can comprise a mixture of sulfonic acid-containing ester molecules having different number of ester group and different number of sulfonic acid groups, the number of groups present in the sulfonate-containing esters can be discussed as an average number of groups per sulfonate-containing ester molecule or as an average ratio per sulfonate-containing ester molecule within a sulfonate-containing ester composition.

The number of ester groups, the average number of ester groups per sulfonate-containing ester molecule, the number of sulfonate groups, the average number of sulfonate groups per sulfonate-containing ester molecule are separate elements of the sulfonate-containing ester, the number of moiety $X^3$'s, the average number of moiety $X^3$'s, the number of moiety $Y^3$'s, the average number of moiety $Y^3$'s, the number of moiety $Z^3$'s, the average number of moiety $Z^3$'s, the number of moiety $X^4$'s, the average number of moiety $X^4$'s, the number of moiety $Y^4$'s, the average number of moiety $Y^4$'s, the number of moiety $Z^4$'s, and the average number of moiety $Z^4$'s. Because the sulfonate-containing esters are produced from the sulfonic acid-containing esters, the sulfonate-containing esters can have any number of ester groups or average number of ester groups per sulfonate-containing ester molecule as described for the sulfonic acid-containing ester. The number and identity of the sulfonate group, moiety $X^3$'s, moiety $Y^3$'s, moiety $Z^3$'s, moiety $X^4$'s, moiety $Y^4$'s, and moiety $Z^4$'s present in the sulfonate-containing esters will be further described herein.

Minimally, in some embodiments, the sulfonate-containing esters have an average of at least one ester group per sulfonate-containing ester molecule and at least one sulfonate group per sulfonate-containing ester molecule. The potential average number of ester groups per sulfonate-containing ester molecule have been previously described. In some embodiments, the sulfonate-containing esters have an average of at least 1.5 sulfonate groups per sulfonate-containing ester molecule; alternatively, have an average of at least 2 sulfonate groups per sulfonate-containing ester molecule; alternatively, an average of at least 2.5 sulfonate groups per sulfonate-containing ester molecule; or alternatively, an average of at least 3 sulfonate groups per sulfonate-containing ester molecule. In other embodiments, the sulfonate-containing esters have an average of from 1.5 to 9 sulfonate groups per sulfonate-containing ester molecule; alternatively, an average of from 3 to 8 sulfonate groups per sulfonate-containing ester molecule; alternatively, an average of from 2 to 4 sulfonate groups per sulfonate-containing ester molecule; or alternatively, an average of from 4 to 8 sulfonate acid groups per sulfonate-containing ester molecule.

In another aspect, the sulfonate-containing ester further contains a hydroxy group. In some embodiments, the sulfonate-containing ester comprises an average of at least 1 hydroxy group per sulfonate-containing ester molecule.

In another independent aspect, the sulfonate-containing ester composition comprises an average of at least one ester group per sulfonate-containing ester molecule and an average of at least one moiety $X^3$ per sulfonate-containing ester mole wherein the moiety $X^3$ has the structure:

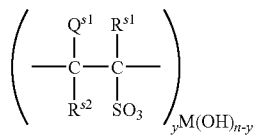

In the moiety $X^3$ structure, $Q^{s1}$ is hydrogen or a hydroxy group, $R^{s1}$ and $R^{s2}$ are independently selected from the consisting of hydrogen, $C_1$ to $C_{20}$ organyl groups, and $C_1$ to $C_{20}$ hydrocarbyl groups, M represents a metal atom having an oxidation number n, y ranges from 1 to the oxidation number n and the unspecified valences of moiety $X^3$ represent the remainder of the sulfonate-containing ester molecule. $Q^{s1}$, $R^{s1}$, $R^{s2}$, M, n, and y are separate elements of moiety $X^3$ that allow moiety $X^3$ to have any combination of further $Q^{s1}$, $R^{s1}$, $R^{s2}$, M, n, and y elements as described herein. In some particular embodiments, $R^{s1}$ and $R^{s2}$ are hydrogen. In other embodiments, n is an integer ranging from 1 to 3. In one aspect, the metal atom is selected from the group consisting of sodium, potassium, calcium, magnesium, barium, and mixtures thereof. In other aspects, the metal atom is sodium. In yet other aspects, the metal atom is calcium or magnesium. In yet other aspects, the metal atom is barium.

In particular embodiments, the sulfonate-containing esters have an average of at least 1.5 moiety $X^3$'s per sulfonate-containing ester molecule. In other embodiments, the sulfonate-containing esters have an average of at least 2 moiety $X^3$'s per sulfonate-containing ester molecule; alternatively, an average of at least 2.5 moiety $X^3$'s per sulfonate-containing ester molecule; or alternatively, an average of at least 3 moiety $X^3$'s per sulfonate-containing ester molecule. In other aspects, the sulfonate-containing esters have an average of from 1.5 to 9 moiety $X^3$'s per sulfonate-containing ester molecule. Alternatively, the sulfonate acid containing ester have an average of from 3 to 8 moiety $X^3$'s per sulfonate-containing ester molecule; alternatively, an average of from 2 to 4 moiety $X^3$'s per sulfonate-containing ester molecule; or alternatively, an average of from 4 to 8 moiety $X^3$'s per sulfonate-containing ester molecule.

In another independent aspect, the sulfonate-containing ester composition comprises an average of at least one ester group per sulfonate-containing ester molecule and an average of at least one moiety $Y^3$ per sulfonate-containing ester mole wherein the moiety $Y^3$ has the structure:

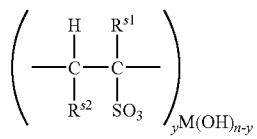

In the moiety $Y^3$ structure, $R^{s1}$ and $R^{s2}$ are independently selected from the consisting of hydrogen, $C_1$ to $C_{20}$ organyl groups, and $C_1$ to $C_{20}$ hydrocarbyl groups, M represents a metal atom having an oxidation number n, y ranges from 1 to the oxidation number n and the unspecified valences of moiety $Y^3$ represent the remainder of the sulfonate-containing ester molecule. $R^{s1}$, $R^{s2}$, M, n, and y are separate elements of moiety $Y^3$ that allow moiety $Y^3$ to have any combination of further $R^{s1}$, $R^{s2}$, M, n, and y elements as described herein. In some particular embodiments, $R^{s1}$ and $R^{s2}$ are hydrogen. In other embodiments, n is an integer ranging from 1 to 3. In one aspect, the metal atom is selected from the group consisting of sodium, potassium, calcium, magnesium, barium, and mixtures thereof. In other aspects, the metal atom is sodium. In yet other aspects, the metal atom is calcium or magnesium. In yet other aspects, the metal atom is barium.

In particular embodiments, the sulfonate-containing esters have an average of at least 1.5 moiety $Y^3$'s per sulfonate-containing ester molecule. In other embodiments, the sulfonate-containing esters have an average of at least 2 moiety $Y^3$'s per sulfonate-containing ester molecule; alternatively, an average of at least 2.5 moiety $Y^3$'s per sulfonate-containing ester molecule; or alternatively, an average of at least 3 moiety $Y^3$'s per sulfonate acid containing ester molecule. In other aspects, the sulfonate-containing esters have an average of from 1.5 to 9 moiety $Y^3$'s per sulfonate-containing ester molecule. Alternatively, the sulfonate-containing esters have an average of from 3 to 8 moiety $Y^3$'s per sulfonate-containing ester molecule; alternatively, an average of from 2 to 4 moiety $Y^3$'s per sulfonate-containing ester molecule; or alternatively, an average of from 4 to 8 moiety $Y^3$'s per sulfonate-containing ester molecule.

In another independent aspect, the sulfonate-containing ester composition comprises an average of at least one ester group per sulfonate-containing ester molecule and an average of at least one moiety $Z^3$ per sulfonate-containing ester mole wherein the moiety $Z^3$ has the structure:

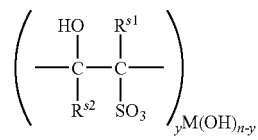

In the moiety $Z^3$ structure, $R^{s1}$ and $R^{s2}$ are independently selected from the consisting of hydrogen, $C_1$ to $C_{20}$ organyl groups, and $C_1$ to $C_{20}$ hydrocarbyl groups, M represents a metal atom having an oxidation number n, y ranges from 1 to the oxidation number n and the unspecified valences of moiety $Z^3$ represent the remainder of the sulfonate-containing ester molecule. $R^{s1}$, $R^{s2}$, M, n, and y are separate elements of moiety $Z^3$ that allow moiety $Z^3$ to have any combination of further $R^{s1}$, $R^{s2}$, M, n, and y elements as described herein. In some particular embodiments, $R^{s1}$ and $R^{s2}$ are hydrogen. In other embodiments, n is an integer ranging from 1 to 3. In one aspect, the metal atom is selected from the group consisting of sodium, potassium, calcium, magnesium, barium, and mixtures thereof. In other aspects, the metal atom is sodium. In yet other aspects, the metal atom is calcium or magnesium. In yet other aspects, the metal atom is barium.

In particular embodiments, the sulfonate-containing esters have an average of at least 1.5 moiety $Z^3$'s per sulfonate-containing ester molecule. In other embodiments, the sulfonate-containing esters have an average of at least 2 moiety $Z^3$'s per sulfonate-containing ester molecule; alternatively, an average of at least 2.5 moiety $Z^3$'s per sulfonate-containing ester molecule; or alternatively, an average of at least 3 moiety $Z^3$'s per sulfonate acid containing ester molecule. In other aspects, the sulfonate-containing esters have an average of from 1.5 to 9 moiety $Z^3$'s per sulfonate-containing ester molecule. Alternatively, the sulfonate-containing esters have an average of from 3 to 8 moiety $Z^3$'s per sulfonate-containing ester molecule; alternatively, an average of from 2 to 4 moiety $Z^3$'s per sulfonate-containing ester molecule; or alternatively, an average of from 4 to 8 moiety $Z^3$'s per sulfonate-containing ester molecule.

In another independent aspect, the sulfonate-containing ester composition comprises an average of at least one ester group per sulfonate-containing ester molecule and an average of at least one moiety $X^4$ per sulfonate-containing ester mole wherein the moiety $X^4$ has the structure:

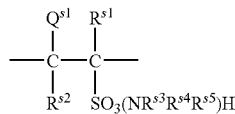

In the moiety $X^4$ structure, $Q^{s1}$ is hydrogen or a hydroxy group; $R^{s1}$ and $R^{s2}$ are independently selected from the consisting of hydrogen, $C_1$ to $C_{20}$ organyl groups, and $C_1$ to $C_{20}$ hydrocarbyl groups; $R^{s3}$, $R^{s4}$, and $R^{s5}$ are independently selected from hydrogen $C_1$ to $C_{20}$ organyl groups, and $C_1$ to $C_{20}$ hydrocarbyl groups; and the unspecified valences of moiety $X^4$ represent the remainder of the sulfonate-containing ester molecule. $Q^{s1}$, $R^{s1}$, $R^{s2}$, $R^{s3}$, $R^{s4}$, and $R^{s5}$ are separate elements of moiety $X^4$ that allow moiety $X^4$ to have any combination of further $Q^{s1}$, $R^{s1}$, $R^{s2}$, $R^{s3}$, $R^{s4}$, and $R^{s5}$ elements as described herein. In some aspects, the structure $NR^{s3}R^{s4}R^{s5}$ represents a compound selected from the group consisting of a trialkylamine, a dialkylamine, and a monoalkylamine. In some embodiments, $NR^{s3}R^{s4}R^{s5}$ represents triethanolamine. In some particular embodiments, $R^{s1}$ and $R^{s2}$ are hydrogen.

In particular embodiments, the sulfonate-containing esters have an average of at least 1.5 moiety $X^4$'s per sulfonate-containing ester molecule. In other embodiments, the sulfonate-containing esters have an average of at least 2 moiety $X^4$'s per sulfonate-containing ester molecule; alternatively, an average of at least 2.5 moiety $X^4$'s per sulfonate-containing ester molecule; or alternatively, an average of at least 3 moiety $X^4$'s per sulfonate-containing ester molecule. In other aspects, the sulfonate-containing esters have an average of from 1.5 to 9 moiety $X^4$'s per sulfonate-containing ester molecule. Alternatively, the sulfonate acid containing ester have an average of from 3 to 8 moiety $X^4$'s per sulfonate-containing ester molecule; alternatively, an average of from 2 to 4 moiety $X^4$'s per sulfonate-containing ester molecule; or alternatively, an average of from 4 to 8 moiety $X^4$'s per sulfonate-containing ester molecule.

In another independent aspect, the sulfonate-containing ester composition comprises an average of at least one ester group per sulfonate-containing ester molecule and an average of at least one moiety $Y^4$ per sulfonate-containing ester mole wherein the moiety $Y^4$ has the structure:

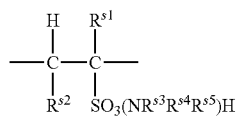

In the moiety $Y^4$ structure, $R^{s1}$ and $R^{s2}$ are independently selected from the consisting of hydrogen, $C_1$ to $C_{20}$ organyl groups, and $C_1$ to $C_{20}$ hydrocarbyl groups, $R^{s3}$, $R^{s4}$, and $R^{s5}$ are independently selected from hydrogen $C_1$ to $C_{20}$ organyl groups, and $C_1$ to $C_{20}$ hydrocarbyl groups, and the unspecified valences of moiety $Y^4$ represent the remainder of the sulfonate-containing ester molecule. $R^{s1}$, $R^{s2}$, $R^{s3}$, $R^{s4}$, and $R^{s5}$ are separate elements of moiety $X^4$ and thus moiety $Y^4$ can have any combination of further $R^{s1}$, $R^{s2}$, $R^{s3}$, $R^{s4}$, and $R^{s5}$ embodiments as described herein. In some aspects, the structure $NR^{s3}R^{s4}R^{s5}$ represents a compound selected from the group consisting of a trialkylamine, a dialkylamine, and a monoalkylamine. In some embodiments, $NR^{s3}R^{s4}R^{s5}$ represents triethanolamine. In some particular embodiments, $R^{s1}$ and $R^{s2}$ are hydrogen.

In particular embodiments, the sulfonate-containing esters have an average of at least 1.5 moiety $Y^4$'s per sulfonate-containing ester molecule. In other embodiments, the sulfonate-containing esters have an average of at least 2 moiety $Y^4$'s per sulfonate-containing ester molecule; alternatively, an average of at least 2.5 moiety $Y^4$'s per sulfonate-containing ester molecule; or alternatively, an average of at least 3 moiety $Y^4$'s per sulfonate-containing ester molecule. In other aspects, the sulfonate-containing esters have an average of from 1.5 to 9 moiety $Y^4$'s per sulfonate-containing ester molecule. Alternatively, the sulfonate acid containing ester have an average of from 3 to 8 moiety $Y^4$'s per sulfonate-containing ester molecule; alternatively, an average of from 2 to 4 moiety $Y^4$'s per sulfonate-containing ester molecule; or alternatively, an average of from 4 to 8 moiety $Y^4$'s per sulfonate-containing ester molecule.

In another independent aspect, the sulfonate-containing ester composition comprises an average of at least one ester group per sulfonate-containing ester molecule and an average of at least one moiety $Z^4$ per sulfonate-containing ester mole wherein the moiety $Z^4$ has the structure:

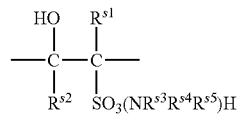

In the moiety $Z^4$ structure, $R^{s1}$ and $R^{s2}$ are independently selected from the consisting of hydrogen, $C_1$ to $C_{20}$ organyl groups, and $C_1$ to $C_{20}$ hydrocarbyl groups, $R^{s3}$, $R^{s4}$, and $R^{s5}$ are independently selected from hydrogen $C_1$ to $C_{20}$ organyl groups, and $C_1$ to $C_{20}$ hydrocarbyl groups, and the unspecified valences of moiety $Z^4$ represent the remainder of the sulfonate-containing ester molecule. $R^{s1}$, $R^{s2}$, $R^{s3}$, $R^{s4}$, and $R^{s5}$ are separate elements of moiety $Z^4$ that allow moiety $Z^4$ to have any combination of further $R^{s1}$, $R^{s2}$, $R^{s3}$, $R^{s4}$, and $R^{s5}$ embodiments as described herein. In some aspects, the structure $NR^{s3}R^{s4}R^{s5}$ represents a compound selected from the group consisting of a trialkylamine, a dialkylamine, and a monoalkylamine. In some embodiments, $NR^{s3}R^{s4}R^{s5}$ represents triethanolamine. In some particular embodiments, $R^{s1}$ and $R^{s2}$ are hydrogen.

In particular embodiments, the sulfonate-containing esters have an average of at least 1.5 moiety $Z^4$'s per sulfonate-containing ester molecule. In other embodiments, the sulfonate-containing esters have an average of at least 2 moiety $Z^4$'s per sulfonate-containing ester molecule; alternatively, an average of at least 2.5 moiety $Z^4$'s per sulfonate-containing ester molecule; or alternatively, an average of at least 3 moiety $Z^4$'s per sulfonate-containing ester molecule. In other aspects, the sulfonate-containing esters have an average of from 1.5 to 9 moiety $Z^4$'s per sulfonate-containing ester molecule. Alternatively, the sulfonate acid containing ester have an average of from 3 to 8 moiety $Z^4$'s per sulfonate-containing ester molecule; alternatively, an average of from 2 to 4 moiety $Z^{4'}$s per sulfonate-containing ester molecule; or alternatively, an average of from 4 to 8 moiety $Z^{4'}$s per sulfonate-containing ester molecule.

In some embodiments, there is provided a sulfonate-containing ester molecule comprising at least one ester group and at least one sulfonate group. The number of ester groups and the number of sulfonate groups are separate elements and the sulfonate-containing ester molecule can contain any number of ester groups and sulfonate groups as described herein.

In some embodiments, the sulfonate-containing ester molecule comprises at least 2 ester groups. Alternatively, in some embodiments, the sulfonate-containing ester molecule comprises at least 3 ester groups. In one aspect, the sulfonate-containing ester molecule comprises from 2 to 9 ester groups. In one aspect, the sulfonate-containing ester molecule comprises from 2 to 8 ester groups; alternatively, from 2 to 7 ester groups; alternatively, from 3 to 5 ester groups; or alternatively, from 3 to 4 ester groups. In yet other embodiments, the sulfonate-containing ester molecule comprises 3 ester groups or alternatively, comprises 4 ester groups.

In further embodiments, the sulfonate-containing ester molecule comprises at least one sulfonate group. In other embodiments, the sulfonate-containing ester molecule comprises at least 2 sulfonate groups; or alternatively, at least 3 sulfonate groups. In other embodiments, the sulfonate-containing ester molecule comprises from 2 to 9 sulfonate groups; alternatively, from 3 to 8 sulfonate groups; alternatively, from 2 to 4 sulfonate groups; or alternatively, from 4 to 8 sulfonate groups.

In some embodiments, the sulfonate-containing ester molecule comprises at least one ester group and a least one moiety $X^3$. In some embodiments, the sulfonate-containing ester molecule comprising ester groups and moiety $X^3$ can comprise any combination of the number of ester groups and any number of moiety $X^{3'}$s as described herein. The number of ester groups within the within the sulfonate-containing ester molecule comprising ester groups and moiety $X^3$ has been described previously. In further embodiments, the sulfonate-containing ester molecule comprising ester groups and moiety $X^3$ can at least 2 moiety $X^{3'}$s, or alternatively, at least 3 moiety $X^{3'}$s. In other embodiments, the sulfonate-containing ester molecule comprising ester groups and moiety $X^3$ comprises from 2 to 9 moiety $X^{3'}$s; alternatively, from 3 to 8 moiety $X^{3'}$s; alternatively, from 2 to 4 moiety $X^{3'}$s; or alternatively, from 4 to 8 moiety $X^{3'}$s.

In some embodiments, the sulfonate-containing ester molecule comprises at least one ester group and a least one moiety $Y^3$. In some embodiments, the sulfonate-containing ester molecule comprising ester groups and moiety $Y^3$ can comprise any combination of the number of ester groups and any number of moiety $Y^{3'}$s as described herein. The number of ester groups within the within the sulfonate-containing ester molecule comprising ester groups and moiety $Y^3$ has been described previously. In further embodiments, the sulfonate-containing ester molecule comprising ester groups and moiety $Y^3$ can at least 2 moiety $Y^{3'}$s, or alternatively, at least 3 moiety $Y^{3'}$s. In other embodiments, the sulfonate-containing ester molecule comprising ester groups and moiety $Y^3$ comprises from 2 to 9 moiety $Y^{3'}$s; alternatively, from 3 to 8 moiety $Y^{3'}$s; alternatively, from 2 to 4 moiety $Y^{3'}$s; or alternatively, from 4 to 8 moiety $Y^{3'}$S.

In some embodiments, the sulfonate-containing ester molecule comprises at least one ester group and a least one moiety $Z^3$. In some embodiments, the sulfonate-containing ester molecule comprising ester groups and moiety $Z^3$ can comprise any combination of the number of ester groups and any number of moiety $Z^{3'}$s as described herein. The number of ester groups within the within the sulfonate-containing ester molecule comprising ester groups and moiety $Z^3$ has been described previously. In further embodiments, the sulfonate-containing ester molecule comprising ester groups and moiety $Z^3$ can at least 2 moiety $Z^{3'}$s, or alternatively, at least 3 moiety $Z^{3'}$s. In other embodiments, the sulfonate-containing ester molecule comprising ester groups and moiety $Z^3$ comprises from 2 to 9 moiety $Z^{3'}$s; alternatively, from 3 to 8 moiety $Z^{3'}$s; alternatively, from 2 to 4 moiety $Z^{3'}$s; or alternatively, from 4 to 8 moiety $Z^{3'}$s.

In some embodiments, the sulfonate-containing ester molecule comprises at least one ester group and a least one moiety $X^4$. In some embodiments, the sulfonate-containing ester molecule comprising ester groups and moiety $X^4$ can comprise any combination of the number of ester groups and any number of moiety $X^{4'}$s as described herein. The number of ester groups within the within the sulfonate-containing ester molecule comprising ester groups and moiety $X^4$ has been described previously. In further embodiments, the sulfonate-containing ester molecule comprising ester groups and moiety $X^4$ can at least 2 moiety $X^{4'}$s, or alternatively, at least 3 moiety $X^{4'}$s. In other embodiments, the sulfonate-containing ester molecule comprising ester groups and moiety $X^4$ comprises from 2 to 9 moiety $X^{4'}$s; alternatively, from 3 to 8 moiety $X^{4'}$s; alternatively, from 2 to 4 moiety $X^{4'}$s; or alternatively, from 4 to 8 moiety $X^{4'}$s.

In some embodiments, the sulfonate-containing ester molecule comprises at least one ester group and a least one moiety $Y^4$ In some embodiments, the sulfonate-containing ester molecule comprising ester groups and moiety $Y^4$ can comprise any combination of the number of ester groups and any number of moiety $Y^{4'}$s as described herein. The number of ester groups within the within the sulfonate-containing ester molecule comprising ester groups and moiety $Y^4$ has been described previously. In further embodiments, the sulfonate-containing ester molecule comprising ester groups and moiety $Y^4$ can at least 2 moiety $Y^{4'}$s, or alternatively, at least 3 moiety $Y^{4'}$s. In other embodiments, the sulfonate-containing ester molecule comprising ester groups and moiety $Y^4$ comprises from 2 to 9 moiety $Y^{4'}$s; alternatively, from 3 to 8 moiety $Y^{4'}$s; alternatively, from 2 to 4 moiety $Y^{4'}$s; or alternatively, from 4 to 8 moiety $Y^{4'}$s.

In some embodiments, the sulfonate-containing ester molecule comprises at least one ester group and a least one moiety $Z^4$. In some embodiments, the sulfonate-containing ester molecule comprising ester groups and moiety $Z^4$ can comprise any combination of the number of ester groups and any number of moiety $Z^{4'}$s as described herein. The number of ester groups within the within the sulfonate-containing ester molecule comprising ester groups and moiety $Z^4$ has been described previously. In further embodiments, the sulfonate-containing ester molecule comprising ester groups and moiety $Z^4$ can at least 2 moiety $Z^{4'}$s, or alternatively, at least 3 moiety $Z^{4'}$s. In other embodiments, the sulfonate-containing ester molecule comprising ester groups and moiety $Z^4$ comprises from 2 to 9 moiety $Z^{4'}$s; alternatively, from 3 to 8 moiety $Z^{4'}$s; alternatively, from 2 to 4 moiety $Z^{4'}$s; or alternatively, from 4 to 8 moiety $Z^{4'}$s.

The sulfonate-containing ester oil compositions may also be described as a product produced by the process comprising contacting a sulfonic acid-containing ester with a base and may be further limited by the process as described herein.

Process for Making a Thiol Ester Composition

The present invention advantageously provides processes for producing a thiol ester composition as embodiments of the present invention. As an embodiment, the present invention advantageously includes a process to produce a thiol ester composition by contacting hydrogen sulfide and an unsaturated ester composition containing unsaturated esters and reacting the hydrogen sulfide and unsaturated esters to form or produce the thiol ester composition. As another embodiment of the present invention, a process to produce the thiol ester composition is advantageously provided. In this embodiment, the process includes contacting a composition comprising a polyol with a composition comprising a thiol containing carboxylic acid composition and reacting the polyol and thiol containing carboxylic acid composition to form the thiol ester composition.

In some embodiments of the present invention that include producing thiol ester compositions, the unsaturated ester composition is a natural source oil. In an aspect, the unsaturated ester composition is soybean oil or alternatively castor oil. Other suitable types of unsaturated ester compositions are described herein and can be used in the processes for producing the thiol ester compositions.

Thiol Esters from Unsaturated Esters

As an embodiment of the present invention, the thiol esters described herein can be produced by a process comprising contacting hydrogen sulfide and an unsaturated ester composition and reacting hydrogen sulfide and the unsaturated ester composition to form the thiol ester composition. In one embodiment, the unsaturated ester composition includes unsaturated esters having an average of at least 1.5 ester groups and an average of at least 1.5 carbon-carbon double bonds per unsaturated ester molecule. In this embodiment, the thiol ester composition includes thiol ester molecules having a molar ratio of cyclic sulfides to thiol groups of less than 1.5.

The processes for producing the thiol ester composition can be applied to any of the unsaturated esters described herein and used to produce any of the thiol esters described herein. The process for producing the thiol ester composition can also include any additional process steps or process conditions described herein.

In some aspects, the reaction between hydrogen sulfide and the unsaturated ester occurs in the presence of a solvent. In other aspects, the reaction between the unsaturated ester and hydrogen sulfide occurs in the substantial absence of a solvent. When the solvent is present, the solvent can be selected from the group consisting of an aliphatic hydrocarbon, an ether, an aromatic compound, an alcohol, or combinations thereof. In further embodiments, the solvent can be an aliphatic hydrocarbon, an ether, or an aromatic compound. Generally, the solvent, regardless of its chemical class, includes from 1 to 20 carbon atoms; or alternatively, from 3 to 10 carbon atoms. When the solvent includes an aliphatic solvent, the aliphatic solvent is butane, isobutane, pentane, hexane, heptane, octane, or any mixture thereof. When the solvent includes an aromatic solvent, the aromatic solvent is benzene, toluene, xylene, ethylbenzene, or any mixtures thereof. When the solvent includes an alcohol, the alcohol is methanol, 1-propanol, 2-propanol, 1-butanol, 2-butanol, 2-methyl-2-propanol, or mixtures thereof. When the solvent includes an ether, the ether is diethyl ether, dipropyl ether, tetrahydrofuran, or mixtures thereof. Other types of suitable solvents will be apparent to those of skill in the art and are to be considered within the scope of the present invention.

When a solvent is used for the reaction between the unsaturated ester and hydrogen sulfide, the quantity of solvent can be any amount that facilitates the reaction. In some embodiments, the mass of the solvent is less than 30 times the mass of the unsaturated ester. In other embodiments, the mass of the solvent is less than 20 times the mass of the unsaturated ester; alternatively, less than 15 times the mass of the unsaturated ester; alternatively, less than 10 times the mass of the unsaturated ester; or alternatively, less than 5 times the mass of the unsaturated ester. In other embodiments, the mass of the solvent is from 2 times to 20 times the mass of the unsaturated ester; alternatively, from 3 times to 15 times the mass of the unsaturated ester; alternatively, 4 times to 15 times the mass of the unsaturated ester; or alternatively, from 5 times to 10 times the mass of the unsaturated ester.

The hydrogen sulfide to molar equivalents of unsaturated ester carbon-carbon double bonds molar ratio utilized in the process to produce the thiol ester composition can be any molar ratio that produces the desired thiol ester. The molar equivalents of unsaturated ester carbon-carbon double bonds is calculated by the equation:

$$\frac{UES\ \text{Mass}}{UES\ GMW} \times UES\ C{=}C$$

In this equation, UES GMW is the average gram molecular weight of the unsaturated ester, UES Mass is the mass of the feedstock unsaturated ester, and UES C=C is the average number of double bonds per unsaturated ester molecule. In some embodiments, the thiol ester molecules have a molar ratio of the hydrogen sulfide to the unsaturated ester carbon-carbon double bonds of greater than 2. In other embodiments, the hydrogen sulfide to unsaturated ester carbon-carbon double bonds molar ratio is greater than 5; alternatively, greater than 10; alternatively, greater than 15; or alternatively, greater than 20. In other embodiments, the hydrogen sulfide to unsaturated ester carbon-carbon double bonds molar ratio can be from 2 to 500; alternatively, from 5 to 200; alternatively, from 10 to 100; or alternatively, from 100 to 200.

In some aspects the reaction between the unsaturated ester and hydrogen sulfide is catalyzed. In some embodiments, the reaction of the unsaturated ester and hydrogen sulfide can be catalyzed by a heterogeneous catalyst or a homogeneous catalyst. In other embodiments, the reaction of the unsaturated ester and hydrogen sulfide is initiated by a free radical initiator or ultraviolet (UV) radiation. Other suitable catalyzing and initiating methods will be apparent to those of skill in the art and are to be considered within the scope of the present invention.

The heterogeneous catalyst is selected from the group consisting of acid clays (such as Filtrol®-24, which is commercially available from Englehard), acid zeolites (such as LZY-84, which is commercially available from UOP), cobalt/molybdenum oxide supported catalysts (such as TK-554, which is commercially available from Haldor-Topsoe), and nickel/molybdenum supported oxide catalysts (such as TK-573, which is commercially available from Haldor-Topsoe). The homogeneous catalyst is methane sulfonic acid or toluene sulfonic acid. Other suitable types of heterogeneous and homogeneous catalysts will be apparent to those of skill in the art and are to be considered within the scope of the present invention.

The free radical initiator can be any free radical initiator capable of forming free radical under thermal or light photolysis. Generally, the free radical initiator is selected from the general class compounds having a —N=N— group or a —O— O— group. Specific classes of free radical initiators include diazo compounds, dialkyl peroxides, hydroperoxides, and peroxy esters. Specific initiators include azobenzene, 2,2'-azobis(2-methylpropionitrile, 4,4'-azobis(4-cyanovaleric acid), 1,1'-azobis(cyclohexanecarbo-nitrile), 2,2'-azobis(2-methylpropane), 2,2'-azobis(2-methylpropionamidine)dihydro-chloride, methylpropionitrile, azodicarboxamide, tert-butyl hyperoxide, di-tert-butyl peroxide, octylperbenzoate. In some embodiments, the free radical initiated reaction is performed at a reaction temperature within ±50° C. of the 1 hour half life of the free radical initiator. In other embodiments, the free radical initiated reaction is performed at a reaction temperature within ±25° C. of the 1 hour half life of the free radical initiator; alternatively, at a reaction temperature within ±20° C. of the 1 hour half life of the free radical initiator; alternatively, at a reaction temperature within ±15° C. of the 1 hour half life of the free radical initiator; alternatively, at a reaction temperature within ±10° C. of the 1 hour half life of the free radical initiator. In embodiments, wherein the free radical initiator catalyst reaction of the unsaturated ester and hydrogen sulfide is initiated by light photolysis, the light can be any light capable of creating free radicals. In some embodiments the light is UV radiation.

In another aspect, the reaction of the unsaturated ester and hydrogen sulfide is initiated by UV radiation. In these embodiments, the UV radiation can be any UV radiation capable of initializing the reaction of the unsaturated ester and hydrogen sulfide. In some embodiments, the UV radiation is generated by a medium pressure mercury lamp. Although UV radiation has been described as the light source, other suitable types of light sources will be apparent to those of skill in the art and are to be considered within the scope of the present invention.

The reaction of the unsaturated ester and hydrogen sulfide can occur in a batch reactor or a continuous reactor. Example continuous reactors include continuous stirred reactors, fixed bed reactors, and the like. Example batch reactors include UV batch reactors. Other types of batch and continuous reactors that can be used in embodiments of the present invention will be apparent to those of skill in the art and are to be considered within the scope of the present invention.

When a continuous reactor is used, a feed unsaturated ester weight hourly space velocity ranging from 0.1 to 5 can be used to produce the desired thiol ester. Alternatively, the feed unsaturated ester weight hourly space velocity ranges between 0.1 to 5; alternatively, from 0.1 to 2. Alternatively, the feed unsaturated ester weight hourly space velocity is 0.1; alternatively, the feed unsaturated ester weight hourly space velocity is 0.25; or alternatively, the feed unsaturated ester weight hourly space velocity is 2.

The time required for the reaction of the unsaturated ester and hydrogen sulfide can be any time required to form the described thiol ester. Generally, the time required for the reaction of the unsaturated ester and hydrogen sulfide is at least 5 minutes. In some embodiments, the time required for the reaction of the unsaturated ester and hydrogen sulfide ranges from 5 minutes to 72 hours; alternatively, from 10 minutes to 48 hours; or alternatively, from 15 minutes to 36 hours.

In embodiments, the process to produce the thiol ester further comprises a step to remove excess or residual hydrogen sulfide after reacting the hydrogen sulfide and the unsaturated ester composition. In some embodiments, the thiol ester is vacuum stripped. In some embodiments, the thiol ester is vacuum stripped at a temperature ranging between 25° C. and 250° C.; or alternatively, between 50° C. and 200° C. In other embodiments, the thiol ester is sparged with an inert gas to remove hydrogen sulfide. In some embodiments, the thiol ester is sparged with an inert gas at a temperature between 25° C. and 250° C.; or alternatively, between 50° C. and 200° C. In some aspects, the inert gas is nitrogen. Generally, the stripped or sparged thiol ester comprises less than 0.1 weight percent hydrogen sulfide. In other embodiments, the stripped or sparged thiol ester comprises less than 0.05 weight percent sulfur; alternatively, less than 0.025 weight percent hydrogen sulfide; or alternatively, less than 0.01 weight percent hydrogen sulfide.

The reaction between the unsaturated ester and hydrogen sulfide can be performed at any temperature capable of forming the thiol ester. In some embodiments, the unsaturated ester and hydrogen sulfide can be reacted at a temperature greater than −20° C. In other embodiments, the unsaturated ester and hydrogen sulfide can be reacted at a temperature greater than 0° C.; alternatively, greater than 20° C.; alternatively, greater than 50° C.; alternatively, greater than 80° C.; or alternatively, greater than 100° C. In yet other embodiments, the unsaturated ester and hydrogen sulfide can be reacted at a temperature from −20° C. to 200° C.; alternatively, from 120° C. to 240° C.; alternatively, from 170° C. to 210° C.; alternatively, from 185° C. to 195° C.; alternatively, from 20° C. to 200° C.; alternatively, from 20° C. to 170° C.; or alternatively, from 80° C. to 140° C.

The reaction between the unsaturated ester and hydrogen sulfide can be performed at any pressure that maintains a portion of the hydrogen sulfide in a liquid state. In some embodiments the unsaturated ester and hydrogen sulfide reaction can be performed at a pressure ranging from 100 psig to 2000 psig. In other embodiments, the unsaturated ester and hydrogen sulfide reaction can be performed at a pressure ranging from 150 to 1000 psig; or alternatively, from 200 to 600 psig.

Thiol esters having a low cyclic sulfide content can be produced using the disclosed process. In an aspect, the process for producing the thiol ester forms or produces a thiol ester having a molar ratio of cyclic sulfide to thiol groups of less than 1.5. Additional cyclic sulfide to thiol groups molar ratios are disclosed herein.

In addition to lower cyclic sulfide content, thiol esters having a low carbon-carbon double bond to thiol group molar ratio can also be produced using the disclosed process. In an aspect, the process described herein produces the thiol ester having a carbon-carbon double bond to thiol group molar ratio of less than 1.5. Additional carbon-carbon double bond to thiol group molar ratios are disclosed herein.

In some aspects, the process described herein produces the thiol ester molecules having an average of greater than 5 weight percent thiol sulfur. Additional thiol sulfur contents are disclosed herein. In other aspects, the process for producing a thiol ester forms a thiol ester having greater than 40 percent of the thiol ester total side chains include sulfur. Other percentages of the thiol ester total side chains that include sulfur are disclosed herein.

In some embodiments, the process for producing a thiol ester composition includes contacting an unsaturated ester and hydrogen sulfide and reacting the unsaturated ester and the hydrogen sulfide to form a thiol ester. The thiol ester comprises thiol ester molecules that have a ratio of cyclic sulfide to thiol groups of less than 1.5.

Thiol Ester from a Polyol and a Thiol Containing Carboxylic Acid Derivative

As another embodiment of the present invention, another process to produce the thiol ester composition is advantageously provided. In this embodiment, the process includes the steps of contacting a composition comprising a polyol with a composition comprising a thiol containing carboxylic acid and/or thiol containing carboxylic acid derivative and reacting the polyol and thiol containing carboxylic acid and/or thiol containing carboxylic acid derivative to produce the thiol ester composition. This process can be applied to any polyol, thiol containing carboxylic acid, or thiol containing carboxylic acid derivative described herein. The process for producing the thiol ester composition can also include any additional process steps or process conditions described herein. Additionally, the process for producing the thiol ester composition can form any thiol ester described herein.

In some embodiments, the thiol ester composition includes thiol ester molecules that have an average of at least 1.5 ester groups and an average of at least 1.5 thiol groups per thiol ester molecule.

The polyol used to produce the thiol ester by contacting a polyol and a thiol carboxylic acid and/or thiol carboxylic acid equivalent (for example a thiol carboxylic acid methyl ester) can be any polyol or mixture of polyols that can produce the described thiol containing ester.

In one aspect, the polyol used to produce the thiol ester can comprise from 2 to 20 carbon atoms. In other embodiments, the polyol comprises from 2 to 10 carbon atoms; alternatively from 2 to 7 carbon atoms; alternatively from 2 to 5 carbon atoms. In further embodiments, the polyol may be a mixture of polyols having an average of 2 to 20 carbon atoms; alternatively, an average of from 2 to 10 carbon atoms; alternatively, an average of 2 to 7 carbon atoms; alternatively an average of 2 to 5 carbon atoms.

In another aspect, the polyol used to produce the thiol ester can have any number of hydroxy groups needed to produce the thiol ester as described herein. In some embodiments, the polyol has 2 hydroxy groups; alternatively 3 hydroxy groups; alternatively, 4 hydroxy groups; alternatively, 5 hydroxy groups; or alternatively, 6 hydroxy groups. In other embodiments, the polyol comprises at least 2 hydroxy groups; alternatively at least 3 hydroxy groups; alternatively, at least 4 hydroxy groups; or alternatively, at least 5 hydroxy groups; at least 6 hydroxy groups. In yet other embodiments, the polyol comprises from 2 to 8 hydroxy groups; alternatively, from 2 to 4 hydroxy groups; or alternatively from 4 to 8 hydroxy groups.

In further aspects, the polyol used to produce the thiol ester is a mixture of polyols. In an embodiment, the mixture of polyols has an average of at least 1.5 hydroxy groups per polyol molecule. In other embodiments, the mixture of polyols has an average of at least 2 hydroxy groups per polyol molecule; alternatively, an average of at least 2.5 hydroxy groups per polyol molecule; alternatively, an average of at least 3.0 hydroxy groups per polyol molecule; or alternatively, an average of at least 4 hydroxy groups per polyol molecule. In yet another embodiments, the mixture of polyols has an average of 1.5 to 8 hydroxy groups per polyol molecule; alternatively, an average of 2 to 6 hydroxy groups per polyol molecule; alternatively, an average of 2.5 to 5 hydroxy groups per polyol molecule; alternatively, an average of 3 to 4 hydroxy groups per polyol molecule; alternatively, an average of 2.5 to 3.5 hydroxy groups per polyol molecule; or alternatively, an average of 2.5 to 4.5 hydroxy groups per polyol molecule.

In yet another aspect, the polyol or mixture of polyols used to produce the thiol ester has a molecular weight or average molecular weight less than 500. In other embodiments, the polyol or mixture of polyols have a molecular weight or average molecular weight less than 300; alternatively less than 200; alternatively, less than 150; or alternatively, less than 100.

The thiol carboxylic acid and/or thiol carboxylic acid equivalent used to produce the thiol ester by contacting a polyol and a thiol carboxylic acid and/or thiol carboxylic acid equivalent can be any thiol carboxylic acid mixture comprising thiol carboxylic acids, thiol carboxylic acid equivalent or mixture comprising thiol carboxylic acid equivalents that can produce the described thiol containing ester. When talking about the characteristics thiol carboxylic acid equivalent or thiol carboxylic acid equivalents, properties such as number of carbon atoms, average number of carbon atom, molecular weight or average molecular weight, number of thiol group, and average number of thiol groups, one will understand the these properties will apply to the portion of the thiol carboxylic acid equivalent which adds to the polyol to form the thiol ester.

In an aspect, the thiol carboxylic acid and/or thiol carboxylic acid equivalent used to produce the thiol ester comprises from 2 to 28 carbon atoms. In an embodiment, the thiol carboxylic acid and/or thiol carboxylic acid equivalent comprises from 4 to 26 carbon atoms; alternatively, from 8 to 24 carbon atoms; alternatively, from 12 to 24 carbon atoms; or alternatively, from 14 to 20 carbon atoms. In other embodiments, a mixture comprising thiol carboxylic acid and/or mixture comprising thiol carboxylic acid equivalents has an average of 2 to 28 carbon atoms per carboxylic acid and/or carboxylic acid equivalent; alternatively, from 4 to 26 carbon atoms per carboxylic acid and/or carboxylic acid equivalent; alternatively, from 8 to 24 carbon atoms per carboxylic acid and/or carboxylic acid equivalent; alternatively, from 12 to 24 carbon atoms per carboxylic acid and/or carboxylic acid equivalent; or alternatively, from 14 to 20 carbon atoms per carboxylic acid and/or carboxylic acid equivalent.

In another aspect, the thiol carboxylic acid and/or thiol carboxylic acid equivalent used to produce the thiol ester has at least 1 thiol group; alternatively 2 thiol groups. In some embodiments, a mixture comprising thiol carboxylic acid and/or mixture comprising thiol carboxylic acid equivalents has an average of from 0.5 to 3 thiol groups per carboxylic acid and/or carboxylic acid equivalent; alternatively, an average of from 1 to 2 thiol groups per carboxylic acid and/or carboxylic acid equivalent.

In another aspect, the thiol carboxylic acid and/or thiol carboxylic acid equivalent used to produce the thiol ester has a molecular weight greater than 100; alternatively greater than 180; alternatively greater than 240; or alternatively greater than 260. In other embodiments, the thiol carboxylic acid and/or thiol carboxylic acid equivalent has a molecular weight from 100 to 500; alternatively, from 120 to 420; alternatively, from 180 to 420; alternatively, from 240 to 420; a mixture or alternatively, from 260 to 360. In some embodiments, a mixture comprising thiol carboxylic acid and/or mixture comprising thiol carboxylic acid equivalents has an average molecular weight greater than 100 per carboxylic acid and/or carboxylic acid equivalent; alternatively greater than 180 per carboxylic acid and/or carboxylic acid equivalent; alternatively greater than 240 per carboxylic acid and/or carboxylic acid equivalent; or alternatively greater than 260 per carboxylic acid and/or carboxylic acid equivalent. In yet other embodiments, the mixture comprising of thiol carboxylic acid and/or mixture comprising thiol carboxylic acid equivalents has an average molecular weight from 100 to 500 per carboxylic acid and/or carboxylic acid equivalent; alternatively, from 120 to 420 per carboxylic acid and/or carboxylic acid equivalent; alternatively, from 180 to 420 per carboxylic acid and/or carboxylic acid equivalent; alternatively, from 240 to 420 per carboxylic acid and/or carboxylic acid equivalent; a mixture or alternatively, from 260 to 360 per carboxylic acid and/or carboxylic acid equivalent.

In some aspects, the reaction between the polyol and the thiol containing carboxylic acid and/or thiol containing carboxylic acid derivative occurs in the presence of a solvent. In other aspects the reaction between the polyol and the thiol containing carboxylic acid and/or thiol containing carboxylic acid derivative occurs in the substantial absence of a solvent. In aspects wherein the reaction between the polyol and the thiol containing carboxylic acid and/or thiol containing carboxylic acid derivative occurs in the presence of a solvent, the solvent is selected from the group consisting of an aliphatic hydrocarbon, an ether, an aromatic compound, or any combination thereof. Generally, the solvent, regardless of its chemical class, can include from 1 to 20 carbon atoms; or alternatively, from 3 to 10 carbon atoms. When the solvent includes the aliphatic hydrocarbon, the aliphatic hydrocarbon is butane, isobutane, pentane, hexane, heptane, octane, or any mixture thereof. When the solvent includes the aromatic compound, the aromatic compound is benzene, toluene, xylene, ethylbenzene, or any mixture thereof. When the solvent includes the ether, the ether is diethyl ether, dipropyl ether, tetrahydrofuran, and any mixture thereof.

When a solvent is used for the reaction between the polyol and the thiol containing carboxylic acid and/or thiol containing carboxylic acid derivative, the quantity of solvent can be any amount that facilitates the reaction. In some embodiments, the mass of the solvent is less than 30 times the mass of the thiol containing carboxylic acid and/or thiol containing carboxylic acid derivative. In other embodiments, the mass of the solvent is less than 20 times the mass of the unsaturated ester oil; alternatively, less than 15 times the mass of the thiol containing carboxylic acid and/or thiol containing carboxylic acid derivative; alternatively, less than 10 times the mass of the thiol containing carboxylic acid and/or thiol containing carboxylic acid derivative; or alternatively, less than 5 times the mass of the thiol containing carboxylic acid and/or thiol containing carboxylic acid derivative. In other embodiments, the mass of the solvent is from 2 times to 20 times the mass of the thiol containing carboxylic acid and/or thiol containing carboxylic acid derivative; alternatively, from 3 times to 15 times the mass of the thiol containing carboxylic acid and/or thiol containing carboxylic acid derivative, or alternatively, from 5 times to 10 times the mass of the thiol containing carboxylic acid and/or thiol containing carboxylic acid derivative.

The equivalent of thiol containing carboxylic acid and/or thiol containing carboxylic acid derivative carboxylic acid groups to equivalents of polyol hydroxy groups molar ratio (hereinafter "carboxylic acid group to polyol hydroxy group molar ratio") utilized in the process to produce the thiol ester composition can be any carboxylic acid group to polyol hydroxy group molar ratio that produces the desired thiol ester composition. In some embodiments, the carboxylic acid group to polyol hydroxy group molar ratio is greater than 0.4. In other embodiments, the carboxylic acid group to polyol hydroxy group molar ratio is greater than 0.6; alternatively, greater than 0.8; alternatively, greater than 1; or alternatively, greater than 1.1. In other embodiments, the carboxylic acid group to polyol hydroxy group molar ratio can range from 0.4 to 1.3; alternatively, from 0.6 to 1.2, or alternatively, from 0.8 to 1.1.

In some aspects, the reaction between the polyol and the thiol containing carboxylic acid and/or thiol containing carboxylic acid derivative is catalyzed. In some embodiments, the catalyst is a mineral acid, such as sulfuric or phosphoric acid. In other embodiments, the catalyst is an organic acid. In embodiments, for example, the organic acid is methane sulfonic acid or toluene sulfonic acid. Other suitable types of catalyst will be apparent to those of skill in the art and are to be considered within the scope of the present invention.

The reaction of the polyol and the thiol containing carboxylic acid and/or thiol containing carboxylic acid derivative can occur in a batch reactor or a continuous reactor, as described herein. The reaction between the polyol and the thiol containing carboxylic acid and/or thiol containing carboxylic acid derivative can be performed at any temperature capable of forming the thiol ester. In some embodiments, the polyol and the thiol containing carboxylic acid and/or thiol containing carboxylic acid derivative can be reacted at a temperature greater than 20° C. In other embodiments, the polyol and the thiol containing carboxylic acid and/or thiol containing carboxylic acid derivative can be reacted at a temperature greater than 50° C.; alternatively, greater than 75° C.; or alternatively, greater than 100° C. In yet other embodiments, the polyol and the thiol containing carboxylic acid and/or thiol containing carboxylic acid derivative can be reacted at a temperature from 20° C. to 250° C.; alternatively, from 50° C. to 200° C.; alternatively, from 75° C. to 175° C.; or alternatively, from 100° C. to 150° C.

The time required for the reaction of the polyol and the thiol containing carboxylic acid and/or thiol containing carboxylic acid derivative can be any time required to form the described thiol ester oil. Generally, the reaction time of the polyol and the thiol containing carboxylic acid and/or thiol containing carboxylic acid derivative is at least 5 minutes. In some embodiments, the reaction time is at least 30 minutes; alternatively, at least 1 hour; or alternatively, at least 2 hours. In yet other embodiments, the reaction time ranges from 5 minutes to 72 hours; alternatively, from 30 minutes to 48 hours; alternatively, from 1 hour minutes to 36 hours; or alternatively, from 2 hours and 24 hours.

When a continuous reactor is used, a feed polyol weight unsaturated ester weight hourly space velocity ranging from 0.1 to 5 can be used to produce the desired thiol ester. Alternatively, the feed polyol weight hourly space velocity ranges between 0.1 to 5; alternatively, from 0.1 to 2. Alternatively, the feed polyol ester weight hourly space velocity is 0.1; alternatively, the feed polyol weight hourly space velocity is 0.25; or alternatively, the feed polyol weight hourly space velocity is 2.

The reaction between the polyol and the thiol containing carboxylic acid and/or thiol containing carboxylic acid derivative can be performed at any reaction pressure that maintains the polyol and the thiol containing carboxylic acid and/or thiol containing carboxylic acid derivative in a liquid state. In some embodiments, the reaction between the polyol and the thiol containing carboxylic acid and/or thiol containing carboxylic acid derivative is performed at a pressure ranging from 0 psia to 2000 psia. In other embodiments, the reaction pressure ranges from 0 psia to 1000 psia; alternatively, from 0 psia and 500 psia; or alternatively, 0 psia to 300 psia.

In some embodiments, the process to produce the thiol ester by reacting a polyol and the thiol containing carboxylic acid and/or thiol containing carboxylic acid derivative can further include a step to remove excess or residual polyol, thiol containing carboxylic acid, and/or thiol containing carboxylic acid derivative once the polyol has reacted with the thiol containing carboxylic acid or thiol containing carboxylic acid derivative. In some embodiments, the thiol ester is vacuum stripped. In some embodiments, the thiol ester is vacuum stripped at a temperature ranging between 25° C. and 250° C.; or alternatively, between 50° C. and 200° C. In other embodiments, the thiol ester is sparged with an inert gas to remove excess polyol, thiol containing carboxylic acid, and/or thiol containing carboxylic acid derivative. In some embodiments, the thiol ester is sparged with an inert gas at a temperature between 25° C. and 250° C.; or alternatively, between 50° C. and 200° C. In some aspects, the inert gas is nitrogen. Generally, the stripped or sparged thiol ester comprises less than 5 excess polyol, thiol containing carboxylic acid, or thiol containing carboxylic acid derivative. In other embodiments, the stripped or sparged thiol ester comprises less than 2 weight percent excess polyol, thiol containing carboxylic acid, and/or thiol containing carboxylic acid derivative; alternatively, less than 1 weight percent excess polyol, thiol containing carboxylic acid, and/or thiol containing carboxylic acid derivative; or alternatively, less than 0.5 weight percent excess polyol, thiol containing carboxylic acid, and/or thiol containing carboxylic acid derivative.

Process for Making Hydroxy Thiol Ester Composition

The present invention advantageously provides processes for producing a hydroxy thiol ester as embodiments of the present invention. As an embodiment, the present invention includes a process to produce the hydroxy thiol ester. The process comprises the steps of contacting hydrogen sulfide and an epoxidized unsaturated ester composition and reacting the hydrogen sulfide and the epoxidized unsaturated ester to form the hydroxy thiol ester. As another embodiment of the present invention, another process to produce the hydroxy thiol ester is provided. In this embodiment, the process comprises the steps of contacting a composition comprising a polyol with a composition comprising an hydroxy thiol containing carboxylic acid or an hydroxy thiol containing carboxylic acid derivative and reacting the polyol and the hydroxy thiol containing carboxylic acid or the hydroxy thiol containing carboxylic acid derivative to form the hydroxy thiol ester.

Hydroxy Thiol Ester from Hydrogen Sulfide and an Epoxidized Unsaturated Ester Composition As an embodiment of the present invention, the hydroxy thiol ester composition is produced by a process comprising the steps of contacting hydrogen sulfide and an epoxidized unsaturated ester composition and reacting the hydrogen sulfide and the epoxidized unsaturated ester to produce the hydroxy thiol ester composition.

In some embodiments, the epoxidized unsaturated ester composition includes epoxidized unsaturated esters that have an average of at least 1 ester groups and an average of at least 1 epoxide groups per epoxidized unsaturated ester molecule.

The process for producing or preparing the hydroxy thiol ester composition can be applied to any of the epoxidized unsaturated esters described herein and used to produce any hydroxy thiol ester described herein. The process for producing the hydroxy thiol ester can also include any additional process steps or process conditions as described herein. Additionally, the process for producing the hydroxy thiol ester can form any hydroxy thiol ester described herein.

In some embodiments, the epoxidized unsaturated ester composition is an epoxidized natural source oil. In some embodiments, the epoxidized unsaturated ester composition is soybean oil. Other suitable types of epoxidized unsaturated ester compositions, including the natural source oils described herein, will be apparent to those of skill in the art and are to be included within the scope of the present invention.

In some aspects, the hydroxy thiol ester is produced by contacting hydrogen sulfide with the epoxidized natural source oil under the reaction conditions to form the hydroxy thiol ester in the presence of an optional catalyst. In some embodiments, the catalyst can be a heterogeneous catalyst or a homogeneous catalyst. Examples of suitable catalysts are described herein. Additional types of suitable catalysts will be apparent to those of skill in the art and are to be considered within the scope of the present invention.

In some aspects the reaction between the epoxidized unsaturated ester occurs in the presence of a solvent. In other aspects the reaction between the epoxidized unsaturated ester and hydrogen sulfide occurs in the substantial absence of a solvent. In aspects that include the presence of a solvent, the solvent is selected from the groups consisting of an aliphatic hydrocarbon, an ether, an aromatic compound, and combinations thereof. Generally, the solvent, regardless of its chemical class, includes from 1 to 20 carbon atoms; or alternatively, from 3 to 10 carbon atoms. When the solvent includes the aliphatic hydrocarbon, the aliphatic hydrocarbon is butane, isobutane, pentane, hexane, heptane, octane, or any mixture thereof. When the solvent includes the aromatic compound, the aromatic compound is benzene, toluene, xylene, ethylbenzene, or any mixture thereof. When the solvent includes the ether, the ether is diethyl ether, dipropyl ether, tetrahydrofuran, or any mixture thereof. Other suitable solvents will be apparent to those of skill in the art and are to be considered within the scope of the present invention.

When a solvent is used for the reaction between the hydrogen sulfide and the epoxidized unsaturated ester, the quantity of solvent can be any amount that facilitates the reaction. In some embodiments, the mass of the solvent is less than 30 times the mass of the epoxidized unsaturated ester. In other embodiments, the mass of the solvent is less than 20 times the mass of the epoxidized unsaturated ester; alternatively, less than 15 times the mass of the epoxidized unsaturated ester; alternatively, less than 10 times the mass of the epoxidized unsaturated ester; or alternatively, less than 5 times the mass of the epoxidized unsaturated ester. In other embodiments, the mass of the solvent is from 2 times to 20 times the mass of the epoxidized unsaturated ester; alternatively, from 3 times to 15 times the mass of the epoxidized unsaturated ester; alternatively; 4 times to 15 times the mass of the epoxidized unsaturated ester; or alternatively, from 5 times to 10 times the mass of the epoxidized unsaturated ester.

The hydrogen sulfide to molar equivalents of epoxide groups in the epoxidized unsaturated ester (hereinafter "hydrogen sulfide to epoxide group molar ratio") utilized in the process to produce the hydroxy thiol ester can be any hydrogen sulfide to epoxide group molar ratio that produces the desired hydroxy thiol ester. The molar equivalents of epoxidized unsaturated ester epoxidized groups can be calculated by the equation:

$$\frac{EUES \text{ Mass}}{EUES \text{ GMW}} \times EUES \text{ Epoxide}$$

In this equation, EUES GMW is the average gram molecular weight of the epoxidized unsaturated ester, EUES Mass is the mass of the epoxidized unsaturated ester, and EUES Epoxide is the average number of epoxide groups per epoxidized unsaturated ester molecule. In some embodiments, the hydrogen sulfide to epoxide group molar ratio is greater than 0.2. In other embodiments, the hydrogen sulfide to epoxide group molar ratio is greater than 0.5; alternatively, greater than 1; or alternatively, greater than 2. In other embodiments, the hydrogen sulfide to epoxide group molar ratio ranges from 0.2 to 5; alternatively, from 0.5 to 4; or alternatively, from 0.75 to 3. In some embodiments, the hydrogen sulfide to epoxide group molar ratio is greater than 2. In other embodiments, the hydrogen sulfide to epoxide group molar ratio is greater than 5; alternatively, greater than 10; alternatively, greater than 15; or alternatively, greater than 20. In other embodiments, the hydrogen sulfide to epoxide group molar ratio can be from 0.2 to 500; alternatively, from 0.5 to 400; alternatively, from 1 to 300; alternatively, from 2 to 250; alternatively, 5 to 200; or alternatively, from 10 to 100.

The reaction of the epoxidized unsaturated ester and hydrogen sulfide can occur in a batch reactor or a continuous reactor. Suitable types of batch and continuous reactors are described herein. Other suitable types of batch and continuous reactors will be apparent to those of skill in the art and are to be considered within the scope of the present invention.

The time required for the reaction of the epoxidized unsaturated ester and hydrogen sulfide can be any time required to form the described hydroxy thiol ester. Generally, the time required for the reaction of the epoxidized unsaturated ester and hydrogen sulfide is at least 15 minutes. In some embodiments, the time required for the reaction of the unsaturated ester and hydrogen sulfide ranges from 15 minutes to 72 hours; alternatively, from 30 minutes to 48 hours; alternatively, from 45 minutes to 36 hours.

In some embodiments, the hydroxy thiol ester composition includes hydroxy thiol ester molecules that have an average of greater than 2.5 weight percent thiol sulfur. In some embodiments, the hydroxy thiol ester composition includes hydroxy thiol ester molecules that have an average of greater than 5 weight percent thiol sulfur. Alternatively, in some embodiments, the hydroxy thiol ester molecules have an average ranging from 8 to 10 weight percent thiol sulfur.

In other aspects, the process producing the hydroxy thiol ester composition includes producing hydroxy thiol ester molecules having an average of greater than 40 percent of the sulfide-containing ester total side chains comprise a sulfide group. Additional embodiments wherein the hydroxy thiol ester comprises a percentage of sulfide-containing ester total side chains are described herein.

In embodiments, the process to produce the hydroxy thiol ester further comprises a step to remove residual hydrogen sulfide after reacting the hydrogen sulfide and the epoxidized unsaturated ester composition. In some embodiments, the hydroxy thiol ester is vacuum stripped. In some embodiments, the hydroxy thiol ester is vacuum stripped at a temperature ranging between 25° C. and 250° C.; or alternatively, between 50° C. and 200° C. In other embodiments, the hydroxy thiol ester is sparged with an inert gas to remove hydrogen sulfide. In some embodiments, the hydroxy thiol ester is sparged with an inert gas at a temperature between 25° C. and 250° C.; or alternatively, between 50° C. and 200° C. In some aspects, the inert gas is nitrogen. Generally, the stripped or sparged hydroxy thiol ester comprises less than 0.1 weight percent hydrogen sulfide. In other embodiments, the stripped or sparged hydroxy thiol ester comprises less than 0.05 weight percent hydrogen sulfide; alternatively, less than 0.025 weight percent hydrogen sulfide; or alternatively, less than 0.01 weight percent hydrogen sulfide.

The reaction between the hydrogen sulfide and the epoxidized unsaturated ester can be performed at any temperature capable of forming the hydroxy thiol ester. In some embodiments, the epoxidized unsaturated ester and hydrogen sulfide can be reacted at a reaction temperature greater than −20° C. In other embodiments, the reaction temperature is greater than 0° C.; alternatively, greater than 20° C.; alternatively, greater than 50° C.; or alternatively, greater than 80° C. In yet other embodiments, the reaction temperature ranges from −20° C. to 200° C.; alternatively, from 20° C. to 170° C.; or alternatively, from 80° C. to 140° C.

The reaction between the epoxidized unsaturated ester and hydrogen sulfide can be performed at any reaction pressure that maintains a substantial portion of the hydrogen sulfide in a liquid state. In some embodiments, the reaction pressure ranges from 100 psig to 2000 psig. In other embodiments, the reaction a pressure ranges from 150 to 1000 psig; or alternatively, from 200 to 600 psig.

In another aspect, the process to produce a hydroxy thiol ester produces a hydroxy thiol ester having an epoxide group to thiol group molar ratio less than 3.3. In another aspect, the process to produce a hydroxy thiol ester produces a hydroxy thiol ester having an epoxide group to thiol group molar ratio less than 2. Other hydroxy thiol ester epoxide group to thiol group molar ratios are described herein. Alternatively, the hydroxy thiol ester epoxide group to thiol group molar ratio can be less than 1.5; alternatively, less than 1.0; alternatively, less than 0.5; alternatively, less that 0.25; or alternatively, less than 0.1. In other embodiments, the hydroxy thiol ester can be substantially free of epoxide groups.

In another aspect, the process to produce hydroxy thiol ester produces a hydroxy thiol ester wherein at least 20 percent of the side chains comprise an α-hydroxy thiol group. Other hydroxy thiol ester embodiments wherein the hydroxy thiol ester contains a percentage of side chains comprising α-hydroxy thiol groups are described herein.

Hydroxy Thiol Ester from a Polyol and a Hydroxy Thiol Containing Carboxylic Acid Derivative As another embodiment of the present invention, another process to prepare the hydroxy thiol ester is advantageously provided. In this embodiment, the process includes the steps of contacting a composition comprising a polyol with a composition comprising a hydroxy thiol containing carboxylic acid and/or thiol containing carboxylic acid derivative and reacting the polyol and hydroxy thiol containing carboxylic acid and/or hydroxy thiol containing carboxylic acid to form a hydroxy thiol ester composition. This process can be applied to any polyol, any hydroxy thiol containing carboxylic acid, or any thiol containing carboxylic acid derivative described herein. The process for producing the hydroxy thiol ester composition can also include any additional process steps or process conditions described herein. Additionally, the process for producing the hydroxy thiol ester composition can form any thiol ester described herein.

In some embodiments, the hydroxy thiol ester composition includes hydroxy thiol ester molecules that have an average of at least 1 ester groups per hydroxy thiol ester molecule and an average of at least 1 α-hydroxy thiol groups per hydroxy thiol ester molecule.

The polyol used to produce the hydroxy thiol ester by contacting a polyol and a hydroxy thiol carboxylic acid and/or hydroxy thiol carboxylic acid equivalent (for example a hydroxy thiol carboxylic acid methyl ester) can be any polyol or mixture of polyols that can produce the described thiol containing ester.

In one aspect, the polyol used to produce the hydroxy thiol ester can comprise from 2 to 20 carbon atoms. In other embodiments, the polyol comprises from 2 to 10 carbon atoms; alternatively from 2 to 7 carbon atoms; alternatively from 2 to 5 carbon atoms. In further embodiments, the polyol may be a mixture of polyols having an average of 2 to 20 carbon atoms; alternatively, an average of from 2 to 10 carbon atoms; alternatively, an average of 2 to 7 carbon atoms; alternatively an average of 2 to 5 carbon atoms.

In another aspect, the polyol used to produce the hydroxy thiol ester can have any number of hydroxy groups needed to produce the hydroxy thiol ester as described herein. In some embodiments, the polyol has 2 hydroxy groups; alternatively 3 hydroxy groups; alternatively, 4 hydroxy groups; alternatively, 5 hydroxy groups; or alternatively, 6 hydroxy groups. In other embodiments, the polyol comprises at least 2 hydroxy groups; alternatively at least 3 hydroxy groups; alternatively, at least 4 hydroxy groups; or alternatively, at least 5 hydroxy groups; at least 6 hydroxy groups. In yet other embodiments, the polyol comprises from 2 to 8 hydroxy groups; alternatively, from 2 to 4 hydroxy groups; or alternatively from 4 to 8 hydroxy groups.

In further aspects, the polyol used to produce the hydroxy thiol ester is a mixture of polyols. In an embodiment, the mixture of polyols has an average of at least 1.5 hydroxy groups per polyol molecule. In other embodiments, the mixture of polyols has an average of at least 2 hydroxy groups per polyol molecule; alternatively, an average of at least 2.5 hydroxy groups per polyol molecule; alternatively, an average of at least 3.0 hydroxy groups per polyol molecule; or alternatively, an average of at least 4 hydroxy groups per polyol molecule. In yet another embodiments, the mixture of polyols has an average of 1.5 to 8 hydroxy groups per polyol molecule; alternatively, an average of 2 to 6 hydroxy groups per polyol molecule; alternatively, an average of 2.5 to 5 hydroxy groups per polyol molecule; alternatively, an average of 3 to 4 hydroxy groups per polyol molecule; alternatively, an average of 2.5 to 3.5 hydroxy groups per polyol molecule; or alternatively, an average of 2.5 to 4.5 hydroxy groups per polyol molecule.

In yet another aspect, the polyol or mixture of polyols used to produce the hydroxy thiol ester has a molecular weight or average molecular weight less than 500. In other embodiments, the polyol or mixture of polyols have a molecular weight or average molecular weight less than 300; alternatively less than 200; alternatively, less than 150; or alternatively, less than 100.

The hydroxy thiol carboxylic acid and/or hydroxy thiol carboxylic acid equivalent used to produce the hydroxy thiol ester by contacting a polyol and a hydroxy thiol carboxylic acid and/or hydroxy thiol carboxylic acid equivalent can be any hydroxy thiol carboxylic acid mixture comprising hydroxy thiol carboxylic acids, hydroxy thiol carboxylic acid equivalent or mixture comprising hydroxy thiol carboxylic acid equivalents that can produce the described hydroxy thiol containing ester. When talking about the characteristics hydroxy thiol carboxylic acid equivalent or hydroxy thiol carboxylic acid equivalents, properties such as number of carbon atoms, average number of carbon atom, molecular weight or average molecular weight, number of thiol group, and average number of thiol groups, one will understand the these properties will apply to the portion of the thiol carboxylic acid equivalent which adds to the polyol to form the thiol ester.

In an aspect, the hydroxy thiol carboxylic acid and/or hydroxy thiol carboxylic acid equivalent used to produce the thiol ester comprises from 2 to 28 carbon atoms. In an embodiment, the hydroxy thiol carboxylic acid and/or hydroxy thiol carboxylic acid equivalents comprises from 4 to 26 carbon atoms; alternatively, from 8 to 24 carbon atoms; alternatively, from 12 to 24 carbon atoms; or alternatively, from 14 to 20 carbon atoms. In other embodiments, a mixture comprising hydroxy thiol carboxylic acids and/or mixture comprising hydroxy thiol carboxylic acid equivalents has an average of 2 to 28 carbon atoms per carboxylic acid and/or carboxylic acid equivalent; alternatively, from 4 to 26 carbon per carboxylic acid and/or carboxylic acid equivalent; alternatively, from 8 to 24 carbon atoms per carboxylic acid and/or carboxylic acid equivalent; alternatively, from 12 to 24 carbon atoms per carboxylic acid and/or carboxylic acid equivalent; or alternatively, from 14 to 20 carbon atoms per carboxylic acid and/or carboxylic acid equivalent.

In another aspect, the hydroxy thiol carboxylic acid and/or hydroxy thiol carboxylic acid equivalent used to produce the thiol ester has at least 1 thiol group, alternatively 2 thiol groups. In some embodiments, a mixture comprising hydroxy thiol carboxylic acids and/or mixture comprising hydroxy thiol carboxylic acid equivalents has an average of from 0.5 to 3 thiol groups per carboxylic acid and/or carboxylic acid equivalent; alternatively, an average of from 1 to 2 thiol groups per carboxylic acid and/or carboxylic acid equivalent.

In another aspect, the hydroxy thiol carboxylic acid and/or hydroxy thiol carboxylic acid equivalent used to produce the thiol ester has at least 1 hydroxy group; alternatively, at least 2 hydroxy groups. In some embodiments, a mixture comprising hydroxy thiol carboxylic acids and/or mixture comprising hydroxy thiol carboxylic acid equivalents has an average of from 0.5 to 3 hydroxy groups per carboxylic acid and/or carboxylic acid equivalent; alternatively, an average of from 1 to 2 hydroxy groups per carboxylic acid and/or carboxylic acid equivalent.

In another aspect, the hydroxy thiol carboxylic acid and/or hydroxy thiol carboxylic acid equivalent used to produce the hydroxy thiol ester has a molecular weight greater than 100; alternatively greater than 180; alternatively greater than 240; or alternatively greater than 260. In other embodiments, the hydroxy thiol carboxylic acid and/or hydroxy thiol carboxylic acid equivalent has a molecular weight from 100 to 500; alternatively, from 120 to 420; alternatively, from 180 to 420; alternatively, from 240 to 420; a mixture or alternatively, from 260 to 360. In some embodiments, a mixture comprising hydroxy thiol carboxylic acids and/or mixture comprising hydroxy thiol carboxylic acid equivalents has an average molecular weight greater than 100 per carboxylic acid and/or carboxylic acid equivalent; alternatively greater than 180 per carboxylic acid and/or carboxylic acid equivalent; alternatively greater than 240 per carboxylic acid and/or carboxylic acid equivalent; or alternatively greater than 260 per carboxylic acid and/or carboxylic acid equivalent. In yet other embodiments, the mixture comprising hydroxy thiol carboxylic acid and/or mixture comprising hydroxy thiol carboxylic acid equivalents has an average molecular weight from 100 to 500 per carboxylic acid and/or carboxylic acid equivalent; alternatively, from 120 to 420 per carboxylic acid and/or carboxylic acid equivalent; alternatively, from 180 to 420 per carboxylic acid and/or carboxylic acid equivalent; alternatively, from 240 to 420 per carboxylic acid and/or carboxylic acid equivalent; a mixture or alternatively, from 260 to 360 per carboxylic acid and/or carboxylic acid equivalent.

In some aspects, the reaction between the polyol and the hydroxy thiol containing carboxylic acid and/or hydroxy thiol containing carboxylic acid derivative occurs in the presence of a solvent. In other aspects, the reaction between the polyol and the hydroxy thiol containing carboxylic acid and/or hydroxy thiol containing carboxylic acid derivative occurs in the substantial absence of a solvent. In aspects wherein the reaction between the polyol and the hydroxy thiol containing carboxylic acid and/or hydroxy thiol containing carboxylic acid derivative occurs in the presence of a solvent, the solvent is selected from the group consisting of an aliphatic hydrocarbon, an ether, an aromatic compound, or any combination thereof. Generally, the solvent, regardless of its chemical class, includes from 1 to 20 carbon atoms; alternatively, from 3 to 10 carbon atoms. When the solvent includes the aliphatic hydrocarbon, the aliphatic hydrocarbon is butane, isobutane, pentane, hexane, heptane, octane, or any mixture thereof. When the solvent includes the aromatic compound, the aromatic compound is benzene, toluene, xylene, ethylbenzene, or any mixture thereof. When the solvent includes the ether, the ether is diethyl ether, dipropyl ether, tetrahydrofuran, and any mixture thereof.

When a solvent is used for the reaction between the polyol and the hydroxy thiol containing carboxylic acid and/or hydroxy thiol containing carboxylic acid derivative, the quantity of solvent can be any amount that facilitates the reaction. In some embodiments, the mass of the solvent is less than 30 times the mass of the hydroxy thiol containing carboxylic acid and/or hydroxy thiol containing carboxylic acid derivative. In other embodiments, the mass of the solvent is less than 20 times the mass of the hydroxy thiol ester; alternatively, less than 15 times the mass of the hydroxy thiol containing carboxylic acid and/or hydroxy thiol containing carboxylic acid derivative; alternatively, less than 10 times the mass of the hydroxy thiol containing carboxylic acid and/or hydroxy thiol containing carboxylic acid derivative; or alternatively, less than 5 times the mass of the hydroxy thiol containing carboxylic acid and/or hydroxy thiol containing carboxylic acid derivative. In other embodiments, the mass of the solvent is from 2 times to 20 times the mass of the hydroxy thiol containing carboxylic acid and/or hydroxy thiol containing carboxylic acid derivative; alternatively, from 3 times to 15 times the mass of the hydroxy thiol containing carboxylic acid and/or hydroxy thiol containing carboxylic acid derivative; or alternatively, from 5 times to 10 times the mass of the hydroxy thiol containing carboxylic acid and/or hydroxy thiol containing carboxylic acid derivative.

The equivalents of hydroxy thiol containing carboxylic acid derivative and/or hydroxy thiol containing carboxylic acid derivative carboxylic acid groups to equivalents of polyol hydroxy groups molar ratio (hereinafter referred to as "carboxylic acid group to polyol hydroxy group molar ratio") utilized in the process to produce the hydroxy thiol ester can be any carboxylic acid group to polyol hydroxy group molar ratio that produces the desired hydroxy thiol ester. In some embodiments, the carboxylic acid group to polyol hydroxy group molar ratio is greater than 0.4. In other embodiments, the carboxylic acid group to polyol hydroxy group molar ratio is greater than 0.6; alternatively, greater than 0.8; alternatively, greater than 1; or alternatively, greater than 1.1. In other embodiments, the carboxylic acid group to polyol hydroxy group molar ratio ranges from 0.4 to 1.3; alternatively, from 0.6 to 1.2, or alternatively, from 0.8 to 1.1.

In some aspects, the reaction between the polyol and the hydroxy thiol containing carboxylic acid and/or hydroxy thiol containing carboxylic acid derivative is catalyzed. In some embodiments, the catalyst is a mineral acid, such as sulfuric or phosphoric acid. In other embodiments, the catalyst is an organic acid. In embodiments, for example, the organic acid is methane sulfonic acid or toluene sulfonic acid. Other suitable types of catalyst will be apparent to those of skill in the art and are to be considered within the scope of the present invention.

The reaction of the polyol and the hydroxy thiol containing carboxylic acid and/or hydroxy thiol containing carboxylic acid derivative can occur in a batch reactor or a continuous reactor, as described herein. The reaction between the polyol and the hydroxy thiol containing carboxylic acid and/or hydroxy thiol containing carboxylic acid derivative can be performed at any temperature capable of forming the hydroxy thiol ester. In some embodiments, the polyol and the hydroxy thiol containing carboxylic acid and/or hydroxy thiol containing carboxylic acid derivative can be reacted at a temperature greater than 20° C. In other embodiments, the polyol and the hydroxy thiol containing carboxylic acid and/or hydroxy thiol containing carboxylic acid derivative can be reacted at a temperature greater than 50° C.; alternatively, greater than 75° C.; or alternatively, greater than 100° C. In yet other embodiments, the polyol and the hydroxy thiol containing carboxylic acid and/or hydroxy thiol containing carboxylic acid derivative can be reacted at a temperature from 20° C. to 250° C.; alternatively, from 50° C. to 200° C.; alternatively, from 75° C. to 175° C.; or alternatively, from 100° C. to 150°.

The time required for the reaction of the polyol and the hydroxy thiol containing carboxylic acid and/or hydroxy thiol containing carboxylic acid derivative can be any time required to form the described hydroxy thiol ester composition. Generally, the reaction time is at least 5 minutes. In some embodiments, the reaction time is at least 30 minutes; alternatively, at least 1 hour; or alternatively, at least 2 hours. In yet other embodiments, the reaction time ranges from 5 minutes to 72 hours; alternatively, from 30 minutes to 48 hours; alternatively, from 1 hour minutes to 36 hours; or alternatively, from 2 hours and 24 hours.

The reaction between the polyol and the hydroxy thiol containing carboxylic acid and/or hydroxy thiol containing carboxylic acid derivative can be performed at any reaction pressure that maintains the polyol and the hydroxy thiol containing carboxylic acid and/or hydroxy thiol containing carboxylic acid derivative in a liquid state. In some embodiments, the reaction pressure ranges from 0 psia to 2000 psia. In other embodiments, the reaction pressure ranges from 0 psia to 1000 psia; alternatively, from 0 psia and 500 psia; or alternatively, from 0 psia to 300 psia.

In some embodiments, the process to produce the hydroxy thiol ester composition by reacting a polyol and the hydroxy thiol containing carboxylic acid and/or hydroxy thiol containing carboxylic acid derivative can further include a step to remove excess or residual polyol, hydroxy thiol containing carboxylic acid, and/or hydroxy thiol containing carboxylic acid derivative once the polyol has reacted with the hydroxy thiol containing carboxylic acid or hydroxy thiol containing carboxylic acid derivative. In some embodiments, the thiol ester is vacuum stripped. In some embodiments, the hydroxy thiol ester is vacuum stripped at a temperature between 25° C. and 250° C.; or alternatively, between 50° C. and 200° C. In other embodiments, the hydroxy thiol ester is sparged with an inert gas to remove excess polyol, hydroxy thiol containing carboxylic acid, and/or hydroxy thiol containing carboxylic acid derivative. In some embodiments, the hydroxy thiol ester is sparged with an inert gas at a temperature between 25° C. and 250° C., or alternatively, between 50° C. and 200° C. In some aspects, the inert gas is nitrogen. Generally, the stripped or sparged hydroxy thiol ester oil comprises less than 5 excess polyol, hydroxy thiol containing carboxylic acid, or hydroxy thiol containing carboxylic acid derivative. In other embodiments, the stripped or sparged hydroxy thiol ester oil comprises less than 2 weight percent excess polyol, hydroxy thiol containing carboxylic acid, and/or hydroxy thiol containing carboxylic acid derivative; less than 1 weight percent excess polyol, hydroxy thiol containing carboxylic acid, and/or hydroxy thiol containing carboxylic acid derivative; or alternatively, less than 0.5 weight percent excess polyol, hydroxy thiol containing carboxylic acid, and/or hydroxy thiol containing carboxylic acid derivative.

Method of Making Thioacrylate Esters

A method of making a thioacrylate containing ester composition is advantageously provided as another embodiment of the present invention. The process for producing the thioacrylate containing ester comprising contacting a thiol ester with an acrylate and converting at least one thiol group to a thiol acrylate group. The process can be applied to any of the thiol esters described herein and used to any thioacrylate ester described herein. The process for producing the thioacrylate ester can also include any additional process steps or process conditions described herein.

The acrylate compound can be any acrylate compound capable of reacting with a thiol group to form the thiol acrylate group. In some embodiments, the acrylate compound can be an acrylic halide. In other embodiments, the acrylate compound can be an acrylic acid. In yet other embodiments, the acrylate compound can be an acrylic anhydride.

In some embodiments of the present invention, the acrylate composition has the following structure:

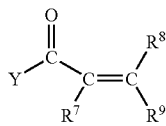

In the acrylate composition structure, Y is selected from the group consisting of hydrogen, a halogen, and $OR^4$; and $R^7$, $R^8$, and $R^9$ are independently selected from the group consisting of hydrogen, $C_1$ to $C_{20}$ organyl groups, and $C_1$ to $C_{20}$ hydrocarbyl groups. In further embodiments, $R^7$, $R^8$, and $R^9$ are selected from hydrogen, $C_1$ to $C_{10}$ organyl groups, and $C_1$ to $C_{10}$ hydrocarbyl groups; or alternatively, selected from $C_1$ to $C_5$ organyl groups, and $C_1$ to $C_5$ hydrocarbyl groups. In certain embodiments, $R^7$, $R^8$, and $R^9$ are independently selected from the group consisting of hydrogen and a methyl group. In some specific embodiments, $R^8$ and $R^9$ are hydrogen and $R^7$ is selected from hydrogen, a methyl group or a mixture thereof; alternatively, $R^8$ and $R^9$ are hydrogen and $R^7$ is a methyl group; or alternatively, $R^7$, $R^8$, and $R^9$ are hydrogen. In some embodiments, $R^4$ is independently selected from the group consisting of $C_1$ to $C_{20}$ organyl groups, and $C_1$ to $C_{20}$ hydrocarbyl groups; alternatively, from $C_1$ to $C_{10}$ organyl groups, and $C_1$ to $C_{10}$ hydrocarbyl groups; or alternatively, selected from $C_1$ to $C_5$ organyl groups, and $C_1$ to $C_5$ hydrocarbyl groups.

In other embodiments, the acrylate compound can be an acrylic anhydride having the structure:

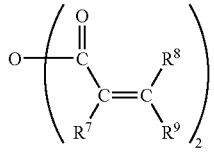

In this acrylic anhydride structure, Y is selected from the group consisting of hydrogen, a halogen, and $OR^4$; and $R^7$, $R^8$, and $R^9$ are independently selected from the group consisting of hydrogen, $C_1$ to $C_{20}$ organyl groups, and $C_1$ to $C_{20}$ hydrocarbyl groups. In further embodiments, $R^7$, $R^8$, and $R^9$ are selected from hydrogen, $C_1$ to $C_{10}$ organyl groups, and $C_1$ to $C_{10}$ hydrocarbyl groups; or alternatively, selected from $C_1$ to $C_5$ organyl groups, and $C_1$ to $C_5$ hydrocarbyl groups. In certain embodiments, $R^7$, $R^8$, and $R^9$ are independently selected from the group consisting of hydrogen and a methyl group. In some specific embodiments, $R^8$ and $R^9$ are hydrogen and $R^7$ is selected from hydrogen, a methyl group or a mixture thereof; alternatively, $R^8$ and $R^9$ are hydrogen and $R^7$ is a methyl group; or alternatively, $R^7$, $R^8$, and $R^9$ can be hydrogen. In some embodiments, $R^4$ is independently selected from the group consisting of $C_1$ to $C_{20}$ organyl groups, and $C_1$ to $C_{20}$ hydrocarbyl groups; alternatively, from $C_1$ to $C_{10}$ organyl groups, and $C_1$ to $C_{10}$ hydrocarbyl groups; or alternatively, selected from $C_1$ to $C_5$ organyl groups, and $C_1$ to $C_5$ hydrocarbyl groups.

In some embodiments of the present invention, the Y within the acrylate composition can be a halide. For example, the halide can be chlorine, bromine and iodine. The acrylate composition can include acryloyl chloride, methacryloyl chloride and mixtures thereof. The acrylic anhydrides compounds can include acrylic anhydride, methacrylic anhydride, or mixtures thereof.

In some aspects, the conversion of the thiol group to a thioacrylate group occurs in the presence of a solvent. In other aspects the conversion of the thiol group to a thioacrylate group occurs in the substantial absence of a solvent. In aspects wherein the conversion of the thiol group to a thioacrylate group occurs in the presence of a solvent, the solvent may be an aliphatic hydrocarbon, an ether, and aromatic compound. Generally, the solvent, regardless of its chemical class, includes from 1 to 20 carbon atoms; or alternatively, from 3 to 10 carbon atoms. When the solvent includes the aliphatic hydrocarbon, the aliphatic hydrocarbon is butane, isobutane, pentane, hexane, heptane, octane, or any mixture thereof. When the solvent includes the aromatic compound, the aromatic compound is benzene, toluene, xylene, ethylbenzene, or any mixture thereof. When the solvent includes the ether, the ether is diethyl ether, dipropyl ether, tetrahydrofuran, or any mixture thereof.

When a solvent is used for the conversion of the thiol group to a thioacrylate group, the quantity of solvent can be any amount that facilitates the reaction. In some embodiments, the mass of the solvent is less than 30 times the mass of the thiol ester. In other embodiments, the mass of the solvent is less than 20 times the mass of the thiol ester; alternatively, less than 15 times the mass of the thiol ester; alternatively, less than 10 times the mass of the thiol ester; or alternatively, less than 5 times the mass of the thiol ester. In other embodiments, the mass of the solvent is from 2 times to 20 times the mass of the thiol ester; alternatively, from 3 times to 15 times the mass of the thiol ester; alternatively, 4 times to 15 times the mass of the thiol ester; or alternatively, from 5 times to 10 times the mass of the thiol ester.

In some aspects the conversion of the thiol group to the thioacrylate group occurs in the presence of a catalyst. In some embodiments, the catalyst is homogeneous. In some embodiments, the catalyst is an organic amine. Examples of suitable organic amines include triethylamine, tripropylamine, tributylamine, and pyridine. In other embodiments, the catalyst is heterogeneous. Examples of suitable catalysts include Amberlyst A-21 and Amberlyst A-26. Other suitable catalysts will be apparent to those of skill in the art and are to be considered within the scope of the present invention.

The conversion of the thiol group to a thioacrylate group can be performed at any conversion temperature that is capable of converting the thiol group to a thioacrylate group. In some embodiments, the conversion temperature is greater than −20° C. In other embodiments, the conversion temperature is greater than 0° C.; alternatively, greater than 20° C.;

alternatively, greater than 50° C.; alternatively, greater than 80° C.; or alternatively, greater than 100° C. In yet other embodiments, the conversion temperature ranges from −20° C. to 250° C.; alternatively, from 20° C. to 200° C.; or alternatively, from 50° C. to 150° C.

The conversion time required for the conversion of the thiol group to a thioacrylate group can be any time required to form the described thioacrylate containing ester. Generally, the conversion time is at least 5 minutes. In some embodiments, the conversion time is at least 15 minutes; alternatively, at least 30 minutes; alternatively, at least 45 minutes; or alternatively, at least 1 hour. In other embodiments, the conversion time ranges from 15 minutes to 12 hours; alternatively, from 30 minutes to 6 hours; or alternatively, from 45 minutes to 3 hours.

The conversion of the thiol group to a thioacrylate group can be performed at any conversion pressure that maintains the thiol ester and the acrylate compound in the liquid state. In some embodiments, the conversion pressure ranges from 0 psia to 2000 psia. In other embodiments, the conversion pressure ranges from 0 psia to 1000 psia; or alternatively, from 0 psia to 500 psia.

Process for Producing Cross-Linked Thiol Ester

As an embodiment of the present invention, a process for producing a cross-linked thiol ester composition is advantageously provided. Minimally, in some embodiments, the process to produce the cross-linked thiol ester composition comprises contacting a thiol ester composition with an oxidizing agent and reacting the thiol ester composition and an oxidizing agent to form the thiol ester oligomer having at least two thiol ester monomers connected by a polysulfide linkage having the structure —$S_Q$—, wherein Q is an integer greater than 1. The disclosed method may be applied to any thiol ester described herein to produce any cross-linked thiol ester composition as described herein. The process to produce the cross-linked thiol ester composition can also include any additional process steps or process conditions as described herein.

In an aspect, the oxidizing agent can be elemental sulfur, oxygen, or hydrogen peroxide. In some embodiments, the oxidizing agent can be elemental sulfur. In other embodiments, the oxidizing agent can be oxygen. In some oxygen oxidizing agent embodiments, the oxidizing agent is air. In further embodiments, the oxidizing agent is hydrogen peroxide.

When elemental sulfur is used as the oxidizing agent, the quantity of elemental sulfur utilized to form the cross-linked thiol ester composition is determined as a function of the thiol sulfur content of the thiol ester composition. In an aspect, the weight ratio of elemental sulfur to thiol sulfur in the thiol ester composition is at least 0.5. In some embodiments, the weight ratio of elemental sulfur to thiol sulfur in the thiol ester composition is at least 5; alternatively, at least 10, alternatively, at least 15, or alternatively, at least 20. In other embodiments, the weight ratio of elemental sulfur to thiol sulfur in the thiol ester composition ranges from 0.5 to 32; alternatively, ranges from 1 to 24; alternatively, ranges from 2 to 16; or alternatively, ranges from 3 to 10.

In an aspect, the reaction of the thiol ester and elemental sulfur occurs in the presence of a catalyst. The catalyst can be any catalyst that catalyzes the formation of the polysulfide linkage between at least two thiol ester monomers. In some embodiments, the catalyst is an amine. In further embodiments, the catalyst is a tertiary amine.

The formation of the cross-linked thiol ester can occur in a batch reactor or a continuous reactor, as described herein. The formation of the cross-linked thiol ester can occur at any temperature capable of forming the thiol ester. In some embodiments, the formation of the cross-linked thiol ester can occurs at a temperature greater than 25° C. In other embodiments, the formation of the cross-linked thiol ester can occurs at a temperature greater than 50° C.; alternatively, greater than 70° C.; or alternatively, greater than 80° C. In yet other embodiments, the formation of the cross-linked thiol ester occurs at a temperature from 25° C. to 150° C.; alternatively, from 50° C. to 150° C.; alternatively, from 70° C. to 120° C.; or alternatively, from 80° C. to 110° C.

The time required to form the cross-linked thiol ester can be any time required to form the desired cross-linked thiol ester. Generally, the time required to form the cross-linked thiol ester is at least 15 minutes. In some embodiments, the time required to form the cross-linked thiol ester is at least 30 minutes; alternatively, at least 1 hour; or alternatively, at least 2 hours. In yet other embodiments, the time required to form the cross-linked thiol ester ranges from 15 minutes to 72 hours; alternatively, from 30 minutes to 48 hours; alternatively, from 1 hour minutes to 36 hours; or alternatively, from 2 hours and 24 hours.

In embodiments, the process to produce the cross-linked thiol ester further comprises a step to remove residual hydrogen sulfide. In some embodiments the cross-linked thiol ester is vacuum stripped. In some embodiments, the cross-linked thiol ester is vacuum striped at a temperature between 25° C. and 250° C.; alternatively, between 50° C. and 200° C.; or alternatively, 75 and 150° C. In some embodiments, the cross-linked thiol ester oil is sparged with an inert gas to remove residual hydrogen sulfide. In other embodiments, the cross-linked thiol ester is sparged with an inert gas at a temperature between 25° C. and 250° C.; alternatively, between 50° C. and 200° C.; or alternatively, between 75 and 150° C. In yet other embodiments, the vacuum stripping is performed while sparging the cross-linked thiol ester with an inert gas. In yet other embodiments, the vacuum stripping is performed while sparging the cross-linked thiol ester an inert gas at a temperature between 25° C. and 250° C.; alternatively, between 50° C. and 200° C.; or alternatively, 75 and 150° C. In some embodiments, the inert gas is nitrogen.

Generally, the stripped or sparged cross-linked thiol ester comprises less than 0.1 weight percent hydrogen sulfide. In other embodiments, the stripped or sparged thiol-containing ester oil comprises less than 0.05 weight percent hydrogen sulfide; alternatively, less than 0.025 weight percent hydrogen sulfide; or alternatively, less than 0.01 weight percent hydrogen sulfide.

Process for Preparing Sulfide-Containing Ester Composition

The present invention advantageously provides processes for producing sulfide-containing esters as embodiments of the present invention. Generally, the sulfide-containing esters can be prepared by two processes. As an embodiment of the present invention, the first process used to produce a sulfide-containing ester comprises contacting an unsaturated ester and a mercaptan and reacting the unsaturated ester and mercaptan to form a sulfide-containing ester. As another embodiment of the present invention, the second process used to produce a sulfide-containing ester comprises contacting an epoxidized unsaturated ester and a mercaptan sulfide and reacting the unsaturated ester and mercaptan to form a sulfide-containing ester. Additional aspects of the two sulfide-containing ester production processes are described below.

Sulfide-Containing Esters from Unsaturated Esters

The sulfide-containing esters and sulfide-containing ester compositions described herein can be produced by a process comprising contacting a mercaptan and an unsaturated ester and reacting the mercaptan and the unsaturated ester to form a sulfide-containing ester. The process can be applied to any of the unsaturated esters and mercaptans described herein. The process for producing the sulfide-containing ester can also include any additional process steps or process conditions described herein. Additionally, the process for producing the sulfide-containing ester can form any sulfide-containing ester described herein.

In some aspects, the reaction between the mercaptan and the unsaturated ester occurs in the presence of a solvent. In other aspects the reaction between the mercaptan and the unsaturated ester occurs in the substantial absence of a solvent. When the reaction occurs in the presence of a solvent, the solvent is selected from an aliphatic hydrocarbon, an ether, an aromatic compound, an alcohol, or any combination thereof. Generally, the solvent, regardless of its chemical class, can comprise from 1 to 20 carbon atoms; alternatively, from 3 to 10 carbon atoms. When the solvent includes an aliphatic hydrocarbon, the aliphatic hydrocarbon is butane, isobutane, pentane, hexane, heptane, octane, or any mixture thereof. When the solvent includes an aromatic compound, the aromatic compound is benzene, toluene, xylene, ethylbenzene, or any mixture thereof. When the solvent includes an alcohol, the alcohol is methanol, 1-propanol, 2-propanol, 1-butanol, 2-butanol, 2-methyl-2-proanol, or any mixture thereof. When the solvent includes an ether, the ether is diethyl ether, dipropyl ether, tetrahydrofuran, or any mixture thereof.

When a solvent is used for the reaction between the mercaptan and the unsaturated ester, the quantity of solvent can be any amount that facilitates the reaction, as understood by those of skill in the art. In some embodiments, the mass of the solvent is less than 30 times the mass of the unsaturated ester. In other embodiments, the mass of the solvent is less than 20 times the mass of the unsaturated ester; alternatively, less than 15 times the mass of the unsaturated ester; alternatively, less than 10 times the mass of the unsaturated ester; or alternatively, less than 5 times the mass of the unsaturated ester. In other embodiments, the mass of the solvent is from 2 times to 20 times the mass of the unsaturated ester; alternatively, from 3 times to 15 times the mass of the unsaturated ester; alternatively, from 4 times to 15 times the mass of the unsaturated ester; or alternatively, from 5 times to 10 times the mass of the unsaturated ester.

The molar ratio of mercaptan to molar equivalents of unsaturated ester carbon-carbon double bonds (herein after "mercaptan to carbon-carbon double bond molar ratio") utilized in the process to produce the sulfide-containing ester can be any mercaptan to carbon-carbon double bond molar ratio that produces the desired sulfide-containing ester. The molar equivalents of unsaturated ester carbon-carbon double bonds is calculated by the equation:

$$\frac{UES\ Mass}{UES\ GMW} \times UES\ C=C$$

In this equation, UES GMW is the average gram molecular weight of the unsaturated ester, UES Mass is the mass of the unsaturated ester, and UES C=C is the average number of double bonds per unsaturated ester molecule. In some embodiments, the mercaptan to carbon-carbon double bond molar ratio is greater than 0.25. In other embodiments, the mercaptan to carbon-carbon double bond molar ratio is greater than 0.5; alternatively, greater than 0.75; alternatively, greater than 1; alternatively, greater than 1.25; or alternatively, greater than 1.5. In other embodiments, the mercaptan to carbon-carbon double bond molar ratio can range from 0.25 to 2; alternatively, from 0.5 to 1.5, or alternatively, from 0.75 to 1.25.

In some aspects the reaction between the mercaptan and the unsaturated ester is catalyzed. The reaction of the mercaptan and the unsaturated ester can be catalyzed by a heterogeneous catalyst or homogeneous catalyst, as described herein. In some aspects, the reaction between the mercaptan and the unsaturated ester is initiated by a free radical initiator or ultraviolet radiation, as described herein.

When the heterogeneous catalyst is used, the heterogeneous acid catalyst is selected from the group consisting of acid clays, zeolites, cobalt/molybdenum oxide supported catalysts, and nickel/molybdenum supported oxide catalysts. Examples of suitable catalysts are described herein.

The free radical initiator can be any free radical initiator capable of forming free radicals under thermal or light photolysis. Generally, the free radical initiator is selected from the general class of compounds having a —N═N— group or a —O—O— group. Specific classes of free radical initiators include diazo compounds, dialkyl peroxides, hydroperoxides, and peroxy esters. Specific initiators include azobenzene, 2,2'-azobis(2-methylpropionitrile), 4,4'-azobis(4-cyanovaleric acid), 1,1'-azobis(cyclohexanecarbo-nitrile), 2,2'-azobis(2methylpropane), 2,2'-azobis(2-methylpropionamidine)dihydro-chloride, methylpropionitrile, azodicarboxamide, tert-butyl hydroperoxide, di-tert-butyl peroxide, octylperbenzoate. In some embodiments, the free radical initiated reaction of the mercaptan and the unsaturated ester is performed at a reaction temperature within ±50° C. of the 1 hour half life of the free radical initiator. In other embodiments, the reaction temperature is within ±25° C. of the 1 hour half life of the free radical initiator; alternatively, the reaction temperature is within ±20° C. of the 1 hour half life of the free radical initiator; alternatively, the reaction temperature is within ±15° C. of the 1 hour half life of the free radical initiator; or alternatively, the reaction temperature is within ±10° C. of the 1 hour half life of the free radical initiator. In embodiments where the free radical initiated reaction of the mercaptan and the unsaturated ester is initiated by light photolysis, the light can be any light capable creating free radicals. In some embodiments, the light is UV radiation. Other sources of light capable of creating free radicals will be apparent to those of skill in the art and are to be considered within the scope of the present invention.

In another aspect, the reaction of the mercaptan and the unsaturated ester is initiated by UV radiation. In these embodiments, the UV radiation may be any UV radiation capable of initiating the reaction of the mercaptan and the unsaturated ester. In some embodiments, the UV radiation is generated by a medium pressure mercury lamp.

The reaction of the mercaptan and the unsaturated ester can occur in a batch reactor of a continuous reactor. Any of the batch or continuous reactors described herein can be used in this reaction. Other suitable reactors will be apparent to those of skill in the art and are to be considered within the scope of the present invention.

The reaction time for reacting the mercaptan and the unsaturated ester can be any time required to form the sulfide-containing ester. Generally, the reaction time is at least 5 minutes. In some embodiments, the reaction time ranges from 5 minutes to 72 hours; alternatively, from 10 minutes to 48 hours; or alternatively, from 15 minutes to 36 hours.

In some embodiments, the process to produce the sulfide-containing ester further comprises a step to remove any residual mercaptan that remains after reacting the mercaptan and the unsaturated ester. In some embodiments, the sulfide-containing ester is vacuum stripped to remove the residual mercaptan. In some embodiments, the sulfide-containing ester is vacuum stripped at a temperature between 25° C. and 250° C.; or alternatively, between 50° C. and 200° C. In other embodiments, the sulfide-containing ester is sparged with an inert gas to remove the residual mercaptan. In some embodiments, the sulfide-containing ester is sparged with an inert gas at a temperature between 25° C. and 250° C.; or alternatively, between 50° C. and 200° C. In some aspects, the inert gas is nitrogen. Generally, the stripped or sparged sulfide-containing ester comprises less than 5 weight percent of the mercaptan. In other embodiments, the stripped or sparged sulfide-containing ester comprises less than 2 weight percent of the mercaptan; alternatively, less than 1 weight percent of the mercaptan; or alternatively, less than 0.5 weight percent of the mercaptan.

The reaction between the mercaptan and the unsaturated ester can be performed at any temperature capable of forming the sulfide-containing ester. In some embodiments, the mercaptan and the unsaturated ester can be reacted at a reaction temperature of greater than −20° C. In other embodiments, the reaction temperature is greater than 0° C.; alternatively, greater than 20° C.; alternatively, greater than 50° C.; alternatively, greater than 80° C.; or alternatively, greater than 100° C. In yet other embodiments, the mercaptan and the unsaturated ester can be reacted at a temperature from −20° C. to 250° C.; alternatively, from 20° C. to 200° C.; or alternatively, from 80° C. to 160° C.

The reaction between the mercaptan and the unsaturated ester can be performed at any pressure that maintains the mercaptan and the unsaturated ester in a substantially liquid state. In some embodiments, the mercaptan and the unsaturated ester can be performed at a reaction pressure ranging from 0 psig to 2000 psig. In other embodiments, the reaction pressure ranges from 0 psig to 1000 psig; alternatively, from 0 psig to 500 psig; or alternatively, from 0 psig to 200 psig.

Using the disclosed process, sulfide-containing ester having a low carbon-carbon double bond to sulfide group molar ratio can be produced. In an aspect, the process for producing the sulfide-containing ester forms a sulfide-containing ester having a carbon-carbon double bond to thiol group molar ratio of less than 1.5. Additional carbon-carbon double bond to sulfide group molar ratios are disclosed herein.

In other aspects, the process producing the sulfide-containing ester includes producing sulfide-containing ester molecules having an average of at least 40 percent of the sulfide-containing ester side chains comprise a sulfide group. Additional embodiments wherein the sulfide-containing ester comprises a percentage of sulfide-containing ester side chains are described herein.

Sulfide-Containing Esters from Epoxidized Unsaturated Esters

As another embodiment of the present invention, another process for producing a class of sulfide-containing esters, which includes hydroxy sulfide-containing esters, is advantageously provided. In this embodiment, the hydroxy sulfide-containing esters and hydroxy sulfide-containing ester compositions can be produced by a process comprising the steps of contacting a mercaptan and an epoxidized unsaturated ester and reacting the mercaptan and the epoxidized unsaturated ester to produce or form the hydroxy sulfide-containing ester. The process can be applied to any mercaptan and/or any epoxidized unsaturated esters described herein. The process for producing the hydroxy sulfide-containing ester can also include any additional process steps or process conditions as described herein. Additionally, the process for producing the hydroxy sulfide-containing ester can form any hydroxy sulfide-containing ester as described herein.

In some aspects, the reaction between the mercaptan and the unsaturated ester occurs in the presence of a solvent. In other aspects the reaction between the mercaptan and the unsaturated ester occurs in the substantial absence of a solvent. When the reaction occurs in the presence of a solvent, the solvent is selected from an aliphatic hydrocarbon, an ether, an aromatic compound, or any combination thereof. Generally, the solvent, regardless of its chemical class, can comprise from 1 to 20 carbon atoms; alternatively, from 3 to 10 carbon atoms. When the solvent includes an aliphatic hydrocarbon, the aliphatic hydrocarbon is butane, isobutane, pentane, hexane, heptane, octane, or any mixture thereof. When the solvent includes an aromatic compound, the aromatic compound is benzene, toluene, xylene, ethylbenzene, or any mixture thereof. When the solvent includes an ether, the ether is diethyl ether, dipropyl ether, tetrahydrofuran, or any mixture thereof.

When a solvent is used for the reaction between the mercaptan and the epoxidized unsaturated ester, the quantity of solvent can be any amount that facilitates the reaction, as understood by those of skill in the art. In some embodiments, the mass of the solvent is less than 30 times the mass of the epoxidized unsaturated ester. In other embodiments, the mass of the solvent is less than 20 times the mass of the epoxidized unsaturated ester; alternatively, less than 15 times the mass of the epoxidized unsaturated ester; alternatively, less than 10 times the mass of the epoxidized unsaturated ester; or alternatively, less than 5 times the mass of the epoxidized unsaturated ester. In other embodiments, the mass of the solvent is from 2 times to 20 times the mass of the epoxidized unsaturated ester; alternatively, from 3 times to 15 times the mass of the epoxidized unsaturated ester; alternatively, from 4 times to 15 times the mass of the epoxidized unsaturated ester; or alternatively, from 5 times to 10 times the mass of the epoxidized unsaturated ester.

The reaction of the mercaptan and the epoxidized unsaturated ester can occur using any mercaptan to molar equivalents of epoxide groups in the epoxidized unsaturated ester (hereinafter referred to as "mercaptan to epoxide group molar ratio") that is capable of producing the herein described α-hydroxy thiol esters. The molar equivalents of epoxidized unsaturated ester epoxidized groups can be calculated by the equation:

$$\frac{EUES\ Mass}{EUES\ GMW} \times EUES\ Epoxide$$

In this equation, EUES GMW is the average gram molecular weight of the epoxidized unsaturated ester, EUES Mass is the mass of the epoxidized unsaturated ester, and EUES Epoxide is the average number of epoxide groups per epoxidized unsaturated ester molecule. In some embodiments, the mercaptan to epoxide group molar ratio is greater than 0.2. In other embodiments, the mercaptan to epoxide group molar ratio is greater than 0.5; alternatively, greater than 1; or alternatively, greater than 2. In other embodiments, the hydrogen sulfide to epoxide group molar ratio ranges from 0.2 to 10; alternatively, from 0.5 to 8; alternatively, from 0.75 to 5; or alternatively, from 1 to 3.

In some aspects, the reaction of the mercaptan and the epoxidized unsaturated ester occurs in the presence of a catalyst. Generally, the catalyst is any catalyst that is capable of catalyzing the reaction of the mercaptan and the epoxidized unsaturated ester to produce the desired hydroxy thiol ester. In one aspect, the catalyst is selected from the group consisting of homogeneous and heterogeneous catalysts. In other aspects, the catalyst is selected from the group consisting of zeolites, heterogeneous catalysts, homogeneous catalysts, and mixtures thereof. In another aspect, the catalyst is an amine. In other aspects, the catalyst is selected from the group consisting of cyclic conjugated amines, 1,8-diazabicylco[5.4.0]undec-7-ene, 1,5-diazabicylco[4.3.0]non-5-ene, and mixtures thereof.

In some aspects, the reaction of the mercaptan and the epoxidized unsaturated ester occurs in the presence of a catalyst. Generally, the catalyst is any catalyst that is capable of catalyzing the reaction of the mercaptan and the epoxidized unsaturated ester to produce the desired hydroxy thiol ester. In some embodiments the catalyst is an organic base. In some embodiments, the catalyst can be 1,8-diazabicyclo[5.4.0]undec-7-ene. (What other catalysts may be used?)

The reaction of the mercaptan and the epoxidized unsaturated ester can occur in a batch reactor of a continuous reactor. Any of the batch or continuous reactors described herein can be used in this reaction. Other suitable reactors will be apparent to those of skill in the art and are to be considered within the scope of the present invention.

The time required for the reaction of the mercaptan and the epoxidized unsaturated ester can be any reaction time required to form the described hydroxy sulfide-containing ester. Generally, the reaction time is at least 15 minutes. In some embodiments, the reaction time ranges from 15 minutes to 72 hours; alternatively, from 30 minutes to 48 hours; or alternatively, from 45 minutes to 36 hours.

In some embodiments, the process to produce the hydroxy sulfide-containing ester further comprises a step to remove the residual mercaptan after reacting the mercaptan and the epoxidized unsaturated ester. In some embodiments the hydroxy sulfide-containing ester is vacuum stripped. In some embodiments, the hydroxy sulfide-containing ester is vacuum stripped at a temperature between 25° C. and 250° C.; or alternatively, between 50° C. and 200° C. In other embodiments, the hydroxy sulfide-containing ester is sparged with an inert gas to remove the mercaptan. In some embodiments, the hydroxy sulfide-containing ester is sparged with an inert gas at a temperature between 25° C. and 250° C.; or alternatively, between 50° C. and 200° C. In some aspects, the inert gas is nitrogen. Generally, the stripped or sparged hydroxy sulfide-containing ester comprises less than 5 weight percent of the mercaptan. In other embodiments, the stripped or sparged hydroxy sulfide-containing ester comprises less than 2 weight percent of the mercaptan; alternatively, less than 1 weight percent of the mercaptan; or alternatively, less than 0.5 weight percent of the mercaptan.

The reaction between the mercaptan and the epoxidized unsaturated ester can be performed at any reaction temperature capable of forming the hydroxy sulfide-containing ester. In some embodiments, the reaction temperature is greater than −20° C. In other embodiments, the reaction temperature is greater than 0° C.; alternatively, greater than 20° C.; alternatively, greater than 50° C.; or alternatively, greater than 80° C. In yet other embodiments, the reaction temperature ranges from −20° C. to 200° C.; alternatively, from 20° C. to 170° C.; or alternatively, from 80° C. to 140° C.

The reaction between the mercaptan and the epoxidized unsaturated ester can be performed at any reaction pressure that maintains the mercaptan and the epoxidized unsaturated ester in a substantially liquid state. In some embodiments, the reaction pressure ranges from 0 psig to 2000 psig. In other embodiments, the reaction pressure ranges from 0 psig to 1000 psig; alternatively, from 0 psig to 500 psig; or alternatively, from 0 psig to 200 psig.

In another aspect, the process to produce a hydroxy sulfide-containing ester produces a hydroxy sulfide-containing ester having an epoxide group to sulfide group molar ratio less than 2. Other hydroxy sulfide-containing ester epoxide group to sulfide group molar ratios are described herein. (The next passage needs to be incorporated into the hydroxy thiol ester section along with the first sentence of this paragraph.) Alternatively, the hydroxy sulfide-containing ester epoxide group to thiol group molar ratio can be less than 1.5; alternatively, less than 1.0; alternatively, less than 0.5, alternatively, less that 0.25; or alternatively, less than 0.1. In other embodiments, the hydroxy sulfide-containing ester can be substantially free of epoxide groups.

In another aspect, the process to produce hydroxy sulfide-containing ester produces a hydroxy sulfide-containing ester wherein at least 20 percent of the side chains comprise a hydroxy sulfide group. Other hydroxy sulfide-containing ester embodiments wherein the hydroxy sulfide-containing ester contains a percentage of side chains comprising a hydroxy sulfide groups are described herein. In other embodiments, the process to produce a hydroxy sulfide-containing ester produces a hydroxy sulfide-containing ester composition comprising hydroxy sulfide-containing ester molecules having an average of at least 20 percent of the side chains contain the moiety Z. In other embodiments, the process to produce a hydroxy sulfide-containing ester produces a hydroxy sulfide-containing ester composition comprising hydroxy sulfide-containing ester molecules having an average of at least 40 percent of the total side chains contain the moiety Z; alternatively, at least 60 percent of the total side chains comprise the moiety Z; alternatively, at least 70 percent of the total side chains comprise the moiety Z; or alternatively, at least 80 percent of the total side chains comprise the moiety Z. (Incorporate the moiety Z embodiments (and moiety X and Y embodiments) into the sulfide-containing ester composition section.

Process for Producing a Sulfonic Acid-Containing Ester or a Sulfonate-Containing Ester As an embodiment of the present invention, processes for producing a sulfonic acid-containing ester and for producing a sulfonate-containing ester are advantageously provided. Generally, the process for producing the sulfonic acid-containing ester comprises the steps of contacting a thiol ester and an oxidizing agent and oxidizing at least one thiol group of the thiol ester to produce a sulfonic acid group. The process for producing the sulfonate-containing ester comprises the steps of contacting a sulfonic acid-containing ester with a base and forming a sulfonate-containing ester.

Process for Producing a Sulfonic Acid-Containing Ester

In an embodiment, the process to prepare a sulfonic acid-containing ester comprises the steps of contacting the thiol ester and the oxidizing agent and oxidizing the thiol ester to produce the sulfonic acid-containing ester. Generally the oxidizing agent oxidizes at least one thiol group of the thiol ester to a sulfonate group. The process to produce the sulfonic acid-containing ester composition can be applied to any thiol ester described herein to prepare any sulfonic acid-containing ester described herein. In some embodiments, the thiol ester includes a hydroxy group. For example, the thiol ester can be any hydroxy thiol ester described herein. The oxidizing agent can be any oxidizing agent described herein.

In some aspects, the oxidation of the thiol ester occurs in the presence of a solvent. In some aspects, the solvent is water.

The oxidizing agent that is contacted with the thiol ester can be any oxidizing agent capable of oxidizing a thiol group to a sulfonic acid group. In some embodiments, the oxidizing agent is oxygen. In other embodiments, the oxidizing agent is chlorine. In other embodiments, the oxidizing agent is dimethyl sulfoxide. In yet other embodiments, the oxidizing agent is a combination of a hydrogen halide and a catalytic amount of a dialkyl sulfide, such as dimethyl sulfoxide. Other suitable oxidizing agents will be apparent to those of skill in the art and are to be considered within the scope of the present invention.

The oxidation of the thiol ester can be performed at any temperature capable of converting the thiol ester to a sulfonic acid-containing ester. In some embodiments, the thiol ester is oxidized a temperature greater than −20° C. In other embodiments, the thiol ester is oxidized at a temperature greater than 0° C.; alternatively, greater than 20° C.; or alternatively, greater than 50° C.

The time required for the oxidation of the thiol ester can be any time required to form the desired sulfonic acid-containing ester. Generally, the time required for the oxidation of the thiol ester is at least 15 minutes; alternatively, at least 30 minutes; alternatively, at least 45 minutes; or alternatively, at least 1 hour. In some embodiments, the time required for the oxidation of the thiol ester ranges from 15 minutes to 12 hours; alternatively, from 30 minutes to 6 hours; alternatively, from 45 minutes to 3 hours.

The oxidation of the thiol ester can be performed at any pressure that maintains the thiol ester and the oxidation agent in the proper state, which is not always a liquid state, to oxidize the thiol ester to a sulfonic acid-containing ester. For example, when the oxidation agent is chlorine, the chlorine can be in the gaseous state. In some embodiments, the oxidation of the thiol ester can performed at a pressure ranging from 0 to 2000 psig. In other embodiments, the oxidation of the thiol ester can be performed at a pressure ranging from 0 to 1000 psig; or alternatively, 0 to 500 psig.

The oxidation of the thiol ester can be performed in a batch reactor or a continuous reactor, as described herein. Additionally, the process to produce the sulfonic acid-containing ester can comprise additional process steps as recognized by those skilled in the art.

Process for Producing a Sulfonate-containing Ester

In an aspect of the present invention, a process to produce the sulfonate-containing ester is advantageously provided. In an embodiment, the process to prepare a sulfonate-containing ester comprises the steps of contacting the sulfonic acid-containing ester and a base and forming the sulfonate-containing ester composition. The process to produce the sulfonate-containing ester can be applied to any sulfonic acid-containing ester described herein to prepare any sulfonate-containing ester described herein. In some aspects, the process to prepare the sulfonate-containing ester includes the steps of the process to prepare the sulfonic acid-containing ester, which are described herein, in addition to the steps of producing the sulfonate-containing ester.

In some aspects, the formation of the sulfonate-containing ester occurs in the presence of a solvent. In some aspects, the solvent is water.

In some aspects, the base can be a metal hydroxide. In some embodiments, the metal hydroxide is selected from the group consisting of sodium, potassium, barium, calcium, magnesium, and mixtures thereof. In particular embodiments, the metal hydroxide is sodium hydroxide. In other aspects, the metal hydroxide is calcium hydroxide or magnesium hydroxide. In yet other aspects, the metal hydroxide is barium hydroxide. In other aspects, the base is an organic amine. In some embodiments, the amine has the structure NRs3Rs4Rs5 wherein Rs3, Rs4, and Rs5 are independently selected from hydrogen, C1 to C10 organyl groups, and C1 to C10 hydrocarbyl groups. In other embodiments, the organic amine is a trialkylamine, a dialkylamine, or a monoalkylamine. In a particular embodiment, NRs3Rs4Rs5 represents triethanolamine.

The formation of the sulfonate-containing ester can be performed at any temperature capable of converting the sulfonic acid group of the sulfonic acid-containing ester to a sulfonate group. In some embodiments, the sulfonate-containing ester is formed at a temperature greater than −20° C. In other embodiments, the thiol ester is oxidized at a temperature greater than 0° C.; alternatively, greater than 20° C.; or alternatively, greater than 50° C. In yet other embodiments, the thiol ester is oxidized at a temperature ranging from 0° C. to 250° C.; alternatively, from 0° C. to 150° C.; or alternatively, from 20° C. to 100° C.

The time required for the formation of the sulfonate-containing ester can be any time required to converting the sulfonic acid group of the sulfonic acid-containing ester to a sulfonate group. Generally, the time required for the formation of the sulfonate-containing ester is at least 15 minutes; alternatively, at least 30 minutes; alternatively, at least 45 minutes; or alternatively, at least 1 hour. In some embodiments, the time required for the formation of the sulfonate-containing ester ranges from 15 minutes to 12 hours; alternatively, from 30 minutes to 6 hours; alternatively, from 45 minutes to 3 hours.

The formation of the sulfonate-containing ester can be performed at any pressure that maintains the sulfonic acid-containing ester, base, and optional solvent in a liquid state. In some embodiments the formation of the sulfonate-containing ester is performed at a pressure ranging from 0 psig to 2000 psig. In other embodiments, the formation of the sulfonate-containing ester is performed at a pressure ranging from 0 to 1000 psig; or alternatively, 0 to 500 psig.

In one aspect the process to prepare a sulfonate-containing ester is performed as a batch process. In another aspect the process to prepare a sulfonate-containing ester is performed as a continuous process.

Polythiourethane and/or Epoxy Polymer Encapsulated Controlled Release Fertilizer Material.

Thus, in one of its aspects, the present invention relates to a polythiourethane and/or epoxy polymer encapsulated controlled release fertilizer material. The terms "controlled release fertilizer material" and "CRF material" are used interchangeably throughout this specification and are intended to have the same meaning. Further, as used throughout this specification, the term "vegetable oil" is intended to have a broad meaning an includes fatty acid triglyceride sources such as soybean oil, corn oil, canola oil, rapeseed oil and the like. The most preferred vegetable oil for use herein is soybean oil.

Generally, the fertilizer material comprises a particulate plant nutrient material. The choice of particulate plant nutrient material useful for the present CRF material is not particularly restricted and is within the purview of a person skilled in the art.

For example, the plant nutrient material used may be selected from those disclosed in Hudson. Preferably, such a plant nutrient comprises a water soluble compound, more preferably a compound containing at least one member selected from the group consisting of nitrogen, phosphorus, potassium, sulfur, micronutrients and mixtures thereof. A preferred such plant nutrient comprises urea. Other useful examples of plant nutrients are taught in U.S. Pat. No. 5,571,303 [Bexton] and/or U.S. Pat. No. 6,663,686 [Geiger et al.]—e.g., ammonium sulfate, ammonium phosphate and mixtures thereof. Non-limiting examples of useful micronutrients may be selected from the group comprising copper, zinc, boron, manganese, iron and mixtures thereof.

Preferably, the coating surrounds the plant nutrient material in an amount in the range of from about 0.1 to about 20 percent by weight, more preferably from about 2.0 to about 15 percent by weight, and most preferably from about 2.5 to about 10 percent by weight, based on the weight of the plant nutrient material.

In a preferred embodiment of the present invention, the sulfur-containing vegetable oil as the sole active hydrogen-containing compound for reaction with the isocyanate (e.g., in the case where the desired coating is a polythiourethane) or for reaction with the epoxy resin component (i.e., in the case where the desired coating is a epoxy polymer). Alternatively, it is possible to use a combination of the sulfur-containing vegetable oil and another active hydrogen-containing compound—e.g., a polyol.

The choice of polyol is not particularly restricted and is within the purview of a person skilled in the art. A polyol here refers to an active hydrogen containing compound reactive with isocyanate. The polyol may be a single type of polyol or a mixture of different polyols. For example, the polyol may be a hydroxyl-terminated backbone of a member selected from the group comprising polyether, polyester, polycarbonate, polydiene and polycaprolactone. Preferably, such a polyol is selected from the group comprising hydroxyl-terminated polyhydrocarbons, fatty acid triglycerides, hydroxyl-terminated polyesters, hydroxymethyl-terminated polyesters, hydroxymethyl-terminated perfluoromethylenes, polyalkyleneether glycols, polyalkylenearyleneether glycols and polyalkyleneether triols. More preferred polyols are selected from the group comprising polyethylene glycols, adipic acid-ethylene glycol polyester, poly(butylene glycol), poly(propylene glycol) and hydroxyl-terminated polybutadiene—see, for example, British patent No. 1,482,213. The most preferred such polyol is a polyether polyol. Preferably, such a polyether polyol has a molecular weight in the range of from about 60 to about 20,000, more preferably from about 60 to about 10,000, and most preferably from about 60 to about 8,000.

If used, a particularly preferred class of polyols are polyols comprising from about 2 to about 12 hydroxyl moieties. Preferably, such polyols are those with low equivalent weight and high functionality. The preferred equivalent weight is 29-400. More preferably, the equivalent weight is 29-200. Most preferably, the equivalent weight is 29-150. The functionality of the polyol as used herein refers to the preferred functionality of the basic unit (or monomer). Preferably, the functionality of the polyol is between about 2 and about 12, more preferably between about 3 and about 8, and most preferably between about 3 and about 6. More preferably, such a polyether polyol is made by using an amine as initiator. Most preferably, the polyol comprises a mixture of Huntsman Jeffol A480TM and another polyol, preferably, castor oil.

Additionally, the polyol, if used, may be derived from fatty acid triglyceride sources such as soybean, corn, canola and the like (i.e., to produce naturally occurring modified oils). An example of such a synthetic polyol comprising a canola base is commercially available from Urethane Soy Systems Corp. (Princeton, Ill.) with a functionality of above 3. A mixture of polyols with a prescribed ratio and molecular weight distribution may be used, for example, Huntsman Jeffol A480TM or 800TM with ethylene glycol, Huntsman Jeffol A480TM or 800TM with oleo polyol, Huntsman Jeffol A480TM or 800TM with polyethylene glycol, Huntsman Jeffol A480TM or 800TM with polypropylene glycol, Huntsman Jeffol A480TM or 800TM with a polypropylene (or polyethylene) glycol mixture of different functionality and molecular weight.

The isocyanate suitable for use in producing the coating is not particularly restricted and the choice thereof is within the purview of a person skilled in the art. The isocyanate may be a single type of isocyanate or a mixture of different isocyanates. Generally, the isocyanate compound suitable for use may be represented by the general formula:

$$Q(NCO)_i$$

wherein i is an integer of two or more and Q is an organic radical having the valence of i. Q may be a substituted or unsubstituted hydrocarbon group (e.g. an alkylene or arylene group). Moreover, Q may be represented by the general formula:

$$Q_1-Z-Q_1$$

wherein $Q_1$ is an alkylene or arylene group and Z is chosen from the group comprising —O—, —O-$Q_1$-, —CO—, —S—, —S-$Q_1$-S— and —SO2-. Examples of isocyanate compounds which fall within the scope of this definition include hexamethylene diisocyanate, 1,8-diisocyanato-p-naphthalene, xylyl diisocyanate, (OCNCH2CH2CH2OCH2O)2, 1-methyl-2,4-diisocyanato-cyclohexane, phenylene diisocyanates, tolylene diisocyanates, chlorophenylene diisocyanates, diphenylmethane-4,4-diisocyanate, naphthalene-1,5-diisocyanate, triphenylmethane-4,4,4-triisocyanate and isopropylbenzene-alpha-4-diisocyanate.

In another embodiment, Q may also represent a polyurethane radical having a valence of i. In this case Q(NCO)i is a compound which is commonly referred to in the art as a prepolymer. Generally, a prepolymer may be prepared by reacting a stoichiometric excess of an isocyanate compound (as discussed hereinabove) with the sulfur-containing vegetable oil (discussed hereinabove) and/or the polyol (discussed hereinabove). In this embodiment, the polyisocyanate may be, for example, used in proportions of from about 5 percent to about 200 percent stoichiometric excess with respect to the proportion of active hydrogen in the sulfur-containing vegetable oil and/or the polyol.

The isocyanate compound suitable for use in the process of the present invention also may be selected from dimers and trimers of isocyanates and diisocyanates, and from polymeric diisocyanates having the general formula:

$$[Q''(NCO)_i]_j$$

wherein both i and j are integers having a value of 2 or more, and Q'' is a polyfunctional organic radical, and/or, as additional components in the reaction mixture, compounds having the general formula:

$$L(NCO)_i$$

wherein i is an integer having a value of 1 or more and L is a monofunctional or polyfunctional atom or radical. Examples of isocyanate compounds which fall with the scope of this definition include ethylphosphonic diisocyanate, phenylphosphonic diisocyanate, compounds which contain a =Si—NCO group, isocyanate compounds derived from sulphonamides ($QSO_2NCO$), cyanic acid and thiocyanic acid.

See also, for example, British patent No. 1,453,258.

Non-limiting examples of suitable isocyanates include: 1,6-hexamethylene diisocyanate, 1,4-butylene diisocyanate, furfurylidene diisocyanate, 2,4-toluene diisocyanate, 2,6-toluene diisocyanate, 2,4'-diphenylmethane diisocyanate, 4,4'-diphenylmethane diisocyanate, 4,4'-diphenylpropane diisocyanate, 4,4'-diphenyl-3,3'-dimethyl methane diisocyanate, 1,5-naphthalene diisocyanate, 1-methyl-2,4-diisocyanate-5-chlorobenzene, 2,4-diisocyanato-s-triazine, 1-methyl-2,4-diisocyanato cyclohexane, p-phenylene diisocyanate, m-phenylene diisocyanate, 1,4-naphthalene diisocyanate, dianisidine diisocyanate, bitoluene diisocyanate, 1,4-xylylene diisocyanate, 1,3-xylylene diisocyanate, bis-(4-isocyanatophenyl)methane, bis-(3-methyl-4-isocyanatophenyl)methane, polymethylene polyphenyl polyisocyanates and mixtures thereof.

A particularly preferred group of isocyanates are those described in Hudson and Markusch.

Preferably, the isocyanate contains from about 1.5 to about 16 NCO groups per molecule. More preferably, the isocyanate contains from about 2 to about 16 NCO groups per molecule. Most preferably, the isocyanate contains from about 3 to about 16 NCO groups per molecule.

Preferably, the isocyanate contains from about 10 to about 50 percent NCO by weight. More preferably, the isocyanate contains from about 12 to about 50 percent NCO by weight. Most preferably, the isocyanate contains from about 15 to about 50 percent NCO by weight.

The sulfur-containing vegetable oil for use in the present CRF material is preferably selected those described in detail herein.

A preferred sulfur-containing vegetable oil is MVO available from Chevron Phillips Chemical Co. under the tradename Polymercaptan 358. Polymercaptan 358 is made by the free radical addition of hydrogen sulfide to the double bonds in soybean oil. Typically, Polymercaptan 358 has a thiol sulfur content of 5 to 10% and equivalent weights of 640 to 320, respectively.

Another preferred sulfur-containing vegetable oil useful as part of the isocyanate-reactive component is a MHVO such as mercapto-hydroxy soybean oil. As described herein, a preferred mercapto-hydroxy soybean oil is made by the free radical addition of hydrogen sulfide to epoxidized soybean oil. Typically, the mercapto and hydroxy functionalities are equal and the mercaptan content is about 8.3% thiol sulfur. The equivalent weight of this material is 192, which includes both mercapto and hydroxy functionalities.

Yet another preferred sulfur-containing vegetable oil useful as part of the isocyanate-reactive component is a CMVO such as sulfur cross-linked mercaptanized soybean oil. Sulfur cross-linked mercaptanized soybean oil is made by the addition of elemental sulfur to mercaptanized soybean oil. In this process, a portion of the mercaptan groups are consumed as cross-linking sites for the sulfur. Typical sulfur cross-linked mercaptanized soybean oil products by Chevron Phillips Chemical Co. include Runs #22, 194, 195, 196 and 197 and have a thiol sulfur content ranging from about 8.0% to 1.4% and equivalent weights ranging from about 400 to about 2250, respectively.

Other isocyanate-reactive components can be used in conjunction with the sulfur-containing vegetable oil in order to increase the cross-link density of the polythiourethane coating. Examples, but not limiting to one skilled in the art for cross-linking agents, include low molecular weight polyethylene and polypropylene glycols, amine initiated polyethylene and polypropylene glycols, aromatic amine inititated polyethylene and propylene glycols, glycerol, sorbitol, neopentyl glycol, ethylene diamine and toluene diamine. The amount and choice of cross-linking agent used is within purview of a person of ordinary skill in the art and is dependent upon the desired physical properties of the coating.

The use of a catalyst for the reaction of the sulfur-containing vegetable oils with the isocyanate is conventional. The selection of the catalyst is within the purview of a person of ordinary skill in the art. Examples, but not limiting, of suitable catalysts include tertiary amines and organo-tin compounds. Particularly useful catalysts are amine initiated polypropylene glycols since they also act as cross-linking agents along with their catalytic effect.

Organic additives can be optionally added to the formulation for coating the CRF material to increase the hydropobicity and/or the handling durability of the coating, if desired. The organic additive can be added to either the isocyanate-reactive component or the polyisocyanate component, prior to applying them to the fertilizer particles. Suitable organic additives include, but not limited to, waxes, both synthetic and natural, petrolatums, asphalts, fatty acids, fatty acid salts, fatty acid esters, higher alcohols, silicones and mixtures thereof. A particularly useful organic additive is synthetic alpha olefin wax (e.g., a $C_{20+}$ alpha olefin wax) made by Chevron Phillips Chemical Co. Another useful organic additive is a microcrystalline wax, such as Calwax™ 170, available from Calwax Corp.

Preferably, the addition of an organic additive or mixture of organic additives is in an amount of up to about 90% by weight of the coating, preferably in the range of from about 0.1% to about 90% by weight of the coating, more preferably in the range of from about 1% to about 80% by weight of the coating and most preferably in the range of from about 2% to 50% by weight of the coating.

It is also possible to include other additives in either the isocyanate-reactive component or the polyisocyanate component, prior to applying them to the fertilizer particles. Possible additives include, for example, flow aids, surfactants, defoamers and other additives know to those of ordinary skill in the art. Any additive, which aids the formation of the polythiourethane coating that encapsulates the fertilizer particles, may be included in one or both of these components.

Suitable epoxy resins to be used in conjunction with mercaptanized vegetable oil for the purpose of this invention include, but not limited to, liquid bisphenol A diglycidyl ethers, such as Dow Plastics D.E.R. 331 and 324, and Resolution Performance Products Epon Resin 282 and 8121 and mixtures thereof. Also, epoxidized soybean oil can be used, such as commercially available AtoChem Vikoflex 7170 and mixtures thereof with other epoxy resins.

For epoxy polymer encapsulated CRF material made from sulfur-containing vegetable oil, it has been found that the use of a tertiary amine catalyst is highly preferred. The amount used is such to be sufficient to give the desired reaction rate for the production of the encapsulated slow release fertilizer product. A non-limiting example of a suitable amine catalyst is diazobicycloundecacene also known as 1,8-diazabicyclo [5,4,0]undec-7-ene [CAS# 6674-22-2] or "DBU", which is preferably used in the range of about 0.1% to 0.5% by weight of the coating. Other suitable catalyst materials will be apparent to those of ordinary skill in the art.

Preferably the amine catalyst is premixed with the sulfur-containing vegetable oil and then this mixture along with the epoxy resin is applied to the fertilizer particles, either simultaneously or either one before the other.

The preferred sulfur-containing vegetable oil to be used in production of an epoxy polymer coated CRF material is MHVO such as mercapto-hydroxy soybean oil. One such material is mercapto-hydroxy soybean oil known as MHSO 566-84 produced by Chevron Phillips Chemical Co. This preferred material contains 8.33% thiol sulfur, with an equivalent weight of 384, based upon the mercaptan functionality.

Organic additives can be optionally added to the formulation to increase the hydropobicity and/or the handling durability of the epoxy polymer coating, if desired. The organic additive can be added to either the epoxy-reactive component and/or the sulfur-containing vegetable component, prior to applying them to the fertilizer particles. Suitable organic additives include, but not limited to, waxes, both synthetic and natural, petrolatums, asphalts, fatty acids, fatty acid salts, fatty acid esters, higher alcohols, silicones and mixtures thereof. A particularly useful organic additive is synthetic alpha olefin wax made by Chevron Phillips Chemical Co.

Preferably, the addition of an organic additive or mixture of organic additives for use with the epoxy polymer is in an amount of up to about 90% by weight of the coating, preferably in the range of from about 0.1% to about 90% by weight of the coating, more preferably in the range of from about 1% to about 80% by weight of the coating and most preferably in the range of from about 2% to 50% by weight of the coating.

It is also possible to include other additives in either the epoxy-reactive component (the sulfur-containing vegetable oil) or the epoxy resin component, prior to applying them to the fertilizer particles. Possible additives include, for example, flow aids, surfactants, defoamers and other additives known to those of ordinary skill in the art. Any additive, which aids the formation of the epoxy polymer coating that encapsulates the fertilizer particles, may be included in one or both of these components.

According to a preferred embodiment, the present CRF material may be produced by applying the isocyanate-reactive component along with the polyisocyanate component at ambient temperature (e.g., from about 20° C. to about 30° C.). Preferably, the fertilizer particles are preheated to a temperature in the range of from about 50° C. to 100° C., more preferably from about 60° C. to 80° C.

According to another preferred embodiment of the invention, the present CRF material may be produced by applying the epoxy-resin reactive components, containing the amine catalyst, along with the epoxy resin component at ambient temperature (e.g., from about 20° C. to about 30° C.) Preferably, the fertilizer particles are preheated to a temperature in the range of from about 50° C. to 100° C., more preferably from about 60° C. to 80° C.

During the coating operation, it is preferred to use a device that maintains the fertilizer particles in a continuous low shear, low impact, motion relative to each other. Examples of suitable mixing apparatus include fluid bed, rotating drum, pan pelletizer and the like that can provide a continuous low shear, motion of the fertilizer particles.

Preferably, polythiourethane encapsulated CRF material may be produced by carrying out the following steps: (i) providing a quantity of fertilizer particles, (ii) agitating the fertilizer particles such that a gentle mixing thereof is maintained, (iii) adding to the agitated fertilizer particles an isocyanate-reactive component comprising the sulfur-containing vegetable oil (with or without one or more of cross-linking agents, hydrophobic organic additives or other additives as described above), (iv) adding to the agitated fertilizer particles an isocyanate (with or without one or more of hydrophobic organic additives or other additives as described above), in such an amount that the ratio of NCO groups to isocyanate-reactive functional groups is from about 0.8:1, to about 2.0:1, preferably from about 0.9:1 to about 1.5:1 and most preferably from about 0.95 to about 1.3:1, (v) allowing isocyanate and isocyanate-reactive component to react, thus forming a solidified polythiourethane coating on the surface of the fertilizer particles, and (vi) cooling the coated fertilizer particles to about or slightly above room temperature, with continuous, gentle agitation.

If multiple coating layers are required to achieve the desired slow release fertilizer, Steps (ii) through (vi) can be repeated a number of times (e.g., from 2 to 10 times).

In accordance with the CRF material of the present invention, it is not necessary that the fertilizer particles contain isocyanate-reactive functional groups.

Polythiourethane encapsulation of the fertilizer particles to obtain the a prescribed release rate profile of the fertilizer depends on a number of factors, including: (i) correct metering of the co-reactants and additives, (ii) relatively precise temperature control, (iii) substantially continuous movement of the fertilizer particles in a gentle, low shear environment, (iv) proper selection of type and amount of catalyst to ensure complete reaction of the isocyanate-reactive components with the polyisocyanate component before successive layers are applied (assuming multiple layers are being applied), and/or (v) cooling of the coated fertilizer particles to avoid agglomeration of the final product.

In accordance with a preferred embodiment, the sulfur-containing vegetable oil, along with the hydrophobic organic additive (if present), is applied as a separate stream to the fertilizer particles, prior to the addition of the isocyanate. Also, preferably, the catalyst and cross-linking agent, if any, are added as a separate stream to the fertilizer particles. The order of addition is not important and is within the purview of one skilled in the art.

Preferably, epoxy polymer encapsulated CRF material may be produced by carrying out the following steps: (i) providing a quantity of fertilizer particles, (ii) agitating the fertilizer particles such that a gentle mixing thereof is maintained, (iii) adding to the agitated fertilizer particles an epoxy-reactive component comprising a sulfur-containing vegetable oil (with or without one or more of the hydrophobic organic additives and other additives as described above), (iv) adding to the agitated fertilizer particles an epoxy resin component (with or without one or more hydrophobic organic additives and other additives as described above), in such an amount that the ratio of oxirane groups in the epoxy resin to epoxy-reactive functional groups is from about 0.8:1, to about 2.0:1, preferably from about 0.9:1 to about 1.5:1; even preferably from about 0.95 to about 1.3:1 and most preferably from about 0.95 to about 1.05:1, (v) allowing the epoxy resin and epoxy-reactive materials to react, thus forming a solidified epoxy polymer coating on the surface of the fertilizer particles, and (vi) cooling the coated fertilizer particles to about or slightly above room temperature, with continuous, gentle agitation.

If multiple coating layers are required to achieve the desired slow release fertilizer, Steps (ii) through (vi) can be repeated a number of times (e.g., 2 to 10 times).

Epoxy polymer encapsulation of the fertilizer particles to obtain the a prescribed release rate profile of the fertilizer depends on a number of factors, including: (i) correct metering of the co-reactants and additives, (ii) relatively precise temperature control, (iii) substantially continuous movement of the fertilizer particles in a gentle, low shear environment, (iv) proper selection of type and amount of catalyst to ensure complete reaction of the epoxy-reactive components with the epoxy resin component before successive layers are applied (assuming multiple layers are being applied), and (v) cooling of the coated fertilizer particles to avoid agglomeration of the final product.

In accordance with a preferred embodiment, the sulfur-containing vegetable oil, along with hydrophobic organic additive (if present), is applied as a separate stream to the fertilizer particles, prior to the addition of the epoxy resin component. Also, preferably, the catalyst and other additives, if any, are added as a separate stream to the fertilizer particles. The order of addition is not important and is within the purview of one skilled in the art.

In a further embodiment of this invention, a combination of epoxy polymer layers and polythiourethane layers can be applied to fertilizer particles to give a composite polymer coating for the CRF material. The epoxy polymer coating and polythiourethane coating can be applied in any order.

FEEDSTOCKS

Unsaturated Ester

The unsaturated ester used as a feedstock to produce the thiol ester compositions described herein can be described using a number of different methods. One method of describing the unsaturated ester feedstock is by the number of ester groups and the number of carbon-carbon double bonds that comprise each unsaturated ester oil molecule. Suitable unsaturated ester used as a feedstock to produce the thiol ester compositions described herein minimally comprise at least 1 ester group and at least 1 carbon-carbon double bond. However, beyond this requirement, the number of ester groups and carbon-carbon double bonds comprising the unsaturated esters are independent elements and can be varied independently of each other. Thus, the unsaturated esters can have any combination of the number of ester groups and the number of carbon-carbon double bonds described separately herein. Suitable, unsaturated esters can also contain additional functional groups such as alcohol, aldehyde, ketone, epoxy, ether, aromatic groups, and combinations thereof. As an example, the unsaturated esters can also comprise hydroxy groups. An example of an unsaturated ester that contains hydroxy groups is castor oil. Other suitable unsaturated esters will be apparent to those of skill in the art and are to be considered within the scope of the present invention.

Minimally the unsaturated ester comprises at least one ester group. In other embodiments, the unsaturated ester comprises at least 2 ester groups. Alternatively, the unsaturated ester comprises 3 ester groups. Alternatively, the unsaturated ester comprises 4 ester groups. Alternatively, the unsaturated ester includes from 2 to 8 ester groups. Alternatively, the unsaturated ester includes from 2 to 7 ester groups. Alternatively, the unsaturated ester includes from 3 to 5 ester groups. As another alternative, the unsaturated ester includes from 3 to 4 ester groups.

In other embodiments, the unsaturated ester comprises a mixture of unsaturated esters. In these situations, the number of ester groups is best described as an average number of ester groups per unsaturated ester molecule comprising the unsaturated ester composition. In some embodiments, the unsaturated esters have an average of at least 1.5 ester groups per unsaturated ester molecule; alternatively, an average of at least 2 ester groups per unsaturated ester molecule; alternatively, an average of at least 2.5 ester groups per unsaturated ester molecule; or alternatively, an average of at least 3 ester groups per unsaturated ester molecule. In other embodiments, the unsaturated esters have an average of from 1.5 to 8 ester groups per unsaturated ester molecule; alternatively, an average of from 2 to 7 ester groups per unsaturated ester molecule; alternatively, an average of from 2.5 to 5 ester groups per unsaturated ester molecule; alternatively, an average of from 3 to 4 ester groups per unsaturated ester molecule. In another embodiment, the unsaturated esters have an average of about 3 ester groups per unsaturated ester molecule or alternatively, an average of about 4 ester groups per unsaturated ester molecule.

Minimally, the unsaturated ester comprises at least one carbon-carbon double bond per unsaturated ester molecule. In an embodiment the unsaturated ester comprises at least 2 carbon-carbon double bonds; alternatively, at least 3 carbon-carbon double bonds; or alternatively, at least 4 carbon-carbon double bonds. In other embodiments, the unsaturated ester comprises from 2 to 9 carbon-carbon double bonds; alternatively, from 2 to 4 carbon-carbon double bonds; alternatively, from 3 to 8 carbon-carbon double bonds; or alternatively, from 4 to 8 carbon-carbon double bonds.

In some embodiments, the unsaturated ester comprises a mixture of unsaturated esters. In this aspect, the number of carbon-carbon double bonds in the mixture of unsaturated ester is best described as an average number of carbon-carbon double bonds per unsaturated ester oil molecule. In some embodiments, the unsaturated esters have an average of at least 1.5 carbon-carbon double bonds per unsaturated ester molecule; alternatively, an average of at least 2 carbon-carbon double bonds per unsaturated ester molecule; alternatively, an average of at least 2.5 carbon-carbon double bonds per unsaturated ester molecule; or alternatively, an average of at least 3 carbon-carbon double bonds per unsaturated ester molecule. In other embodiments, the unsaturated esters have average of from 1.5 to 9 carbon-carbon double bonds per unsaturated ester molecule; alternatively, an average of from 3 to 8 carbon-carbon double bonds per unsaturated ester molecule; alternatively, an average of from 2 to 4 carbon-carbon double bonds per unsaturated ester molecule; or alternatively, from of 4 to 8 carbon-carbon double bonds per unsaturated ester molecule.

While the number (or average number) of ester groups and the number (or average number) double bonds are independent elements of the unsaturated esters, particular embodiments are mentioned for illustrative purposes. In an embodiment, the unsaturated ester molecules have an average of at least 1.5 ester groups per unsaturated ester molecule and have an average of at least 1.5 carbon-carbon double bonds per unsaturated ester molecule. Alternatively, the unsaturated ester molecules have an average of at least 3 ester groups per unsaturated ester molecule and have an average of at least 1.5 carbon-carbon double bonds per unsaturated ester molecule. Alternatively, the unsaturated ester molecules have an average of at least 3 ester groups per unsaturated ester molecule and have an average of from 1.5 to 9 carbon-carbon double bonds per unsaturated ester molecule. As another alternative, the unsaturated ester molecules have an average of from 2 to 8 ester groups per unsaturated ester molecule and have an average of from 1.5 to 9 carbon-carbon double bonds per unsaturated ester oil.

In addition to the number (or average number) of ester groups and the number (or average number) of carbon-carbon double bonds present in the unsaturated ester molecules, the disposition of the carbon-carbon double bonds in unsaturated ester molecules having 2 or more carbon-carbon double bonds can be a consideration. In some embodiments where the unsaturated ester molecules have 2 or more carbon-carbon double bonds, the carbon-carbon double bonds can be conjugated. In other embodiments, the carbon-carbon double bonds can be separated from each other by only one carbon atom. When two carbon-carbon double bonds are separated by a carbon atom having two hydrogen atoms attached to it, e.g. a methylene group, these carbon-carbon double bonds can be termed as methylene interrupted double bonds. In yet other embodiments, the carbon-carbon double bonds are isolated, e.g. the carbon-carbon double bonds are separated from each other by 2 or more carbon atoms. In further embodiments, the carbon-carbon double bonds can be conjugated with a carbonyl group.

In some aspects, the unsaturated ester may be described as an ester of a polyol and unsaturated carboxylic acids. Within this description, the unsaturated carboxylic acid portion of the unsaturated ester can be called a polyol side chain (or more simply a side chain). In some embodiments, the unsaturated ester comprises less than 30 percent of side chains comprising methylene interrupted double bonds. In other embodiments, embodiments the unsaturated ester comprises greater than 30 percent of the side chains comprise methylene interrupted double bonds. In yet other embodiments, the unsaturated ester comprises less than 25 percent of side chains having 3 contiguous methylene interrupted carbon-carbon double bonds. In further embodiments, the unsaturated ester comprises less than 25 percent linolenic acid side chains. In further embodiments, the unsaturated ester comprises greater than 25 percent of side chains having 3 contiguous methylene interrupted carbon-carbon double bonds. In further embodiments, the unsaturated ester comprises greater than 25 percent linolenic acid side chains. In additional embodiments, the unsaturated ester comprises at least 30 percent side chains having 2 contiguous methylene interrupted carbon-carbon double bonds and less than 25 percent of side chains having 3 contiguous methylene interrupted carbon-carbon double bonds.

Additional functional groups can also be present in the unsaturated ester. A non-limiting list of functional groups include a hydroxy group, an ether group, aldehyde group, a ketone group, an amine group, a carboxylic acid group among others, and combinations thereof. In an aspect, the unsaturated ester can comprise hydroxy groups. In some embodiments, the unsaturated esters have an average of at least 1.5 hydroxy groups per unsaturated ester molecule; alternatively, an average of at least 2 hydroxy groups per unsaturated ester molecule; alternatively, an average of at least 2.5 hydroxy groups per unsaturated ester molecule; or alternatively, an average of at least 3 hydroxy groups per unsaturated ester molecule. In other embodiments, the unsaturated esters have average of from 1.5 to 9 hydroxy groups per unsaturated ester molecule; alternatively, an average of from 3 to 8 hydroxy groups per unsaturated ester molecule; alternatively, an average of from 2 to 4 hydroxy groups per unsaturated ester molecule; or alternatively, from of 4 to 8 hydroxy groups per unsaturated ester molecule. In an embodiment the unsaturated ester comprises at least 2 hydroxy groups; alternatively, at least 3 hydroxy groups; or alternatively, at least 4 hydroxy groups. In other embodiments, the unsaturated ester comprises from 2 to 9 hydroxy groups; alternatively, from 2 to 4 hydroxy groups; alternatively, from 3 to 8 hydroxy groups; or alternatively, from 4 to 8 hydroxy groups.

Sources of Unsaturated Ester Oils

The unsaturated ester oil utilized as a feedstock of this invention can be any unsaturated ester oil having the number of ester groups and carbon-carbon double bonds per unsaturated ester oil described herein. The unsaturated ester oil can be derived from natural sources, synthetically produced from natural source raw materials, produced from synthetic raw materials, produced from a mixture of natural and synthetic materials, or a combination thereof.

Unsaturated Natural Source Oil

In an embodiment, the unsaturated ester oil is unsaturated natural source oil. The unsaturated natural source oil can derived from naturally occurring nut, vegetable, plant and animal sources. In an embodiment, the unsaturated ester oil is derived from genetically modified nuts, vegetables, plant, and animal sources. In an embodiment, the unsaturated ester oil comprises a triglyceride derived from genetically modified nuts, vegetables, plant, and animal sources.

In an aspect, the unsaturated natural source oil can be tallow, olive, peanut, castor bean, sunflower, sesame, poppy, seed, palm, almond seed, hazel-nut, rapeseed, canola, soybean, corn, safflower, canola, cottonseed, camelina, flaxseed, or walnut oil. In some embodiment, the unsaturated natural source oil can be soybean, corn, castor bean, safflower, canola, cottonseed, camelina, flaxseed, or walnut oil. In further embodiments, the unsaturated natural source oil can be soybean oil; alternatively corn oil; alternatively castor bean oil; or alternatively, canola oil.

The unsaturated natural source oils are comprised of triglycerides that can be described as an ester of glycerol and an unsaturated carboxylic acid. Within this description, the unsaturated carboxylic acid portion of the triglyceride can be called a glycerol side chain (or more simply a side chain). In some embodiments, the triglyceride comprises less than 30 percent of side chains comprising methylene interrupted double bonds. In other embodiments, embodiments the triglyceride comprises greater than 30 percent of the side chains comprise methylene interrupted double bonds. In yet other embodiments, the triglyceride comprises less than 25 percent of side chains having 3 contiguous methylene interrupted carbon-carbon double bonds. In further embodiments, the triglyceride comprises less than 25 percent linolenic acid side chains. In further embodiments, the triglyceride comprises greater than 25 percent of side chains having 3 contiguous methylene interrupted carbon-carbon double bonds. In further embodiments, the triglyceride comprises greater than 25 percent linolenic acid side chains. In additional embodiments, the triglyceride comprises at least 30 percent side chains having 2 contiguous methylene interrupted carbon-carbon double bonds and less than 25 percent of side chains having 3 contiguous methylene interrupted carbon-carbon double bonds.

In another embodiment, the unsaturated natural ester oil comprises "natural" triglycerides derived from unsaturated natural source oils. In an embodiment, the unsaturated ester oil is synthetic. In an embodiment, the unsaturated ester oil comprises both synthetic and natural raw materials. In an embodiment, the unsaturated ester oil comprises synthetic triglycerides.

Synthetic Unsaturated Esters

Synthetic unsaturated esters used as feedstock for aspects of this invention can be produced using methods for producing an ester group known to those skilled in the art. The term "ester group" means a moiety formed from the reaction of a hydroxy group and a carboxylic acid or a carboxylic acid derivative. Typically, the esters can be produced by reacting an alcohol with a carboxylic acid, transesterification of carboxylic acid ester with an alcohol, reacting an alcohol with a carboxylic acid anhydride, or reacting an alcohol with a carboxylic acid halide. Any of these methods can be used to produce the synthetic unsaturated ester oils used as a feedstock in an aspect of this invention. The alcohol, unsaturated carboxylic acid, unsaturated carboxylic acid ester, unsaturated carboxylic acid anhydride raw materials for the production of the unsaturated ester oil can be derived from natural, synthetic, genetic, or any combination of natural, genetic, and synthetic sources.

The polyols and the unsaturated carboxylic acids, simple unsaturated carboxylic acid esters, or unsaturated carboxylic acid anhydrides used to produce the unsaturated esters used as a feedstock in various aspects of this invention are independent elements. That is, these elements can be varied independently of each other and thus, can be used in any combination to produce an unsaturated ester utilized a feedstock to produce the compositions described in this application or as a feedstock for the processes described in this application.

Synthetic Unsaturated Ester Oils—Polyol Component

The polyol used to produce the unsaturated ester oil can be any polyol or mixture of polyols capable of reacting with an unsaturated carboxylic acid, unsaturated simple carboxylic acid ester, carboxylic acid anhydride, or carboxylic acid halide under reaction condition known to those skilled in the art.

The number of carbon atoms in the polyol is not particularly important. In one aspect, the polyol used to produce the unsaturated ester can comprise from 2 to 20 carbon atoms. In other embodiments, the polyol comprises from 2 to 10 carbon atoms; alternatively from 2 to 7 carbon atoms; alternatively from 2 to 5 carbon atoms. In further embodiments, the polyol may be a mixture of polyols having an average of 2 to 20 carbon atoms; alternatively, an average of from 2 to 10 carbon atoms; alternatively, an average of 2 to 7 carbon atoms; alternatively an average of 2 to 5 carbon atoms.

In another aspect, the polyol used to produce the unsaturated ester can have any number of hydroxy groups needed to produce the unsaturated ester as described herein. In some embodiments, the polyol has 2 hydroxy groups; alternatively 3 hydroxy groups; alternatively, 4 hydroxy groups; alternatively, 5 hydroxy groups; or alternatively, 6 hydroxy groups. In other embodiments, the polyol comprises at least 2 hydroxy groups; alternatively at least 3 hydroxy groups; alternatively, at least 4 hydroxy groups; or alternatively, at least 5 hydroxy groups; at least 6 hydroxy groups. In yet other embodiments, the polyol comprises from 2 to 8 hydroxy groups; alternatively, from 2 to 4 hydroxy groups; or alternatively from 4 to 8 hydroxy groups.

In further aspects, the polyol used to produce the unsaturated ester is a mixture of polyols. In an embodiment, the mixture of polyols has an average of at least 1.5 hydroxy groups per polyol molecule. In other embodiments, the mixture of polyols has an average of at least 2 hydroxy groups per polyol molecule; alternatively, an average of at least 2.5 hydroxy groups per polyol molecule; alternatively, an average of at least 3.0 hydroxy groups per polyol molecule; or alternatively, an average of at least 4 hydroxy groups per polyol molecule. In yet another embodiments, the mixture of polyols has an average of 1.5 to 8 hydroxy groups per polyol molecule; alternatively, an average of 2 to 6 hydroxy groups per polyol molecule; alternatively, an average of 2.5 to 5 hydroxy groups per polyol molecule; alternatively, an average of 3 to 4 hydroxy groups per polyol molecule; alternatively, an average of 2.5 to 3.5 hydroxy groups per polyol molecule; or alternatively, an average of 2.5 to 4.5 hydroxy groups per polyol molecule.

In yet another aspect, the polyol or mixture of polyols used to produce the unsaturated thiol ester has a molecular weight or average molecular weight less than 500. In other embodiments, the polyol or mixture of polyols have a molecular weight or average molecular weight less than 300; alternatively less than 200; alternatively, less than 150; or alternatively, less than 100.

In some embodiments, suitable polyols include 1,2-ethanediol, 1,3-propanediol, 1,4-butanediol, 1,5-pentanediol, 1,6-hexanediol, dimethylolpropane, neopentylpropane, 2-propyl-2-ethyl-1,3-propanediol, 1,2-propanediol, 1,3-butanediol, diethylene glycol, triethylene glycol, polyethylene glycol, dipropylene glycol, tripropylene glycol, and polypropylene glycol; cyclohexanedimethanol, 1,3-dioxane-5,5-dimethanol; and 1,4-xylylenedimethanol and 1-phenyl-1,2-ethanediol, trimethylolpropane, trimethylolethane, trimethylolbutane, glycerol, 1,2,5-hexanetriol, pentaerythritol, ditrimethylolpropane, diglycerol, ditrimethylolethane, 1,3,5-trihydroxybenzene, 1,4-xylylenedimethanol, and 1-phenyl-1,2-ethanediol, or any combination thereof. In further embodiments, the polyol is glycerol, pentaerythritol, or mixtures thereof. In other embodiments, the polyol is glycerol, or alternatively pentaerythritol.

Synthetic Unsaturated Ester—Carboxylic Acid or Carboxylic Acid Equivalent Component The carboxylic acid component of the unsaturated ester oil can be any carboxylic acid or mixture of carboxylic acids comprising a carbon-carbon double bond. As the carboxylic acid component will be combined with a polyol or polyol mixture comprising an average of greater than 1.5 hydroxy groups or any other number of hydroxy groups described herein, the carboxylic acid component can be any mixture comprising unsaturated carboxylic acids that produces an unsaturated ester oil meeting the feedstock requirement described herein. In some embodiments, the carboxylic acid component can be any mixture of saturated carboxylic acids and unsaturated carboxylic acid that produces an unsaturated ester oil meeting the feedstock requirement described herein. Thus, the carboxylic acid or carboxylic acid mixture used to produce the synthetic unsaturated ester oil can be described as having an average number of a specified element per carboxylic acid.

Independent elements of the carboxylic acid include the average number of carboxylic acid groups per carboxylic acid molecule, the average number of carbon atoms present in the carboxylic acid, and the average number of carbon-carbon double bonds per carboxylic acid. Additional independent elements include the position of the double bond in the carbon chain and the relative position of the double bonds in respect to each other when there are multiple double bonds.

Specific carboxylic acids used as a component of the carboxylic acid composition used to produce the unsaturated ester oil can have from 3 to 30 carbon atoms per carboxylic acid molecule. In some embodiments the carboxylic acid is linear. In some embodiments the carboxylic acid is branched. In some embodiments the carboxylic acid is a mixture of linear and branched carboxylic acids. In some embodiments the carboxylic acid can also comprise additional functional groups including alcohols, aldehydes, ketones, and epoxides, among others.

Suitable carboxylic acids that can be used as a component of unsaturated carboxylic acid composition can have from about 3 to about 30 carbon atoms; alternatively 8 to 25 carbon atoms; or alternatively, from 12 to 20 carbon atoms. In other embodiments, the carboxylic acids comprising the unsaturated carboxylic acid composition comprise an average of 2 to 30 carbon atoms; alternatively an average of 8 to 25 carbon atoms; or alternatively, and average of from 12 to 20 carbon atoms.

The carbon-carbon double bond can be located anywhere along the length of the carbon-carbon chain. In one embodiment, the double bond can be located at a terminal position. In another embodiment, the carbon-carbon double bond can be located at internal position. In yet another embodiment, the carboxylic acid or mixture of carboxylic acids can comprise both terminal and internal carbon-carbon double bonds. The double bond can also be described by indicating the number of substitutes that are attached to carbon-carbon double bond. In some embodiments, the carbon-carbon double bond can be mono-substituted, disubstituted, trisubstituted, tetrasubstituted, or a mixture of unsaturated carboxylic acids that can have any combination of monosubstituted, disubstituted, trisubstituted and tetrasubstituted carbon-carbon double bonds.

Suitable unsaturated carboxylic acid include acrylic, agonandoic, agonandric, alchornoic, ambrettolic, angelic, asclepic, auricolic, avenoleic, axillarenic, brassidic, caproleic, cetelaidic, cetoleic, civetic, CLA, coriolic, coronaric, crepenynic, densipolic, dihomolinoleic, dihomotaxoleic, dimorphecolic, elaidic, ephedrenic, erucic, gadelaidic, gadoleic, gaidic, gondolo, gondoleic, gorlic, helenynolic, hydrosorbic, isoricinoleic, keteleeronic, labellenic, lauroleic, lesquerolic, linelaidic, linderic, linoleic, lumequic, malvalic, mangold's acid, margarolic, megatomic, mikusch's acid, mycolipenic, myristelaidic, nervoic, obtusilic, oleic, palmitelaidic, petroselaidic, petroselinic, phlomic, physeteric, phytenoic, pyrulic, ricinelaidic, rumenic, selacholeic, sorbic, stearolic, sterculic, sterculynic, stillingic, strophanthus, tariric, taxoleic, traumatic, tsuduic, tsuzuic, undecylenic, vaccenic, vernolic, ximenic, ximenynic, ximenynolic, and combinations thereof. In further embodiments, suitable unsaturated carboxylic acids include oleic, palmitoleic, ricinoleic, linoleic, and combination thereof.

In some embodiments the unsaturated ester can be produced by transesterification of a simple ester of the carboxylic acid or mixture of carboxylic acids described herein with the polyol compositions described herein. In some embodiment, the simple ester, is a methyl or ethyl ester of the carboxylic acid or mixture of carboxylic acids. In further embodiments the simple carboxylic acid ester is a methyl ester of the carboxylic acids as described herein.

Epoxidized Unsaturated Esters

In an aspect, epoxidized unsaturated esters are used as a feedstock to produce materials described herein and for the process to produce the material described herein. Generally, the epoxidized unsaturated ester can be derived by epoxidizing any unsaturated ester described herein. The unsaturated ester oil can be derived from natural sources, synthetically produced from natural source raw materials, produced from synthetic raw materials, produced from a mixture of natural and synthetic materials, or a combination thereof.

Minimally, the epoxidized unsaturated ester comprises at least one epoxide group. In an embodiment the epoxidized unsaturated ester comprises at least 2 epoxide groups; alternatively, at least 3 epoxide groups; or alternatively, at least 4 epoxide. In other embodiments, the epoxidized unsaturated ester comprises from 2 to 9 epoxide groups; alternatively, from 2 to 4 epoxide groups; alternatively, from 3 to 8 epoxide groups; or alternatively, from 4 to 8 epoxide groups.

In some embodiments, the unsaturated ester comprises a mixture of epoxidized unsaturated esters. In this aspect, the number of epoxide groups in the epoxidized unsaturated ester is best described as an average number of epoxide groups per epoxidized unsaturated ester molecule. In some embodiments, the epoxidized unsaturated esters have an average of at least 1.5 epoxide groups per epoxidized unsaturated ester molecule; alternatively, an average of at least 2 epoxide groups per epoxidized unsaturated ester molecule; alternatively, an average of at least 2.5 epoxide groups per epoxidized unsaturated ester molecule; or alternatively, an average of at least 3 epoxide groups per epoxidized unsaturated ester molecule. In other embodiments, the epoxidized unsaturated esters have average of from 1.5 to 9 epoxide groups per epoxidized unsaturated ester molecule; alternatively, an average of from 3 to 8 epoxide groups per epoxidized unsaturated ester molecule; alternatively, an average of from 2 to 4 epoxide groups per epoxidized unsaturated ester molecule; or alternatively, from of 4 to 8 epoxide group per epoxidized unsaturated ester molecule.

In an aspect the epoxidized unsaturated ester can be an epoxidized unsaturated natural source oil (epoxidized natural source oil). The unsaturated natural source oil can be derived from naturally occurring nut, vegetable, plant and animal sources. In an embodiment, the unsaturated ester oil is derived from genetically modified nuts, vegetables, plant, and animal sources. In an embodiment, the unsaturated ester oil comprises a triglyceride derived from genetically modified nuts, vegetables, plant, and animal sources.

In an aspect, the epoxidized natural source oil can be tallow, olive, peanut, castor bean, sunflower, sesame, poppy, seed, palm, almond seed, hazel-nut, rapeseed, canola, soybean, corn, safflower, canola, cottonseed, camelina, flaxseed, or walnut oil. In some embodiment, the epoxidized natural source oil can be soybean, corn, castor bean, safflower, canola, cottonseed, camelina, flaxseed, or walnut oil. In further embodiments, the epoxidized natural source oil can be soybean oil; alternatively corn oil; alternatively castor bean oil; or alternatively, canola oil.

The thiol composition can include an average of greater than 0 to about 4 epoxide groups per triglyceride. The thiol composition can also include an average of greater than 1.5 to about 9 epoxide groups per triglyceride.

Mercaptans

Within some embodiments, an unsaturated ester or an epoxidized unsaturated ester is contacted with mercaptan. Within these embodiments, the mercaptan can be any mercaptan comprising from 1 to 20 carbon atoms. Generally, the mercaptan can have the following structure:

HS—R$^3$ wherein R3 is a C1 to C20 organyl groups or a C1 to C20 hydrocarbyl groups. In further embodiments the R3 can be a C2 to C10 organyl group or a C2 to C10 hydrocarbyl group. In some embodiments, the mercaptan composition comprises a solvent. In one aspect, the mercaptan composition comprises at least one other functional group.

The at least one other functional group can be selected from several different groups. For example, the at least one other functional group is an alcohol group, a carboxylic alcohol group, a carboxylic ester group, an amine group, a sulfide group, a thiol group, a methyl or ethyl ester of a carboxylic acid group, or combinations thereof. Other types of functional groups will be apparent to those of skill in the art and are to be considered within the scope of the present invention.

In some embodiments, the mercaptan is selected from the group consisting of 3-mercaptopropyl-trimethoxysilane, 2-mercaptopyridine, 4-mercaptopyridine, 2-mercaptopyrimidine, mercaptopyruvic acid, mercaptosuccinic acid, 2-mercaptonicotinic acid, 6-mercaptonicotinic acid, 2-mercaptophenol, 4-mercaptophenol, 3-mercapto-1,2-propanediol, 3-mercapto-1,2-propanediol, 3-mercapto-1-propanesulfonic acid, 1-mercapto-2-propanol, 3-mercapto-1-propanol, 2-mercaptopropionic acid, 3-mercaptopropionic acid, 2-mercaptobenzyl alcohol, 3-mercapto-2-butanol, 4-mercapto-1-butanol, 2-mercaptoethanesulfonic acid, 2-mercaptoethanol, 2-mercaptoethyl ether, 2-mercaptoethyl sulfide, 16-mercaptohexadecanoic acid, 6-mercapto-1-hexanol, 4'-mercaptoacetanilide, mercaptoacetic acid, 2-mercaptobenzoic acid, 3-mercaptobenzoic acid, 4-mercaptobenzoic acid, 2-mercaptothiazoline, 3-mercapto-1H-1,2,4-triazole, 11-mercaptoundecanoic acid, 1-mercapto-1-undecanol, or combinations thereof.

In some embodiments, the mercaptan is selected from the group consisting of beta-mercaptoethanol, 2-mercaptophenol, 3-mercaptophenol, 4-mercaptophenol, I-mercapto-2-propanol, 1-mercapto-3-propanol, mercaptoacetic acid, 2-mercaptopropionic acid, 3-mercaptopropionic acid, 2-mercaptobenzoic acid, 3-mercaptobenzoic acid, 4-mercaptobenzoic acid, 2-mercaptobenzylalcohol, 3-mercapto-2-butanol, 4-mercapto-1-butanol, 2-mercaptoethyl ether, 2-mercaptoethyl sulfide, 6-mercapto-hexanol, 3-mercapto-1,2-propanediol, mercaptosuccinic acid, and mixtures thereof. In further embodiments, the mercaptan is selected from the group consisting of beta-mercaptoethanol, 1-mercapto-2-propanol, 1-mercapto-3-propanol, 2-mercaptobenzylalcohol, 3-mercapto-2-butanol, 4-mercapto-1-butanol, 6-mercapto-hexanol, 3-mercapto-1,2-propanediol, and mixtures thereof. In further embodiments, the mercaptan is selected from the group consisting 2-mercaptophenol, 3-mercaptophenol, 4-mercaptophenol, and mixtures thereof. In yet further embodiments, the mercaptan is selected from the group consisting mercaptoacetic acid, 2-mercaptopropionic acid, 3-mercaptopropionic acid, 2-mercaptobenzoic acid, 3-mercaptobenzoic acid, 4-mercaptobenzoic acid, mercaptosuccinic acid, and mixtures thereof.

Isocyanates

Within some embodiments, the inventive compositions described herein are reacted with an isocyanate compound to produce a polythiourethane composition. The isocyanate may be any isocyanates capable of reacting with the thiol esters, hydroxy thiol esters, and a cross-linked thiol esters described herein to form a polyurethane composition. Generally, the isocyanate compound has at least two isocyanate groups.

In an aspect the isocyanates can be selected from the group consisting of 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis-(isocyanatomethyl)-cyclohexane, bis-(4-isocyanatocyclohexyl)-methane, 2,4'-diisocyanato-dicyclohexyl methane, bis-(4-isocyanato-3-methyl-cyclohexyl)-methane, (.alpha., .alpha.,.alpha.',.alpha.'-tetramethyl-1,3- and/or -1,4-xylylene diisocyanate, 1-isocyanato-1-methyl-4(3)-isocyanatomethyl cyclohexane, 2,4- and/or 2,6-hexahydro-toluylene diisocyanate, 1,3- and/or 1,4-phenylene diisocyanate, 2,4- and/or 2,6-toluylene diisocyanate, 2,4- and/or 4,4'-diphenylmethane diisocyanate and 1,5-diisocyanato naphthalene and mixtures thereof. In some embodiments, the isocyanate compound is selected from the group consisting of bis-(4-isocyanatocyclohexyl)-methane, 1,6-hexamethylene diisocyanate, isophorone diisocyanate, .alpha.,.alpha.,.alpha.',.alpha.'-tetramethyl-1,3- and/or -1,4-xylylene diisocyanate, 2,4- and/or 2,6-toluylene diisocyanate, and 2,4- and/or 4,4'-diphenylmethane diisocyanate. In other embodiments, the isocyanate compound is selected from the group consisting of isophorone diisocyanate, 2,4-toluylene diisocyanate and mixtures of 2,4- and 2,6-toluylene diisocyanate. In yet further embodiments, the isocyanate compound can be 4,4'-methylenebis(phenyl) diisocyanate (MDI), 4,4'-methylenebis(cyclohexyl) diisocyanate (Hydrogenated MDI), tolylene 2,4-diisocyanate (TDI), 1,6-diisocyanatohexane (HDI), and Luprinate™ M20S.

EXAMPLES

Mercaptanized Soybean Oil

Soybean oil was reacted with hydrogen sulfide in the presence of an initiator to produce mercaptanized soybean oil in accordance with the method steps described herein. Several examples follow utilizing the same procedure.

In the examples that included reacting soybean oil with hydrogen sulfide in the presence of UV light, the following feedstocks were utilized: Refined (Food Grade) Soybean Oil (Cargill); Unrefined Non-degummed Soybean Oil (ADM Supplier); Hydrogen Sulfide (Tessenderlo Sourcing, Air Products >99.9% Purity); and Tri-n-butylphosphite (Aldrich, 90%).

In order to quantitatively measure the thiol sulfur, the thiol sulfur analyses were conducted using silver nitrate titration in accordance with ASTM D3227, with the following modifications designed to minimize probe fouling by silver salts: the samples were diluted in a known mass of tetrahydrofuran. The silver nitrate concentration was 0.01 N standardized against potassium iodide.

Example 1

The soybean oil (see sourcing above, 500 mL) was charged to a 5 liter stainless steel autoclave reactor fitted with a horizontal quartz tube containing a 100 Watt Hanovia Medium Pressure UV lamp. The system was flushed with nitrogen and sealed at ambient pressure. Liquid hydrogen sulfide (1.96 kg) was charged to the reactor. The reactor pressure was 307 psig. Excess heat was dissipated by means of a circulating bath operating at 18° C. The reactor agitator was started The lamp was switched on for a period of 30 minutes. The reactor was slowly depressurized to a high-pressure flare line through a top portal vent. The product was then sparged with nitrogen to the high-pressure flare. The crude mercaptanized soybean oil was then drained out through a bottom drain valve.

The resulting mercaptanized soybean oil was subjected to nitrogen sparging under reduced pressure at 100° C. for a period of 4 hours to remove any residual hydrogen sulfide.

Thiol sulfur was analyzed by three different tests. The first test used was the modified ASTM D3227, which resulted in a thiol sulfur measurement of 4.64%. The second test used to measure the thiol sulfur was SLP-1204, which is a test developed by Chevron Phillips Chemical Company LLP. By using the SLP-1204 test, the resulting thiol sulfur measurement was 4.28%. Lastly, the total sulfur was measured by combustion analysis, which resulted in a total sulfur measurement of 4.27%.

Example 2

Vegetable oil (42 kg) was charged to a 100-gallon holding vessel. The vessel was purged with nitrogen and returned to atmospheric pressure. Hydrogen sulfide (174 kg) was charged to the holding vessel. The vessel temperature was controlled from 25-30° C. while the pressure was typically maintained between 380-400 psig. The reactants were continuously rolled from the holding tank through a stainless steel tubular photochemical reactor containing a 7.5 KW Hanovia medium pressure mercury lamp contained within a quartz tube. Reactor temperature, pressure, and composition were monitored over the course of the reaction. The reaction time was dependent upon reaching a desired composition of thiol sulfur. Upon completion, the unreacted hydrogen sulfide was slowly vented from the system. Residual $H_2S$ was removed at 100° C. and reduced pressure while passing nitrogen through a nitrogen sparge tube. The product was drained from the bottom of the reactor into a clean drum. The thiol sulfur measurements were 11.0% when using the modified ASTM D3227, 8.74% when using SLP-1204, and the total sulfur was 11.21% when using combustion analysis (total sulfur).

Example 3

The soybean oil (see sourcing above, 180 mL) and tri-n-butylphosphite (1.8 mL) was charged to a 1.5 liter stainless steel autoclave reactor fitted with a horizontal quartz tube containing a 100 Watt Hanovia Medium Pressure UV lamp. The system was flushed with nitrogen and sealed at ambient pressure. Liquid hydrogen sulfide (1.96 kg) was charged to the reactor. The reactor pressure was 307 psig. The circulating bath was started and bath temperature set at 18° C. The reactor agitator was started. The lamp was switched on for a period of 30 minutes. The reactor was slowly depressurized to a high-pressure flare line through a top portal vent. The reactor product was then sparged with nitrogen to the high-pressure flare. The crude mercaptanized soybean oil was then drained out through a bottom drain valve.

The resulting mercaptanized soybean oil was subjected to nitrogen sparging under reduced pressure at 100° C. for a period of 4 hours to remove any residual hydrogen sulfide. The thiol sulfur measurements were 13.0% when using the modified ASTM D3227, 9.82% when using SLP-1204, and 11.69% when using combustion analysis.

Table 1 provides the properties of the mercaptanized soybean oil produced in examples 1-3.

TABLE 1

Mercaptanized Soybean Oil Product Properties

| Example | Thiol Sulfur† (wt %) | Cyclic Sulfide to Thiol Group Molar Ratio | C=C to Thiol groups Molar Ratio |
|---|---|---|---|
| 1 | 4.28 | 0.02 | 2.79 |
| 2 | 11.0 | 0.03 | 0.26 |
| 3 | 13.0 | 0.03 | 0.51 |

†Thiol sulfur content determined by the modified ASTM D3227

Samples of modified soybean oil and modified linseed oil were also subjected to methanolysis substantially according to the procedure described in U.S. Pat. No. 3,991,089, which is incorporated herein by reference. 1 gram of mercaptanized soybean oil was placed in a round bottom flask. A solution of sodium methoxide in methanol (25%, 2.0 mL) was added to the mercaptanized oil and the mixture was stirred for about 1 hour at room temperature. Toluene (10 mL) and distilled water (5 mL) were added. The mixture was acidified with 0.5 N HCl until a pH of about 2-3 was obtained. The resulting layers were separated and the top layer was dried over $MgSO_4$ prior to filtering. The resulting samples were analyzed by GC-MS.

Example 4

Soybean oil was reacted with hydrogen sulfide in a 1000 gallon reactor having six medium pressure ultraviolet 7500 watt UV lamps. The general procedure for five mercaptanized soybean production runs is provided below.

Soybean oil was charged to a 1000 gallon stirred reactor. Hydrogen sulfide was then charged to the reactor. After the hydrogen sulfide was charged to the reactor, the stirrers and the UV lamps were turned on and the reaction allowed to build temperature and pressure as the reaction proceed. The reaction was continued until a minimum thiol sulfur content of 8 weight percent was achieved. After reaction was completion, the excess hydrogen sulfide was flashed from the reactor. For runs 2-5, the mercaptanized soybean oil product underwent an additional hydrogen sulfide stripping step comprising stripping hydrogen sulfide from the product under vacuum, 50 mm Hg, at 250° F. (only true for runs 2-5).

Table 2 provides the soybean oil and hydrogen sulfide charges to the reactor for five 1000 gallon reactor runs. The Table 2 also provides the approximate hydrogen sulfide to carbon-carbon double bond molar ratio based upon an average of 4.5 carbon-carbon double bonds per soybean oil molecule. Additionally, Table 2 provides the temperature and pressure ranges of the reactor during the reaction of soybean oil with hydrogen sulfide.

TABLE 2

1000 gallon reactor Mercaptanized Soybean Oil Production Run Conditions

| Run Number | Soybean oil (lbs) | Hydrogen Sulfide (lbs) | $H_2S$ to C=C Molar Ratio | Time (hours) | Temperature (° C.) | Pressure (psig) |
|---|---|---|---|---|---|---|
| 1 | 2264 | 4526 | 12 | 35 | 29-41 | 295-384 |
| 2 | 971 | 6039 | 38 | 10 | 31-44 | 323-429 |
| 3 | 513 | 6500 | 78 | <5.1 | 29-48 | 309-449 |
| 4 | 524 | 6528 | 77 | 3 | 26-43 | 279-424 |
| 5 | 276 | 6648 | 148 | 2 | 40-43 | 241-355 |

Table 3 provides the details of the analysis of the mercaptanized soybean oil producing in the five 1000 gallon reactor runs.

TABLE 3

1000 gallon reactor Mercaptanized Soybean Oil Product Properties

| Run Number | Thiol Sulfur† (wt %) | Cyclic Sulfide to Thiol Group Molar Ratio | C=C to Thiol groups Molar Ratio | Side Chain Containing Thiol Groups (%) |
|---|---|---|---|---|
| 1 | 9.3 | — | — | 71.6 |
| 2 | 9.6 | 0.04 | 0.48 | 72.3 |
| 3 | 9.2 | 0.03 | 0.59 | 69.1 |
| 4 | 9.3 | 0.03 | 0.62 | 71.6 |
| 5 | 10.1 | 0.03 | 0.54 | 72.3 |

†Thiol sulfur content determined by Raman spectroscopy

Mercaptanized Castor Bean Oil

Castor oil was reacted with hydrogen sulfide in the presence of an initiator to produce mercaptanized castor bean oil in accordance with the method steps described herein. Several examples follow utilizing the same procedure. In the examples that included reacting castor bean oil with hydrogen sulfide the following feedstocks were utilized: Castor Oil (Aldrich); Hydrogen Sulfide (Tessenderlo Sourcing, Air Products >99.9% Purity); and Tri-n-butylphosphite (Aldrich, 90%).

Example 1

Castor oil, 140 mL was charged to a 1.5 liter stainless steel autoclave reactor fitted with a horizontal quartz tube containing a 100 Watt Hanovia Medium Pressure UV lamp. The system was flushed with nitrogen and sealed at ambient pressure. Liquid hydrogen sulfide (0.76 kg) was charged to the reactor. The reactor pressure was 419 psig. The reactor agitator was started and adjusted to 800 rpm. The lamp was switched on for a period of 2 hours. The reaction temperature varied from 33.9 to 40.8° C. The final reactor pressure was 448 psig. The lamp was switched off and the reactor was slowly depressurized to a high-pressure flare line through a top portal vent. The reactor product was then sparged with nitrogen to the high-pressure flare. The crude mercaptanized soybean oil was then drained out through a bottom drain valve.

Example 2

Castor oil (140 mL) and tri-n-butylphosphite (1.4 mL) was charged to a 1.5 liter stainless steel autoclave reactor fitted with a horizontal quartz tube containing a 100 Watt Hanovia Medium Pressure UV lamp. The system was flushed with nitrogen and sealed at ambient pressure. Liquid hydrogen sulfide (0.76 kg) was charged to the reactor. The reactor pressure was 418 psig. The reactor agitator was started and adjusted to 800 rpm. The lamp was switched on for a period of 4 hours. The reaction temperature varied from 33.2 to 40.9° C. The final reactor pressure was 456 psig. The lamp was switched off and the reactor was slowly depressurized to a high-pressure flare line through a top portal vent. The reactor product was then sparged with nitrogen to the high-pressure flare. The crude mercaptanized soybean oil was then drained out through a bottom drain valve.

The analytical properties of the two mercaptanized castor oil products are provide in Table 4.

TABLE 4

Mercaptanized Castor Oil Product Properties

| Example | Thiol Sulfur[†] (wt %) | C=C to Thiol groups Molar Ratio | Side Chain Containing Thiol Groups (%) |
|---|---|---|---|
| 1 | 6.4 | 0.52 | 64.1 |
| 2 | 7.4 | 0.26 | 77.7 |

[†]Thiol sulfur content determined by Raman spectroscopy

Mercaptohydroxy Soybean Oil Synthetic Procedure

Example 1 (CPC407-81D)

Epoxidized Soybean Oil (700 g, ~0.7 mol) and 1,8-diazabicyclo[5.4.0]undec-7-ene (DBU, 4.7 g, 30.5 mmol) were charged to a 1-L Hastelloy C autoclave reactor that was pressure tested to 630 psig. Hydrogen sulfide ($H_2S$, 132.0 g, 3.87 mol) was then pressured into the stirred reactor contents through a dip tube in the liquid space. The reaction mixture was heated and maintained at 85° C. with stirring for 8 hrs, during which time the reactor pressure decreased from a maximum of 351 psig to 219 psig. The stirrer was stopped and while still warm (80-85° C.), excess $H_2S$ was slowly vented to a low-pressure flare. The reactor vapor space was then swept with $N_2$ for 1 hr and the reactor contents drained warm (80-85° C.). The reaction product was $N_2$ sparged under vacuum (<5 mmHg) at 130-140° C. for 16 hrs to remove residual $H_2S$. The resulting light yellow, viscous sticky oil had a thiol sulfur (titration by modified ASTM D3227) content of 7.53 wt. %, 2.5 SH/molecule, or 2.35 meq SH/g. Combustion analysis indicated C, 64.37%, H, 10.20%, N, <0.15%, and S, 9.51%.

Example 2 (CPC407-83)

Epoxidized Soybean Oil (600 g, ~0.6 mol) and 1,8-diazabicyclo[5.4.0]undec-7-ene (DBU, 5.0 g, 32.4 mmol) were charged to a 1-L Hastelloy C autoclave reactor, and the vessel was pressure tested to 630 psig. Hydrogen sulfide ($H_2S$, 204.0 g, 5.99 mol) was then pressured into the stirred reactor contents through a dip tube in the liquid space. The reaction mixture was heated and maintained at 97° C. with stirring for 14 hrs, during which time the reactor pressure decreased from a maximum of 509 psig to 229 psig. The stirrer was stopped and while still warm (90-95° C.), excess $H_2S$ was slowly vented to a low-pressure flare. The reactor vapor space was then swept with $N_2$ for 1 hr and the reactor contents drained warm (80-85° C.). The reaction product was $N_2$ sparged under vacuum (<50 mmHg) at 130-140° C. for 16 hrs to remove residual $H_2S$. The resulting light yellow, viscous sticky oil had a thiol sulfur (titration by modified ASTM D3227) content of 4.14 wt. %, 1.4 SH/molecule, or 1.29 meq SH/g. Combustion analysis indicated C, 65.18%, H, 10.17%, N, <0.15%, and S, 7.80%.

Example 3 (CPC407-86)

Epoxidized Soybean Oil (600 g, ~0.6 mol) and 1,8-diazabicyclo[5.4.0]undec-7-ene (DBU, 5.0 g, 32.4 mmol) were charged to a 1-L Hastelloy C autoclave reactor, and the vessel was pressure tested to 630 psig. Hydrogen sulfide ($H_2S$, 204.0 g, 5.99 mol) was then pressured into the stirred reactor contents through a dip tube in the liquid space. The reaction mixture was heated and maintained at 85° C. with stirring for 10 hrs, during which time the reactor pressure decreased from a maximum of 578 psig to 489 psig. The stirrer was stopped and while still warm (80-85° C.), excess $H_2S$ was slowly vented to a low-pressure flare. The reactor vapor space was then swept with $N_2$ for 1 hr and the reactor contents drained warm (80-85° C.). The reaction product was $N_2$ sparged under vacuum (<50 mmHg) at 130-140° C. for 16 hrs to remove residual $H_2S$. The resulting light yellow, viscous sticky oil had a thiol sulfur (titration with modified ASTM D3227) content of 8.28 wt. %, 2.8 SH/molecule, or 2.58 meq SH/g. Combustion analysis indicated C, 65.24%, H, 9.52%, N, 0.18%, and S, 9.53%.

Example 4 (CPC407-88)

Epoxidized soybean oil (600 g, ~0.6 mol) and 1,8-diazabicyclo[5.4.0]undec-7-ene (DBU, 5.0 g, 32.4 mmol) were charged to a 1-L Hastelloy C autoclave reactor that was pressure tested to 630 psig. Hydrogen sulfide ($H_2S$, 204.0 g, 5.99 mol) was then pressured into the stirred reactor contents through a dip tube in the liquid space. The reaction mixture was heated and maintained at 85° C. with stirring for 12 hrs, during which time the reactor pressure decreased from a maximum of 587 psig to 498 psig. The stirrer was stopped and while still warm (80-85° C.), excess H$_2$S was slowly vented to a low-pressure flare. The reactor vapor space was then swept with N$_2$ for 1 hr and the reactor contents drained warm (80-85° C.). The reaction product was N$_2$ sparged under vacuum (<50 mmHg) at 130-140° C. for 16 hrs to remove residual H$_2$S. The resulting light yellow, viscous sticky oil had a thiol sulfur (titration by modified ASTM D3227) content of 8.24 wt. %, 2.8 SH/molecule, or 2.57 meq SH/g. Combustion analysis indicated C, 63.39%, H, 10.01%, N, <0.15%, and S, 8.76%.

Example 5 (CPC407-93)

Epoxidized soybean oil (600 g, ~0.6 mol) and 1,8-diazabicyclo[5.4.0]undec-7-ene (DBU, 5.0 g, 32.4 mmol) were charged to a 1-L Hastelloy C autoclave reactor, and the vessel was pressure tested to 630 psig. Hydrogen sulfide (H$_2$S, 204.0 g, 5.99 mol) was then pressured into the stirred reactor contents through a dip tube in the liquid space. The reaction mixture was heated and maintained at 85° C. with stirring for 8 hrs, during which time the reactor pressure decreased from a maximum of 606 psig to 537 psig. The stirrer was stopped and while still warm (80-85° C.), excess H$_2$S was slowly vented to a low-pressure flare. The reactor vapor space was then swept with N$_2$ for 1 hr and the reactor contents drained warm (80-85° C.). The reaction product was N$_2$ sparged under vacuum (<50 mmHg) at 130-140° C. for 16 hrs to remove residual H$_2$S. The resulting light yellow, viscous sticky oil had a thiol sulfur (titration by modified ASTM D3227) content of 7.34 wt. %, 2.5 SH/molecule, or 2.29 meq SH/g. Combustion analysis indicated C, 64.47%, H, 10.18%, N, <0.15%, and S, 8.40%.

Example 6 (CPC407-94)

Epoxidized soybean oil (600 g, ~0.6 mol) and 1,8-diazabicyclo[5.4.0]undec-7-ene (DBU, 5.0 g, 32.4 mmol) were charged to a 1-L Hastelloy C autoclave reactor that was pressure tested to 630 psig. Hydrogen sulfide (H$_2$S, 204.0 g, 5.99 mol) was then pressured into the stirred reactor contents through a dip tube in the liquid space. The reaction mixture was heated and maintained at 85° C. with stirring for 6 hrs, during which time the reactor pressure decreased from a maximum of 586 psig to 556 psig. The stirrer was stopped and while still warm (80-85° C.), excess H$_2$S was slowly vented to a low-pressure flare. The reactor vapor space was then swept with N$_2$ for 1 hr and the reactor contents drained warm (80-85° C.). The reaction product was N$_2$ sparged under vacuum (<50 mmHg) at 130-140° C. for 16 hrs to remove residual H$_2$S. The resulting light yellow, viscous sticky oil had a thiol sulfur (titration by modified ASTM D3227) content of 5.93 wt. %, 2.0 SH/molecule, or 1.85 meq SH/g. Combustion analysis indicated C, 65.26%, H, 10.19%, N, <0.15%, and S, 8.43%.

Example 7 (CPC407-95)

Epoxidized soybean oil (600 g, ~0.6 mol) and 1,8-diazabicyclo[5.4.0]undec-7-ene (DBU, 5.0 g, 32.4 mmol) were charged to a 1-L Hastelloy C autoclave reactor, and the vessel was pressure tested to 630 psig. Hydrogen sulfide (H$_2$S, 204.0 g, 5.99 mol) was then pressured into the stirred reactor contents through a dip tube in the liquid space. The reaction mixture was heated and maintained at 85° C. with stirring for 4 hrs, during which time the reactor pressure decreased from a maximum of 595 psig to 554 psig. The stirrer was stopped and while still warm (80-85° C.), excess H$_2$S was slowly vented to a low-pressure flare. The reactor vapor space was then swept with N$_2$ for 1 hr and the reactor contents drained warm (80-85° C.). The reaction product was N$_2$ sparged under vacuum (<50 mmHg) at 130-140° C. for 16 hrs to remove residual H$_2$S. The resulting light yellow, viscous sticky oil had a thiol sulfur (titration by modified ASTM D3227) content of 5.36 wt. %, 1.8 SH/molecule, or 1.67 meq SH/g. Combustion analysis indicated C, 65.67%, H, 10.17%, N, 0.34%, and S, 9.84%.

Example 8 (CPC407-97)

Epoxidized soybean oil (600 g, ~0.6 mol) and 1,8-diazabicyclo[5.4.0]undec-7-ene (DBU, 5.0 g, 32.4 mmol) were charged to a 1-L Hastelloy C autoclave reactor that was pressure tested to 630 psig. Hydrogen sulfide (H$_2$S, 204.0 g, 5.99 mol) was then pressured into the stirred reactor contents through a dip tube in the liquid space. The reaction mixture was heated and maintained at 85° C. with stirring for 4 hrs, during which time the reactor pressure decreased from a maximum of 577 psig to 519 psig. The stirrer was stopped and while still warm (80-85° C.), excess H$_2$S was slowly vented to a low-pressure flare. The reactor vapor space was then swept with N$_2$ for 1 hr and the reactor contents drained warm (80-85° C.). The reaction product was N$_2$ sparged under vacuum (<50 mmHg) at 130-140° C. for 16 hrs to remove residual H$_2$S. The resulting light yellow, viscous sticky oil had a thiol sulfur (titration with AgNO$_3$) content of 5.85 wt. %, 2.0 SH/molecule, or 1.82 meq SH/g. Combustion analysis indicated C, 65.09%, H, 10.15%, N, 0.35%, and S, 10.63%.

Example 9 (CPC407-98)

Epoxidized soybean oil (600 g, ~0.6 mol) and 1,8-diazabicyclo[5.4.0]undec-7-ene (DBU, 5.0 g, 32.4 mmol) were charged to a 1-L Hastelloy C autoclave reactor, and the vessel was pressure tested to 630 psig. Hydrogen sulfide (H$_2$S, 204.0 g, 5.99 mol) was then pressured into the stirred reactor contents through a dip tube in the liquid space. The reaction mixture was heated and maintained at 85° C. with stirring for 2 hrs, during which time the reactor pressure decreased from a maximum of 577 psig to 508 psig. The stirrer was stopped and while still warm (80-85° C.), excess H$_2$S was slowly vented to a low-pressure flare. The reactor vapor space was then swept with N$_2$ for 1 hr and the reactor contents drained warm (80-85° C.). The reaction product was N$_2$ sparged under vacuum (<5 mmHg) at 130-140° C. for 16 hrs to remove residual H$_2$S. The resulting light yellow, viscous sticky oil had a thiol sulfur (titration by modified ASTM D3227) content of 5.07 wt. %, 1.7 SH/molecule, or 1.58 meq SH/g. Combustion analysis indicated C, 63.96%, H, 10.01%, N, 0.35%, and S, 11.22%.

Table 5 provides the properties of the mercaptohydroxy soybean oil samples produced in Examples 1-10.

TABLE 5

| Example | Reaction Time (hrs) | Reaction Temp (° C.) | Mercaptan Sulfur (wt. %)[1] | SH per molecule[2] | Epoxides groups left per molecule[3] | Epoxide:SH Molar Ratio |
|---|---|---|---|---|---|---|
| 1 | 0 | N/A | N/A | 0 | 4.3 | — |
| 2 | 8 | 85 | 7.53 | 2.5 | 1.8 | 0.72 |
| 3 | 14 | 97 | 4.14 | 1.4 | 2.9 | 2.07 |
| 4 | 10 | 85 | 8.28 | 2.8 | 1.5 | 0.54 |
| 5 | 12 | 85 | 8.24 | 2.8 | 1.5 | 0.54 |
| 6 | 8 | 85 | 7.34 | 2.5 | 1.8 | 0.72 |
| 7 | 6 | 85 | 5.93 | 2.0 | 2.3 | 1.15 |
| 8 | 4 | 85 | 5.36 | 1.8 | 2.5 | 1.40 |
| 9 | 4 | 85 | 5.85 | 2.0 | 2.3 | 1.15 |
| 10 | 2 | 85 | 5.07 | 1.7 | 2.6 | 1.529 |

[1]Thiol sulfur was determined by silver nitrate oxidation using ASTM D 3227
[2]Determined by wt. % thiol sulfur
[3]Determined by subtracting the SH/molecule from the starting material epoxide content Example 1L Additional mercaptohydroxy soybean oils were prepared using different quantities of epoxidized soybean oil, hydrogen sulfide, and catalyst using different temperature and reaction times. The general procedure used to produce the mercaptohydroxy soybean oils is provided as follows.

Epoxidized soybean oil and the catalyst were charged to a 1-L Hastelloy C autoclave reactor, and the vessel was pressure tested to 1000 psig. Hydrogen sulfide was then pressured into the stirred reactor contents through a dip tube in the liquid space. The reaction mixture was heated and maintained at temperature a set period of time with stirring for 12 hrs. During the reaction time the reactor pressure usually decreased. At the end of the reaction time, the stirrer was stopped and excess $H_2S$ was slowly vented while the reaction mixture was warm to a low-pressure flare. The reactor vapor space was then swept with $N_2$ for 1 hr and the reactor contents drained. The reaction product was $N_2$ sparged under vacuum (<50 mmHg) at 100° C. for 16 hrs to remove residual $H_2S$. Table 6 provides the reaction conditions used to produce the mercaptohydroxy soybean oils for several runs and the thiol sulfur content of the mercaptohydroxy soybean oils produced.

Run number 407-86 was subjected to the sodium methoxide methanolysis procedure and subsequently analyzed by GC/MS. The GS/MS analysis indicated that the product had epoxide group to thiol group molar ratio of approximately 0.14. The methanolysis data also indicated that an average of 80.4 percent of the product mercaptohydroxy soybean oil contained sulfur.

Oligomerized MSO (Mercaptanized Soybean Oil)

Example 1

Mercaptanized soybean oil (900.1 g; 10.92 wt. % thiol sulfur,) was charged to a three necked flask along with elemental sulfur pellets (9.6 g). The reaction mixture was heated to 120° C. until sulfur dissolved and then cooled to 99° C. Tributylamine (4.8 g) was charged to the reaction mixture with an addition funnel drop wise. The reaction mixture was mixed at 90° C. for 2 hrs. $H_2S$ evolution was observed. The reaction product (904.8 g) was sparged with $N_2$ under vacuum at 110° C. for 4 hrs to remove residual $H_2S$. The final product was a light yellow oil with a thiol sulfur of 6.33 wt. % (by modified ASTM D3227). The elemental combustion analysis was 70.19% C, 10.37% H; and 11.21% S.

Example 2

Mercaptanized soybean oil (900.0 g; 10.92 wt. % thiol sulfur,) was charged to a three necked flask along with

TABLE 6

Mecaptohydroxy Soybean Oil Production Runs

| Run | Epoxidized Soybean Oil (g) | Catalyst (g) | $H_2S$ (g) | $H_2S$:Epoxide Molar Ratio | Temperature (° C.) | Time (minutes) | Thiol Sulfur[a] (wt. %) |
|---|---|---|---|---|---|---|---|
| 556-41[†] | 249.6 | 1.950 | 214.0 | 5.86 | 64 | 728 | 5.69 |
| 556-53[†] | 250.0 | 2.000 | 213.0 | 5.81 | 100 | 370 | 9.04 |
| 556-47[†] | 250.5 | 1.050 | 213.0 | 5.81 | 101 | 720 | 10.47 |
| 407-81D[†] | 500.0 | 4.200 | 255.0 | 3.49 | 85 | 480 | 7.53 |
| 407-86[†] | 600.0 | 5.000 | 204.0 | 2.07 | 85 | 600 | 8.28 |
| 556-79[‡] | 250.0 | 2.600 | 214.0 | 5.83 | 100 | 720 | 6.68 |
| 556-80[‡] | 251.0 | 5.000 | 214.0 | 5.81 | 100 | 720 | 9.51 |

[†]Catalyst was DBU
[‡]catalyst was triethylamine (TEA)
[a]Thiol sulfur measured by silver nitrate titration using modified ASTM D 3227 elemental sulfur pellets (36.0 g). The reaction mixture was heated to 120° C. until sulfur dissolved and then cooled to 100° C. Tributylamine (4.8 g) was charged to the reaction mixture with an addition funnel drop wise. The reaction mixture was mixed at 90° C. for 36 hrs. $H_2S$ evolution was observed. The reaction product (825.6 g) was sparged with $N_2$ under vacuum at 90° C. for 36 hrs to remove residual $H_2S$. The reaction product was then sparged with $N_2$ under vacuum at 110° C. for 3 hrs to remove residual $H_2S$. The final product was a light yellow oil with a thiol sulfur of 2.36 wt. % (by modified ASTM D3227). The elemental combustion analysis was 68.90% C; 11.07% H; and 12.25% S.

Example 3

Mercaptanized soybean oil (900.1 g; 10.92 wt. % thiol sulfur,) was charged to a three necked flask along with elemental sulfur pellets (18.0 g). The reaction mixture was heated to 125° C. until sulfur dissolved and then cooled to 101° C. Tributylamine (4.8 g) was charged to the reaction mixture with an addition funnel drop wise. The reaction mixture was mixed at 90° C. for 2 hrs. $H_2S$ evolution was observed. The reaction product (901.5 g) was sparged with $N_2$ under vacuum at 110° C. for 4 hrs to remove residual $H_2S$. The final product was a light yellow oil with a thiol sulfur of 4.9 wt. % (by modified ASTM D3227). The elemental combustion analysis was 69.58% C, 11.25% H; and 11.31% S.

Example 4

Mercaptanized soybean oil (900.2 g; 10.92 wt. % thiol sulfur,) was charged to a three necked flask along with elemental sulfur pellets (45.0 g). The reaction mixture was heated to 125° C. until sulfur dissolved and then cooled to 100° C. Tributylamine (4.8 g) was charged to the reaction mixture with an addition funnel drop wise. The reaction mixture was mixed at 90° C. for 2 hrs. $H_2S$ evolution was observed. The reaction product (915.0 g) was sparged with $N_2$ under vacuum at 110° C. for 4 hrs to remove residual $H_2S$. The final product was a light yellow oil with a thiol sulfur of 1.41 wt. % (by modified ASTM D3227). The elemental combustion analysis was 68.35% C, 10.98% H; and 13.28% S.

Table 7 provides the viscosities of the oligomerized mercaptanized soybean oil (cross-linked mercaptanized soybean oil) produced in examples 1-4 at several different temperature.

TABLE 7

| | Viscosities of Oligomerized MSO | | | |
|---|---|---|---|---|
| Example | 25° C. Viscosity (cP) | 50° C. Viscosity (cP) | 75° C. Viscosity (cP) | 100° C. Viscosity (cP) |
| 1 | 610.5 | 162.8 | 52.14 | 29.60 |
| 2 | 3240 | — | 200 | 106.3 |
| 3 | 843 | 321.7 | 68.8 | 38.5 |
| 4 | >10000 | 1502 | 398 | 213 |

Determined by Brookfield Viscometer

The different oligomeric mixtures were analyzed by GPC. The GPC data showed the presence of various oligomers including up to 20 triglyceride units linked together.

Polythiourethane Polymer Preparation

Mercaptanized Soybean Oil (MSO), Mercaptohydroxy Soybean Oil (MHSO), or Cross-linked Mercaptanized Soybean Oil (CMSO—Oligomerized MSO) (all referred to hereafter as cross-linking agent) was weighed into a polyethylene beaker. To the cross-linking agent was added the desired polyisocyanate. To this reaction mixture was added the desired catalyst. The three-component reaction mixture was then manually stirred with a wooden Popsicle stick. The entire pre-polymer mixture was then poured into the appropriate mold for curing. Example molds include 50 mm diameter or 70 mm diameter aluminum pans. The sample was then cured via the desired profile, A, B, or C. After the cure time was complete, the sample was stored at room temperature in plastic, resealing, sandwich bags for 2 weeks. The sample was then removed from the aluminum mold and either tested by ASTM D2240-02B, ASTM E1545-95A and/or E228-95 or resealed in the sandwich bag for storage.

Polythiourethane Compositions

TABLE 8

| R&T Feedstocks | Diisocyanates | Stoichiometry | Catalysts |
|---|---|---|---|
| MSO - trifunctional | LuprinateTM - PolyMDI | ≈0.9 | DABCO |
| MSO - difunctional | MDI | ≈1 | DBTDL |
| MSO - TBP treated | HMDI | ≈1.25 | Jeffol ® A-480 |
| MHSO - trimercaptan | TDI | | |
| MHSO - dimercaptan | HDI | | |
| CMSO - hi cross-link | | | |
| CMSO - med cross-link | | | |
| CMSO - low cross-link | | | |
| Castor Oil | | | |

Numerous polythiourethane compositions were prepared by reacting a thiol ester composition with a diisocyanate in the presence of a catalyst by using the processes described herein for preparing such polythiourethane compositions. The compositions were produced using the different variables of feedstocks, diisocyanates, stoichiometry, and catalysts shown in Table 8. Once every combination of variable was used, over 1200 compositions were produced. Each of the feedstocks were reacted with each of the diisocyanates at each of the stoichiometries with each of the catalysts listed to produce the 1200+ compositions. The stoichiometry was based upon a thiol ester composition (MSO, MHSO, CMSO, MCO) active hydrogen (thiol and hydroxyl group) to diisocyanate equivalent ratio. For example, caster oil was reacted with toluene diisocyanate at a stoichiometric value of 1.25 while using Jeffol® A-480 as the catalyst. As another example, a thiol ester composition was reacted with methane diisocyanate at a stoichiometric value of 0.9 while using the DABCO catalyst.

In addition polythiourethanes produced from the matrix above two polythiourethanes were produced from mercaptanized castor oil (MCO).

In the first MCO polythiourethane example, MCO was weighed into a polyethylene beaker. To the MCO agent was added Luprinate at a thiol to isocyanate mole ratio of 0.95. To this reaction mixture was added dibutyl tin dilaurate (DBTDL) at a weight percent of 0.125 based upon the total weight of the ingredients. The three-component reaction mixture was then manually stirred with a wooden Popsicle stick. The entire pre-polymer mixture was then poured into a mold for curing and cured using curing profile B. After the curing time was complete it was determined that the preparation produced a polythiourethane polymer.

In the second MCO polythiourethane example, MCO was weighed into a polyethylene beaker. To the MCO agent was added Luprinate M20S at a thiol to isocyanate mole ratio of 1.00. To this reaction mixture was added dibutyl tin dilaurate (DBTDL) at a weight percent of 0.125 based upon the total weight of the ingredients. The three-component reaction mixture was then manually stirred with a wooden Popsicle stick. The entire pre-polymer mixture was then poured into a mold for curing and cured using curing profile B. After the curing time was complete it was determined that the preparation produced a polythiourethane polymer.

In the polythiourethane compositions, the feedstock thiol ester compositions that were used included MSO (mercaptanized soybean oil), MHSO (mercaptohydroxy soybean oil), CMSO (cross-linked mercaptanized soybean oil), castor oil, and MCO (mercaptanized caster oil). The diisocyanates that were used to produce these compositions included MDI (4,4'-methylenebis(phenyl) diisocyanate), HMDI (4,4'-methylenebis(cyclohexyl) diisocyanate, which is also known as hydrogenated MDI), TDI (tolylene 2,4-diisocyanate), HDI (1,6-diisocyanatohexane, which is also known as hexamethylene diisocyanate), and Luprinate™ M20S (which is an oligomerized form of MDI and is also referred to as polymeric MDI that is produced by BASF Corporation). The catalysts that were used included DABCO (diazabicyclooctane-di-tertiary amine), DBTDL (dibutyl tin dilaurate—organometallic catalyst), Jeffol® A-480 (which is a tertiary amine polyol produced by Huntsman Based Chemicals), and BDMA (benzyldimethylamine).

Various physical properties were determined for randomly selected polythiourethane compositions of the 1200+ compositions, the results of which are included in tables that are attached as FIGS. 7A-7F. The curing profiles that were used are as follows: A=curing for 1-8 hours at room temperature, followed by curing at 65° C. overnight, and then curing at 95° C. for 8 hours; B=curing at 65° C. overnight, followed by curing at 95° C. for 24 hours; and C=curing at 120° C. for 3 hours, followed by curing at 95° C. for 24 hours. CTE 1 represents the coefficient of thermal expansion between the glass transition temperature and a first transition temperature. CTE 2 represents the coefficient of thermal expansion between the first transition temperature and a second transition temperature.

FERTILIZER EXAMPLES

Embodiments of the present invention will be illustrated with reference to the following examples that should not be used to limit or construe the invention. Those of ordinary skill in the art will readily appreciate that the specific conditions and methodology noted in the Fertilizer Examples can be varied to produce the same or similar compositions. Unless otherwise noted, all temperatures are degrees Celsius and all ingredient amounts percentages are by weight.

In the Fertilizer Examples, the following materials were used:

A: Fertilizer particles—granular fertilizer grade urea, SGN 250, commercially available from Agrium;

B1: Mercaptanized soybean oil (an example of MVO discussed above)—Polymercaptan 358, available from Chevron Phillips Chemical Co.; 8.65% thiol sulfur; 370 equivalent weight; viscosity of 510.6 cSt @ 21° C.;

B2: Mercapto-hydroxy soybean oil (an examples of MHVO discussed above)—A mercapto-hydroxy soybean oil made by the free radical addition of hydrogen sulfide to epoxidized soybean oil; the mercapto and hydroxy functionalities are equal; 8.335% thiol sulfur; equivalent weight 192 (including both mercapto and hydroxy functionalities);

B3: Sulfur cross-linked mercaptanized soybean oil (an example of CMVO discussed above)—A sulfur cross-linked mercaptanized soybean oil made by the addition of elemental sulfur to mercaptanized soybean oil; thiol sulfur content 6.33%; equivalent weight 506;

B4: Sulfur cross-linked mercaptanized soybean oil (an example of CMVO discussed above)—A sulfur cross-linked mercaptanized soybean oil made by the addition of elemental sulfur to mercaptanized soybean oil; thiol sulfur content 7.64%; equivalent weight 419; cross-linkcross-link C1: Isocyanate #17—A polymeric MDI, commercially available from BASF Canada, equivalent weight of 133;

C2: Epoxy resin—5 minute epoxy resin, commercially available from ITW Devcon, Danvers, Mass. 01923 USA, equivalent weight 198;

D1: Organic additive—Gulftene C30-HA alpha olefin wax, commercially available from Chevron Phillips Chemical Co., melting point 65° C.-80° C.;

D2: Organic additive—Calwax 170, a microcrystalline wax commercially available from Calwax Corporation;

E: Cross-linking agent—Jeffol A480, commercially available from Huntsman Polyurethanes; equivalent weight of 120; functionality 4.0; viscosity of 4000 cPs @25C;

F1: Amine catalyst: Exp-9, commercially available from Huntsman Polyurethanes; and F2: Amine catalyst: 1,8-Diazabicyclo[5,4,0]undec-7-ene (DBU), CAS# 6674-22-2.

Fertilizer Examples 1-6

A series of CRF materials were produced using the formulations set out in Table 4 using the following methodology. The amount of fertilizers particles (A) coated in each Fertilizer Example was 1000 g.

A stainless steel coating drum, 12 inches in diameter by 6 inches deep, with an enclosed back plate and a front plate that had an 8 inch central opening was used. The coating drum was fitted with four evenly spaced longitudinal baffles, each about ½ inch high. The coating drum was connected to a variable speed drive, set to rotate the drum at 18 rpm.

During the process, the internal temperature of the drum and its contents was maintained at about 70° C. by using a variable speed electric heating gun. The coating components were added using individual automatic macro pipettes capable of adding ⅓ the weight of each coating component in a single addition. In other words, the coating was applied in 3 layers—the total coating weight is reported in Table 4. In Fertilizer Examples, 2, 3 and 6, a wax overcoat was applied after application of the 3-layered coating. At the end of the process, the drum and its contents were cooled to 40° C. by blowing a stream of room temperature air into the drum. The contents were removed and stored in a plastic bag.

A Paint shaker test was used to evaluate the mechanical handling durability of each product of the Fertilizer Examples. The "Paint shaker simulation" test used to simulate the damage to the controlled release coating is conducted in a paint shaker machine using the following methodology.

First 200 grams of the slow release fertilizer is placed in a 6" diameter by 5.5" deep metal can with lid. Then 8 (¼ inch by ½ inch) machine bolts with slotted heads and 8 (¼ inch) square head nuts are added in the can. The can with the slow release fertilizer, nuts, and bolts is then placed securely in a paint conditioner/shaker (Red Devil, ¼ H.P. model). The test sample is vigorously conditioned in the paint shaker at frequency of 730 cycles per minute for 6 minutes. The operating time is controlled with an electronic timer (Gralab model 451) that automatically stops the paint shaker at the preset time. After the paint shaker cycling is complete the can is removed and the nuts and bolts are removed by passing the contents through a 3½ mesh screen. The slow release fertilizer is collected in a pan and returned to its sample bag for the release rate analysis.

A comparison test has been conducted to correlate the simulation effect of the paint shaker with the damage in some commercial fertilizer blenders. The operating time of the paint shaker and the number of the bolts and nuts are determined based on the comparison test. The presetting of these parameters in the test for the work in this patent can simulate properly the damage in the commercial fertilizer blenders.

The water release rate profile for the slow release fertilizer material before and after the Paint shaker simulation test was then determined. In the analysis, a Technicon AutoAnalyzer™ was calibrated and used pursuant to the teachings of *Automated Determination of Urea and Ammoniacal Nitrogen* (University of Missouri, 1980). The following procedure was used:

1. Accurately weigh 15 grams (±0.1 mg) of the sample into a weigh dish. Record the weight of sample. Transfer the sample to 125 mL Erlenmeyer flask.
2. Add 75 mL of demineralized water and stopper the flask.
3. Gently swirl the sample and water until all the particles are submersed.
4. Let the sample stand for a specified time at a constant temperature (typically at room temperature).
5. Gently swirl the flask to mix the solution and decant only the solution to a 100 mL volumetric flask.
6. Rinse the sample with demineralized water adding to the volumetric flask.
7. Bulk to volume of volumetric flask and mix thoroughly.
8. If the test is to be repeated for another time period, repeat starting at Step 2.
9. Once the Technicon AutoAnalyzer II is on line, transfer some of this solution (or perform the required dilutions if necessary) to the Technicon sample cups for analysis.
10. Record the results as parts per million N—$NH_3$ (read directly from a Shimadzu Integrator)

Figure 8:
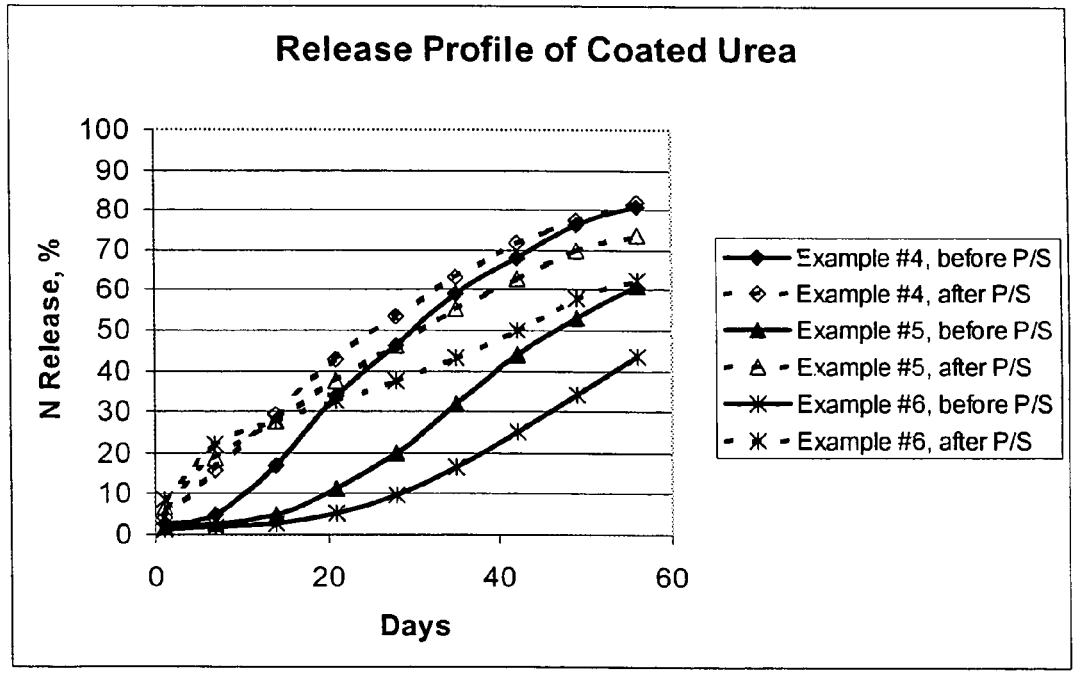
FIG. 8 illustrates the water release performance of a CRF material produced in Fertilizer Examples 4-6 in accordance with an embodiment of the present invention.
Figure 9:
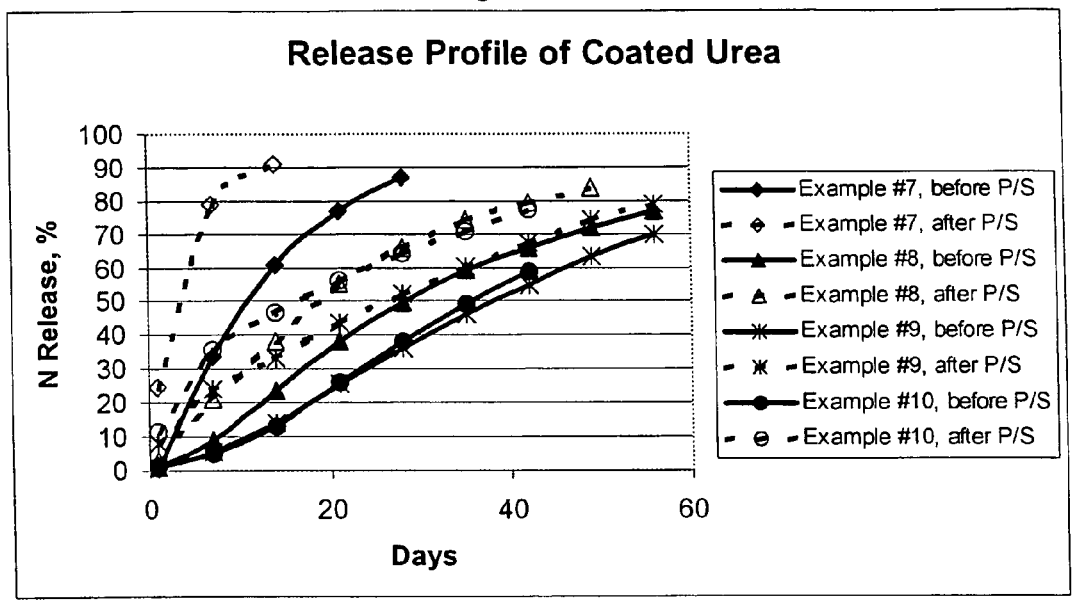
FIG. 9 illustrates the water release performance of a CRF material produced in Fertilizer Examples 7-10 in accordance with an embodiment of the present invention.

The water release performance for the CRF material produced in Fertilizer Examples 1-3 is shown in FIG. 8—in each case, the water release performance is shown both before and after Paintshaker handling test. The water release performance for the CRF material produced in Fertilizer Examples 4-6 is shown in FIG. 9—in each case, the water release performance is shown both before and after Paintshaker handling test.

Figure 7:
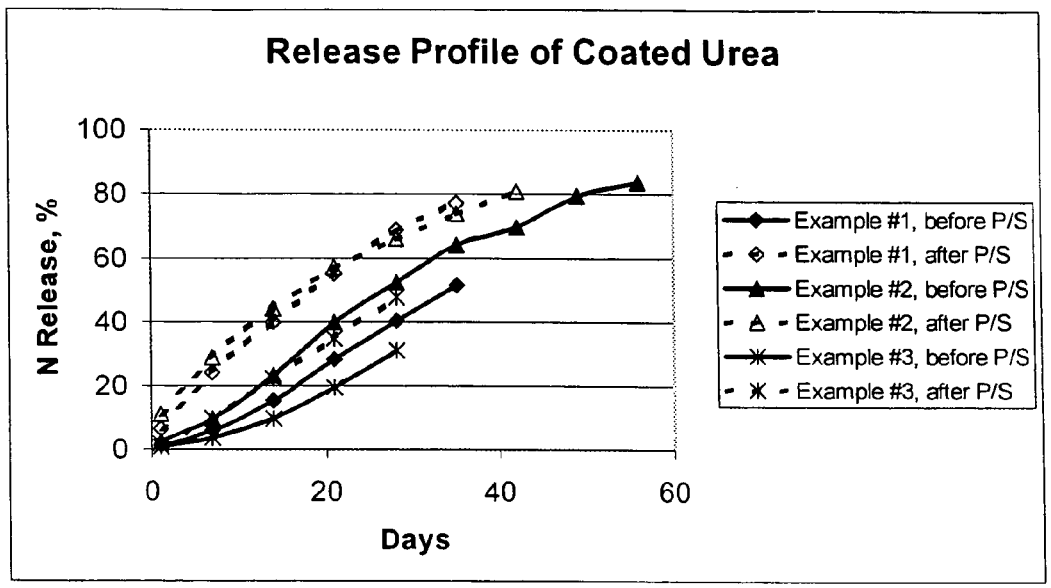
FIG. 7 illustrates the water release performance of a CRF material produced in Fertilizer Examples 1-3 in accordance with an embodiment of the present invention.

The results in FIGS. 7 and 8 illustrate that a polythiourethane coating can be made using mercaptanized soybean oil to produce a CRF material having desirable slow release properties. These results also illustrate that the release performance can be controlled by selection of the organic additive (e.g., wax).

Fertilizer Examples 7-10

A series of CRF materials were produced and tested using the methodology reported above for Fertilizer Examples 1-6 and the formulations set out in Table 5.

The water release performance for the CRF material produced in Fertilizer Examples 7-10 is shown in FIG. 9—in each case, the water release performance is shown both before and after Paintshaker handling test.

The results in FIG. 9 illustrate that a polythiourethane coating can be made using sulfur cross-linked mercaptanized soybean oil to produce a CRF material having desirable slow release properties. These results also illustrate that the addition of a cross-linking agent to the coating formulation can be used to reduce the release rate of the coated fertilizer.

Fertilizer Examples 11-14

A series of CRF materials were produced and tested using the methodology reported above for Fertilizer Examples 1-6 and the formulations set out in Table 6.

Figure 10:
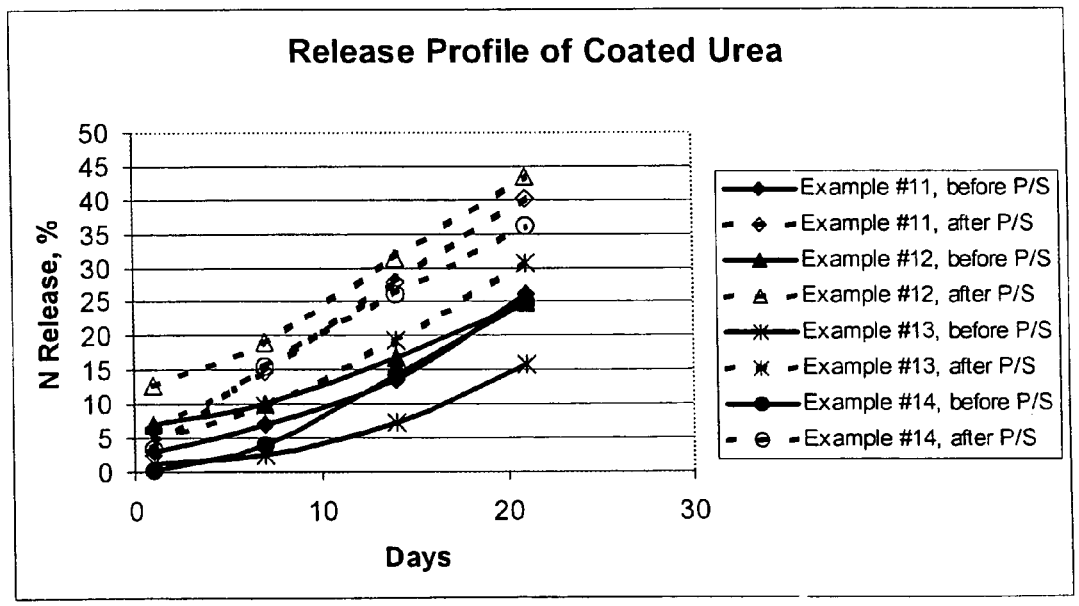
FIG. 10 illustrates the water release performance of a CRF material produced in Fertilizer Examples 11-14 in accordance with an embodiment of the present invention.

The water release performance for the CRF materials produced in Fertilizer Examples 11-14 is shown in FIG. 10—in each case, the water release performance is shown both before and after Paintshaker handling test.

The results in FIG. 10 illustrate that a polythiourethane coating can be made using mercapto-hydroxy soybean oil to produce a CRF material having desirable slow release properties. These results also illustrate that a polythiourethane coating can be made using a mixture of a mercaptanized soybean oil and a mercapto-hydroxy soybean oil to produce a CRF material having desirable slow release properties.

Fertilizer Examples 15-17

A series of CRF materials were produced and tested using the methodology reported above for Fertilizer Examples 1-6 and the formulations set out in Table 7.

Figure 11:
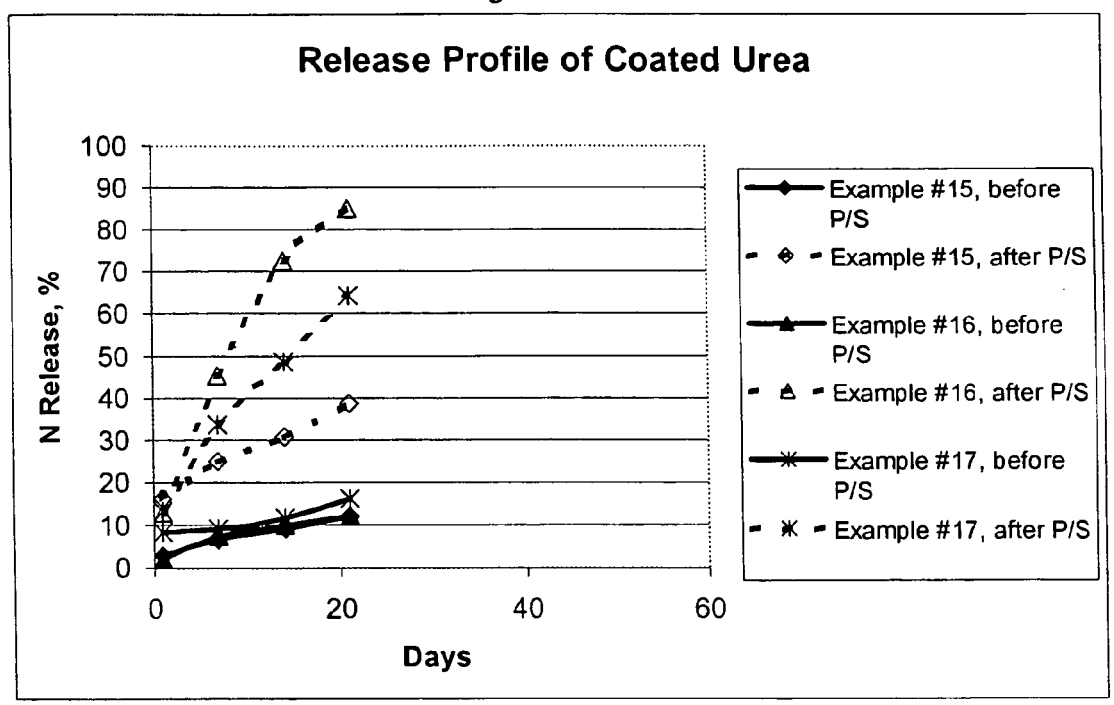
FIG. 11 illustrates the water release performance of a CRF material produced in Fertilizer Examples 15-17 in accordance with an embodiment of the present invention.

The water release performance for the CRF materials produced in Fertilizer Examples 15-17 is shown in FIG. 11—in each case, the water release performance is shown both before and after Paintshaker handling test.

The results in FIG. 11 illustrate that an epoxy polymer coating can be made using mercapto-hydroxy soybean oil to produce a CRF material having desirable slow release properties.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

ANALYSIS

Analysis of the Thiol Containing Esters, Hydroxy Thiol Containing Esters and Cross-Linked Thiol Containing Ester Particular aspects of the thiol containing esters, hydroxy thiol containing esters, cross-linked thiol ester, unsaturated esters and epoxidized unsaturated esters are measured particular analytical techniques. Thiol sulfur values were obtained using a silver nitrate titration as described in ASTM D3227 or by Raman spectroscopy. Carbon-carbon double bond to thiol group molar ratio, cyclic sulfide to thiol group molar ratios were determined by $^{13}C$ NMR and/or GC analysis of the thiol containing ester or hydroxy thiol containing ester side chains.

Thiol Sulfur Content by Raman Spectroscopy

Thiol sulfur content was measured by both silver nitrate titration, ASTM D3227, and/or Raman spectroscopy. The Raman spectroscopy method is practiced by measuring the Raman spectra of the thiol containing ester, hydroxy thiol containing ester, cross-linked thiol ester and comparing the spectra to calibration standards containing know thiol compounds having know amounts of thiol groups. Generally, the calibration standard thiol compound has a similar structure to the thiol containing esters analyzed.

The thiol containing esters, hydroxy thiol containing esters and cross-linked thiol ester thiol content were determined by comparing the Raman spectra of the thiol containing esters, hydroxy thiol containing esters and cross-linked thiol ester to calibration standards prepared from mercaptanized methyl oleate diluted in soybean oil to known thiol sulfur contents. Thiol sulfur calibration standards were prepared using standards using various known concentration of mercaptanized methyl oleate diluted in soybean oil.

Raman spectra of the calibration standards and the thiol containing esters, hydroxy thiol containing esters and cross-linked thiol ester were measured using a Kaiser Hololab 5000 Process Raman spectrometer, using a 785 nm laser. Thiol containing esters, hydroxy thiol containing esters and cross-linked thiol ester samples and the thiol sulfur calibration standard Raman spectra were obtained by collecting four 10 second scans which were then processed using Holoreact software. Thiol sulfur values for the thiol containing esters, hydroxy thiol containing esters and cross-linked thiol ester were then calculated using the ratio of the peak area values of the thiol SH peak (center: 2575 cm−1; area 2500-2650 cm−1), and the C═O peak (center—1745 cm−1; area—1700-1800 cm−1) and comparing them to the peak area values for the calibration standards and interpolating the containing esters, hydroxy thiol containing esters and cross-linked thiol ester thiol sulfur contents. Repeatability of the thiol sulfur values as measured by Raman spectroscopy have been shown to have a standard deviation of 0.05-0.1 and a % RSD of 0.6-1.5 using 5 samples having a % thiol sulfur content ranging from 3.1-10.6 weight percent as measured over a two month period.

The Raman spectroscopy technique for determining the thiol sulfur content of a thiol containing ester, hydroxy thiol containing ester, and a cross-linked thiol containing ester has been illustrated using a thiol containing ester produced from soybean oil. However, one skilled in the art may adapt and apply the Raman spectroscopy technique for determining the thiol sulfur content of other thiol containing esters, hydroxy thiol containing esters, and a cross-linked thiol containing esters described herein.

C═C to Thiol Group and Cyclic Sulfide Group to Tool Group Molar Ratios by $^{13}$C NMR Carbon-carbon double bond to thiol group molar ratio and cyclic sulfide group to thiol group molar ratios were determined by $^{13}$C NMR. Thiol containing ester $^{13}$C NMR spectra were obtained on a Varian Mercury INOVA400 NMR, a Varian Mercury Plus 300 NMR, or equivalent spectrometer (75.5 MHz $^{13}$C NMR). Peak areas were determined for the cyclic sulfide carbon atoms, thiol group HS—C carbon atoms and carbon-carbon double bonds carbon atoms using the $^{13}$C NMR regions indicated in the table below:

| Functional Group | $^{13}$C NMR Region | Number of Carbon Atoms/Group |
|---|---|---|
| Cyclic Sulfide Carbon Atoms | 49-49.5 ppm | 2 |
| HS—C Carbon Atoms | 40-41.5 ppm | 1 |
| C═C Carbon Atoms | 120-140 ppm | 2 |

The thiol containing ester cyclic sulfide to thiol group molar ratio were calculated by dividing the cyclic sulfide carbon atoms $^{13}$C NMR peak area by 2 (to account for the 2 carbon atoms per cyclic sulfide group) and dividing the result-ant number by the thiol group HS—C carbon atoms $^{13}$C NMR peak area. The thiol containing ester carbon-carbon double bond to thiol group molar ratio were calculated by dividing the C═C carbon atoms $^{13}$C NMR peak area by 2 (to account for the 2 carbon atoms per carbon-carbon double bond) and dividing the result number by the thiol group HS—C carbon atoms $^{13}$C NMR peak area Offset sample $^{13}$C NMR's for soybean oil and a thiol containing ester produced from soybean oil using the disclosed process is provided as FIG. 1.

The number of average number carbon-carbon double bonds per unsaturated ester molecule can be determined utilizing similar methods utilizing either the carbonyl group carbon atom or the C—O ester group carbon atom $^{13}$C NMR peak areas in conjunction with the carbon-carbon double bond $^{13}$C NMR peak area.

The NMR technique for analyzing the unsaturated ester and the thiol containing ester produced from an unsaturated ester have been illustrated using $^{13}$C NMR on soybean oil the thiol containing ester produced from soybean oil. However, one skilled in the art may adapt and apply either the $^{13}$C NMR or $^{1}$H NMR technique to analyze the unsaturated esters and thiol containing ester produced from the unsaturated ester described herein.

Epoxide Group to Thiol Group Molar Ratios by $^{13}$C or $^{1}$H NMR

The epoxide group to thiol group molar ratios were determined using $^{1}$H or $^{13}$C NMR. Hydroxy thiol containing ester $^{1}$H or $^{13}$C NMR spectra were obtained on a Varian Mercury INOVA400 NMR, a Varian Mercury Plus 300 NMR, or equivalent spectrometer (300 MHz $^{1}$H NMR-75.5 MHz $^{13}$C NMR). Peak areas were determined for the epoxide group and sulfide group using the $^{13}$C and or $^{1}$H regions indicated in the table below:

| Functional Group | $^{1}$H NMR Region | $^{13}$C NMR Region | Number of Carbon Atoms/Group | Number of Hydrogen Atoms/Group |
|---|---|---|---|---|
| Epoxide Group Carbon Atoms | 2.75-3.2 ppm | 53.6-56.6 ppm | 2 | 2 |
| HS—C Carbon Atoms | 3.2-4 ppm | 40-41.5 ppm | 1 | 1 |

The hydroxy thiol containing ester epoxide group to thiol group molar ratio were calculated by dividing the epoxide group carbon atoms $^{1}$H NMR peak area by 2 (to account for the 2 hydrogen atoms attached to the epoxide group carbon atoms) and dividing the result number by the thiol group HS—C carbon atom hydrogens 1C NMR peak area. Similarly, the hydroxy thiol containing ester epoxide group to thiol group molar ratio were calculated using 13H NMR peak areas.

Figure 2:
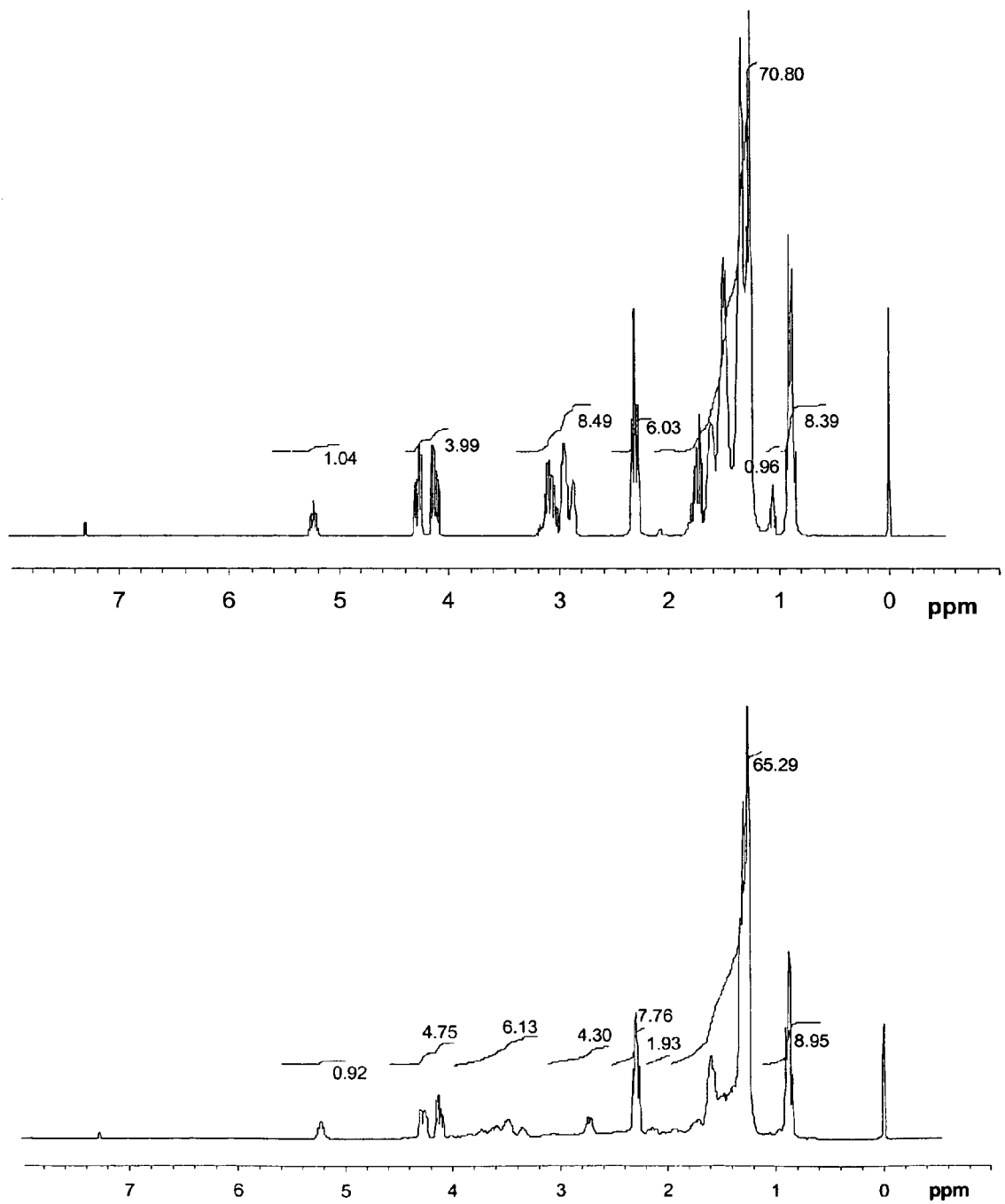
FIG. 2 includes two graphs that compare the NMR's of epoxidized soybean oil, which is shown in the top graph, and a thiol containing ester produced from epoxidized soybean oil in accordance with an embodiment of the present invention, which is shown in the bottom graph.

The average number of epoxide group per epoxidized unsaturated ester molecule can be determined utilizing similar methods utilizing either the carbonyl group carbon atom or the C—O ester group carbon atoms $^{13}$C NMR peak areas in conjunction with the epoxide group $^{13}$C NMR peak area. Sample $^{1}$H NMR's epoxidized soybean oil and a thiol containing ester produced from epoxidized soybean oil 1 are provided in FIG. 2.

The NMR technique for analyzing the epoxidized unsaturated ester and the thiol containing ester produced from an epoxidized unsaturated ester (a hydroxy thiol containing ester) has been illustrated using $^{1}$H NMR on epoxidized soybean oil the thiol containing ester produced from epoxidized soybean oil. However, one skilled in the art may adapt and apply either the $^1$H NMR or $^{13}$C NMR technique to analyze the epoxidized unsaturated esters and thiol containing ester produced from the epoxidized unsaturated ester described herein.

Analysis of Unsaturated Esters, Epoxidized Unsaturated Esters, Thiol Containing Esters, and Hydroxy Thiol Containing Esters by Methanolysis Many properties of the unsaturated esters, epoxidized unsaturated esters, thiol containing esters, and hydroxy thiol containing ester were and/or can be determined by converting the complex ester molecules into their component polyols and carboxylic acid methyl esters. The converted esters are then analyzed by gas chromatography (GC) and/or gas chromatography/mass spectrometry (GCMS) to determine the composition of the complex ester side chains. Properties that are or can be determined by the methanolysis followed by GC or GC/MS of the carboxylic acid methyl esters include the number of side chain that contain thiol groups, the percent of thiol group sulfur, the number of (or average number) of double bonds per ester molecule, the molecular weight distribution (or average molecular weight) of the ester side chains, The number of (or average number of) epoxide groups per ester molecule, the cyclic sulfide to thiol group molar ratio, the carbon-carbon double bond to thiol group molar ratio, and the epoxide group to thiol group molar ratio, among others.

Depending upon the material being subjected to the methanolysis procedure, there are two methanolysis procedures that were practiced upon the unsaturated ester, epoxidized esters, thiol containing ester, and hydroxy thiol containing esters described within the experimental section.

Unsaturated esters and thiol containing ester produced from unsaturated ester were subjected to a hydrogen chloride based methanolysis procedure. In the hydrogen chloride methanolysis procedure, a 50 to 100 mg sample of the thiol containing ester is contacted with 3 mL of 3 N methanolic HCl and reacted for 2 hours a 50° C. The solution is then allowed to cool and the neutralized with a dilute sodium bicarbonate solution. The solution's organic components are then extracted with ethyl ether and analyzed by GC and/or GC/MS. Additional details for the methanolic hydrogen chloride methanolysis procedure may be found in the product specification sheet for methanolic HCl, 0.5 N and 3 N as supplied by Supelco.

Epoxidized unsaturated esters and hydroxy thiol containing esters produced from epoxidized unsaturated esters were subjected to a sodium methoxide based methanolysis procedure. The sodium methoxide methanolysis procedure was based upon the procedure disclosed in U.S. Pat. No. 3,991,089. In the sodium methoxide methanolysis procedure, approximately 1 g of the ester was placed in a 50 mL vial with 5.0 mL 25% sodium methoxide in methanol, and 10 mL methanol. The mixture was shaken for approximately 1 hour at room temperature, during which time the solution became one phase. The mixture was then poured into 25 mL of distilled water. Diethyl ether, 25 mL, was added to the solution and the mixture was acidified with 0.5 N HCL to a pH of approximately 5. The organic layer was separated from the aqueous layer using a separatory funnel. The organic layer was washed successively with distilled water (15 mL) and brine solution (15 mL) and then dried over magnesium sulfate. The magnesium sulfate was separated from the organic solution by filtration and the solvent removed by rotary evaporation.

The products of the methanolysized esters of either methanolysis procedure were then subjected to GC and or GC/MS analysis. Two potential GC and/or GC/MS columns and analysis conditions are provided below:

TABLE 8

Methanolysis Products - GC or GC/MS Analysis Conditions 1
Analysis Column
HP-5 30 m × 0.32 mm id × 0.25 μm film thickness GC Column GC Analysis Conditions:

| | |
|---|---|
| Initial Oven Temperature | 60° C. |
| Initial Time | 5 minutes |
| Oven Temperature Ramp Rate | 8° C./minute |
| Final Oven Temperature | 260° C. |
| Final Time | 20 minutes |
| Injector Temperature | 250° C. |
| Detector Temperature | 300° C. |
| Column Helium flow | 1 mL/minute |

TABLE 9

Methanolysis Products - GC or GC/MS Analysis Conditions 2
Analysis Column
DB 30 m × 0.25 mm id × 0.25 μm film thickness GC Analysis Conditions:

| | |
|---|---|
| Initial Oven Temperature | 100° C. |
| Initial Time | 10 minutes |
| Oven Temperature Ramp Rate | 5° C./minute |
| Final Oven Temperature | 270° C. |
| Final Time | 10 minutes |
| Injector Temperature | 250° C. |
| Detector Temperature | 300° C. |
| Column Helium flow | 2 mL/minute |

Table 10 provides the GC/MS trace peak assignments for a GC/MS trace of a soybean oil subjected to the methanolysis procedure and analyzed by GC/MS using a HP-5 30 m×0.32 mm id×0.25 μm film thickness GC Column.

TABLE 10

GC/MS Data for Methanolysis of Soybean Oil

| GC Retention time | Methyl Ester Carboxylic Acid Assignment |
|---|---|
| 21.58 | Methyl hexadecanoate |
| 23.66 | Methyl (C18 monoene)oate |
| 23.74 | Methyl (C18 monoene)oate |
| 23.96 | Methyl octadecanoate |

FIG. 3 provides a GC/MS trace of a mercaptanized soybean oil subjected to the methanolysis procedure and analyzed by GC/MS using a HP-5 30 m×0.32 mm id×0.25 μm film thickness GC Column. Table 11 provides the GC/MS trace peak assignments.

TABLE 11

GC/MS Data for Methanolysis of A Thiol Containing Ester Produced from Soybean Oil

| GC Retention time | Methyl Ester Carboxylic Acid Assignment |
|---|---|
| 21.58 | Methyl hexadecanoate |
| 23.66 | Methyl (C18 monoene)oate |
| 23.74 | Methyl (C18 monoene)oate |
| 23.96 | Methyl octadecanoate |
| 26.46 | Methyl (C18 Monoene monomercaptan)oate |
| 26.59 | Methyl (C18 Monoene monomercaptan)oate |

TABLE 11-continued

GC/MS Data for Methanolysis of A Thiol Containing Ester Produced from Soybean Oil

| GC Retention time | Methyl Ester Carboxylic Acid Assignment |
|---|---|
| 26.66 | Methyl (C18 Monoene monomercaptan)oate |
| 26.80 | Methyl (C18 monomercaptan)oate |
| 27.31 | Methyl (C18 cyclic sulfide)oate |
| 27.44 | Methyl (C18 cyclic sulfide)oate |
| 29.04 | Methyl (C18 dimercaptan)oate |
| 29.15 | Methyl (C18 dimercaptan)oate |
| 29.37 | Methyl (C18 monoene dimercaptan)oate |
| 29.46 | Methyl (C18 monoene dimercaptan)oate |
| 30.50 | Methyl (C18 di (cyclic sulfide))oate |

Peaks at 29.37 or 29.46 could also contain Methyl (C18 cyclic sulfide monomercaptan)oate isomers as part of those peaks.

FIG. 4 provides a GC/MS trace of epoxidized soybean oil subjected to the methanolysis procedure and analyzed by GC/MS using a HP-5 30 m×0.32 mm id×0.25 μm film thickness GC Column. Table 12 provides the GC/MS trace peak assignments.

TABLE 12

GC/MS Data for Methanolysis of Epoxidized Soybean Oil

| GC Retention time | Methyl Ester Carboxylic Acid Assignment |
|---|---|
| 16.09 | Methyl hexadecanoate |
| 17.68 | Methyl octadecanoate |
| 18.94 | Methyl (C18 monoepoxide)oate |
| 19.94 | Methyl (C18 diepoxide)oate |
| 20.14 | Methyl (C18 diepoxide)oate |
| 21-21.5 | Methyl (C18 triepoxide)oate |

FIG. 5 provides a GC/MS trace of an epoxidized soybean oil contacted with hydrogen sulfide (a hydroxy thiol containing ester) subjected to the methanolysis procedure and analyzed by GC/MS using a HP-5 30 m×0.32 mm id×0.25 μm film thickness GC Column. Table 13 provides the GC/MS trace peak assignments.

TABLE 13

GC/MS Data for Methanolysis of a Hydroxy Thiol Containing Ester Produced from Epoxidized Soybean Oil

| GC Retention time | Methyl Ester Carboxylic Acid Assignment |
|---|---|
| 16.09 | Methyl hexadecanoate |
| 17.68 | Methyl octadecanoate |
| 18.94 | Methyl (C18 monoepoxide)oate |
| 19.94 | Methyl (C18 diepoxide)oate |
| 20.14 | Methyl (C18 diepoxide)oate |
| 20.75 | Methyl (C18 monohydroxy monothiol)oate |
| 21-21.5 | Methyl (C18 triepoxide)oate |
| 22.82 | Methyl (C18 dihydroxy dithiol)oate |
| 22.90 | Methyl (C18 monoepoxide monohydroxy monothiol)oate |
| 27-27.5 | Unidentified mixture of C18 sulfur containing methyl esters |

The methanolysis procedure and GC/MS procedure has been illustrate using soybean oil, epoxidized soybean oil, and the thiol containing products derived from soybean oil and epoxidized soybean oil. However, one skilled in the art can easily adapt the procedures to the analysis of other unsaturated esters, epoxidized unsaturated ester, and the thiol containing products derived from the unsaturated esters and epoxidized unsaturated esters as described herein.

Analysis of the Polythiourethanes

The polythiourethane produced from the thiol containing esters, hydroxy thiol containing esters, and cross linked thiol containing ester were analyzed using ASTM E1545-95A and E228-95 to provide the glass transition temperatures and the coefficients of thermal expansion. Shore hardness of the polythiourethanes were determined using ASTM D2240-02A. The polythiourethane were also subject to a subjective analysis classifying the polythiourethanes as hard, flexible, rubbery, rigid, tough, brittle, and other characteristics.

Applications

In addition to the uses related to fertilizers described herein, embodiments of the present invention are useful in other numerous applications. For example, embodiments of the invention are useful in various polymer applications that include, but are not limited to, as polythiourethanes, foams, adhesives, epoxy hardening agents, polyacrylates and polymethacrylate templates for paints and polyester resins, printing ink binder polymers, alkyd resin cross-linkers, sulfur based paint template, radiation cured polymers, mining and drilling chemicals, specialty chain transfer agents, rubber modifiers, and the like. Because the feedstock materials are economical and readily available, it is believed that embodiments of the present would be useful in such applications and others.

The invention has been described with reference to certain preferred embodiments. However, as obvious variations thereon will become apparent to those of skill in the art, the invention is not to be limited thereto.

TABLE 4

| | Example | | | | | |
|---|---|---|---|---|---|---|
| Ingredient | #1 | #2 | #3 | #4 | #5 | #6 |
| B1 (g) | 14.16 | 11.04 | 8.19 | 13.38 | 13.38 | 11.91 |
| D1 (g) | — | — | 1.35 | 1.5 | — | — |
| D2 (g) | — | — | — | — | 1.5 | 1.35 |
| E (g) | 2.73 | 2.13 | 4.59 | 2.58 | 2.58 | 2.28 |
| F1 (g) | 0.15 | 0.09 | — | 0.15 | 0.15 | 0.12 |
| C1 (b) | 9.96 | 7.74 | 9.87 | 9.39 | 9.39 | 8.34 |
| Total coating (g) | 27.00 | 21.00 | 24.00 | 27.00 | 27.00 | 24.00 |
| D1 overcoat (g) | — | 6.00 | 3.00 | — | — | 3.00 |
| Total coat (%) | 2.7 | 2.7 | 2.7 | 2.7 | 2.7 | 2.7 |

TABLE 5

| | Example | | | |
|---|---|---|---|---|
| Ingredient | #7 | #8 | #9 | #10 |
| B3 (g) | 15.12 | 12.45 | — | — |
| B4 (g) | — | — | 11.01 | 11.01 |
| D1 (g) | 6.00 | 6.00 | 6.00 | — |
| E (g) | 0 | 1.68 | 2.13 | 2.13 |
| F1 (g) | 0.09 | 0.06 | 0.12 | 0.12 |
| C1 (b) | 5.79 | 6.81 | 7.74 | 7.74 |
| Total coating (g) | 27.00 | 27.00 | 27.00 | 21.00 |
| D1 overcoat (g) | — | — | — | 6.00 |
| Total coat (%) | 2.7 | 2.7 | 2.7 | 2.7 |

TABLE 6

| Ingredient | Example #11 | Example #12 | Example #13 | Example #14 |
|---|---|---|---|---|
| B2 (g) | 9.33 | 13.86 | 11.34 | 6.09 |
| B1 (g) | — | — | — | 3.18 |
| D1 (g) | 1.35 | 1.35 | 6.00 | 6.00 |
| E (g) | 2.28 | — | — | 2.67 |
| F1 (g) | — | — | — | — |
| C1 (b) | 11.04 | 11.79 | 9.66 | 9.06 |
| Total coating (g) | 24.00 | 27.00 | 27.00 | 27.00 |
| D1 overcoat (g) | 3.00 | — | — | — |
| Total coat (%) | 2.7 | 2.7 | 2.7 | 2.7 |

TABLE 7

| Ingredient | Example #15 | Example #16 | Example #17 |
|---|---|---|---|
| B2 (g) | 14.37 | 13.89 | 14.37 |
| D1 (g) | 4.95 | 4.8 | — |
| D2 (g) | — | — | 1.95 |
| F2 (g) | 0.12 | 0.12 | 0.12 |
| C1 (g) | — | 0.90 | — |
| C2 (b) | 7.56 | 7.29 | 7.56 |
| Total coating (g) | 27.00 | 27.00 | 24.00 |
| D1 overcoat (g) | — | — | 3.00 |
| Total coat (%) | 2.7 | 2.7 | 2.7 |

What is claimed is:

1. A composition comprising thiol ester oligomers having at least two thiol ester monomers that are
   a) thiol ester molecules derived from an unsaturated natural source oil or unsaturated triglyceride or
   b) hydroxy thiol ester molecules derived from an epoxidized unsaturated natural source oil or epoxidized unsaturated triglyceride connected by a polysulfide linkage having a structure —$S_Q$—, wherein Q is greater than 1.

2. The composition of claim 1, wherein the thiol ester oligomers have at least three thiol ester monomers connected by polysulfide linkages.

3. The composition of claim 1, wherein the thiol ester oligomers have from 3 to 20 thiol ester monomers connected by polysulfide linkages.

4. The composition of claim 1, wherein the composition comprises thiol ester monomers and thiol ester oligomers.

5. The composition of claim 4, wherein the combined thiol ester monomers and thiol ester oligomers have a total thiol sulfur content from 0.5 to 8 weight percent.

6. The composition of claim 4, wherein the combined thiol ester monomers and thiol ester oligomers have an average molecular weight greater than 2000.

7. The composition of claim 4, wherein the combined thiol ester monomers and thiol ester oligomers have an average molecular weight from 2000 to 20,000.

8. The composition of claim 4, wherein the combined thiol ester monomers and thiol ester oligomers have a total sulfur content ranging from 8 to 15 weight percent.

9. A process to produce a composition comprising:
   a) contacting a thiol ester composition comprising thiol ester molecules with an oxidizing agent; and
   b) reacting the thiol ester molecules and the oxidizing agent to form thiol ester oligomers having at least two thiol ester molecules connected by a polysulfide linkage having a structure —$S_Q$—, wherein Q is greater than 1;
wherein the thiol ester molecules are derived from a) an unsaturated natural source oil or unsaturated triglyceride or b) an epoxidized unsaturated natural source oil or epoxidized unsaturated triglyceride.

10. The process of claim 9, wherein the oxidizing agent is elemental sulfur, oxygen, or hydrogen peroxide.

11. The process of claim 9, wherein the oxidizing agent is elemental sulfur.

12. The process of claim 9, wherein the thiol ester molecules are hydroxy thiol ester molecules.

13. The process of claim 9, wherein a weight ratio of elemental sulfur to thiol sulfur in the thiol ester molecules ranges from 0.5 to 32.

14. The process of claim 9, wherein step of the reacting the thiol ester molecules and the oxidizing agent is performed at a temperature ranging from 25° C. to 150° C.

15. The process of claim 9, wherein residual hydrogen sulfide is stripped from the composition produced.

16. The process of claim 11, wherein the reaction of the thiol ester molecules and the elemental sulfur is catalyzed.

17. The process of claim 16, wherein the catalyst is an amine.

18. The process of claim 9, wherein the thiol ester molecules have an average of at least 1.5 ester groups per thiol ester molecule and have an average of at least 1.5 thiol groups per thiol ester molecule.

19. The process of claim 9, wherein the thiol ester molecules have an average of from 2 to 7 ester groups per thiol ester molecule and have an average of from 2 to 4 thiol groups per thiol ester molecule.

20. The process of claim 9, wherein the thiol ester molecules are derived from an unsaturated natural source oil or an unsaturated triglyceride.

21. The process of claim 20, wherein the thiol ester molecules have an average of from 2.5 to 5 ester groups per thiol ester molecule, have an average of 1.5 to 9 thiol groups per thiol ester molecule, and have an average molar ratio of cyclic sulfide groups to thiol group per thiol ester molecule less than 1.5.

22. The process of claim 20, wherein the thiol ester molecules have an average of from 2.5 to 5 ester groups per thiol ester molecule, have an average of 2 to 4 thiol groups per thiol ester molecule, and have an average molar ratio of cyclic sulfide groups to thiol group per thiol ester molecule less than 0.5.

23. The process of claim 20, wherein the thiol ester molecules have an average of greater than 5 weight percent thiol sulfur.

24. The process of claim 20, wherein the thiol ester molecules have an average ranging from 8 to 10 weight percent thiol sulfur.

25. The process of claim 20, wherein the unsaturated natural source oil comprises soybean oil, corn oil, castor bean oil, or canola oil.

26. The process of claim 20, wherein the unsaturated natural source oil comprises soybean oil.

27. The process of claim 12, wherein the hydroxy thiol ester molecules have an average of at least 1.5 ester groups per hydroxy thiol ester molecule, have an average of at least 1.5 thiol groups per hydroxy thiol ester molecule, and have an average of at least 1.5 hydroxy groups per hydroxy thiol ester molecule.

28. The process of claim 12, the hydroxy thiol ester molecules have an average of from 2 to 7 thiol groups per hydroxy thiol ester molecule, have an average of from 2 to 7 hydroxy groups per hydroxy thiol ester molecule, have an average of 2 to 7 ester groups per hydroxy thiol ester molecule, and have an average of 5 to 25 weight percent thiol sulfur.

29. The process of claim 12, wherein the hydroxy thiol ester molecules are derived from an epoxidized unsaturated natural source oil or an epoxidized unsaturated triglyceride.

30. The process of claim 29, wherein the hydroxy thiol ester molecules have an average of at least 2.5 weight percent thiol sulfur.

31. The process of claim 29, wherein the hydroxy thiol ester molecules have an average of from 5 to 20 weight percent thiol sulfur.

32. The process of claim 29, wherein the hydroxy thiol ester molecules have an average of from 1.5 to 9 thiol groups per hydroxy thiol ester molecule, have an average of from 1.5 to 9 hydroxy groups per hydroxy thiol ester molecule, have an average of from 2.5 to 5 ester groups per hydroxy thiol ester molecule, and have an average of 5 to 25 weight percent thiol sulfur.

33. The process of claim 29, wherein the hydroxy thiol ester molecules have an average of from 2 to 4 thiol groups per hydroxy thiol ester molecule, have an average of from 2 to 4 hydroxy groups per hydroxy thiol ester molecule, have an average of from 2.5 to 5 ester groups per hydroxy thiol ester molecule, and have an average of from 5 to 25 weight percent thiol sulfur.

34. The process of claim 29, the epoxidized unsaturated natural source oil comprises epoxidized soybean oil, epoxidized corn oil, epoxidized castor bean oil, or epoxidized canola oil.

35. The process of claim 29, the epoxidized unsaturated natural source oil comprises epoxidized soybean oil.

36. The composition of claim 1, wherein the thiol ester monomers that are thiol ester molecules derived from the unsaturated natural source oil or unsaturated triglyceride have an average of at least 1.5 ester groups per thiol ester molecule and have an average of at least 1.5 thiol groups per thiol ester molecule.

37. The composition of claim 1, wherein the thiol ester monomers that are thiol ester molecules derived from the unsaturated natural source oil or unsaturated triglyceride have an average of from 2 to 7 ester groups per thiol ester molecule and have an average of from 2 to 4 thiol groups per thiol ester molecule.

38. The composition of claim 1, wherein the composition comprises thiol ester oligomers having at least three thiol ester monomers that are thiol ester molecules derived from an unsaturated natural source oil or an unsaturated triglyceride.

39. The composition of claim 38, wherein the thiol ester molecules have an average of from 2.5 to 5 ester groups per thiol ester molecule, have an average of 1.5 to 9 thiol groups per thiol ester molecule, and have an average molar ratio of cyclic sulfide groups to thiol group per thiol ester molecule less than 1.5.

40. The composition of claim 38, wherein the thiol ester molecules have an average of from 2.5 to 5 ester groups per thiol ester molecule, have an average of 2 to 4 thiol groups per thiol ester molecule, and have an average molar ratio of cyclic sulfide groups to thiol group per thiol ester molecule less than 0.5.

41. The composition of claim 38, wherein the thiol ester molecules have an average of greater than 5 weight percent thiol sulfur.

42. The composition of claim 38, wherein the thiol ester molecules have an average ranging from 8 to 10 weight percent thiol sulfur.

43. The composition of claim 38, wherein the unsaturated natural source oil comprises soybean oil, corn oil, castor bean oil, or canola oil.

44. The composition of claim 38, wherein the unsaturated natural source oil comprises soybean oil.

45. The composition of claim 1, wherein the thiol ester monomers that are hydroxy thiol ester molecules derived from the epoxidized unsaturated natural source oil or epoxidized unsaturated triglyceride have an average of at least 1.5 ester groups per hydroxy thiol ester molecule, have an average of at least 1.5 thiol groups per hydroxy thiol ester molecule, and have an average of at least 1.5 hydroxy groups per hydroxy thiol ester molecule.

46. The composition of claim 1, wherein the thiol ester monomers that are hydroxy thiol ester molecules derived from the epoxidized unsaturated natural source oil or epoxidized unsaturated triglyceride have an average of from 2 to 7 thiol groups per hydroxy thiol ester molecule, have an average of from 2 to 7 hydroxy groups per hydroxy thiol ester molecule, have an average of 2 to 7 ester groups per hydroxy thiol ester molecule, and have an average of 5 to 25 weight percent thiol sulfur.

47. The composition of claim 1, wherein the composition comprises thiol ester oligomers having at least three thiol ester monomers that are hydroxy thiol ester molecules derived from an epoxidized unsaturated natural source oil or an epoxidized unsaturated triglyceride.

48. The composition of claim 47, wherein the hydroxy thiol ester molecules have an average of at least 2.5 weight percent thiol sulfur.

49. The composition of claim 47, wherein the hydroxy thiol ester molecules have an average of from 5 to 20 weight percent thiol sulfur.

50. The composition of claim 47, wherein the hydroxy thiol ester molecules have an average of from 1.5 to 9 thiol groups per hydroxy thiol ester molecule, have an average of from 1.5 to 9 hydroxy groups per hydroxy thiol ester molecule, have an average of from 2.5 to 5 ester groups per hydroxy thiol ester molecule, and have an average of 5 to 25 weight percent thiol sulfur.

51. The composition of claim 47, wherein the hydroxy thiol ester molecules have an average of from 2 to 4 thiol groups per hydroxy thiol ester molecule, have an average of from 2 to 4 hydroxy groups per hydroxy thiol ester molecule, have an average of from 2.5 to 5 ester groups per hydroxy thiol ester molecule, and have an average of from 5 to 25 weight percent thiol sulfur.

52. The composition of claim 47, wherein the epoxidized unsaturated natural source oil comprises epoxidized soybean oil, epoxidized corn oil, epoxidized castor bean oil, or epoxidized canola oil.

53. The composition of claim 47, wherein the epoxidized unsaturated natural source oil comprises epoxidized soybean oil.

* * * * *